(12) United States Patent
Burkin et al.

(10) Patent No.: US 10,398,749 B2
(45) Date of Patent: Sep. 3, 2019

(54) METHODS OF TREATING MUSCULAR DYSTROPHY

(71) Applicant: BOARD OF REGENTS OF THE NEVADA SYSTEM OF HIGHER EDUCATION ON BEHALF OF THE UNIVERSITY OF NEVADA, Reno, NV (US)

(72) Inventors: Dean Burkin, Sparks, NV (US); Ryan Wuebbles, Sparks, NV (US)

(73) Assignee: BOARD OF REGENTS OF THE NEVADA SYSTEM OF HIGHER EDUCATION ON BEHALF OF THE UNIVERSITY OF NEVADA, RENO, Reno, NV (US)

( * ) Notice: Subject to any disclaimer, the term of this patent is extended or adjusted under 35 U.S.C. 154(b) by 0 days.

(21) Appl. No.: 16/019,194

(22) Filed: Jun. 26, 2018

(65) Prior Publication Data
US 2018/0318380 A1 Nov. 8, 2018

Related U.S. Application Data

(63) Continuation of application No. 14/426,928, filed as application No. PCT/US2013/059074 on Sep. 10, (Continued)

(51) Int. Cl.
| | |
|---|---|
| *A61K 38/05* | (2006.01) |
| *A61K 31/496* | (2006.01) |
| *A61K 31/4985* | (2006.01) |
| *A61K 31/506* | (2006.01) |
| *A61K 38/39* | (2006.01) |
| *A61K 31/5375* | (2006.01) |
| *A61K 31/343* | (2006.01) |
| *A61K 31/4418* | (2006.01) |
| *A61K 31/444* | (2006.01) |
| *A61K 31/4709* | (2006.01) |
| *A61K 31/53* | (2006.01) |
| *A61K 45/06* | (2006.01) |
| *A61K 31/5377* | (2006.01) |
| *A61K 31/5383* | (2006.01) |
| *A61K 31/551* | (2006.01) |
| *A61K 31/57* | (2006.01) |
| *A61K 31/661* | (2006.01) |
| *A61K 31/16* | (2006.01) |
| *A61K 31/575* | (2006.01) |
| *A61K 31/5365* | (2006.01) |
| *A61K 31/4178* | (2006.01) |
| *A61K 31/20* | (2006.01) |
| *A61K 31/519* | (2006.01) |

(Continued)

(52) U.S. Cl.
CPC .............. *A61K 38/05* (2013.01); *A61K 31/16* (2013.01); *A61K 31/19* (2013.01); *A61K 31/20* (2013.01); *A61K 31/277* (2013.01); *A61K 31/341* (2013.01); *A61K 31/343* (2013.01); *A61K 31/36* (2013.01); *A61K 31/37* (2013.01); *A61K 31/381* (2013.01); *A61K 31/4025* (2013.01); *A61K 31/4035* (2013.01); *A61K 31/41* (2013.01); *A61K 31/415* (2013.01); *A61K 31/4178* (2013.01); *A61K 31/4196* (2013.01); *A61K 31/421* (2013.01); *A61K 31/426* (2013.01); *A61K 31/4365* (2013.01); *A61K 31/4402* (2013.01); *A61K 31/444* (2013.01); *A61K 31/4418* (2013.01); *A61K 31/47* (2013.01); *A61K 31/473* (2013.01); *A61K 31/4709* (2013.01); *A61K 31/496* (2013.01); *A61K 31/498* (2013.01); *A61K 31/4985* (2013.01); *A61K 31/506* (2013.01); *A61K 31/519* (2013.01); *A61K 31/53* (2013.01); *A61K 31/5365* (2013.01); *A61K 31/5375* (2013.01); *A61K 31/5377* (2013.01); *A61K 31/5383* (2013.01); *A61K 31/541* (2013.01); *A61K 31/551* (2013.01); *A61K 31/57* (2013.01); *A61K 31/575* (2013.01); *A61K 31/661* (2013.01); *A61K 38/39* (2013.01); *A61K 45/06* (2013.01); *A61K 31/404* (2013.01); *A61K 31/4164* (2013.01); *A61P 21/00* (2018.01)

(58) Field of Classification Search
CPC .... A61K 31/404; A61K 31/4164; A61P 21/00
USPC .................................................. 514/385, 415
See application file for complete search history.

(56) References Cited

U.S. PATENT DOCUMENTS 9,566,310 B2 * 2/2017 Burkin ................. A61K 31/498

* cited by examiner

*Primary Examiner* — Kevin E Weddington
(74) *Attorney, Agent, or Firm* — Schwabe Williamson & Wyatt, P.C.

(57) ABSTRACT

Disclosed herein are α7β1 integrin modulatory agents and methods of using such to treat conditions associated with decreased α7β1 integrin expression or activity, including muscular dystrophy. In one example, methods for treating a subject with muscular dystrophy are disclosed. The methods include administering an effective amount of an α7β1 integrin modulatory agent to the subject with muscular dystrophy, wherein the α7β1 integrin modulatory agent increases α7β1 integrin expression or activity as compared to α7β1 integrin expression or activity prior to treatment, thereby treating the subject with muscular dystrophy. Also disclosed are methods of enhancing muscle regeneration, repair, or maintenance in a subject and methods of enhancing α7β1 integrin expression by use of the disclosed α7β1 integrin modulatory agents. Methods of prospectively preventing or reducing muscle injury or damage in a subject are also disclosed.

18 Claims, 37 Drawing Sheets

Related U.S. Application Data 2013, now Pat. No. 10,028,992, and a continuation-in-part of application No. 13/842,781, filed on Mar. 15, 2013, now Pat. No. 9,566,310.

(60) Provisional application No. 61/798,479, filed on Mar. 15, 2013, provisional application No. 61/699,189, filed on Sep. 10, 2012.

(51) Int. Cl.
| | |
|---|---|
| *A61K 31/541* | (2006.01) |
| *A61K 31/19* | (2006.01) |
| *A61K 31/277* | (2006.01) |
| *A61K 31/341* | (2006.01) |
| *A61K 31/36* | (2006.01) |
| *A61K 31/37* | (2006.01) |
| *A61K 31/381* | (2006.01) |
| *A61K 31/4025* | (2006.01) |
| *A61K 31/4035* | (2006.01) |
| *A61K 31/41* | (2006.01) |
| *A61K 31/415* | (2006.01) |
| *A61K 31/4196* | (2006.01) |
| *A61K 31/421* | (2006.01) |
| *A61K 31/426* | (2006.01) |
| *A61K 31/4365* | (2006.01) |
| *A61K 31/4402* | (2006.01) |
| *A61K 31/47* | (2006.01) |
| *A61K 31/473* | (2006.01) |
| *A61K 31/498* | (2006.01) |
| *A61K 31/404* | (2006.01) |
| *A61K 31/4164* | (2006.01) |
| *A61P 21/00* | (2006.01) |

FIG. 5
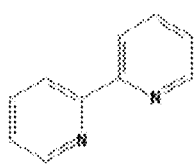
2,2-Dipyridyl
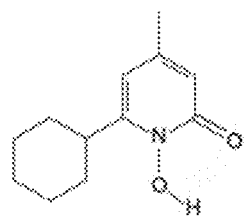
Ciclopirox
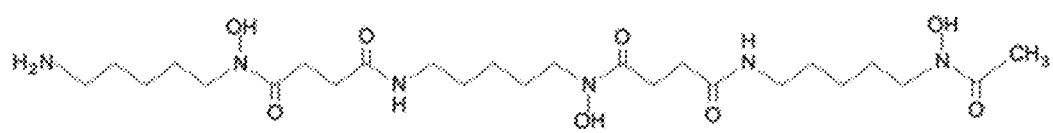
Deferoxamine

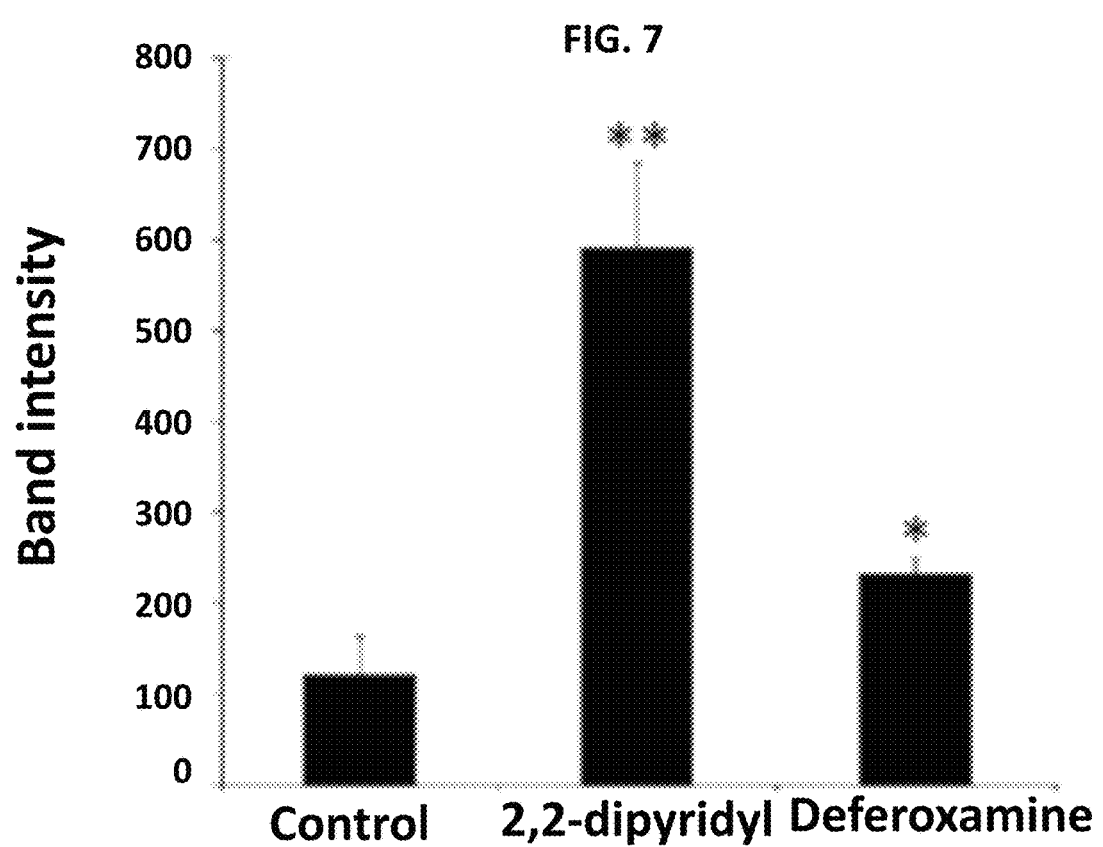

FIG. 8
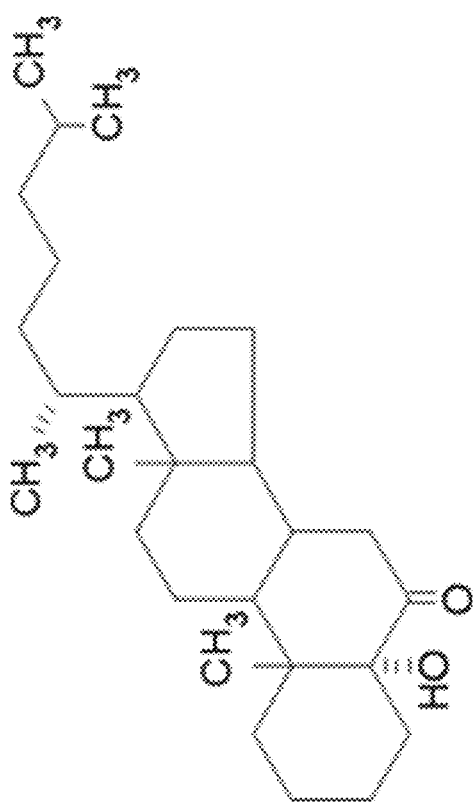
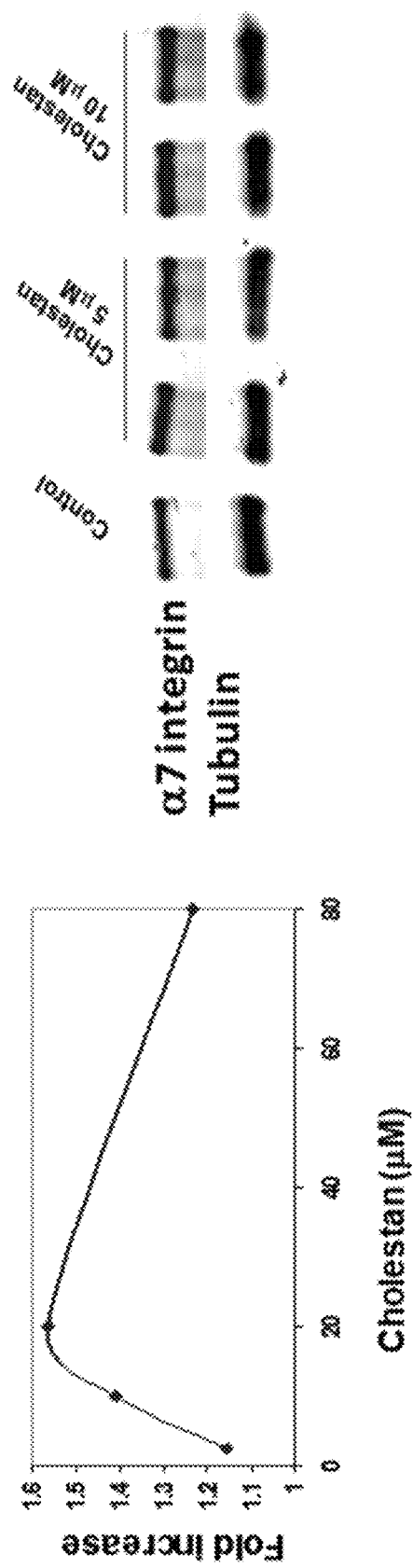

FIG. 9
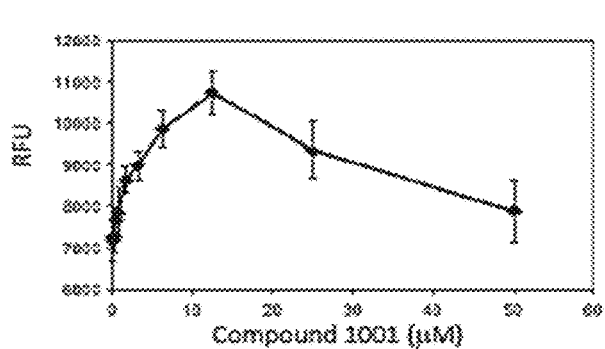
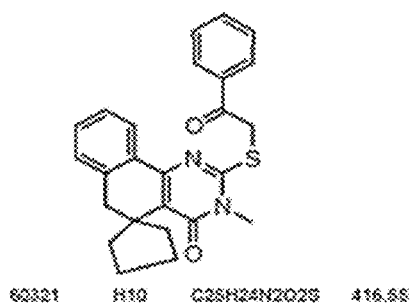
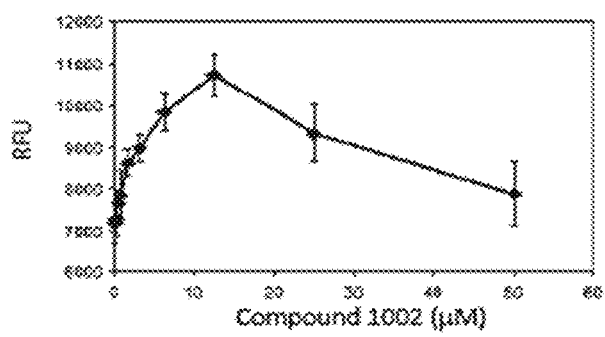
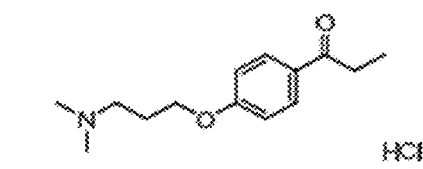
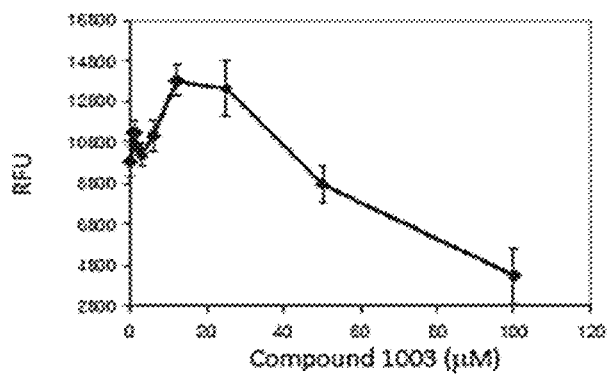
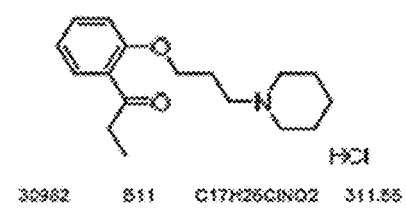

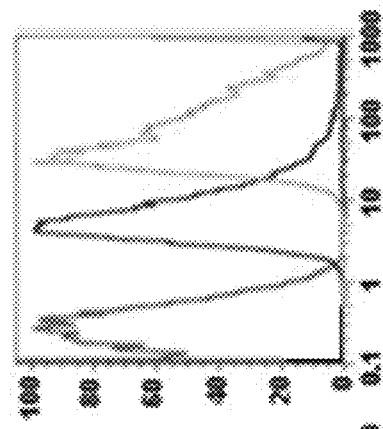
FIG. 12A  FIG. 12B  FIG. 12C  FIG. 12D
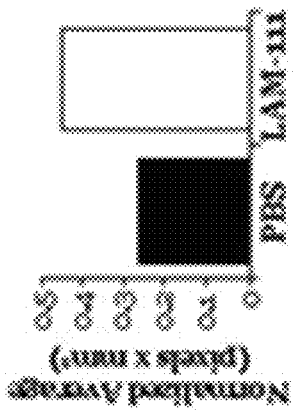
FIG. 13A
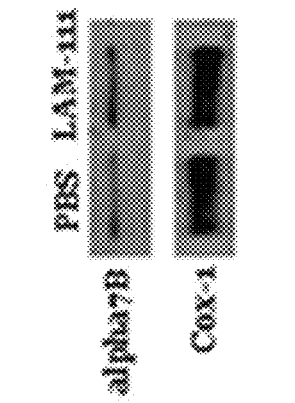
FIG. 13B
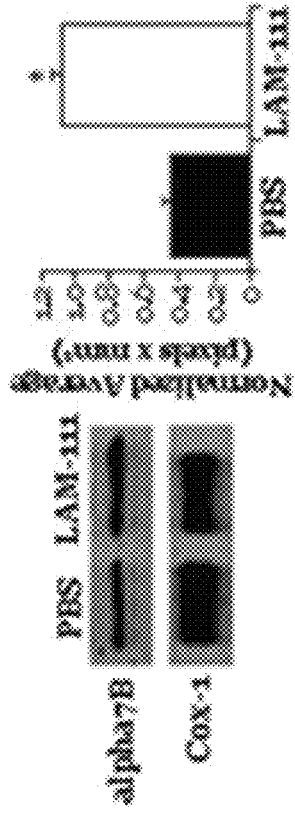
FIG. 13C
FIG. 13D

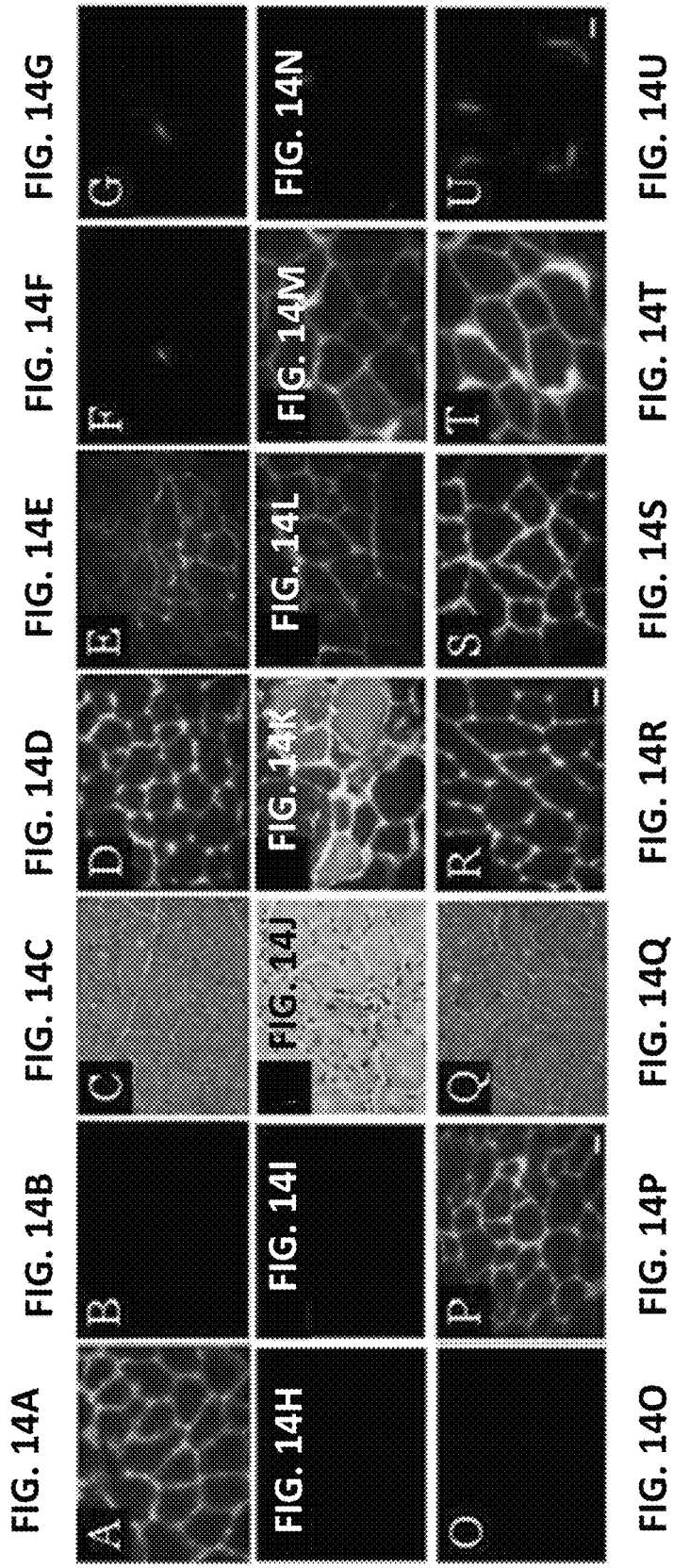

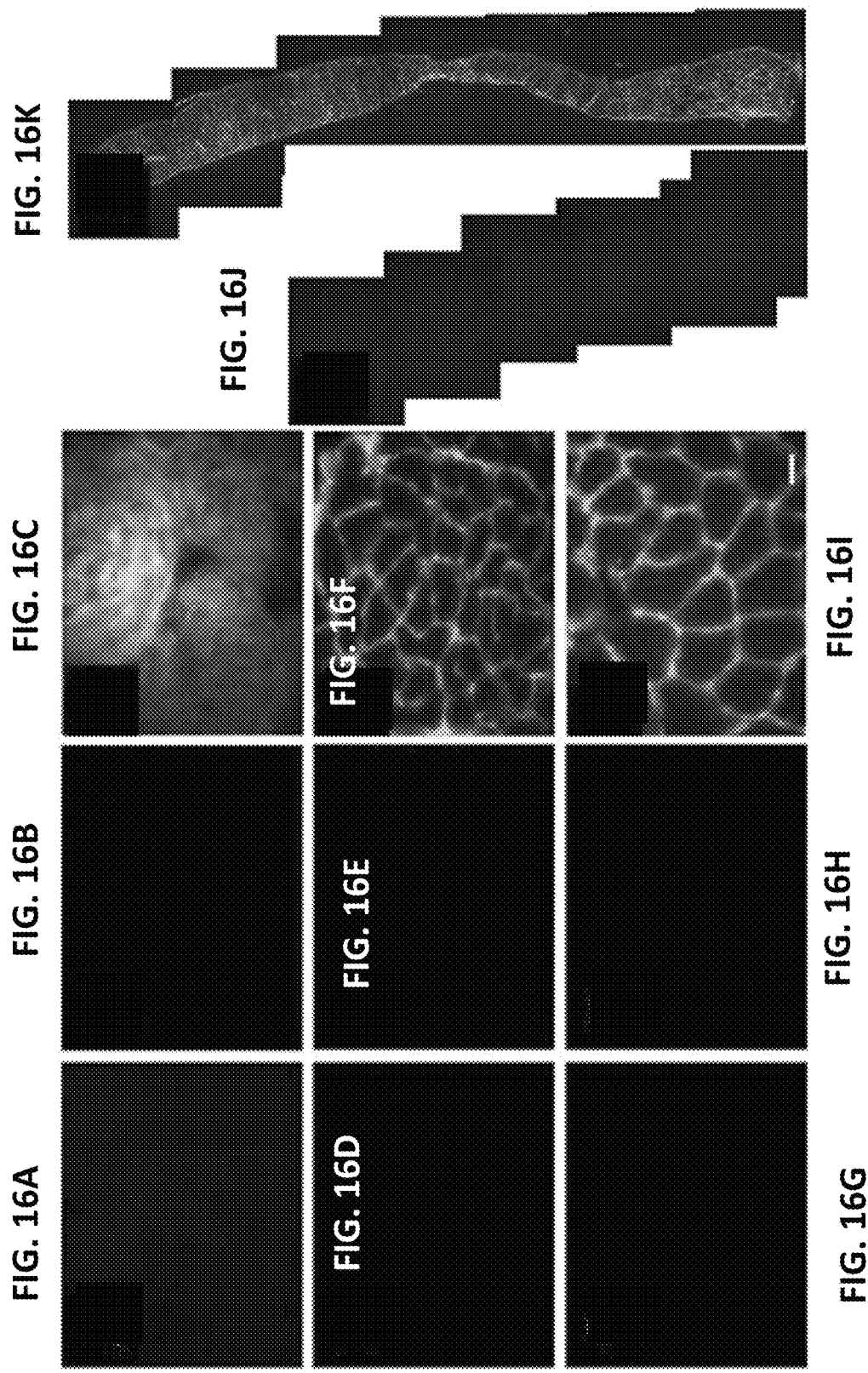

FIG. 29C Rational Drug Design for PRTH-002-F: Tail Piece
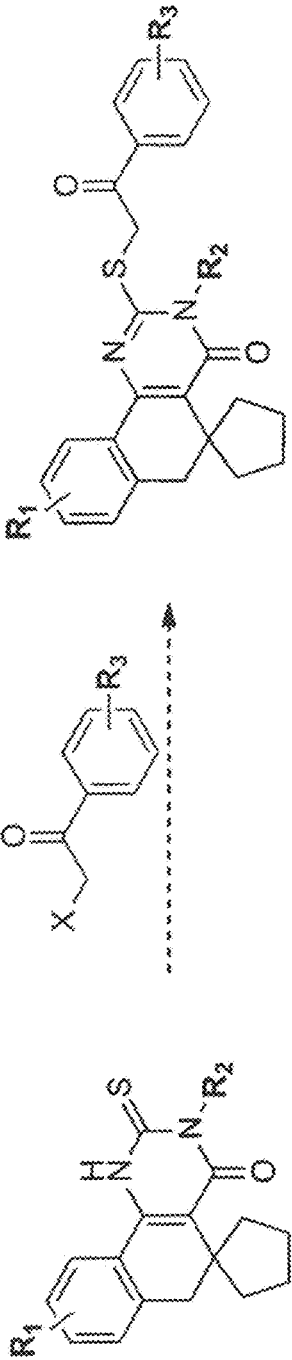

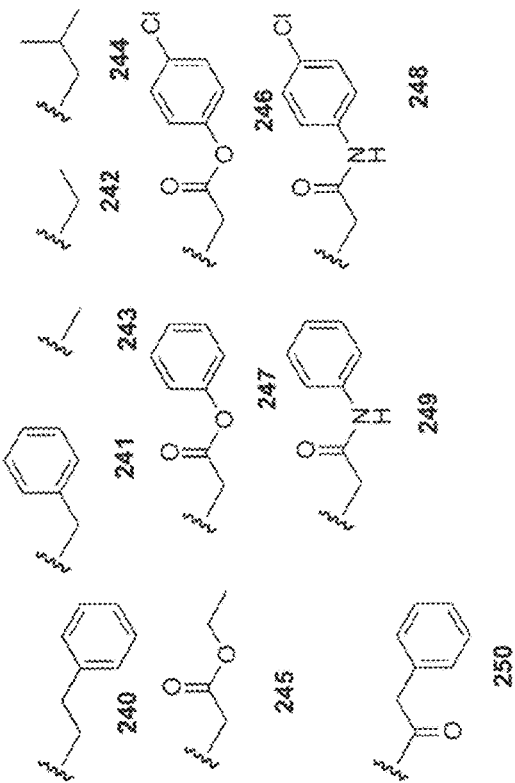
FIG. 29D
Rational Drug Design for PRTH-002-F: Tail Piece
- Focus on modifying the Tail Piece
- Round 1 : 11 analogs
Compounds 240-250
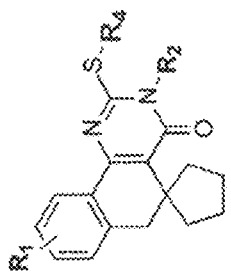
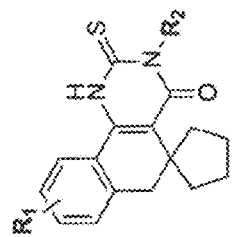
Intermediate 1

FIG. 29E Rational Drug Design for PRTH-002-F: A Ring
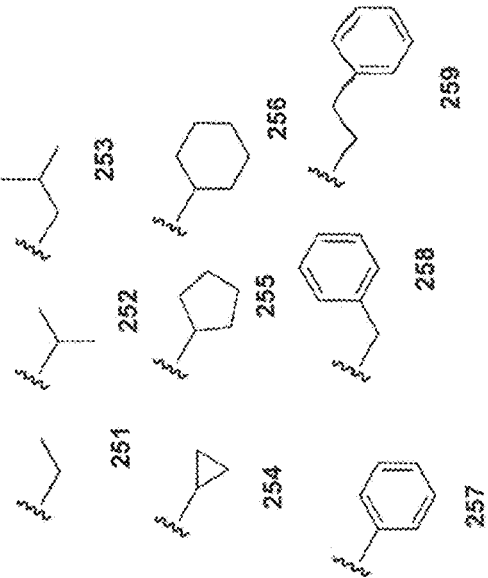
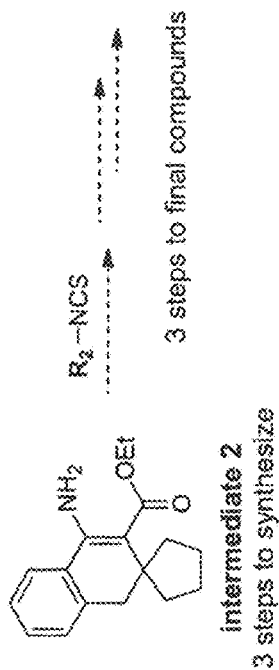
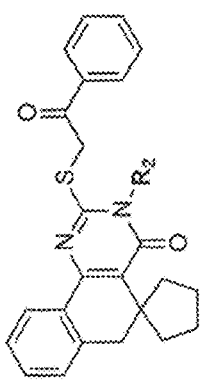
- Focus on A-Ring
- Round 2 : 9 analogs

Rational Drug Design For PRTH-002-E

- Round 1 : 22 analogs

PRTH-002-E
2,2'-dipyridyl

⟹

PRTH-002-E6 to E27

$R_1$ = OMe, tBu, $CF_3$, F, $NMe_2$, $NO_2$, $CO_2Me$, $CONH_2$, CONHMe, $CONMe_2$
$R_2$ = H $R_1$ = Cl, Br, Me, OH, $CO_2H$, $NH_2$
$R_2$ = H $R_1$ = Cl
$R_2$ = Cl, Br, OH $R_1$ = Me
$R_2$ = Br, Me $R_1$ = $CO_2H$
$R_2$ = $CO_2H$

PRTH-002-E6 to E27

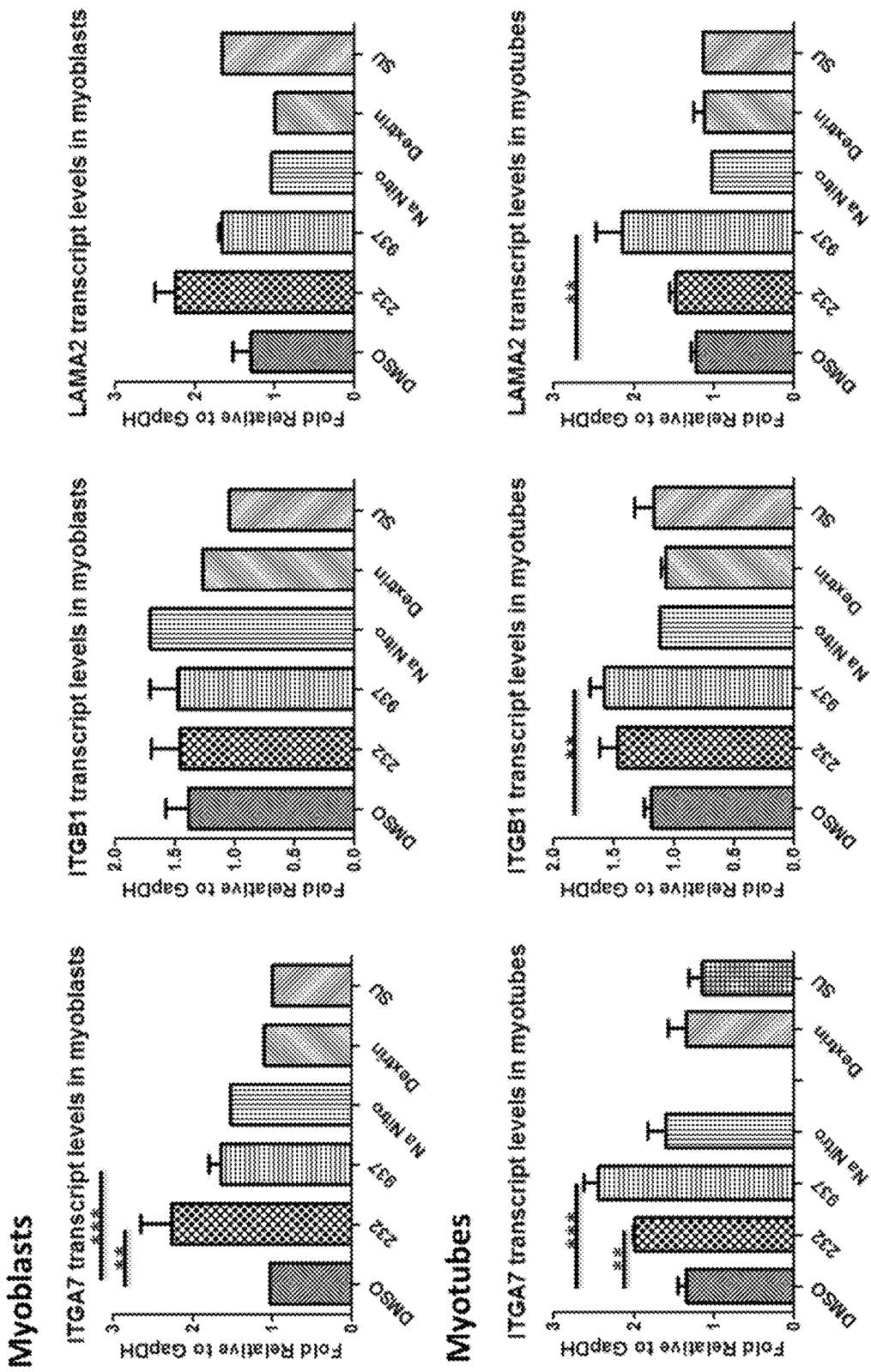
FIG. 30 Quantitative Real-time Analysis in C2C12 cells treated for 24 hours

METHODS OF TREATING MUSCULAR DYSTROPHY

CROSS REFERENCE TO RELATED APPLICATIONS

This application is a continuation of U.S. application Ser. No. 14/426,928, filed Mar. 9, 2015, which is the 371 U.S. National Stage of International Application No. PCT/US2013/059074, filed Sep. 10, 2013, which was published in English under PCT Article21(2), which in turn claims the benefit of U.S. Provisional Patent Application Nos. 61/699,189, filed on Sep. 10, 2012, and 61/798,479, filed on Mar. 15, 2013, each of these provisional applications is herein incorporated by reference in its entirety. PCT/US2013/059074 is a Continuation in Part of U.S. patent application Ser. No. 13/842,781 filed on Mar. 15, 2013, now issued as U.S. Pat. No. 9,566,310. U.S. patent application Ser. No. 13/842,781, which in turn claims the benefit of U.S. Provisional Patent Application Nos. 61/699,189, filed on Sept. 10, 2012, and 61/798,479, filed on Mar. 15, 2013 each of which is herein incorporated by reference in its entirety.

ACKNOWLEDGMENT OF GOVERNMENT SUPPORT

This invention was made with government support under Grant Numbers R43 AR060030, R21 NS058429-01, and R21 AR060769 awarded by the National Institutes of Health. The government has certain rights in the invention.

FIELD

This disclosure relates to the field of muscular dystrophy and in particular, to compositions and methods for treating muscular dystrophy, such as Duchenne muscular dystrophy, Fukuyama congenital muscular dystrophy or merosin deficient congenital muscular dystrophy type 1A or 1D.

BACKGROUND

Mutations in the $\alpha 7$ integrin gene are responsible for congenital myopathy in man The $\alpha 7 \beta 1$ integrin is also a major modifier of muscle disease progression in various genetic muscle diseases including various types of muscular dystrophy, such as Duchenne muscular dystrophy (DMD), Fukuyama congenital muscular dystrophy (FCMD) and merosin deficient congenital muscular dystrophy type 1A (MDC1A). However, transcriptional regulation of the $\alpha 7$ integrin gene, including such role in muscular dystrophy (e.g., DMD, FCMD and/or MDC1A), remains poorly understood.

Duchenne muscular dystrophy (DMD) is an X-chromosome-linked disease and the most common form of muscular dystrophy. DMD affects 1 in 3500 live male births with patients suffering from chronic muscle degeneration and weakness. Clinical symptoms are first detected between the ages of 2 and 5 years and, by the time the patient is in their teens, the ability for independent ambulation is lost. Death typically occurs in the patient before they are 30 years old due to cardiopulmonary failure.

Fukuyama congenital muscular dystrophy (FCMD) and MDC1A are congenital muscular dystrophies that are heritable neuromuscular disorders. MDC1A is characterized by muscle weakness at birth or in infancy. Affected infants will present with poor muscle tone and few movements. The quality of life and life span of the child is affected through progressive muscle wasting, respiratory compromise, and spinal rigidity. MDC1A is the most common and severe form of congenital muscular dystrophy, accounting for 30-40% of all congenital muscular dystrophy (CMD) diagnosed cases. MDC1A is characterized by congenital hypotonia, distinct joint contractures, and a lack of independent ambulation. Feeding tube placement and positive pressure ventilation is often required for the respiratory problems that occur. Patients afflicted with MDC1A often die before they reach the age of ten years. FCMD is caused by mutations in the fukutin gene, located at human chromosome 9q31. The disease is inherited in an autosomal recessive manner FCMD is a type of Limb-Girdle muscular dystrophy. Currently there is no cure for DMD, FCMD or MDC1A.

SUMMARY

The muscular dystrophies are a group of diverse, heritable neuromuscular disorders which represent a group of devastating neuromuscular diseases characterized by primary or secondary skeletal muscle involvement. Currently, there are no cures for such diseases.

Disclosed herein are $\alpha 7 \beta 1$ integrin expression modulatory agents and methods of using such to treat a condition associated with impaired $\alpha 7$ integrin expression, such as muscular dystrophy. In one embodiment, a method for treating a subject with muscular dystrophy is disclosed. The method includes administering an effective amount of an $\alpha 7 \beta 1$ integrin modulatory agent to the subject with muscular dystrophy, wherein the $\alpha 7 \beta 1$ integrin modulatory agent is ciclopirox ethanolamine, deferoxamine, 2,2-dipyridyl; 5$\alpha$-cholestan-3$\beta$-ol-6-one, Compound ID #1001, Compound ID #1002, Compound ID #1003, N032-0003, N066-0070, N069-0071, N069-0075, N064-0028, N066-0053, N069-0073, 1080-0573, a compound provided herein, such as in Table 10, Table 11, Table 6 (see Appendix I in U.S. Provisional Patent Application No. 61/798,479, filed on Mar. 15, 2013, which is hereby incorporated by reference in its entirety), Table 7 (see Appendix II in U.S. Provisional Patent Application No. 61/798,479, filed on Mar. 15, 2013, which is hereby incorporated by reference in its entirety), Table 13, or a combination thereof, wherein the $\alpha 7 \beta 1$ integrin modulatory agent increases $\alpha 7 \beta 1$ integrin expression or activity as compared to $\alpha 7 \beta 1$ integrin expression or activity prior to treatment, thereby treating the subject with muscular dystrophy (such as MDC1A, MDC1D, LGMD, DMD, FCMD or FHMD).

Also disclosed are methods of enhancing muscle regeneration, repair, or maintenance in a subject. In some embodiments, the method includes administering an effective amount of an $\alpha 7 \beta 1$ integrin modulatory agent to the subject in need of muscle regeneration, repair or maintenance, wherein the $\alpha 7 \beta 1$ integrin modulatory agent comprises ciclopirox ethanolamine, deferoxamine, 2,2-dipyridyl; 5$\alpha$-cholestan-3$\beta$-ol-6-one, Compound ID #1001, Compound ID #1002, Compound ID #1003, N032-0003, N066-0070, N069-0071, N069-0075, N064-0028, N066-0053, N069-0073, 1080-0573, a compound provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or a combination thereof, wherein the $\alpha 7 \beta 1$ integrin modulatory agent increases $\alpha 7 \beta 1$ integrin expression or activity as compared to $\alpha 7 \beta 1$ integrin expression or activity prior to treatment, thereby enhancing muscle regeneration, repair or maintenance in a subject.

In a specific embodiment, the present disclosure provides a method for increasing muscle regeneration in a subject. For example, geriatric subjects, subjects suffering from muscle disorders, and subjects suffering from muscle injury, including activity induced muscle injury, such as injury caused by exercise, may benefit from this embodiment.

In yet further embodiments of the disclosed method, the α7β1 integrin modulatory agent is administered in a preventative manner, such as to prevent or reduce muscular damage or injury (such as activity or exercise induced injury). For example, geriatric subjects, subjects prone to muscle damage, or subjects at risk for muscular injury, such as athletes, may be treated in order to eliminate or ameliorate muscular damage, injury, or disease.

Further disclosed are methods of enhancing α7β1 integrin expression. In some embodiments, the method includes contacting a cell with an effective amount of an α7β1 integrin modulatory agent, wherein the α7β1 integrin modulatory agent includes ciclopirox ethanolamine, deferoxamine, 2,2-dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, a compound provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or a combination thereof and increases α7β1 integrin expression in the treated cell relative to α7β1 integrin expression in an untreated cell, thereby enhancing α7β1 integrin expression.

The methods of the present disclosure can include administering the α7β1 integrin modulatory agent with one or more additional pharmacological substances, such as a therapeutic agent. In some aspects, the additional therapeutic agent enhances the therapeutic effect of the α7β1 integrin modulatory agent. In further aspects, the therapeutic agent provides independent therapeutic benefit for the condition being treated. In various examples, the additional therapeutic agent is a component of the extracellular matrix, such as an integrin, dystrophin, dystroglycan, utrophin, or a growth factor. In further examples, the therapeutic agent reduces or enhances expression of a substance that enhances the formation or maintenance of the extracellular matrix. In some examples, the therapeutic agent is an additional α7β1 integrin modulatory agent such as laminin-111, a laminin-111 fragment, valproic acid or a valproic acid analog.

In some examples, the α7β1 integrin modulatory agent is applied to a particular area of the subject to be treated. For example, the α7β1 integrin modulatory agent may be injected into a particular area to be treated, such as a muscle. In further examples, the α7β1 integrin modulatory agent is administered such that it is distributed to multiple areas of the subject, such as systemic administration or regional administration.

A α7β1 integrin modulatory agent, can be administered by any suitable method, such as topically, parenterally (such as intravenously or intraperitoneally), or orally. In a specific example, the α7β1 integrin modulatory agent is administered systemically, such as through parenteral administration, such as stomach injection or peritoneal injection.

Although the disclosed methods generally have been described with respect to muscle regeneration, the disclosed methods also may be used to enhance repair or maintenance, or prevent damage to, other tissues and organs. For example, the methods of the present disclosure can be used to treat symptoms of muscular dystrophy stemming from effects to cells or tissue other than skeletal muscle, such as impaired or altered brain function, smooth muscles, or cardiac muscles.

The foregoing and other features of the disclosure will become more apparent from the following detailed description, which proceeds with reference to the accompanying figures.

BRIEF DESCRIPTION OF THE DRAWINGS

FIG. 5 shows the chemical structures for Ciclopirox, Deferoxamine and 2,2-dipyridyl.

FIG. 7 shows the iron chelators 2,2-dipyridyl and Deferoxamine increase α7 protein in DMD myotubes. DMD myotubes treated with either 2,2-dipyridyl or deferoxamine showed increased α7 integrin protein as determined by western analysis. N=3 replicates, **P<0.01; *P<0.05.

FIG. 8 shows Cholestan increases α7 integrin promoter activity in mouse and DMD muscle cells. A typical dose response was obtained using Cholestan in α7βgal$^{+/-}$ myotubes. Treatment of DMD myotubes with cholestan resulted in increased α7 integrin protein compared to control.

FIG. 9 shows Compounds 1001, 1002 and 1003 activate α7 integrin promoter activity. Typical dose response curves showing the fold increase in reporter activity vs drug dose were obtained for compounds 1001, 1002 and 1003 using α7βgal$^{+/-}$ myotubes.

FIGS. 12A-12D are scatter plots from fluorescence-activated cell sorting (FACS) analyses demonstrating that a 24 hour treatment of α7β1-gal+/− myoblasts with 100 nM LAM-111 and a fluorescent β-gal substrate resulted increase α7 integrin expression compared to PBS treatment. FACS of α7βgal+/− myoblasts treated for 24 hours with PBS (A), PBS followed by fluorescent β-gal substrate FDG (Molecular Probes) (B), and 100 nM LAM-111 followed by FDG (C). (D) Peak fluorescence of α7betagal+/− myoblasts treated with PBS (red), PBS+FDG (blue), and LAM-111+ FDG (green). Samples were run on the Beckman Coulter XL/MCI flow cytometer and analyzed using FlowJo software. X-axis: FITC fluorescence, (A-C); Y-axis: # of cells, (D); Y-axis: % maximal fluorescence.

FIGS. 13A-13D illustrate western blot studies in which protein extracts from C2C12 (A, B) and DMD (C, D) myoblasts were first treated with PBS or 100 nM LAM-111 and then subjected to western analysis of the α7B integrin and the Cox-1 loading standard. *=p<0.05.

FIGS. 14A-14U are digital images of sections of TA muscle from wild-type (A through G), PBS-treated mdx mice (H through N), and LAM-111-treated mdx mice (O through U). Detection of dystrophin (A, H, O), LAM-111 (B, I, P), hematoxylin and eosin (C, J, Q), Evans blue dye uptake (D, K, R), α7 integrin (E, L, S), utrophin (F, M, T), and α-bungarotoxin (G, N, U).

FIGS. 16A-16K are digital images showing intraperitoneal delivery of LAM-111 distributes throughout mdx skeletal and cardiac muscles Immunofluorescence detection of LAM-111 in the heart (A, B, C), diaphragm (D, E, F, J, K), and gastrocnemius (G, H, I) of wild-type (A, D, G), PBS-treated mdx (B, E, H, J), and LAM-111 treated mdx mice (C, F, I, K). FIGS. 16A-16C: 100×, FIGS. 16D-16I: 63×.

FIGS. 20A-20C show that systemic LAM-111 decreases muscle pathology of dyW skeletal muscle Multiple systemic doses of LAM-111 to dyW mice result in a decreased percentage of centrally nucleated myofibers (FIG. 20A), decreased percentage of Evans Blue dye positive myofibers (FIG. 20B), and decreased percentage of TUNEL positive myofibers (FIG. 20C). PBS-treated dyW (black), LAM-111-treated dy W (gray) and WT (white) mice. Animals were injected i.p. twice weekly with 1 mg/kg of LAM-111 beginning at 10 days of age. Tissues were harvested at 7 weeks of age. *=p<0.05, **=p<0.001.

FIGS. 29A-29H illustrate the synthesis of compounds provided in Table 11.

FIG. 30 is a digital image illustrating the results of quantitative real-time PCR used to assess Itga7, Itgb1, and Lama2 transcript levels in C2C12 myoblasts and myotubes treated for 24 hours with DMSO control, 10 μM MLS000683232-01 (IED-232), 10 μM MLS001165937-01 (IED-937), Hydroxylpropyl-Beta-Cyclodextrin (HPBCD) control, or 12 μM SU9516 in HPBCD. * denotes a significant difference in relative transcript levels with p-value <0.01 and *p <0.001.

DETAILED DESCRIPTION OF SEVERAL EMBODIMENTS

I. Overview of Several Embodiments

Figure 1A:
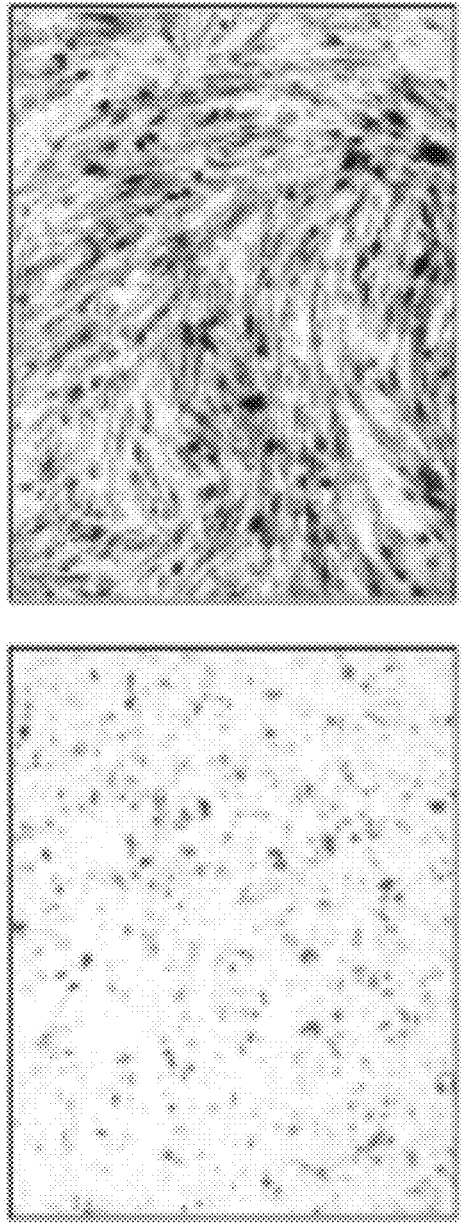
FIG. 1A is two digital images of X-gal staining demonstrating that α7βgal$^{+/-}$ myoblasts express β-galactosidase which increases upon differentiation to myotubes.

Disclosed herein are α7β1 integrin expression modulatory agents and methods of using such to treat a condition associated with impaired α7 integrin expression, such as muscular dystrophy. The present disclosure is related to the subject matter disclosed in U.S. Provisional Patent Application No. 61/533,059, which is incorporated herein by reference in its entirety. Furthermore, the compounds of the present disclosure may be as identified in and have the features described in Appendix I (Table 6), and Appendix II (Table 7) of U.S. Provisional Patent Application No. 61/798,479. The described features are considered to contribute to solving the technical problem underlying the invention of the present application. The described features include, for example, α7β1 integrin modulatory activity suitable for treating a subject with muscular dystrophy, enhancing α7β1 integrin expression, preventing or reducing muscle injury or damage in a subject, enhancing muscle regeneration, repair, or maintenance in a subject, and combinations thereof.

In one embodiment, a method for treating a subject with muscular dystrophy is disclosed. The method includes administering an effective amount of an α7β1 integrin modulatory agent to the subject with muscular dystrophy, wherein the α7β1 integrin modulatory agent is ciclopirox ethanolamine, deferoxamine, 2,2-dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, or any one of the compounds provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or a combination thereof, wherein the α7β1 integrin modulatory agent increases α7β1 integrin expression or activity as compared to α7β1 integrin expression or activity prior to treatment, thereby treating the subject with muscular dystrophy.

In some embodiments, a method for treating a subject with muscular dystrophy, comprises administering an effective amount of an α7β1 integrin modulatory agent to the subject with muscular dystrophy, wherein the α7β1 integrin modulatory agent comprises ciclopirox ethanolamine, deferoxamine, 2,2-dipyridyl; 5α-cholestan-3β-ol-6-one, N032-0003, N066-0070, N069-0071, N069-0075, N064-0028, N066-0053, N069-0073, 1080-0573, an agent having a formula selected from

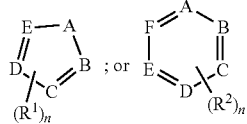

wherein each $R^1$ and $R^2$ independently is selected from $C_{1-10}$alkyl, substituted $C_{1-10}$alkyl, $C_{1-10}$alkoxy, substituted $C_{1-10}$alkoxy, acyl, acylamino, acyloxy, acyl$C_{1-10}$alkyloxy, amino, substituted amino, aminoacyl, aminocarbonyl$C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester)amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, halo, hydroxyl, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, and substituted $C_{1-10}$alkythio, thiocarbonyl; or two $R^1$ substituents, together with the atom to which each is bound, may form ring selected from a $C_{6-15}$aryl, substituted $C_{6-15}$aryl, $C_{3-8}$cycloalkyl, substituted $C_{3-8}$cycloalkyl, $C_{1-10}$heteroaryl, substituted $C_{1-10}$heteroaryl, $C_{2-10}$substituted heterocyclyl, and $C_{2-10}$heterocyclyloxy, substituted;

two $R^2$ substituents, together with the atom to which each is bound, may form ring selected from a $C_{6-15}$aryl, substituted $C_{6-15}$aryl, $C_{3-8}$cycloalkyl, substituted $C_{3-8}$cycloalkyl, $C_{1-10}$heteroaryl, substituted $C_{1-10}$heteroaryl, $C_{2-10}$substituted heterocyclyl, and $C_{2-10}$heterocyclyloxy, substituted;

each of A, B, C, D, E, and F independently may be selected from carbon, nitrogen, oxygen, and sulfur; and n may be zero, 1, 2, 3, 4, or 5; or a combination of any of these compounds, wherein the α7β1 integrin modulatory agent increases α7β1 integrin expression or activity as compared to α7β1 integrin expression or activity prior to treatment, thereby treating the subject with muscular dystrophy. Particular disclosed embodiments concerning one or more of the compounds provided in Tables 10, 11, 6 and/or 7 (see Appendix I of U.S. Provisional Pat. App. No. 61/796,476 for Table 6 and Appendix II of U.S. Provisional Pat. App. No. 61/796,476 for Table 7).

In some embodiments, the muscular dystrophy is merosin deficient congenital muscular dystrophy Type 1A (MDC1A), merosin deficient congenital muscular dystrophy Type 1D (MDC1D), limb-girdle muscular dystrophy (LGMD), Duchenne muscular dystrophy (DMD), Fukuyama congenital muscular dystrophy (FCMD) or Facioscapulohumeral muscular dystrophy (FHMD).

In some particular embodiments, the muscular dystrophy is DMD, MDC1A or FCMD.

In one particular embodiment, the muscular dystrophy is DMD.

In some embodiments, the α7β1 integrin modulatory agent is administered with an additional therapeutic agent.

In some embodiments, the additional therapeutic agent is a costameric protein, a growth factor, satellite cells, stem cells, myocytes or an additional α7β1 integrin modulatory agent.

In some embodiments, the additional α7β1 integrin modulatory agent is laminin-111, a laminin-111 fragment, valproic acid, or a valproic acid analog.

In some embodiments, the method further includes selecting a subject with muscular dystrophy.

In some embodiments, the selecting a subject with muscular dystrophy includes diagnosing the subject with muscular dystrophy prior to administering an effective amount of the α7β1 integrin modulatory agent to the subject.

In other embodiments, a method of enhancing muscle regeneration, repair, or maintenance in a subject is disclosed.

In some embodiments, the method includes administering an effective amount of an α7β1 integrin modulatory agent to the subject with muscular dystrophy, wherein the α7β1 integrin modulatory agent comprises ciclopirox ethanolamine, deferoxamine, 2,2-dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, or any one of the compounds provided herein, such as in Table 10, Table 11, Table 6 (see Appendix I of U.S. Provisional Pat. App. No. 61/796,476), and/or Table 7 (see Appendix II of U.S. Provisional Pat. App. No. 61/796,476), Table 13, or a combination thereof, wherein the α7β1 integrin modulatory agent increases α7β1 integrin expression or activity as compared to α7β1 integrin expression or activity prior to treatment, thereby enhancing muscle regeneration, repair or maintenance in a subject.

In some embodiments, the method includes administering the α7β1 modulatory agent prior to the subject experiencing muscle damage or disease.

In some embodiments, the method is a method of enhancing muscle maintenance in a subject.

In some embodiments, the α7β1 integrin modulatory agent is administered to the subject prior to the subject exercising.

In some embodiments, the α7β1 integrin modulatory agent is administered to a subject at risk of acquiring a muscle disease or damage, such as an elderly subject.

In some embodiments, the method also includes selecting a subject in need of enhancing muscle regeneration, repair, or maintenance.

In some embodiments, selecting a subject in need of enhancing muscle regeneration, repair, or maintenance includes diagnosing the subject with a condition characterized by impaired muscle regeneration prior to administering an effective amount of the α7β1 integrin modulatory agent to the subject.

In some embodiments, selecting a subject in need of enhancing muscle regeneration, repair, or maintenance comprises diagnosing the subject with a condition characterized by impaired production of a component of α7β1 integrin prior to administering an effective amount of the α7β1 integrin modulatory agent to the subject.

In some embodiments, the α7β1 integrin modulatory agent is administered with an additional therapeutic agent.

In some embodiments, the additional therapeutic agent is a costameric protein, a growth factor, satellite cells, stem cells, myocytes or an additional α7β1 integrin modulatory agent.

In some embodiments, the additional α7β1 integrin modulatory agent is laminin-111, a laminin-111 fragment, valproic acid, or a valproic acid analog.

In further embodiments, a method of prospectively preventing or reducing muscle injury or damage in a subject is disclosed.

In some embodiments, the method includes administering an effective amount of an α7β1 integrin modulatory agent to the subject wherein the α7β1 integrin modulatory agent includes ciclopirox ethanolamine, deferoxamine, 2,2-dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, or any one of the compounds provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or a combination thereof, wherein the α7β1 integrin modulatory agent increases α7β1 integrin expression or activity as compared to α7β1 integrin expression or activity prior to treatment, thereby prospectively preventing or reducing muscle injury or damage in the subject.

In some embodiments, the subject is at risk of developing a muscle injury or damage.

In some embodiments, the α7β1 integrin modulatory agent is administered with an additional therapeutic agent.

In some embodiments, the additional therapeutic agent is a costameric protein, a growth factor, satellite cells, stem cells, myocytes or an additional α7β1 integrin modulatory agent.

In some embodiments, the additional α7β1 integrin modulatory agent is laminin-111, a laminin-111 fragment, valproic acid, or a valproic acid analog.

In even further embodiments, a method of enhancing α7β1 integrin expression is provided.

In some embodiments, the method includes contacting a cell with an effective amount of an α7β1 integrin modulatory agent, wherein the α7β1 integrin modulatory agent includes ciclopirox ethanolamine, deferoxamine, 2,2-dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, or any one of the compounds provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or a combination thereof and increases α7β1 integrin expression in the treated cell relative to α7β1 integrin expression in an untreated cell, thereby enhancing α7β1 integrin expression.

In some embodiments, the cell is a muscle cell.

In some embodiments, the muscle cell is present in a mammal, and wherein contacting the cell with an agent comprises administering the agent to the mammal.

II. Terms

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless indicated otherwise, the nomenclature of substituents that are not explicitly defined herein are arrived at by naming the terminal portion of the functionality followed by the adjacent functionality toward the point of attachment.

A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art.

All publications, patent applications, patents, and other references mentioned herein are incorporated by reference in their entirety. All sequences provided in the disclosed Genbank Accession numbers are incorporated herein by reference as available on Aug. 11, 2011. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Administration: To provide or give a subject one or more agents, such as an agent that increases α7β1 expression and/or treats one or more symptoms associated with muscular dystrophy, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Agent: Any protein, nucleic acid molecule (including chemically modified nucleic acids), compound, antibody, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including treating a subject with a muscular dystrophy).

In some examples, an agent can act directly or indirectly to alter the expression and/or activity of α7β1. In a particular example, a therapeutic agent significantly increases the expression and/or activity of α7β1 (which is a muscular dystrophy associated molecule) thereby treating one or more signs or symptoms associated with muscular dystrophy. An example of a therapeutic agent is one that can increase the expression and/or activity of the α7β1 gene or gene product, for example as measured by a clinical response (such as a decrease in one or more signs or symptoms associated with the muscular dystrophy, an improvement in muscular health, regeneration, repair or maintenance of a muscle cell or tissue). "Improving muscular health" refers to an improvement in muscular health compared with a preexisting state or compared with a state which would occur in the absence of treatment. For example, improving muscular health may include enhancing muscle regeneration, maintenance, or repair. Improving muscular health may also include prospectively treating a subject to prevent or reduce muscular damage or injury. "Regeneration" refers to the repair of cells or tissue, such as muscle cells or tissue (or organs) which includes muscle cells, following injury or damage to at least partially restore the muscle or tissue to a condition similar to which the cells or tissue existed before the injury or damage occurred. Regeneration also refers to facilitating repair of cells or tissue in a subject having a disease affecting such cells or tissue to eliminate or ameliorate the effects of the disease. In more specific examples, regeneration places the cells or tissue in the same condition or an improved physiological condition as before the injury or damage occurred or the condition which would exist in the absence of disease. "Maintenance" of cells or tissue, such as muscle cells or tissue (or organs) which includes muscle cells, refers to maintaining the cells or tissue in at least substantially the same physiological condition, such as maintaining such condition even in the presence of stimulus which would normally cause damage, injury, or disease. "Repair" of cells or tissue, such as muscle cells or tissue (or organs) which includes muscle cells, refers to the physiological process of healing damage to the cells or tissue following damage or other trauma.

A "pharmaceutical agent" is a chemical compound or composition capable of inducing a desired therapeutic or prophylactic effect when administered to a subject, alone or in combination with another therapeutic agent(s) or pharmaceutically acceptable carriers. In a particular example, a pharmaceutical agent significantly increases the expression and/or activity of α7β1 thereby treating a condition or disease associated with decreased α7β1 expression/activity, such as muscular dystrophy.

Acyl: H—C(O)—, alkyl-C(O)—, substituted alkyl-C(O)—, cycloalkyl-C(O)—, substituted cycloalkyl-C(O)—, substituted aryl-C(O)—, heteroaryl-C(O)—, substituted heteroaryl-C(O)—, heterocyclyl-C(O)—, and substituted heterocyclyl-C(O)—.

Acylamino: —NR$^a$C(O)alkyl, —NR$^a$C(O)substituted alkyl, —NR$^a$C(O)cycloalkyl, —NR$^a$C(O)substituted cycloalkyl, —NR$^a$C(O)cycloalkenyl, —NR$^a$C(O)substituted cycloalkenyl, —NR$^a$C(O)alkenyl, —NR$^a$C(O)substituted alkenyl, —NR$^a$C(O)alkynyl, —NR$^a$C(O)substituted alkynyl, —NR$^a$C(O)aryl, —NR$^a$C(O)substituted aryl, —NR$^a$C(O)heteroaryl, —NR$^a$C(O)substituted heteroaryl, —NR$^a$C(O)heterocyclyl, and —NR$^a$C(O)substituted heterocyclyl, wherein R$^a$ is selected from hydrogen, alkyl, aryl, and cycloalkyl.

Acyloxy: alkyl-C(O)O—, substituted alkyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclyl-C(O)O—, and substituted heterocyclyl-C(O)O—.

Acylalkyloxy: alkyl-C(O)alkylO—, substituted alkyl-C(O)alkylO—, aryl-C(O)alkylO—, substituted aryl-C(O)alkylO—, cycloalkyl-C(O)alkylO—, substituted cycloalkyl-C(O)alkylO—, heteroaryl-C(O)alkylO—, substituted heteroaryl-C(O)alkylO—, heterocyclyl-C(O)alkylO—, and substituted heterocyclyl-C(O)alkylO—.

Alkyl: A saturated or unsaturated monovalent hydrocarbon having a number of carbon atoms ranging from one to ten (e.g., $C_{1-10}$alkyl), which is derived from removing one hydrogen atom from one carbon atom of a parent compound (e.g., alkane, alkene, alkyne). An alkyl group may be branched or straight-chain.

Alkenyl: A unsaturated monovalent hydrocarbon having a number of carbon atoms ranging from one to ten (e.g., $C_{2-10}$alkenyl), which has at least one carbon-carbon double bond and is derived from removing one hydrogen atom from one carbon atom of a parent alkene. An alkenyl group may be branched, straight-chain, cyclic, cis, or trans (e.g., E or Z).

Alkynyl: A unsaturated monovalent hydrocarbon having a number of carbon atoms ranging from one to ten (e.g., $C_{2-10}$alkynyl), which has at least one carbon-carbon triple bond and is derived from removing one hydrogen atom from one carbon atom of a parent alkyne. An alkynyl group may be branched, straight-chain, or cyclic.

Alkoxy: —O-alkyl (e.g., methoxy, ethoxy, n-propoxy, isopropoxy, n-butoxy, t-butoxy, sec-butoxy, n-pentoxy).

Alkylthio: —S-alkyl, wherein alkyl is as defined herein. This term also encompasses oxidized forms of sulfur, such as —S(O)-alkyl, or —S(O)$_2$-alkyl.

Amino: —NH$_2$.

Aminocarbonyl: —C(O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen.

Aminocarbonylalkyl: -alkylC(O)N($R^b$)$_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen.

Aminocarbonylamino: —NR$^a$C(O)N($R^b$)$_2$, wherein $R^a$ and each $R^b$ are as defined herein.

Aminodicarbonylamino: —NR$^a$C(O)C(O)N($R^b$)$_2$, wherein $R^a$ and each $R^b$ are as defined herein.

Aminocarbonyloxy: —O—C(O)N($R^b$)$_2$, wherein each $R^b$ independently is as defined herein.

Aminosulfonyl: —SO$_2$N($R^b$)$_2$, wherein each $R^b$ independently is as defined herein.

Analog or Derivative: A compound which is sufficiently homologous to a compound such that it has a similar functional activity for a desired purpose as the original compound. Analogs or derivatives refers to a form of a substance, such as cholestan, which has at least one functional group altered, added, or removed, compared with the parent compound. In some examples, examples of an analog are provided in Table 11, for example "Functional group" refers to a radical, other than a hydrocarbon radical, that adds a physical or chemical property to a substance.

Aryl: a monovalent aromatic carbocyclic group of from 6 to 15 carbon atoms having a single ring (e.g., phenyl) or multiple condensed rings (e.g., naphthyl), which condensed rings may or may not be aromatic provided that the point of attachment is through an atom of the aromatic aryl group.

Aryloxy —O-aryl.

Arylthio —S-aryl, wherein aryl is as defined herein. This term also encompasses oxidized forms of sulfur, such as —S(O)-aryl, or —S(O)$_2$-aryl.

Biological activity: The beneficial or adverse effects of an agent on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, the agent significantly increases the biological activity of α7β1 which reduces one or more signs or symptoms associated with the muscular dystrophy.

Contacting: Placement in direct physical association, including both a solid and liquid form. Contacting an agent with a cell can occur in vitro by adding the agent to isolated cells or in vivo by administering the agent to a subject.

Control: A sample or standard used for comparison with a test sample, such as a biological sample obtained from a patient (or plurality of patients) without a particular disease or condition, such as a muscular dystrophy. In some embodiments, the control is a sample obtained from a healthy patient (or plurality of patients) (also referred to herein as a "normal" control), such as a normal biological sample. In some embodiments, the control is a historical control or standard value (e.g., a previously tested control sample or group of samples that represent baseline or normal values (e.g., expression values), such as baseline or normal values of a particular gene such as a α7β1 gene, gene product in a subject without a muscular dystrophy). In some examples, the control is a standard value representing the average value (or average range of values) obtained from a plurality of patient samples (such as an average value or range of values of the gene or gene products, such as the α7β1 gene or gene products, in the subjects without a muscular dystrophy).

Carboxyl: —COOH or salts thereof.

Carboxyester: —C(O)O-alkyl, —C(O)O— substituted alkyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclyl, and —C(O)O-substituted heterocyclyl.

(Carboxyester)amino: —NR$^a$—C(O)O-alkyl, —NR$^a$—C(O)O— substituted alkyl, —NR$^a$—C(O)O-aryl, —NR$^a$—C(O)O-substituted aryl, —NR$^a$—C(O)O-cycloalkyl, —NR$^a$—C(O)O-substituted cycloalkyl, —NR$^a$—C(O)O-heteroaryl, —NR$^a$—C(O)O-substituted heteroaryl, —NR$^a$—C(O)O-heterocyclyl, and —NR$^a$—C(O)O-substituted heterocyclyl, wherein $R^a$ is as recited herein.

(Carboxyester)oxy: —O—C(O)O-alkyl, —O—C(O)O— substituted alkyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclyl, and —O—C(O)O-substituted heterocyclyl.

Cyano: —CN.

Cycloalkyl: cyclic alkyl (or alkenyl, or alkynyl) groups of from 3 to 10 carbon atoms having single or multiple cyclic rings including fused, bridged, and spiro ring systems (e.g., cyclopropyl, cyclobutyl, etc.).

(Cycloalkyl)oxy: —O-cycloalkyl.

(Cycloalkyl)thio: —S-cycloalkyl. This term also encompasses oxidized forms of sulfur, such as —S(O)-cycloalkyl, or —S(O)$_2$-cycloalkyl.

Decrease: To reduce the quality, amount, or strength of something. In one example, a therapy decreases one or more symptoms associated with the muscular dystrophy, for example as compared to the response in the absence of the therapy.

Diagnosis: The process of identifying a disease, such as muscular dystrophy, by its signs, symptoms and results of various tests. The conclusion reached through that process is also called "a diagnosis." Forms of testing commonly performed include blood tests, medical imaging, urinalysis, and biopsy.

Effective amount: An amount of agent that is sufficient to generate a desired response, such as reducing or inhibiting one or more signs or symptoms associated with a condition or disease. When administered to a subject, a dosage will generally be used that will achieve target tissue/cell concentrations. In some examples, an "effective amount" is one that treats one or more symptoms and/or underlying causes of any of a disorder or disease. In some examples, an "effective amount" is a therapeutically effective amount in which the agent alone with an additional therapeutic agent(s) (for example anti-pathogenic agents), induces the desired response such as treatment of a muscular dystrophy, such as DMD, FCMD or MDC1A.

In particular examples, it is an amount of an agent capable of increasing α7β1 gene expression or activity by least 20%, at least 50%, at least 60%, at least 70%, at least 80%, at least 90%, at least 95%, at least 98%, or even at least 100% (elimination of the disease to a point beyond detection).

In some examples, an effective amount is an amount of a pharmaceutical preparation that alone, or together with a pharmaceutically acceptable carrier or one or more additional therapeutic agents, induces the desired response.

In one example, a desired response is to increase the subject's survival time by slowing the progression of the disease, such as slowing the progression of muscular dystrophy. The disease does not need to be completely inhibited for the pharmaceutical preparation to be effective. For example, a pharmaceutical preparation can decrease the progression of the disease by a desired amount, for example by at least 20%, at least 50%, at least 60%, at least 70%, at least 80%, at least 90%, at least 95%, at least 98%, or even at least 100%, as compared to the progression typical in the absence of the pharmaceutical preparation.

In another or additional example, it is an amount sufficient to partially or completely alleviate symptoms of the muscular dystrophy within the subject. Treatment can involve only slowing the progression of the disease temporarily, but can also include halting or reversing the progression of the disease permanently.

Effective amounts of the agents described herein can be determined in many different ways, such as assaying for a reduction in of one or more signs or symptoms associated with the muscular dystrophy in the subject or measuring the expression level of one or more molecules known to be associated with the muscular dystrophy. Effective amounts also can be determined through various in vitro, in vivo or in situ assays, including the assays described herein.

The disclosed therapeutic agents can be administered in a single dose, or in several doses, for example daily, during a course of treatment. However, the effective amount can be dependent on the source applied (for example a nucleic acid molecule isolated from a cellular extract versus a chemically synthesized and purified nucleic acid), the subject being treated, the severity and type of the condition being treated, and the manner of administration.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, expression, such as expression of α7β1, can be regulated to treat one or more signs or symptoms associated with muscular dystrophy.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or subdomain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have muscular dystrophy, such as DMD, FCMD or MDC1A) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

Extracellular matrix: An extracellular structure of a tissue or a layer thereof, including the arrangement, composition, and forms of one or more matrix components, such as proteins, including structural proteins such as collagen and elastin, proteins such as fibronectin and laminins, and proteoglycans. The matrix may comprise fibrillic collagen, having a network of fibers. In some examples, the extracellular matrix is connected to cells through the costameric protein network.

Halogen or Halo: fluoro, chloro, bromo, and iodo.

Heteroaryl: an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl or furyl) or multiple condensed rings (e.g., indolizinyl or benzothienyl), wherein the condensed rings may or may not be aromatic and/or contain a heteroatom, provided that the point of attachment is through an atom of the aromatic heteroaryl group. In one embodiment, the nitrogen and/or sulfur ring atom(s) of the heteroaryl group are optionally oxidized to provide for the N-oxide (N→O), sulfinyl, or sulfonyl moieties.

Heteroaryloxy: —O-heteroaryl.

Heteroarylthio: —S-heteroaryl. This term also encompasses oxidized forms of sulfur, such as —S(O)—heteroaryl, or —S(O)$_2$-heteoaryl.

Heterocyclyl: a saturated, unsaturated group, or combinations thereof, having a single ring or multiple condensed rings, including fused bridged and spiro ring systems, and having from 3 to 15 ring atoms, including 1 to 4 heteroatoms, selected from nitrogen, sulfur, or oxygen. These groups may be substituted with one or more of the substituents disclosed herein for substituted aryl and/or substituted alkyl. These groups encompass, for example, a saturated heterocyclyl fused with one or more aromatic hydrocarbons or heteroaryl groups.

Heterocyclyloxy: —O-heterocycyl.

Heterocyclylthio: —S-heterocycyl. This term also encompasses oxidized forms of sulfur, such as —S(O)-heterocyclyl, or —S(O)$_2$-heterocyclyl.

Hydroxyl or Hydroxy: —OH.

Imino: —N=$R^c$ wherein $R^c$ may be selected from hydrogen, aminocarbonylalkyloxy, substituted aminocarbonylalkyloxy, aminocarbonylalkylamino, and substituted aminocarbonylalkylamino Increase: To enhance the quality, amount, or strength of something. In one example, an agent increases the activity or expression of α7β1, for example relative to an absence of the agent. In a particular example, an agent increases the activity or expression of α7β1 by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such increases can be measured using the methods disclosed herein.

In a particular example, a therapy increases (also known as up-regulates) the expression of α7β1, such as an increase of at least 10%, at least 20%, at least 50%, or even at least 90% in α7β1 expression, thereby treating/alleviating one or more signs or symptoms associated with muscular dystrophy. In some examples, an increase in expression refers to an increase in a α7β1 gene product. An α7β1 gene product can be RNA (such as mRNA, rRNA, tRNA, and structural RNA) or protein.

Gene upregulation includes any detectable increase in the production of a α7β1 gene product. In certain examples, production of a α7β1 gene product increases by at least 2-fold, for example at least 3-fold or at least 4-fold, as compared to a control (such an amount of gene expression in a normal cell). In one example, a control is a relative amount of α7 gene expression or protein expression in a biological sample taken from a subject who does not have muscular dystrophy, such as DMD, FCMD or MDC1A. Such increases can be measured using the methods disclosed herein. For example, "detecting or measuring expression of α7β1" includes quantifying the amount of the gene, gene product or modulator thereof present in a sample. Quantification can be either numerical or relative. Detecting expression of the gene, gene product or modulators thereof can be achieved using any method known in the art or described herein, such as by measuring nucleic acids by PCR (such as RT-PCR) and proteins by ELISA. In primary embodiments, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include samples believed to be normal (in that they are not altered for the desired characteristic, for example a sample from a subject who does not have muscular dystrophy, such as DMD, FCMD or MDC1A) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

In other embodiments of the methods, the increase or decrease is of a diagnostically significant amount, which refers to a change of a sufficient magnitude to provide a statistical probability of the diagnosis.

The level of expression in either a qualitative or quantitative manner can detect nucleic acid or protein. Exemplary methods include microarray analysis, RT-PCR, Northern blot, Western blot, and mass spectrometry.

Inhibiting a disease or condition: A phrase referring to reducing the development of a disease or condition, for example, in a subject who is at risk for a disease or who has a particular disease. Particular methods of the present disclosure provide methods for inhibiting muscular dystrophy.

Integrin: A cell surface transmembrane glycoprotein receptor. Integrins are involved in many biological processes such as wound healing, blood clot formation, gene regulation, and immune responses. Integrins can regulate tissue specific cell adhesion molecules. Integrins are heterodimeric non-covalently associated glycoproteins composed of two subunits. The subunits, which are designated a and beta, have approximate molecular weights of 150-180 kilodaltons and 90-110 kilodaltons, respectively.

The α7β1 integrin is a major laminin receptor expressed in skeletal muscle. The α7β1 integrin plays a role in the development of neuromuscular and myotendinous junctions. In the adult, the α7β1 integrin is concentrated at junctional sites and found in extrajunctional regions where it mediates the adhesion of the muscle fibers to the extracellular matrix. Mice that lack the α7 chain develop muscular dystrophy that affects the myotendinous junctions. The absence of α7 integrin results in defective matrix deposition at the myotendinous junction. Loss of the α7 integrin in γ-sarcoglycan mice results in severe muscle pathology. Absence of the α7 integrin in mdx mice also results in severe muscular dystrophy, confirming that the α7β1 integrin serves as a major genetic modifier for Duchenne and other muscular dystrophies.

Mutations in the α7 gene are responsible for muscular dystrophy in humans. A screen of 117 muscle biopsies from patients with undefined muscle disease revealed 3 which lacked the α7 integrin chain and had reduced levels of β1D integrin chain. These patients exhibited delayed developmental milestones and impaired mobility consistent with the role for the α7β1 integrin in neuromuscular and myotendinous junction development and function.

Several lines of evidence suggest the α7 integrin may be important for muscle regeneration. For example, during embryonic development, the α7β1 integrin regulates myoblast migration to regions of myofiber formation. It has been found that MyoD (myogenic determination protein) transactivates α7 integrin gene expression in vitro, which would increase α7 integrin levels in activated satellite cells. Human, mouse and rat myoblast cell lines derived from satellite cells express high levels of α7 integrin. Elevated α7 integrin mRNA and protein are detected in the skeletal muscle of 5 week old mdx mice, which correlates with the period of maximum muscle degeneration and regeneration. In addition, the α7β1 integrin associates with muscle specific β1-integrin binding protein (MIBP), which regulates laminin deposition in C2C12 myoblasts Laminin provides an environment that supports myoblast migration and proliferation. Finally, enhanced expression of the α7 integrin in dystrophic skeletal muscle results in increased numbers of satellite cells.

The sequences for α7β1 integrin subunits are publicly available on GenBank, see, for example Gene Accession No. NM_001144116 (human) and NM_008398.2 (mouse) for α7 integrin, and Gene Accession No. NM_002211 for β1 integrin (also known as CD29), each of which is herein incorporated by reference as available on Sep. 8, 2011. Exemplary α7β1 integrin modulatory agents are disclosed herein, such as in Tables 8, 9 and 10, including ciclopirox ethanolamine, deferoxamine, 2,2-dipyridyl, 5α-cholestan-3β-ol-6-one, Compound ID #1001, Compound ID #1002, Compound ID #1003, N032-0003, N066-0070, N069-0071, N069-0075, 1080-0573, N064-0028, N066-0053, or N069-0073 or analogs provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or combinations thereof.

A α7β1 integrin-associated condition is a condition associated with altered α7β1 integrin expression or activity, including muscular dystrophy, such as DMD, FCMD, LGMD, FHMD, Beckers muscular dystrophy and/or MDC1A.

Laminin: Any of the family of glycoproteins that are typically involved in the formation and maintenance of extracellular matrices Laminin is a heterotrimers formed from an α chain, a β chain, and a γ chain The various chains of a particular laminin can affect the properties of the molecule. In some aspects of the present disclosure, fragments, derivatives, or analogs of various laminins can be used, such as laminins having at least a portion at least substantially homologous to the laminin α1 chain A "fragment of laminin," as used herein, refers to a portion of a substance, such as laminin A fragment may be, in some examples, a particular domain or chain of a protein. For example, particular embodiments of the present disclosure involve administering a fragment of laminin-1 corresponding to at least a portion of (or all of) the laminin α1 chain. Fragments may be synthetic or may be derived from larger parent substances.

In some aspects, laminins may be administered as a mixture of laminins, including fragments, analogs, and derivatives thereof. Suitable methods for preparing analogs of laminin domains are disclosed in U.S. Pat. No. 6,933,280, incorporated by reference herein to the extent not inconsistent with this disclosure.

The laminin materials or compositions of the present disclosure may be delivered as discrete molecules or may be complexed with, or conjugated to, another substance. For example, the laminin may be combined with a carrier, such as to aid in delivery of the laminin to a site of interest or to increase physiological uptake or incorporation of the laminin.

In specific examples, the laminin administered includes or consists of laminin-1 (LAM-111), which includes the chains α1β1γ1. In further examples, the laminin administered includes or consists of laminin-2, which includes the chains α2β1γ1. In yet further examples, the laminin administered includes or consists of laminin-4, which includes the chains α2β2γ1.

Laminins may be obtained from any suitable source. For example, laminin-1 may be obtained from placental tissue or from Engelbreth-Holm-Swarm murine sarcoma. Suitable methods of isolating various laminins are disclosed in U.S. Pat. No. 5,444,158, incorporated by reference herein to the extent not inconsistent with the present disclosure.

Muscle: Any myoblast, myocyte, myofiber, myotube or other structure composed of muscle cells. Muscles or myocytes can be skeletal, smooth, or cardiac. Muscle may also refer to, in particular implementations of the present disclosure, cells or other materials capable of forming myocytes, such as stem cells and satellite cells.

Muscular dystrophy: A term used to refer to a group of genetic disorders that lead to progressive muscle weakness. Muscular dystrophy can result in skeletal muscle weakness and defects in skeletal muscle proteins, leading to a variety of impaired physiological functions. No satisfactory treatment of muscular dystrophy exists. Existing treatments typically focus on ameliorating the effects of the disease and improving the patient's quality of life, such as through physical therapy or through the provision of orthopedic devices.

Mutated genes associated with muscular dystrophy are responsible for encoding a number of proteins associated with the costameric protein network. Such proteins include laminin-2, collagen, dystroglycan, integrins, caveolin-3, ankyrin, dystrophin, α-dystrobrevin, vinculin, plectin, BPAG1b, muscle LIM protein, desmin, actinin-associated LIM protein, α-actin, titin, telethonin, cypher, myotilin, and the sarcoglycan/sarcospan complex.

The most common form of muscular dystrophy is DMD, affecting 1 in 3,500 live male births. DMD is an X-linked recessive disorder characterized by a mutation in the gene that codes for dystrophin. Dystrophin is a cytoskeletal protein about 430 kDa in size. This protein works to connect the cell's cytoskeleton and extracellular matrix. The loss of dystrophin in DMD patients leads to a loss of muscle fiber attachment at the extracellular matrix during contraction, which ultimately leads to progressive fiber damage, membrane leakage and a loss of muscle function. Most patients die before they reach the age of 30 due to respiratory or cardiac failure.

Beckers muscular dystrophy (also known as Benign pseudohypertrophic muscular dystrophy) is related to DMD in that both result from a mutation in the dystrophin gene, but in DMD no functional dystrophin is produced making DMD much more severe than BMD. BMD is an X-linked recessive inherited disorder characterized by slowly progressive muscle weakness of the legs and pelvis. BMD is a type of dystrophinopathy, which includes a spectrum of muscle diseases in which there is insufficient dystrophin produced in the muscle cells, results in instability in the structure of muscle cell membrane. This is caused by mutations in the dystrophin gene, which encodes the protein dystrophin. The pattern of symptom development of BMD is similar to DMD, but with a later, and much slower rate of progression.

Congenital muscular dystrophies are caused by gene mutations. FCMD and MDC1A are examples of congenital muscular dystrophies. MDC1A is a congenital muscular dystrophy due to a genetic mutation in the LAMA2 gene which results in lack of or complete loss of laminin-α2 protein. This loss of laminin-α2 leads to an absence of laminins-211/221. Laminins-211/221 are major components of the extracellular matrix and play a key role in muscle cell development. During muscle cell differentiation laminin binds to the α7β1 integrin. Without laminin-α2, muscle fibers are unable to adhere to the basement membrane and myotubes undergo apotosis. Muscle regeneration also fails, leading to a loss of muscle repair and an increase in muscle fibrosis and inflammation. This chronic tissue injury is a major cause of morbidity and mortality in MDC1A.

Congenital Muscular Dystrophies (CMD) and Limb-Girdle muscular dystrophy (LGMD) are common forms of highly heterogeneous muscular dystrophies which can be distinguished by their age at onset. In CMD, onset of symptoms is at birth or within the first 6 months of life; in LGMD onset of symptoms is in late childhood, adolescence or even adult life. Inheritance in LGMD can be autosomal dominant (LGMD type 1) or autosomal recessive (LGMD type 2), CMD is recessively inherited. CMD and LGMD can overlap both clinically and genetically MDC1A is a progressive muscle wasting disease that results in children being confined to a wheelchair, requiring ventilator assistance to breathe and premature death. Symptoms are detected at birth with poor muscle tone and "floppy" baby syndrome. DMD, BMD and LGMD are progressive muscle degenerative diseases usually diagnosed at 3-5 years of age when children show developmental delay including ability to walk and climb stairs. The disease is progressive and children are usually confined to a wheelchair in their teens and require ventilator assistance.

Fukuyama congenital muscular dystrophy (FCMD) is an inherited condition that predominantly affects the muscles, brain, and eyes. Congenital muscular dystrophies are a group of genetic conditions that cause muscle weakness and wasting (atrophy) beginning very early in life. Fukuyama congenital muscular dystrophy affects the skeletal muscles, which are muscles the body uses for movement. The first signs of the disorder appear in early infancy and include a weak cry, poor feeding, and weak muscle tone (hypotonia). Weakness of the facial muscles often leads to a distinctive facial appearance including droopy eyelids (ptosis) and an open mouth. In childhood, muscle weakness and joint deformities (contractures) restrict movement and interfere with the development of motor skills such as sitting, standing, and walking Fukuyama congenital muscular dystrophy also impairs brain development. People with this condition have a brain abnormality called cobblestone lissencephaly, in which the surface of the brain develops a bumpy, irregular appearance (like that of cobblestones). These changes in the structure of the brain lead to significantly delayed development of speech and motor skills and moderate to severe intellectual disability. Social skills are less severely impaired. Most children with Fukuyama congenital muscular dystrophy are never able to stand or walk, although some can sit without support and slide across the floor in a seated position. More than half of all affected children also experience seizures. Other signs and symptoms of Fukuyama congenital muscular dystrophy include impaired vision, other eye abnormalities, and slowly progressive heart problems after age 10. As the disease progresses, affected people may develop swallowing difficulties that can lead to a bacterial lung infection called aspiration pneumonia. Because of the serious medical problems associated with Fukuyama congenital muscular dystrophy, most people with the disorder live only into late childhood or adolescence.

Fukuyama congenital muscular dystrophy is seen almost exclusively in Japan, where it is the second most common form of childhood muscular dystrophy (after Duchenne muscular dystrophy). Fukuyama congenital muscular dystrophy has an estimated incidence of 2 to 4 per 100,000 Japanese infants.

Fukuyama congenital muscular dystrophy is caused by mutations in the FKTN gene which encodes fukutin. The most common mutation in the FKTN gene reduces the amount of fukutin produced within cells. A shortage of fukutin likely prevents the normal modification of α-dystroglycan, which disrupts that protein's normal function. Without functional α-dystroglycan to stabilize muscle cells, muscle fibers become damaged as they repeatedly contract and relax with use. The damaged fibers weaken and die over time, leading to progressive weakness and atrophy of the skeletal muscles.

Defective α-dystroglycan also affects the migration of neurons during the early development of the brain. Instead of stopping when they reach their intended destinations, some neurons migrate past the surface of the brain into the fluid-filled space that surrounds it. Because Fukuyama congenital muscular dystrophy involves a malfunction of α-dystroglycan, this condition is described as a dystroglycanopathy.

Facioscapulohumeral muscular dystrophy (FHMD) is a form of muscular dystrophy associated with progressive muscle weakness and loss of muscle tissue. Unlike DMD and BMD which mainly affect the lower body, FSHD affects the upper body mainly the face, shoulder and upper arm muscles. However, it can affect muscles around the pelvis, hips, and lower leg. Symptoms for FSHD often do not appear until age 10-26, but it is not uncommon for symptoms to appear much later. In some cases, symptoms never develop.

Symptoms are usually mild and very slowly become worse. Facial muscle weakness is common, and may include eyelid drooping, inability to whistle, decreased facial expression, depressed or angry facial expression, difficulty pronouncing words, shoulder muscle weakness (leading to deformities such as pronounced shoulder blades (scapular winging) and sloping shoulders), weakness of the lower, hearing loss and possible heart conditions.

Oxo: (=O).

Pharmaceutically acceptable carriers: The pharmaceutically acceptable carriers (vehicles) useful in this disclosure are conventional. Remington's Pharmaceutical Sciences, by E. W. Martin, Mack Publishing Co., Easton, Pa., 19th Edition (1995), describes compositions and formulations suitable for pharmaceutical delivery of one or more agents, such as one or more α7β1 modulatory agents.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical agents to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Prodrug: A compound that is transformed in vivo to yield a parent compound, for example, by hydrolysis in the gut or enzymatic conversion in blood.

Sample (or biological sample): A biological specimen containing genomic DNA, RNA (including mRNA), protein, or combinations thereof, obtained from a subject. Examples include, but are not limited to, peripheral blood, urine, saliva, tissue biopsy, surgical specimen, and autopsy material. In one example, a sample includes muscle biopsy, such as from a subject with DMD, FCMD, or MDC1A.

Signs or symptoms: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting muscular dystrophy, including measuring creatine kinase levels, electromyography (to determine if weakness is caused by destruction of muscle tissue rather than by damage to nerves) or immunohistochemistry/immunoblotting/immunoassay (e.g., ELISA) to measure muscular dystrophy-associated molecules, such as α7β1 integrin. In one example, reducing or inhibiting one or more symptoms or signs associated with muscular dystrophy, includes increasing the activity or expression of α7β1 integrin by a desired amount, for example by at least 20%, at least 50%, at least 60%, at least 70%, at least 80%, at least 90%, at least 95%, at least 98%, or even at least 100%, as compared to the activity and/or expression in the absence of the treatment. Symptoms of muscular dystrophy include, but are not limited to, muscle weakness and loss, difficulty running, difficulty hopping, difficulty jumping, difficulty walking, difficulty breathing, fatigue, skeletal deformities, muscle deformities (contractions of heels; pseudohypertrophy of calf muscles), heart disease (such as dilated cardiomyopathy), elevated creatine phosphokinase (CK) levels in blood or combinations thereof.

Subject: Living multi-cellular vertebrate organisms, a category that includes human and non-human mammals.

Substituted Alkyl: an alkyl (or alkenyl, or alkynyl) group having from 1 to 5 hydrogen atoms replaced with substituents selected alkoxy, substituted alkoxy, acyl, acylamino, acyloxy, acylalkyloxy, amino, substituted amino, aminocarbonyl, aminocarbonylamino, aminocarbonyloxy, aminodicarbonylamino, aminocarbonylalkyl, aminosulfonyl, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, aminodiacylamino, cycloalkyloxy, substituted cycloalkyloxy, cycloalkylthio, substituted cycloalkylthio, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, imino, oxo, sulfonylamino, nitro, $SO_3H$, sulfonyl, thiol, imino, substituted imino, alkylthio, and substituted alkylthio. The alkyl may be substituted with 1 to 2, 1 to 3, or 1 to 4 of these groups, which are defined herein.

Substituted Alkoxy: —O-(substituted alkyl).

Substituted Alkylthio: —S-(substituted alkyl). This term also encompasses oxidized forms of sulfur, such as —S(O)-substituted alkyl, or —S(O)$_2$-substituted alkyl.

Substituted Amino: —N($R^b$)$_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen.

Substituted Aryl: aryl groups having 1 to 5 hydrogens replaced with substituents independently selected from alkoxy, substituted alkoxy, acyl, acylamino, acyloxy, amino, substituted amino, aminocarbonyl, aminocarbonylamino, aminocarbonyloxy, aminosulfonyl, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, $SO_3H$, sulfonyl, thiol, alkylthio, and substituted alkylthio. The aryl group may be substituted with 1 to 2, 1 to 3, or 1 to 4 of these groups, which are defined herein.

Substituted Aryloxy: —O-(substituted aryl).

Substituted Arylthio: —S-(substituted aryl), wherein substituted aryl is as defined herein. This term also encompasses oxidized forms of sulfur, such as —S(O)-substituted aryl, or —S(O)$_2$-substituted aryl.

Substituted Cycloalkyl: cycloalkyl, cycloalkenyl, or cycloalkynyl group having from 1 to 5 substituents selected from the group consisting of oxo, alkoxy, substituted alkoxy, acyl, acylamino, acyloxy, amino, substituted amino, aminocarbonyl, aminocarbonylamino, aminocarbonyloxy, aminosulfonyl, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, halo, hydroxy, heteroaryl, substituted heteroaryl, heteroaryloxy, substituted heteroaryloxy, heteroarylthio, substituted heteroarylthio, heterocyclyl, substituted heterocyclyl, heterocyclyloxy, substituted heterocyclyloxy, heterocyclylthio, substituted heterocyclylthio, nitro, $SO_3H$, sulfonyl, thiol, alkylthio, and substituted alkylthio. The aryl group may be substituted with 1 to 2, 1 to 3, or 1 to 4 of these groups, which are defined herein. In some embodiments, the cycloalkyl group may have multiple condensed rings (e.g. tetrahydronaphthyl or tetrahydroanthacenyl), provided that the point of attachment is through an atom of the nonaromatic ring.

Substituted (Cycloalkyl)oxy: —O-(substituted cycloalkyl).

Substituted (Cycloalkyl)thio: refers to —S-(substituted cycloalkyl). This term also encompasses oxidized forms of sulfur, such as —S(O)-substituted cycloalkyl, or —S(O)$_2$-substituted cycloalkyl.

Substituted Heteroaryl: heteroaryl groups that are substituted with from 1 to 5 substituents selected from the group consisting of the same group of substituents defined for substituted aryl.

Substituted Heteroaryloxy: —O-(substituted heteroaryl).

Substituted Heteroarylthio: —S-(substituted heteroaryl). This term also encompasses oxidized forms of sulfur, such as —S(O)-substituted heteroaryl, or —S(O)$_2$-substituted heteoaryl.

Substituted Heterocycyloxy: —O-(substituted heterocyclyl) wherein the heterocyclyl group is substituted with one or more of the substituents recited for substituted alkyl.

Substituted Heterocyclthio: —S-(substituted heterocycyl). This term also encompasses oxidized forms of sulfur, such as —S(O)-substituted heterocyclyl, or —S(O)$_2$-substituted heterocyclyl.

Sulfonyl: —SO$_2$-alkyl, —SO$_2$-substituted alkyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclyl, and —SO$_2$-substituted heterocyclyl.

Sulfonylamino: —NR$^a$SO$_2$alkyl, —NR$^a$SO$_2$substituted alkyl, —NR$^a$SO$_2$cycloalkyl, —NR$^a$SO$_2$substituted cycloalkyl, —NR$^a$SO$_2$aryl, —NR$^a$SO$_2$substituted aryl, —NR$^a$SO$_2$heteroaryl, —NR$^a$SO$_2$substituted heteroaryl, —NR$^a$SO$_2$heterocyclyl, —NR$^a$SO$_2$substituted heterocyclyl, wherein each $R^a$ independently is as defined herein.

Thiol: —SH.

Thiocarbonyl: (=S)

Tissue: An aggregate of cells, usually of a particular kind, together with their intercellular substance that form one of the structural materials of an animal and that in animals include connective tissue, epithelium, muscle tissue, and nerve tissue.

Treating a disease: A therapeutic intervention that ameliorates a sign or symptom of a disease or pathological condition related to a muscular dystrophy, such as a sign or symptom of muscular dystrophy. Treatment can induce remission or cure of a condition or slow progression, for example, in some instances can include inhibiting the full development of a disease, for example preventing development of a muscular dystrophy. Prevention of a disease does not require a total absence of disease. For example, a decrease of at least 50% can be sufficient.

Treating a disease can be a reduction in severity of some or all clinical symptoms of the disease or condition, a reduction in the number of relapses of the disease or condition, an improvement in the overall health or well-being of the subject, by other parameters well known in the art that are specific to the particular disease or condition, and combinations of such factors.

Under conditions sufficient for: A phrase that is used to describe any environment that permits the desired activity. In one example, includes administering a disclosed agent to a subject sufficient to allow the desired activity. In particular examples, the desired activity is increasing the expression or activity of α7β1.

III. Compounds for Treating Muscular Dystrophy

Disclosed herein are compounds that may be used as α1β7 integrin modulatory agents in methods disclosed herein. In particular disclosed embodiments, the compound is effective in treating muscular dystrophy. The compound is a small-molecule therapeutic. In particular disclosed embodiments, the small-molecule therapeutic is a cyclic compound comprising a heteroatom-containing skeleton. In other disclosed embodiments, the small-molecule therapeutic is a cyclic compound comprising an all-carbon skeleton. In certain disclosed embodiments, the cyclic compound comprising a heteroatom-containing skeleton has a formula illustrated below:

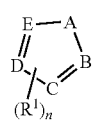

Formula 1 wherein each $R^1$ independently is selected from $C_{1-10}$alkyl, substituted $C_{1-10}$alkyl, $C_{1-10}$alkoxy, substituted $C_{1-10}$alkoxy, acyl, acylamino, acyloxy, acyl$C_{1-10}$alkyloxy, amino, substituted amino, aminoacyl, aminocarbonyl$C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester) amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, halo, hydroxyl, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, and substituted $C_{1-10}$alkythio, thiocarbonyl; or two $R^1$ substituents, together with the atom to which each is bound, may form ring selected from a $C_{6-15}$aryl, substituted $C_{6-15}$aryl, $C_{3-8}$cycloalkyl, substituted $C_{3-8}$cycloalkyl, $C_{1-10}$heteroaryl, substituted $C_{1-10}$heteroaryl, $C_{2-10}$substituted heterocyclyl, and $C_{2-10}$heterocyclyloxy, substituted;

each of A, B, C, D, and E independently may be selected from carbon, nitrogen, oxygen, and sulfur; and n may be zero, 1, 2, 3, 4, or 5.

In other embodiments, the cyclic compound comprising a heteroatom-containing moiety has a formula illustrated below:

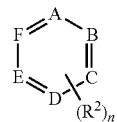

Formula 2 wherein each $R^2$ independently is selected from $C_{1-10}$alkyl, substituted $C_{1-10}$alkyl, $C_{1-10}$alkoxy, substituted $C_{1-10}$alkoxy, acyl, acylamino, acyloxy, acyl$C_{1-10}$alkyloxy, amino, substituted amino, aminoacyl, aminocarbonyl$C_{1-10}$alkyl, aminocarbonylamino, aminodicarbonylamino, aminocarbonyloxy, aminosulfonyl, $C_{6-15}$aryl, substituted $C_{6-15}$aryl, $C_{6-15}$aryloxy, substituted $C_{6-15}$aryloxy, $C_{6-15}$arylthio, substituted $C_{6-15}$arylthio, carboxyl, carboxyester, (carboxyester) amino, (carboxyester)oxy, cyano, $C_{3-8}$cycloalkyl, substituted $C_{3-8}$cycloalkyl, ($C_{3-8}$cycloalkyl)oxy, substituted ($C_{3-8}$cycloalkyl)oxy, ($C_{3-8}$cycloalkyl)thio, substituted ($C_{3-8}$cycloalkyl)thio, halo, hydroxyl, $C_{1-10}$heteroaryl, substituted $C_{1-10}$heteroaryl, $C_{1-10}$heteroaryloxy, substituted $C_{1-10}$heteroaryloxy, $C_{1-10}$heteroarylthio, substituted $C_{1-10}$heteroarylthio, $C_{2-10}$heterocyclyl, $C_{2-10}$substituted heterocyclyl, $C_{2-10}$heterocyclyloxy, substituted $C_{2-10}$heterocyclyloxy, $C_{2-10}$heterocyclylthio, substituted $C_{2-10}$heterocyclylthio, imino, oxo, sulfonyl, sulfonylamino, thiol, $C_{1-10}$alkylthio, and substituted $C_{1-10}$alkythio, thiocarbonyl; or two $R^2$ substituents, together with the atom to which each is bound, may form ring selected from a $C_{6-15}$aryl, substituted $C_{6-15}$aryl, $C_{3-8}$cycloalkyl, substituted $C_{3-8}$cycloalkyl, $C_{1-10}$heteroaryl, substituted $C_{1-10}$heteroaryl, $C_{2-10}$substituted heterocyclyl, and $C_{2-10}$heterocyclyloxy, substituted;

each of A, B, C, D, E, and F independently may be selected from carbon, nitrogen, oxygen, and sulfur; and n may be zero, 1, 2, 3, 4, or 5.

In particular disclosed embodiments, the cyclic compound comprising an all-carbon skeleton may have a general formula provided below:

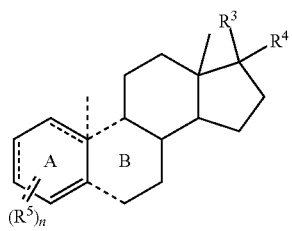

Formula 3 wherein $R^3$ and $R^4$ independently may be selected from hydroxyl, hydrogen, $C_{1-10}$alkyl, substituted $C_{1-10}$alkyl, carboxyl, acyl, aminoacyl, acylamino, amino, substituted amino, $C_{6-15}$aryl, substituted $C_{6-15}$aryl, and $C_{1-10}$alkoxy; $R^5$ is selected from amino, substituted amino, oxo, hydroxyl, $C_{1-10}$alkoxy, and imino; and n may be zero, 1, 2, 3, 4, or 5. A person of ordinary skill in the art will recognize that the dashed lines indicate optional bonds which may be present in certain compounds and not present in others.

In particular disclosed embodiments, rings A and B are connected via the optional bonds to form a steroid-based skeleton. In embodiments wherein rings A and B are connected, $R^5$ may be bound to ring A via a double bond or a single bond, a feature that is indicated with the optional dashed bond in Formula 13. For example, if $R^5$ is amino, hydroxyl, substituted amino, or $C_{1-10}$alkoxy, then $R^5$ is attached to ring A via a single bond, whereas if $R^5$ is oxo or imino, then $R_5$ is attached to ring A via a double bond.

In particular disclosed embodiments, $C_{6-15}$aryl may be selected from phenyl, biphenyl, naphthalene, anthracene, and the like; substituted $C_{6-15}$aryl may be selected from phenyl, biphenyl, naphthalene, and anthracene substituted with one or more substituents as defined herein; $C_{1-10}$alkyl may be selected from $C_{1-10}$alkane, $C_{2-10}$alkene, and $C_{2-10}$alkyne; more typically from methyl, ethyl, propyl, butyl, pentyl, hexyl, and the like; ethylene, propylene, butylene, and the like; and ethyne, propyne, butyne, and the like; substituted $C_{1-10}$alkyl may be selected from $C_{1-10}$alkane, $C_{2-10}$alkene, and $C_{2-10}$alkyne substituted with one or of the substituents as provided herein.

Exemplary embodiments concerning hetercyclyl and heteroaryl substituents include, but are not limited to, epoxy, pyrrolyl, imidazole, pyrazole, pyridinyl, pyrazine, pyrimidine, oxanyl, thianyl, dioxanyl, dithianyl, coumarin, pyridazine, indolizine, isoindole, indolyl, indolinyl (or dihydroindole), indazole, purine, isoquinoline, quinoline, benzo[d]pyridazine, naphthyridine, quinoxaline, quinazoline, benzopyridazine, pteridine, carbazole, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl, piperidinyl, pyrrolidinyl, piperazinyl, oxazolidinyl, oxazolyl, thiophenyl, isooxazolidinyl, and tetrahydrofuranyl.

Exemplary substituents wherein at least two $R^1$ groups have been joined together include the following:

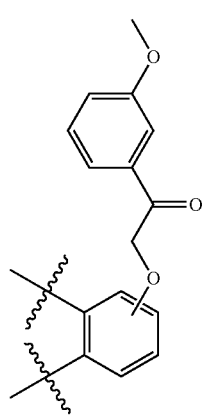

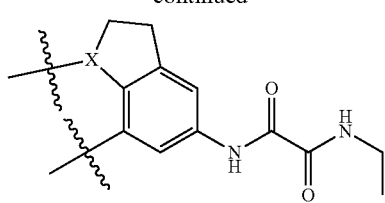

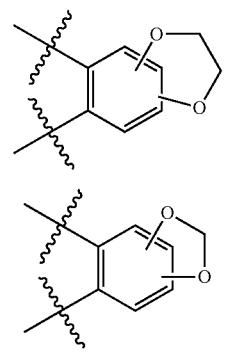

Particular disclosed embodiments concern cyclic compounds comprising a five-membered heteroatom-containing skeleton having a formula selected from those provided below.

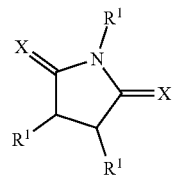

Formula 4

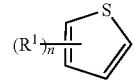

Formula 5

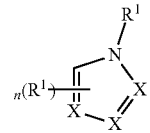

Formula 6

With reference to Formulas 4-6, $R^1$ and n are as recited herein, and each X independently may be selected from carbon, oxygen, nitrogen, and sulfur.

In yet other embodiments, the cyclic compound comprising a five-membered heteroatom-containing skeleton may have any one of the following formulas

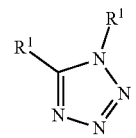

Formula 7

Formula 8
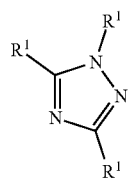
Formula 9
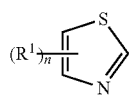
Formula 10
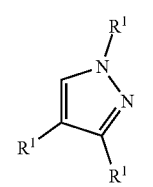
Formula 11
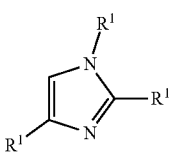
wherein R¹ is as recited herein.
Exemplary compounds are provided below.
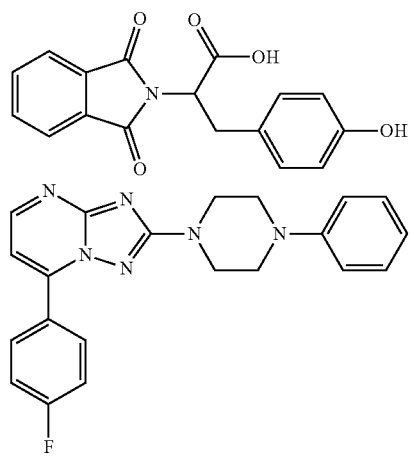
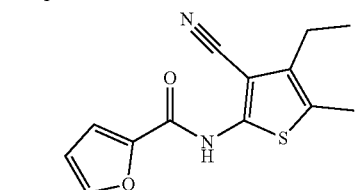
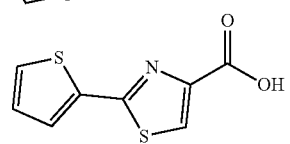
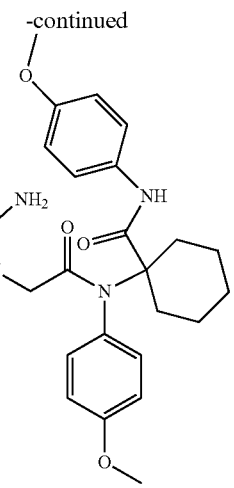
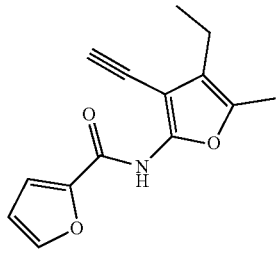
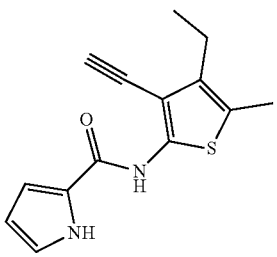
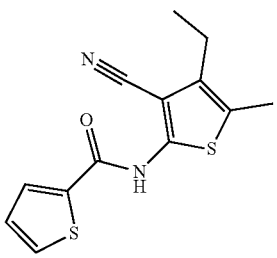
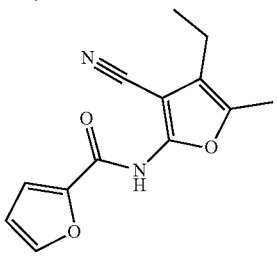
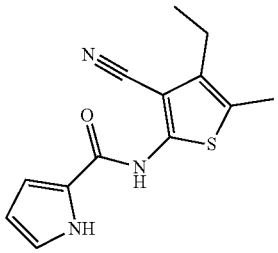

-continued
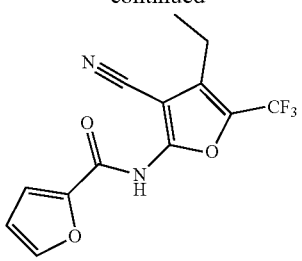
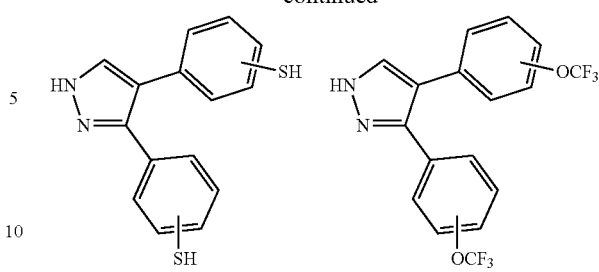
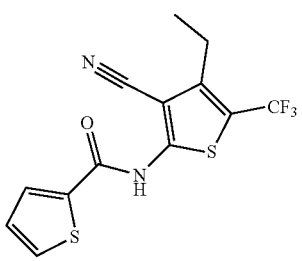
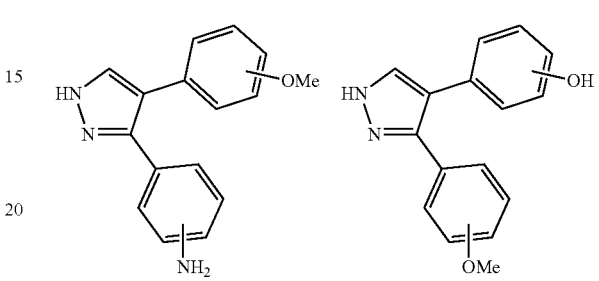
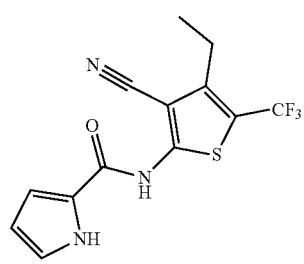
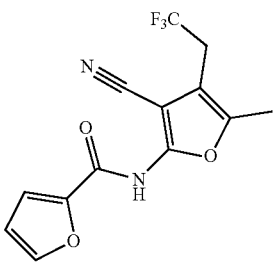
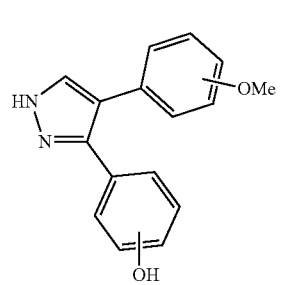
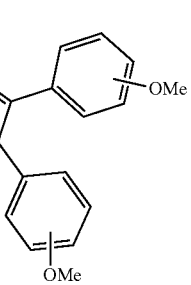
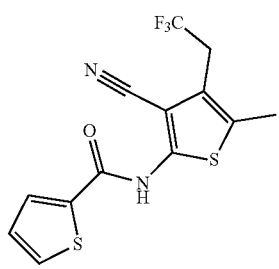
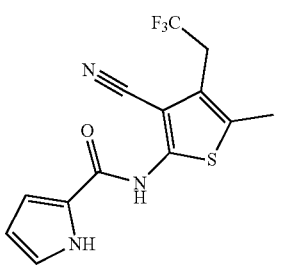
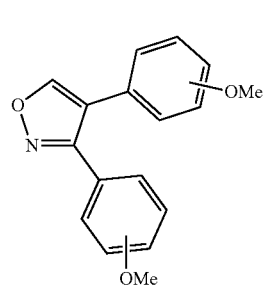
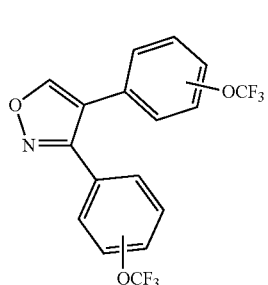
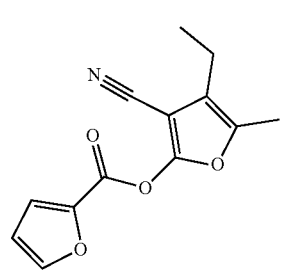
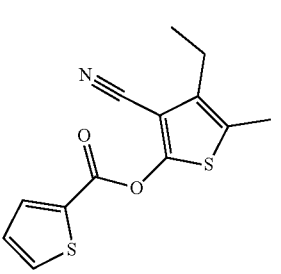
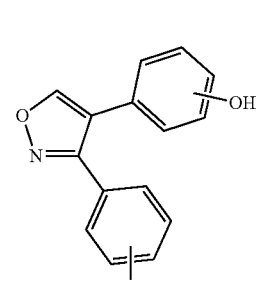
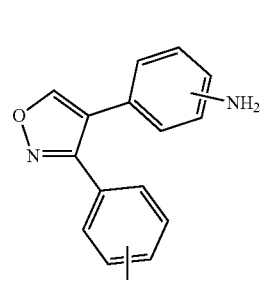
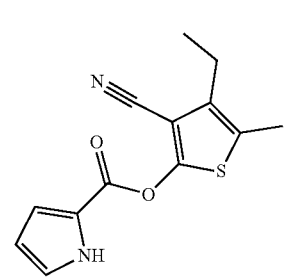
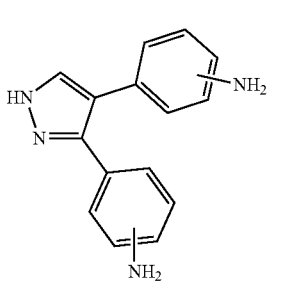
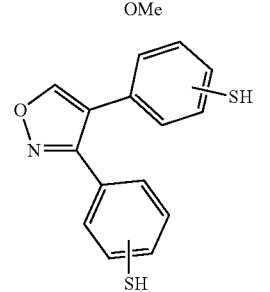
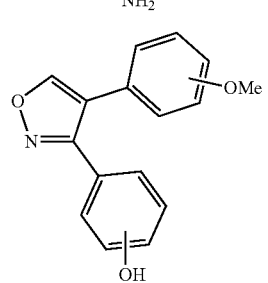

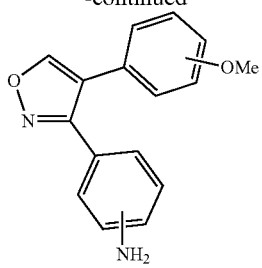

Particular embodiments concern cyclic compounds comprising a six-membered heteroatom-containing skeleton having any one of the formulas provided below:

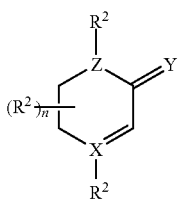

Formula 12

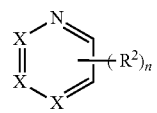

Formula 13

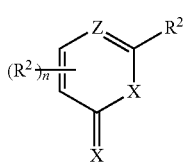

Formula 14 wherein $R^2$ and n are as recited herein, Z may be selected from carbon and nitrogen, Y may be selected from nitrogen and oxygen, and each X independently may be selected from nitrogen and carbon. A person of ordinary skill in the art will recognize that the dashed lines indicate variable bonds which may or may not be present, depending on the valency of the atom to which each variable bond is attached. For example, if the variable bond indicated in Formula 11 is present, X typically is carbon, as a carbon atom can accommodate four bonds. X may be nitrogen in such a compound; however, a person of ordinary skill in the art would recognize that the nitrogen atom would be positively charged due to the fact that its lone pairs are used to accommodate a fourth bond.

Exemplary compounds are provided below solely as illustrative examples.

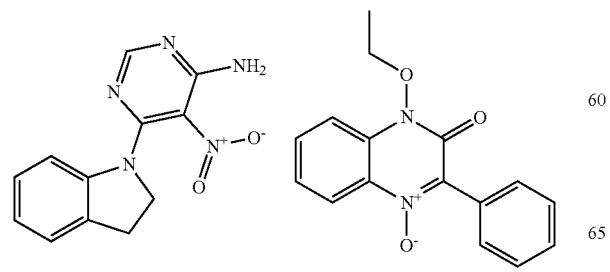

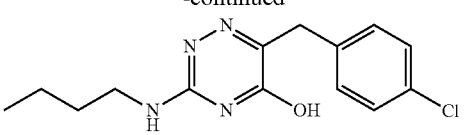

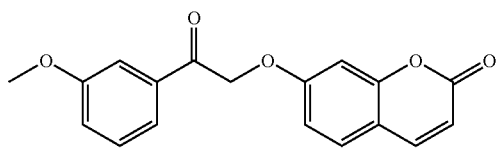

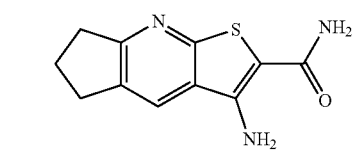

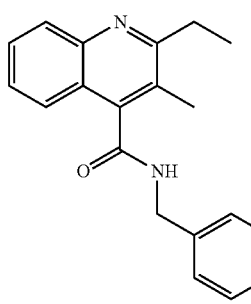

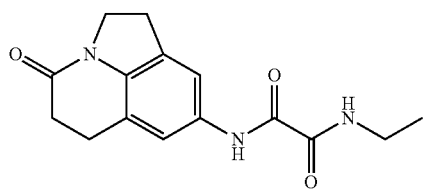

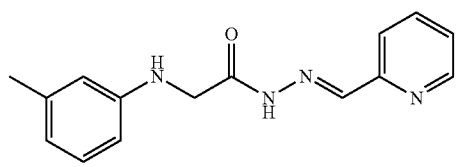

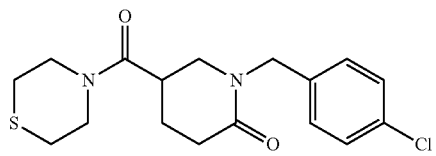

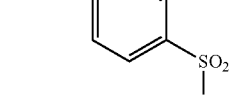

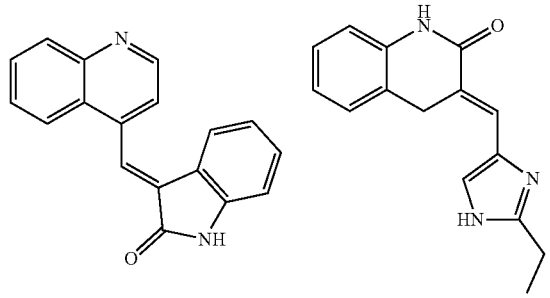

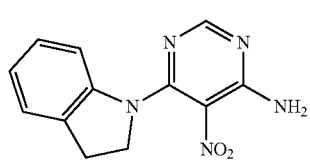

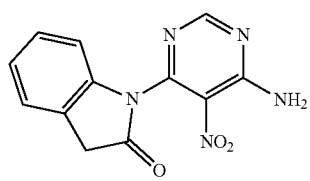

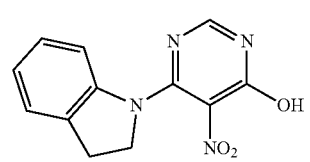

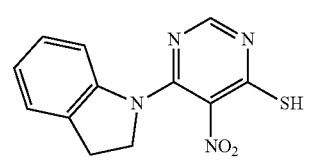

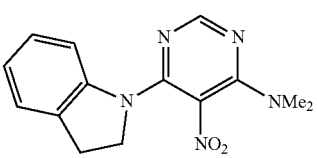

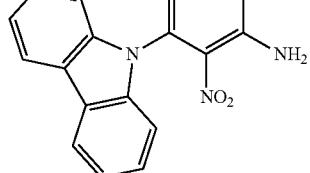

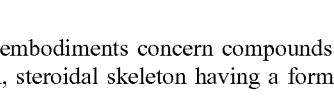

Particular embodiments concern compounds comprising an all-carbon, steroidal skeleton having a formula as illustrated below.

Formula 15

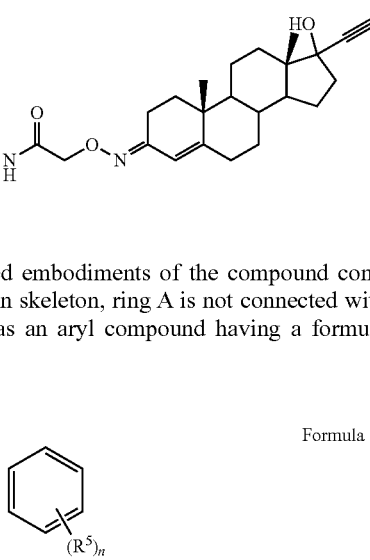

An exemplary compound is provided below.

In other disclosed embodiments of the compound comprising an all-carbon skeleton, ring A is not connected with ring B and exists as an aryl compound having a formula illustrated below.

Formula 16

Exemplary compounds are illustrated below.

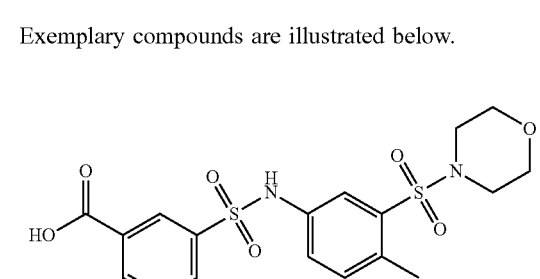

In yet other embodiments, the compound may have any one of the following formulas:

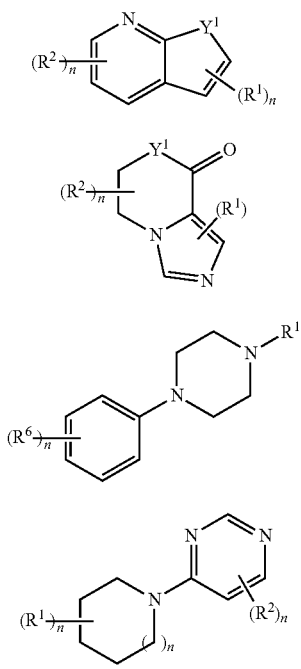

Formula 17

Formula 18

Formula 19

Formula 20

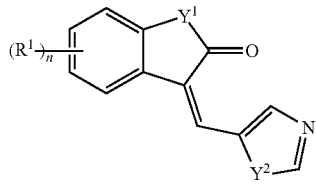

Formula 21

-continued wherein each $Y^1$ and $Y^2$ independently may be selected from oxygen, sulfur, and $NR^b$ wherein $R^b$ is as disclosed herein; and $R^6$ is selected from those substituents provided for $R^1$. Any of the compounds disclosed herein may also be used in an alternate chemical form, such as a pharmaceutically acceptable salt, a N-oxide, a prodrug, and/or a solvate. In particular disclosed embodiments, the compound may be a pharmaceutically acceptable salt, such as a hydrochloride salt, a hydrobromide salt, a hydroiodide salt, a nitrate salt, a sulfate salt, a bisulfate salt, a phosphate salt, an acid phosphate salt, an isonicotinate salt, an acetate salt, a lactate salt, a salicylate salt, a citrate salt, a tartrate salt, an ascorbate salt, a succinate salt, a maleate salt, a fumarate salt, a gluconate salt, a saccharate salt, a formate salt, a benzoate salt, a glutamate salt, a methanesulfonate salt, an ethanesulfonate salt, a benzensulfonate salt, a p-toluenesulfonate salt, and combinations thereof. Exemplary compounds are provided below in Tables 1-6A.

TABLE 1

| $R^1$ | $R^{1'}$ | $R^2$ | $Y^1$ |
|---|---|---|---|
| $C(O)NH_2$ | $NH_2$ | $N[(CH_2)_{0-5}CH_3]_2$ | S |
| $C(O)N[(CH_2)_{0-5}CH_3]_2$ | $NH_2$ | $N[(CH_2)_{0-5}CH_3]_2$ | S |
| $C(O)OH$ | $NH_2$ | $N[(CH_2)_{0-5}CH_3]_2$ | S |
| $C(O)OP(O)(OH)_2$ | $NH_2$ | $N[(CH_2)_{0-5}CH_3]_2$ | S |
| $C(O)OC(O)C(CH_3)_3$ | $NH_2$ | $N[(CH_2)_{0-5}CH_3]_2$ | S |
| $C(O)OC(O)NMe_2$ | $NH_2$ | $N[(CH_2)_{0-5}CH_3]_2$ | S |
| $C(O)O(CH_2)_{0-5}CH_3$ | $NH_2$ | $N[(CH_2)_{0-5}CH_3]_2$ | S |
| $C(O)NH_2$ | $NH_2$ | $N[(CH_2)_{0-5}CH_3]_2$ | $N(CH_2)_{0-5}CH_3$ |
| $C(O)N[(CH_2)_{0-5}CH_3]_2$ | $NH_2$ | $N[(CH_2)_{0-5}CH_3]_2$ | $N(CH_2)_{0-5}CH_3$ |
| $C(O)OH$ | $NH_2$ | $N[(CH_2)_{0-5}CH_3]_2$ | $N(CH_2)_{0-5}CH_3$ |
| $C(O)OP(O)(OH)_2$ | $NH_2$ | $N[(CH_2)_{0-5}CH_3]_2$ | $N(CH_2)_{0-5}CH_3$ |
| $C(O)OC(O)C(CH_3)_3$ | $NH_2$ | $N[(CH_2)_{0-5}CH_3]_2$ | $N(CH_2)_{0-5}CH_3$ |
| $C(O)OC(O)NMe_2$ | $NH_2$ | $N[(CH_2)_{0-5}CH_3]_2$ | $N(CH_2)_{0-5}CH_3$ |
| $C(O)O(CH_2)_{0-5}CH_3$ | $NH_2$ | $N[(CH_2)_{0-5}CH_3]_2$ | $N(CH_2)_{0-5}CH_3$ |
| $C(O)NH_2$ | $NH_2$ | $N[(CH_2)_{0-5}CH_3]_2$ | O |
| $C(O)N[(CH_2)_{0-5}CH_3]_2$ | $NH_2$ | $N[(CH_2)_{0-5}CH_3]_2$ | O |
| $C(O)OH$ | $NH_2$ | $N[(CH_2)_{0-5}CH_3]_2$ | O |
| $C(O)OP(O)(OH)_2$ | $NH_2$ | $N[(CH_2)_{0-5}CH_3]_2$ | O |
| $C(O)OC(O)C(CH_3)_3$ | $NH_2$ | $N[(CH_2)_{0-5}CH_3]_2$ | O |
| $C(O)OC(O)NMe_2$ | $NH_2$ | $N[(CH_2)_{0-5}CH_3]_2$ | O |
| $C(O)O(CH_2)_{0-5}CH_3$ | $NH_2$ | $N[(CH_2)_{0-5}CH_3]_2$ | O |
| $C(O)NH_2$ | $NH_2$ | $N[(CH_2)_{0-5}CH_3]_2$ | NH |
| $C(O)N[(CH_2)_{0-5}CH_3]_2$ | $NH_2$ | $N[(CH_2)_{0-5}CH_3]_2$ | NH |
| $C(O)OH$ | $NH_2$ | $N[(CH_2)_{0-5}CH_3]_2$ | NH |
| $C(O)OP(O)(OH)_2$ | $NH_2$ | $N[(CH_2)_{0-5}CH_3]_2$ | NH |
| $C(O)OC(O)C(CH_3)_3$ | $NH_2$ | $N[(CH_2)_{0-5}CH_3]_2$ | NH |
| $C(O)OC(O)NMe_2$ | $NH_2$ | $N[(CH_2)_{0-5}CH_3]_2$ | NH |
| $C(O)O(CH_2)_{0-5}CH_3$ | $NH_2$ | $N[(CH_2)_{0-5}CH_3]_2$ | NH |
| $C(O)NH_2$ | $N[(CH_2)_{0-5}CH_3]_2$ | $N[(CH_2)_{0-5}CH_3]_2$ | S |
| $C(O)N[(CH_2)_{0-5}CH_3]_2$ | $N[(CH_2)_{0-5}CH_3]_2$ | $N[(CH_2)_{0-5}CH_3]_2$ | S |
| $C(O)OH$ | $N[(CH_2)_{0-5}CH_3]_2$ | $N[(CH_2)_{0-5}CH_3]_2$ | S |
| $C(O)OP(O)(OH)_2$ | $N[(CH_2)_{0-5}CH_3]_2$ | $N[(CH_2)_{0-5}CH_3]_2$ | S |
| $C(O)OC(O)C(CH_3)_3$ | $N[(CH_2)_{0-5}CH_3]_2$ | $N[(CH_2)_{0-5}CH_3]_2$ | S |
| $C(O)OC(O)NMe_2$ | $N[(CH_2)_{0-5}CH_3]_2$ | $N[(CH_2)_{0-5}CH_3]_2$ | S |

TABLE 1-continued

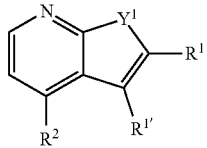

| R¹ | R¹' | R² | Y¹ |
|---|---|---|---|
| $C(O)O(CH_2)_{0-5}CH_3$ | $N[(CH_2)_{0-5}CH_3]_2$ | $N[(CH_2)_{0-5}CH_3]_2$ | S |
| $C(O)NH_2$ | $N[(CH_2)_{0-5}CH_3]_2$ | $N[(CH_2)_{0-5}CH_3]_2$ | O |
| $C(O)N[(CH_2)_{0-5}CH_3]_2$ | $N[(CH_2)_{0-5}CH_3]_2$ | $N[(CH_2)_{0-5}CH_3]_2$ | O |
| $C(O)OH$ | $N[(CH_2)_{0-5}CH_3]_2$ | $N[(CH_2)_{0-5}CH_3]_2$ | O |
| $C(O)OP(O)(OH)_2$ | $N[(CH_2)_{0-5}CH_3]_2$ | $N[(CH_2)_{0-5}CH_3]_2$ | O |
| $C(O)OC(O)C(CH_3)_3$ | $N[(CH_2)_{0-5}CH_3]_2$ | $N[(CH_2)_{0-5}CH_3]_2$ | O |
| $C(O)OC(O)NMe_2$ | $N[(CH_2)_{0-5}CH_3]_2$ | $N[(CH_2)_{0-5}CH_3]_2$ | O |
| $C(O)O(CH_2)_{0-5}CH_3$ | $N[(CH_2)_{0-5}CH_3]_2$ | $N[(CH_2)_{0-5}CH_3]_2$ | O |
| $C(O)NH_2$ | $N[(CH_2)_{0-5}CH_3]_2$ | $N[(CH_2)_{0-5}CH_3]_2$ | $N(CH_2)_{0-5}CH_3$ |
| $C(O)N[(CH_2)_{0-5}CH_3]_2$ | $N[(CH_2)_{0-5}CH_3]_2$ | $N[(CH_2)_{0-5}CH_3]_2$ | $N(CH_2)_{0-5}CH_3$ |
| $C(O)OH$ | $N[(CH_2)_{0-5}CH_3]_2$ | $N[(CH_2)_{0-5}CH_3]_2$ | $N(CH_2)_{0-5}CH_3$ |
| $C(O)OP(O)(OH)_2$ | $N[(CH_2)_{0-5}CH_3]_2$ | $N[(CH_2)_{0-5}CH_3]_2$ | $N(CH_2)_{0-5}CH_3$ |
| $C(O)OC(O)C(CH_3)_3$ | $N[(CH_2)_{0-5}CH_3]_2$ | $N[(CH_2)_{0-5}CH_3]_2$ | $N(CH_2)_{0-5}CH_3$ |
| $C(O)OC(O)NMe_2$ | $N[(CH_2)_{0-5}CH_3]_2$ | $N[(CH_2)_{0-5}CH_3]_2$ | $N(CH_2)_{0-5}CH_3$ |
| $C(O)O(CH_2)_{0-5}CH_3$ | $N[(CH_2)_{0-5}CH_3]_2$ | $N[(CH_2)_{0-5}CH_3]_2$ | $N(CH_2)_{0-5}CH_3$ |
| $C(O)NH_2$ | $N[(CH_2)_{0-5}CH_3]_2$ | $N[(CH_2)_{0-5}CH_3]_2$ | NH |
| $C(O)N[(CH_2)_{0-5}CH_3]_2$ | $N[(CH_2)_{0-5}CH_3]_2$ | $N[(CH_2)_{0-5}CH_3]_2$ | NH |
| $C(O)OH$ | $N[(CH_2)_{0-5}CH_3]_2$ | $N[(CH_2)_{0-5}CH_3]_2$ | NH |
| $C(O)OP(O)(OH)_2$ | $N[(CH_2)_{0-5}CH_3]_2$ | $N[(CH_2)_{0-5}CH_3]_2$ | NH |
| $C(O)OC(O)C(CH_3)_3$ | $N[(CH_2)_{0-5}CH_3]_2$ | $N[(CH_2)_{0-5}CH_3]_2$ | NH |
| $C(O)OC(O)NMe_2$ | $N[(CH_2)_{0-5}CH_3]_2$ | $N[(CH_2)_{0-5}CH_3]_2$ | NH |
| $C(O)O(CH_2)_{0-5}CH_3$ | $N[(CH_2)_{0-5}CH_3]_2$ | $N[(CH_2)_{0-5}CH_3]_2$ | NH |
| $C(O)NH_2$ | $N[(CH_2)_{0-5}CH_3]_2$ | $N[(CH_2)_{0-5}CH_3]_2$ | $NCH_2OP(O)(OH)_2$ |
| $C(O)N[(CH_2)_{0-5}CH_3]_2$ | $N[(CH_2)_{0-5}CH_3]_2$ | $N[(CH_2)_{0-5}CH_3]_2$ | $NCH_2OP(O)(OH)_2$ |
| $C(O)OH$ | $N[(CH_2)_{0-5}CH_3]_2$ | $N[(CH_2)_{0-5}CH_3]_2$ | $NCH_2OP(O)(OH)_2$ |
| $C(O)O(CH_2)_{0-5}CH_3$ | $N[(CH_2)_{0-5}CH_3]_2$ | $N[(CH_2)_{0-5}CH_3]_2$ | $NCH_2OP(O)(OH)_2$ |
| $C(O)OP(O)(OH)_2$ | $N[(CH_2)_{0-5}CH_3]_2$ | $N[(CH_2)_{0-5}CH_3]_2$ | $NCH_2OP(O)(OH)_2$ |
| $C(O)OC(O)C(CH_3)_3$ | $N[(CH_2)_{0-5}CH_3]_2$ | $N[(CH_2)_{0-5}CH_3]_2$ | $NCH_2OP(O)(OH)_2$ |
| $C(O)OC(O)NMe_2$ | $N[(CH_2)_{0-5}CH_3]_2$ | $N[(CH_2)_{0-5}CH_3]_2$ | $NCH_2OP(O)(OH)_2$ |

TABLE 2

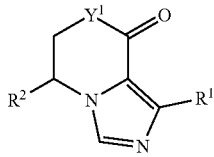

| R¹ | R² | Y¹ |
|---|---|---|
| $C(O)NH(Ph)pCH_2NHC(O)Ot\text{-}Bu$ | $(CH_2)_{0-5}CH_3$ | NH |
| $C(O)N[CH_2OP(O)(OH)_2](Ph)pCH_2NHC(O)Ot\text{-}Bu$ | $(CH_2)_{0-5}CH_3$ | NH |
| $C(O)N[CH_2OP(O)(OH)_2](Ph)pCH_2N[CH_2OP(O)(OH)_2]C(O)Ot\text{-}Bu$ | $(CH_2)_{0-5}CH_3$ | NH |
| $C(O)NH(Ph)pCH_2N[CH_2OP(O)(OH)_2]C(O)Ot\text{-}Bu$ | $(CH_2)_{0-5}CH_3$ | NH |
| $C(O)NH(Ph)pCH_2NHC(O)OH$ | $(CH_2)_{0-5}CH_3$ | NH |
| $C(O)N[CH_2OP(O)(OH)_2](Ph)pCH_2NHC(O)OH$ | $(CH_2)_{0-5}CH_3$ | NH |
| $C(O)NH(Ph)pCH_2NHC(O)OMe$ | $(CH_2)_{0-5}CH_3$ | NH |
| $C(O)N[CH_2OP(O)(OH)_2](Ph)pCH_2NHC(O)OMe$ | $(CH_2)_{0-5}CH_3$ | NH |
| $C(O)N[CH_2OP(O)(OH)_2](Ph)pCH_2N[CH_2OP(O)(OH)_2]C(O)OMe$ | $(CH_2)_{0-5}CH_3$ | NH |
| $C(O)N[(CH_2)_{0-5}CH_3](Ph)pCH_2NHC(O)Ot\text{-}Bu$ | $(CH_2)_{0-5}CH_3$ | NH |
| $C(O)N[(CH_2)_{0-5}CH_3](Ph)pCH_2N[CH_2OP(O)(OH)_2]C(O)Ot\text{-}Bu$ | $(CH_2)_{0-5}CH_3$ | NH |
| $C(O)N[(CH_2)_{0-5}CH_3](Ph)pCH_2NHC(O)OH$ | $(CH_2)_{0-5}CH_3$ | NH |
| $C(O)N[(CH_2)_{0-5}CH_3](Ph)pCH_2N[CH_2OP(O)(OH)_2]C(O)OH$ | $(CH_2)_{0-5}CH_3$ | NH |
| $C(O)N[(CH_2)_{0-5}CH_3](Ph)pCH_2NHC(O)OMe$ | $(CH_2)_{0-5}CH_3$ | NH |
| $C(O)N[(CH_2)_{0-5}CH_3](Ph)pCH_2N[CH_2OP(O)(OH)_2]C(O)OMe$ | $(CH_2)_{0-5}CH_3$ | NH |
| $C(O)NH(Ph)pCH_2NH_2$ | $(CH_2)_{0-5}CH_3$ | NH |
| $C(O)N[CH_2OP(O)(OH)_2](Ph)pCH_2NH_2$ | $(CH_2)_{0-5}CH_3$ | NH |
| $C(O)NH(Ph)pCH_2OH$ | $(CH_2)_{0-5}CH_3$ | NH |
| $C(O)N[CH_2OP(O)(OH)_2](Ph)pCH_2OH$ | $(CH_2)_{0-5}CH_3$ | NH |
| $C(O)NH(Ph)pCH_2N[(CH_2)_{0-5}CH_3]_2$ | $(CH_2)_{0-5}CH_3$ | NH |
| $C(O)N[CH_2OP(O)(OH)_2](Ph)pCH_2N[(CH_2)_{0-5}CH_3]_2$ | $(CH_2)_{0-5}CH_3$ | NH |
| $C(O)NH(Ph)pCH_2OMe$ | $(CH_2)_{0-5}CH_3$ | NH |
| $C(O)N[CH_2OP(O)(OH)_2](Ph)pCH_2OMe$ | $(CH_2)_{0-5}CH_3$ | NH |
| $C(O)NH(Ph)pCH_2SH$ | $(CH_2)_{0-5}CH_3$ | NH |
| $C(O)N[CH_2OP(O)(OH)_2](Ph)pCH_2SH$ | $(CH_2)_{0-5}CH_3$ | NH |

TABLE 2-continued

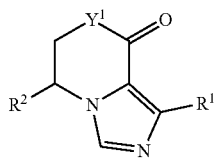

| R[1] | R[2] | Y[1] |
|---|---|---|
| C(O)NH(Ph)pCH$_2$SMe | (CH$_2$)$_{0-5}$CH$_3$ | NH |
| C(O)N[CH$_2$OP(O)(OH)$_2$](Ph)pCH$_2$SMe | (CH$_2$)$_{0-5}$CH$_3$ | NH |
| C(O)N[(CH$_2$)$_{0-5}$CH$_3$](Ph)pCH$_2$NH$_2$ | (CH$_2$)$_{0-5}$CH$_3$ | NH |
| C(O)N[CH$_2$OP(O)(OH)$_2$](Ph)pCH$_2$NH$_2$ | (CH$_2$)$_{0-5}$CH$_3$ | NH |
| C(O)N[(CH$_2$)$_{0-5}$CH$_3$](Ph)pCH$_2$OH | (CH$_2$)$_{0-5}$CH$_3$ | NH |
| C(O)N[CH$_2$OP(O)(OH)$_2$](Ph)pCH$_2$OH | (CH$_2$)$_{0-5}$CH$_3$ | NH |
| C(O)N[(CH$_2$)$_{0-5}$CH$_3$](Ph)pCH$_2$N[(CH$_2$)$_{0-5}$CH$_3$]$_2$ | (CH$_2$)$_{0-5}$CH$_3$ | NH |
| C(O)N[CH$_2$OP(O)(OH)$_2$](Ph)pCH$_2$N[(CH$_2$)$_{0-5}$CH$_3$]$_2$ | (CH$_2$)$_{0-5}$CH$_3$ | NH |
| C(O)N[(CH$_2$)$_{0-5}$CH$_3$](Ph)pCH$_2$OMe | (CH$_2$)$_{0-5}$CH$_3$ | NH |
| C(O)N[CH$_2$OP(O)(OH)$_2$](Ph)pCH$_2$OMe | (CH$_2$)$_{0-5}$CH$_3$ | NH |
| C(O)N[(CH$_2$)$_{0-5}$CH$_3$](Ph)pCH$_2$SH | (CH$_2$)$_{0-5}$CH$_3$ | NH |
| C(O)N[CH$_2$OP(O)(OH)$_2$](Ph)pCH$_2$SH | (CH$_2$)$_{0-5}$CH$_3$ | NH |
| C(O)N[(CH$_2$)$_{0-5}$CH$_3$](Ph)pCH$_2$SMe | (CH$_2$)$_{0-5}$CH$_3$ | NH |
| C(O)N[CH$_2$OP(O)(OH)$_2$](Ph)pCH$_2$SMe | (CH$_2$)$_{0-5}$CH$_3$ | NH |
| C(O)NH(Ph)pCH$_2$NHC(O)Ot-Bu | (CH$_2$)$_{0-5}$CH$_3$ | O |
| C(O)N[CH$_2$OP(O)(OH)$_2$](Ph)pCH$_2$NHC(O)Ot-Bu | (CH$_2$)$_{0-5}$CH$_3$ | O |
| C(O)N[CH$_2$OP(O)(OH)$_2$](Ph)pCH$_2$N[CH$_2$OP(O)(OH)$_2$]C(O)Ot-Bu | (CH$_2$)$_{0-5}$CH$_3$ | O |
| C(O)NH(Ph)pCH$_2$N[CH$_2$OP(O)(OH)$_2$]C(O)Ot-Bu | (CH$_2$)$_{0-5}$CH$_3$ | O |
| C(O)NH(Ph)pCH$_2$NHC(O)OH | (CH$_2$)$_{0-5}$CH$_3$ | O |
| C(O)N[CH$_2$OP(O)(OH)$_2$](Ph)pCH$_2$NHC(O)OH | (CH$_2$)$_{0-5}$CH$_3$ | O |
| C(O)NH(Ph)pCH$_2$NHC(O)OMe | (CH$_2$)$_{0-5}$CH$_3$ | O |
| C(O)N[CH$_2$OP(O)(OH)$_2$](Ph)pCH$_2$NHC(O)OMe | (CH$_2$)$_{0-5}$CH$_3$ | O |
| C(O)N[CH$_2$OP(O)(OH)$_2$](Ph)pCH$_2$N[CH$_2$OP(O)(OH)$_2$]C(O)OMe | (CH$_2$)$_{0-5}$CH$_3$ | O |
| C(O)N[(CH$_2$)$_{0-5}$CH$_3$](Ph)pCH$_2$NHC(O)Ot-Bu | (CH$_2$)$_{0-5}$CH$_3$ | O |
| C(O)N[(CH$_2$)$_{0-5}$CH$_3$](Ph)pCH$_2$N[CH$_2$OP(O)(OH)$_2$]C(O)Ot-Bu | (CH$_2$)$_{0-5}$CH$_3$ | O |
| C(O)N[(CH$_2$)$_{0-5}$CH$_3$](Ph)pCH$_2$NHC(O)OH | (CH$_2$)$_{0-5}$CH$_3$ | O |
| C(O)N[(CH$_2$)$_{0-5}$CH$_3$](Ph)pCH$_2$N[CH$_2$OP(O)(OH)$_2$]C(O)OH | (CH$_2$)$_{0-5}$CH$_3$ | O |
| C(O)N[(CH$_2$)$_{0-5}$CH$_3$](Ph)pCH$_2$NHC(O)OMe | (CH$_2$)$_{0-5}$CH$_3$ | O |
| C(O)N[(CH$_2$)$_{0-5}$CH$_3$](Ph)pCH$_2$N[CH$_2$OP(O)(OH)$_2$]C(O)OMe | (CH$_2$)$_{0-5}$CH$_3$ | O |
| C(O)NH(Ph)pCH$_2$NH$_2$ | (CH$_2$)$_{0-5}$CH$_3$ | O |
| C(O)N[CH$_2$OP(O)(OH)$_2$](Ph)pCH$_2$NH$_2$ | (CH$_2$)$_{0-5}$CH$_3$ | O |
| C(O)NH(Ph)pCH$_2$OH | (CH$_2$)$_{0-5}$CH$_3$ | O |
| C(O)N[CH$_2$OP(O)(OH)$_2$](Ph)pCH$_2$OH | (CH$_2$)$_{0-5}$CH$_3$ | O |
| C(O)NH(Ph)pCH$_2$N[(CH$_2$)$_{0-5}$CH$_3$]$_2$ | (CH$_2$)$_{0-5}$CH$_3$ | O |
| C(O)N[CH$_2$OP(O)(OH)$_2$](Ph)pCH$_2$N[(CH$_2$)$_{0-5}$CH$_3$]$_2$ | (CH$_2$)$_{0-5}$CH$_3$ | O |
| C(O)NH(Ph)pCH$_2$OMe | (CH$_2$)$_{0-5}$CH$_3$ | O |
| C(O)N[CH$_2$OP(O)(OH)$_2$](Ph)pCH$_2$OMe | (CH$_2$)$_{0-5}$CH$_3$ | O |
| C(O)NH(Ph)pCH$_2$SH | (CH$_2$)$_{0-5}$CH$_3$ | O |
| C(O)N[CH$_2$OP(O)(OH)$_2$](Ph)pCH$_2$SH | (CH$_2$)$_{0-5}$CH$_3$ | O |
| C(O)NH(Ph)pCH$_2$SMe | (CH$_2$)$_{0-5}$CH$_3$ | O |
| C(O)N[CH$_2$OP(O)(OH)$_2$](Ph)pCH$_2$SMe | (CH$_2$)$_{0-5}$CH$_3$ | O |
| C(O)N[(CH$_2$)$_{0-5}$CH$_3$](Ph)pCH$_2$NH$_2$ | (CH$_2$)$_{0-5}$CH$_3$ | O |
| C(O)N[CH$_2$OP(O)(OH)$_2$](Ph)pCH$_2$NH$_2$ | (CH$_2$)$_{0-5}$CH$_3$ | O |
| C(O)N[(CH$_2$)$_{0-5}$CH$_3$](Ph)pCH$_2$OH | (CH$_2$)$_{0-5}$CH$_3$ | O |
| C(O)N[CH$_2$OP(O)(OH)$_2$](Ph)pCH$_2$OH | (CH$_2$)$_{0-5}$CH$_3$ | O |
| C(O)N[(CH$_2$)$_{0-5}$CH$_3$](Ph)pCH$_2$N[(CH$_2$)$_{0-5}$CH$_3$]$_2$ | (CH$_2$)$_{0-5}$CH$_3$ | O |
| C(O)N[CH$_2$OP(O)(OH)$_2$](Ph)pCH$_2$N[(CH$_2$)$_{0-5}$CH$_3$]$_2$ | (CH$_2$)$_{0-5}$CH$_3$ | O |
| C(O)N[(CH$_2$)$_{0-5}$CH$_3$](Ph)pCH$_2$OMe | (CH$_2$)$_{0-5}$CH$_3$ | O |
| C(O)N[(CH$_2$)$_{0-5}$CH$_3$](Ph)pCH$_2$SH | (CH$_2$)$_{0-5}$CH$_3$ | O |
| C(O)N[CH$_2$OP(O)(OH)$_2$](Ph)pCH$_2$SH | (CH$_2$)$_{0-5}$CH$_3$ | O |
| C(O)N[(CH$_2$)$_{0-5}$CH$_3$](Ph)pCH$_2$SMe | (CH$_2$)$_{0-5}$CH$_3$ | O |
| C(O)N[CH$_2$OP(O)(OH)$_2$](Ph)pCH$_2$SMe | (CH$_2$)$_{0-5}$CH$_3$ | O |
| C(O)NH(Ph)pCH$_2$NHC(O)Ot-Bu | (CH$_2$)$_{0-5}$CH$_3$ | NCH$_2$OP(O)(OH)$_2$ |
| C(O)N[CH$_2$OP(O)(OH)$_2$](Ph)pCH$_2$NHC(O)Ot-Bu | (CH$_2$)$_{0-5}$CH$_3$ | NCH$_2$OP(O)(OH)$_2$ |
| C(O)N[CH$_2$OP(O)(OH)$_2$](Ph)pCH$_2$N[CH$_2$OP(O)(OH)$_2$]C(O)Ot-Bu | (CH$_2$)$_{0-5}$CH$_3$ | NCH$_2$OP(O)(OH)$_2$ |
| C(O)NH(Ph)pCH$_2$N[CH$_2$OP(O)(OH)$_2$]C(O)Ot-Bu | (CH$_2$)$_{0-5}$CH$_3$ | NCH$_2$OP(O)(OH)$_2$ |
| C(O)NH(Ph)pCH$_2$NHC(O)OH | (CH$_2$)$_{0-5}$CH$_3$ | NCH$_2$OP(O)(OH)$_2$ |
| C(O)N[CH$_2$OP(O)(OH)$_2$](Ph)pCH$_2$NHC(O)OH | (CH$_2$)$_{0-5}$CH$_3$ | NCH$_2$OP(O)(OH)$_2$ |
| C(O)NH(Ph)pCH$_2$NHC(O)OMe | (CH$_2$)$_{0-5}$CH$_3$ | NCH$_2$OP(O)(OH)$_2$ |
| C(O)N[CH$_2$OP(O)(OH)$_2$](Ph)pCH$_2$NHC(O)OMe | (CH$_2$)$_{0-5}$CH$_3$ | NCH$_2$OP(O)(OH)$_2$ |
| C(O)N[CH$_2$OP(O)(OH)$_2$](Ph)pCH$_2$N[CH$_2$OP(O)(OH)$_2$]C(O)OMe | (CH$_2$)$_{0-5}$CH$_3$ | NCH$_2$OP(O)(OH)$_2$ |
| C(O)N[(CH$_2$)$_{0-5}$CH$_3$](Ph)pCH$_2$NHC(O)Ot-Bu | (CH$_2$)$_{0-5}$CH$_3$ | NCH$_2$OP(O)(OH)$_2$ |
| C(O)N[(CH$_2$)$_{0-5}$CH$_3$](Ph)pCH$_2$N[CH$_2$OP(O)(OH)$_2$]C(O)Ot-Bu | (CH$_2$)$_{0-5}$CH$_3$ | NCH$_2$OP(O)(OH)$_2$ |
| C(O)N[(CH$_2$)$_{0-5}$CH$_3$](Ph)pCH$_2$NHC(O)OH | (CH$_2$)$_{0-5}$CH$_3$ | NCH$_2$OP(O)(OH)$_2$ |
| C(O)N[(CH$_2$)$_{0-5}$CH$_3$](Ph)pCH$_2$N[CH$_2$OP(O)(OH)$_2$]C(O)OH | (CH$_2$)$_{0-5}$CH$_3$ | NCH$_2$OP(O)(OH)$_2$ |
| C(O)N[(CH$_2$)$_{0-5}$CH$_3$](Ph)pCH$_2$NHC(O)OMe | (CH$_2$)$_{0-5}$CH$_3$ | NCH$_2$OP(O)(OH)$_2$ |
| C(O)N[(CH$_2$)$_{0-5}$CH$_3$](Ph)pCH$_2$N[CH$_2$OP(O)(OH)$_2$]C(O)OMe | (CH$_2$)$_{0-5}$CH$_3$ | NCH$_2$OP(O)(OH)$_2$ |
| C(O)NH(Ph)pCH$_2$NH$_2$ | (CH$_2$)$_{0-5}$CH$_3$ | NCH$_2$OP(O)(OH)$_2$ |
| C(O)N[CH$_2$OP(O)(OH)$_2$](Ph)pCH$_2$NH$_2$ | (CH$_2$)$_{0-5}$CH$_3$ | NCH$_2$OP(O)(OH)$_2$ |

TABLE 2-continued

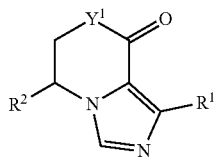

| R$^1$ | R$^2$ | Y$^1$ |
|---|---|---|
| C(O)NH(Ph)pCH$_2$OH | (CH$_2$)$_{0-5}$CH$_3$ | NCH$_2$OP(O)(OH)$_2$ |
| C(O)N[CH$_2$OP(O)(OH)$_2$](Ph)pCH$_2$OH | (CH$_2$)$_{0-5}$CH$_3$ | NCH$_2$OP(O)(OH)$_2$ |
| C(O)NH(Ph)pCH$_2$N[(CH$_2$)$_{0-5}$CH$_3$]$_2$ | (CH$_2$)$_{0-5}$CH$_3$ | NCH$_2$OP(O)(OH)$_2$ |
| C(O)N[CH$_2$OP(O)(OH)$_2$](Ph)pCH$_2$N[(CH$_2$)$_{0-5}$CH$_3$]$_2$ | (CH$_2$)$_{0-5}$CH$_3$ | NCH$_2$OP(O)(OH)$_2$ |
| C(O)NH(Ph)pCH$_2$OMe | (CH$_2$)$_{0-5}$CH$_3$ | NCH$_2$OP(O)(OH)$_2$ |
| C(O)N[CH$_2$OP(O)(OH)$_2$](Ph)pCH$_2$OMe | (CH$_2$)$_{0-5}$CH$_3$ | NCH$_2$OP(O)(OH)$_2$ |
| C(O)NH(Ph)pCH$_2$SH | (CH$_2$)$_{0-5}$CH$_3$ | NCH$_2$OP(O)(OH)$_2$ |
| C(O)N[CH$_2$OP(O)(OH)$_2$](Ph)pCH$_2$SH | (CH$_2$)$_{0-5}$CH$_3$ | NCH$_2$OP(O)(OH)$_2$ |
| C(O)NH(Ph)pCH$_2$SMe | (CH$_2$)$_{0-5}$CH$_3$ | NCH$_2$OP(O)(OH)$_2$ |
| C(O)N[CH$_2$OP(O)(OH)$_2$](Ph)pCH$_2$SMe | (CH$_2$)$_{0-5}$CH$_3$ | NCH$_2$OP(O)(OH)$_2$ |
| C(O)N[(CH$_2$)$_{0-5}$CH$_3$](Ph)pCH$_2$NH$_2$ | (CH$_2$)$_{0-5}$CH$_3$ | NCH$_2$OP(O)(OH)$_2$ |
| C(O)N[CH$_2$OP(O)(OH)$_2$](Ph)pCH$_2$NH$_2$ | (CH$_2$)$_{0-5}$CH$_3$ | NCH$_2$OP(O)(OH)$_2$ |
| C(O)N[(CH$_2$)$_{0-5}$CH$_3$](Ph)pCH$_2$OH | (CH$_2$)$_{0-5}$CH$_3$ | NCH$_2$OP(O)(OH)$_2$ |
| C(O)N[CH$_2$OP(O)(OH)$_2$](Ph)pCH$_2$OH | (CH$_2$)$_{0-5}$CH$_3$ | NCH$_2$OP(O)(OH)$_2$ |
| C(O)N[(CH$_2$)$_{0-5}$CH$_3$](Ph)pCH$_2$N[(CH$_2$)$_{0-5}$CH$_3$]$_2$ | (CH$_2$)$_{0-5}$CH$_3$ | NCH$_2$OP(O)(OH)$_2$ |
| C(O)N[CH$_2$OP(O)(OH)$_2$](Ph)pCH$_2$N[(CH$_2$)$_{0-5}$CH$_3$]$_2$ | (CH$_2$)$_{0-5}$CH$_3$ | NCH$_2$OP(O)(OH)$_2$ |
| C(O)N[(CH$_2$)$_{0-5}$CH$_3$](Ph)pCH$_2$OMe | (CH$_2$)$_{0-5}$CH$_3$ | NCH$_2$OP(O)(OH)$_2$ |
| C(O)N[(CH$_2$)$_{0-5}$CH$_3$](Ph)pCH$_2$SH | (CH$_2$)$_{0-5}$CH$_3$ | NCH$_2$OP(O)(OH)$_2$ |
| C(O)N[CH$_2$OP(O)(OH)$_2$](Ph)pCH$_2$SH | (CH$_2$)$_{0-5}$CH$_3$ | NCH$_2$OP(O)(OH)$_2$ |
| C(O)N[(CH$_2$)$_{0-5}$CH$_3$](Ph)pCH$_2$SMe | (CH$_2$)$_{0-5}$CH$_3$ | NCH$_2$OP(O)(OH)$_2$ |
| C(O)N[CH$_2$OP(O)(OH)$_2$](Ph)pCH$_2$SMe | (CH$_2$)$_{0-5}$CH$_3$ | NCH$_2$OP(O)(OH)$_2$ |
| C(O)NH(Ph)pCH$_2$NHC(O)Ot-Bu | (CH$_2$)$_{0-5}$CH$_3$ | N(CH$_2$)$_{0-5}$CH$_3$ |
| C(O)N[CH$_2$OP(O)(OH)$_2$](Ph)pCH$_2$NHC(O)Ot-Bu | (CH$_2$)$_{0-5}$CH$_3$ | N(CH$_2$)$_{0-5}$CH$_3$ |
| C(O)N[CH$_2$OP(O)(OH)$_2$](Ph)pCH$_2$N[CH$_2$OP(O)(OH)$_2$]C(O)Ot-Bu | (CH$_2$)$_{0-5}$CH$_3$ | N(CH$_2$)$_{0-5}$CH$_3$ |
| C(O)NH(Ph)pCH$_2$N[CH$_2$OP(O)(OH)$_2$]C(O)Ot-Bu | (CH$_2$)$_{0-5}$CH$_3$ | N(CH$_2$)$_{0-5}$CH$_3$ |
| C(O)NH(Ph)pCH$_2$NHC(O)OH | (CH$_2$)$_{0-5}$CH$_3$ | N(CH$_2$)$_{0-5}$CH$_3$ |
| C(O)N[CH$_2$OP(O)(OH)$_2$](Ph)pCH$_2$NHC(O)OH | (CH$_2$)$_{0-5}$CH$_3$ | N(CH$_2$)$_{0-5}$CH$_3$ |
| C(O)NH(Ph)pCH$_2$NHC(O)OMe | (CH$_2$)$_{0-5}$CH$_3$ | N(CH$_2$)$_{0-5}$CH$_3$ |
| C(O)N[CH$_2$OP(O)(OH)$_2$](Ph)pCH$_2$NHC(O)OMe | (CH$_2$)$_{0-5}$CH$_3$ | N(CH$_2$)$_{0-5}$CH$_3$ |
| C(O)N[CH$_2$OP(O)(OH)$_2$](Ph)pCH$_2$N[CH$_2$OP(O)(OH)$_2$]C(O)OMe | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$NHC(O)Ot-Bu | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$N[CH$_2$OP(O)(OH)$_2$]C(O)Ot-Bu | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$NHC(O)OH | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$N[CH$_2$OP(O)(OH)$_2$]C(O)OH | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$NHC(O)OMe | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$N[CH$_2$OP(O)(OH)$_2$]C(O)OMe | (CH$_2$)$_{0-5}$CH$_3$ | N(CH$_2$)$_{0-5}$CH$_3$ |
| C(O)NH(Ph)pCH$_2$NH$_2$ | (CH$_2$)$_{0-5}$CH$_3$ | N(CH$_2$)$_{0-5}$CH$_3$ |
| C(O)N[CH$_2$OP(O)(OH)$_2$](Ph)pCH$_2$NH$_2$ | (CH$_2$)$_{0-5}$CH$_3$ | N(CH$_2$)$_{0-5}$CH$_3$ |
| C(O)NH(Ph)pCH$_2$OH | (CH$_2$)$_{0-5}$CH$_3$ | N(CH$_2$)$_{0-5}$CH$_3$ |
| C(O)N[CH$_2$OP(O)(OH)$_2$](Ph)pCH$_2$OH | (CH$_2$)$_{0-5}$CH$_3$ | N(CH$_2$)$_{0-5}$CH$_3$ |
| C(O)NH(Ph)pCH$_2$N[(CH$_2$)$_{0-5}$CH$_3$]$_2$ | (CH$_2$)$_{0-5}$CH$_3$ | N(CH$_2$)$_{0-5}$CH$_3$ |
| C(O)N[CH$_2$OP(O)(OH)$_2$](Ph)pCH$_2$N[(CH$_2$)$_{0-5}$CH$_3$]$_2$ | (CH$_2$)$_{0-5}$CH$_3$ | N(CH$_2$)$_{0-5}$CH$_3$ |
| C(O)NH(Ph)pCH$_2$OMe | (CH$_2$)$_{0-5}$CH$_3$ | N(CH$_2$)$_{0-5}$CH$_3$ |
| C(O)N[CH$_2$OP(O)(OH)$_2$](Ph)pCH$_2$OMe | (CH$_2$)$_{0-5}$CH$_3$ | N(CH$_2$)$_{0-5}$CH$_3$ |
| C(O)NH(Ph)pCH$_2$SH | (CH$_2$)$_{0-5}$CH$_3$ | N(CH$_2$)$_{0-5}$CH$_3$ |
| C(O)N[CH$_2$OP(O)(OH)$_2$](Ph)pCH$_2$SH | (CH$_2$)$_{0-5}$CH$_3$ | N(CH$_2$)$_{0-5}$CH$_3$ |
| C(O)NH(Ph)pCH$_2$SMe | (CH$_2$)$_{0-5}$CH$_3$ | N(CH$_2$)$_{0-5}$CH$_3$ |
| C(O)N[CH$_2$OP(O)(OH)$_2$](Ph)pCH$_2$SMe | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$NH$_2$ | (CH$_2$)$_{0-5}$CH$_3$ | N(CH$_2$)$_{0-5}$CH$_3$ |
| C(O)N[CH$_2$OP(O)(OH)$_2$](Ph)pCH$_2$NH$_2$ | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$OH | (CH$_2$)$_{0-5}$CH$_3$ | N(CH$_2$)$_{0-5}$CH$_3$ |
| C(O)N[CH$_2$OP(O)(OH)$_2$](Ph)pCH$_2$OH | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$N[(CH$_2$)$_{0-5}$CH$_3$]$_2$ | (CH$_2$)$_{0-5}$CH$_3$ | N(CH$_2$)$_{0-5}$CH$_3$ |
| C(O)N[CH$_2$OP(O)(OH)$_2$](Ph)pCH$_2$N[(CH$_2$)$_{0-5}$CH$_3$]$_2$ | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$OMe | (CH$_2$)$_{0-5}$CH$_3$ | N(CH$_2$)$_{0-5}$CH$_3$ |
| C(O)N[CH$_2$OP(O)(OH)$_2$](Ph)pCH$_2$OMe | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$SH | (CH$_2$)$_{0-5}$CH$_3$ | N(CH$_2$)$_{0-5}$CH$_3$ |
| C(O)N[CH$_2$OP(O)(OH)$_2$](Ph)pCH$_2$SH | (CH$_2$)$_{0-5}$CH$_3$ | N(CH$_2$)$_{0-5}$CH$_3$ |
| C(O)N[(CH$_2$)$_{0-5}$CH$_3$](Ph)pCH$_2$SMe | (CH$_2$)$_{0-5}$CH$_3$ | N(CH$_2$)$_{0-5}$CH$_3$ |
| C(O)N[CH$_2$OP(O)(OH)$_2$](Ph)pCH$_2$SMe | (CH$_2$)$_{0-5}$CH$_3$ | N(CH$_2$)$_{0-5}$CH$_3$ |

TABLE 3

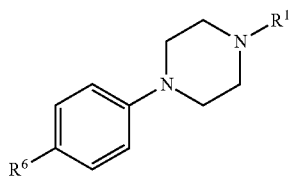

| R¹ | R⁶ | R¹ | R⁶ |
| --- | --- | --- | --- |
| C(O)—Ph-p-Br | NHC(O)-3-bromo-5-pyridyl | C(O)—Ph-p-Br | NHC(O)-3-fluoro-5-pyridyl |
| C(O)—Ph-p-Cl | NHC(O)-3-bromo-5-pyridyl | C(O)—Ph-p-Cl | NHC(O)-3-fluoro-5-pyridyl |
| C(O)—Ph-p-F | NHC(O)-3-bromo-5-pyridyl | C(O)—Ph-p-F | NHC(O)-3-fluoro-5-pyridyl |
| C(O)—Ph-p-I | NHC(O)-3-bromo-5-pyridyl | C(O)—Ph-p-I | NHC(O)-3-fluoro-5-pyridyl |
| C(O)—Ph-p-CF₃ | NHC(O)-3-bromo-5-pyridyl | C(O)—Ph-p-CF₃ | NHC(O)-3-fluoro-5-pyridyl |
| C(O)—Ph-p-Br | N[CH₂OP(O)(OH)₂]C(O)-3-bromo-5-pyridyl | C(O)—Ph-p-Br | N[CH₂OP(O)(OH)₂]C(O)-3-fluoro-5-pyridyl |
| C(O)—Ph-p-Cl | N[CH₂OP(O)(OH)₂]C(O)-3-bromo-5-pyridyl | C(O)—Ph-p-Cl | N[CH₂OP(O)(OH)₂]C(O)-3-fluoro-5-pyridyl |
| C(O)—Ph-p-F | N[CH₂OP(O)(OH)₂]C(O)-3-bromo-5-pyridyl | C(O)—Ph-p-F | N[CH₂OP(O)(OH)₂]C(O)-3-fluoro-5-pyridyl |
| C(O)—Ph-p-I | N[CH₂OP(O)(OH)₂]C(O)-3-bromo-5-pyridyl | C(O)—Ph-p-I | N[CH₂OP(O)(OH)₂]C(O)-3-fluoro-5-pyridyl |
| C(O)—Ph-p-CF₃ | N[CH₂OP(O)(OH)₂]C(O)-3-bromo-5-pyridyl | C(O)—Ph-p-CF₃ | N[CH₂OP(O)(OH)₂]C(O)-3-fluoro-5-pyridyl |
| C(O)—Ph-o-Br | NHC(O)-3-bromo-5-pyridyl | C(O)—Ph-o-Br | NHC(O)-3-fluoro-5-pyridyl |
| C(O)—Ph-o-Cl | NHC(O)-3-bromo-5-pyridyl | C(O)—Ph-o-Cl | NHC(O)-3-fluoro-5-pyridyl |
| C(O)—Ph-o-F | NHC(O)-3-bromo-5-pyridyl | C(O)—Ph-o-F | NHC(O)-3-fluoro-5-pyridyl |
| C(O)—Ph-o-I | NHC(O)-3-bromo-5-pyridyl | C(O)—Ph-o-I | NHC(O)-3-fluoro-5-pyridyl |
| C(O)—Ph-o-CF₃ | NHC(O)-3-bromo-5-pyridyl | C(O)—Ph-o-CF₃ | NHC(O)-3-fluoro-5-pyridyl |
| C(O)—Ph-o-Br | N[CH₂OP(O)(OH)₂]C(O)-3-bromo-5-pyridyl | C(O)—Ph-o-Br | N[CH₂OP(O)(OH)₂]C(O)-3-fluoro-5-pyridyl |
| C(O)—Ph-o-Cl | N[CH₂OP(O)(OH)₂]C(O)-3-bromo-5-pyridyl | C(O)—Ph-o-Cl | N[CH₂OP(O)(OH)₂]C(O)-3-fluoro-5-pyridyl |
| C(O)—Ph-o-F | N[CH₂OP(O)(OH)₂]C(O)-3-bromo-5-pyridyl | C(O)—Ph-o-F | N[CH₂OP(O)(OH)₂]C(O)-3-fluoro-5-pyridyl |
| C(O)—Ph-o-I | N[CH₂OP(O)(OH)₂]C(O)-3-bromo-5-pyridyl | C(O)—Ph-o-I | N[CH₂OP(O)(OH)₂]C(O)-3-fluoro-5-pyridyl |
| C(O)—Ph-o-CF₃ | N[CH₂OP(O)(OH)₂]C(O)-3-bromo-5-pyridyl | C(O)—Ph-o-CF₃ | N[CH₂OP(O)(OH)₂]C(O)-3-fluoro-5-pyridyl |
| C(O)—Ph-m-Br | NHC(O)-3-bromo-5-pyridyl | C(O)—Ph-m-Br | NHC(O)-3-fluoro-5-pyridyl |
| C(O)—Ph-m-Cl | NHC(O)-3-bromo-5-pyridyl | C(O)—Ph-m-Cl | NHC(O)-3-fluoro-5-pyridyl |
| C(O)—Ph-m-F | NHC(O)-3-bromo-5-pyridyl | C(O)—Ph-m-F | NHC(O)-3-fluoro-5-pyridyl |
| C(O)—Ph-m-I | NHC(O)-3-bromo-5-pyridyl | C(O)—Ph-m-I | NHC(O)-3-fluoro-5-pyridyl |
| C(O)—Ph-m-CF₃ | NHC(O)-3-bromo-5-pyridyl | C(O)—Ph-m-CF₃ | NHC(O)-3-fluoro-5-pyridyl |
| C(O)—Ph-m-Br | N[CH₂OP(O)(OH)₂]C(O)-3-bromo-5-pyridyl | C(O)—Ph-m-Br | N[CH₂OP(O)(OH)₂]C(O)-3-fluoro-5-pyridyl |
| C(O)—Ph-m-Cl | N[CH₂OP(O)(OH)₂]C(O)-3-bromo-5-pyridyl | C(O)—Ph-m-Cl | N[CH₂OP(O)(OH)₂]C(O)-3-fluoro-5-pyridyl |
| C(O)—Ph-m-F | N[CH₂OP(O)(OH)₂]C(O)-3-bromo-5-pyridyl | C(O)—Ph-m-F | N[CH₂OP(O)(OH)₂]C(O)-3-fluoro-5-pyridyl |
| C(O)—Ph-m-I | N[CH₂OP(O)(OH)₂]C(O)-3-bromo-5-pyridyl | C(O)—Ph-m-I | N[CH₂OP(O)(OH)₂]C(O)-3-fluoro-5-pyridyl |
| C(O)—Ph-m-CF₃ | N[CH₂OP(O)(OH)₂]C(O)-3-bromo-5-pyridyl | C(O)—Ph-m-CF₃ | N[CH₂OP(O)(OH)₂]C(O)-3-fluoro-5-pyridyl |
| H | NHC(O)-3-bromo-5-pyridyl | H | NHC(O)-3-fluoro-5-pyridyl |
| H | N[CH₂OP(O)(OH)₂]C(O)-3-bromo-5-pyridyl | H | N[CH₂OP(O)(OH)₂]C(O)-3-fluoro-5-pyridyl |
| (CH₂)₀₋₅CH₃ | NHC(O)-3-bromo-5-pyridyl | (CH₂)₀₋₅CH₃ | NHC(O)-3-fluoro-5-pyridyl |
| (CH₂)₀₋₅CH₃ | N[CH₂OP(O)(OH)₂]C(O)-3-bromo-5-pyridyl | (CH₂)₀₋₅CH₃ | N[CH₂OP(O)(OH)₂]C(O)-3-fluoro-5-pyridyl |
| C(O)—Ph-p-Br | N[(CH₂)₀₋₅CH₃]C(O)-3-bromo-5-pyridyl | C(O)—Ph-p-Br | N[(CH₂)₀₋₅CH₃]C(O)-3-fluoro-5-pyridyl |
| C(O)—Ph-p-Cl | N[(CH₂)₀₋₅CH₃]C(O)-3-bromo-5-pyridyl | C(O)—Ph-p-Cl | N[(CH₂)₀₋₅CH₃]C(O)-3-fluoro-5-pyridyl |
| C(O)—Ph-p-F | N[(CH₂)₀₋₅CH₃]C(O)-3-bromo-5-pyridyl | C(O)—Ph-p-F | N[(CH₂)₀₋₅CH₃]C(O)-3-fluoro-5-pyridyl |
| C(O)—Ph-p-I | N[(CH₂)₀₋₅CH₃]C(O)-3-bromo-5-pyridyl | C(O)—Ph-p-I | N[(CH₂)₀₋₅CH₃]C(O)-3-fluoro-5-pyridyl |
| C(O)—Ph-p-CF₃ | N[(CH₂)₀₋₅CH₃]C(O)-3-bromo-5-pyridyl | C(O)—Ph-p-CF₃ | N[(CH₂)₀₋₅CH₃]C(O)-3-fluoro-5-pyridyl |
| C(O)—Ph-o-Br | N[(CH₂)₀₋₅CH₃]C(O)-3-bromo-5-pyridyl | C(O)—Ph-o-Br | N[(CH₂)₀₋₅CH₃]C(O)-3-fluoro-5-pyridyl |
| C(O)—Ph-o-Cl | N[(CH₂)₀₋₅CH₃]C(O)-3-bromo-5-pyridyl | C(O)—Ph-o-Cl | N[(CH₂)₀₋₅CH₃]C(O)-3-fluoro-5-pyridyl |
| C(O)—Ph-o-F | N[(CH₂)₀₋₅CH₃]C(O)-3-bromo-5-pyridyl | C(O)—Ph-o-F | N[(CH₂)₀₋₅CH₃]C(O)-3-fluoro-5-pyridyl |
| C(O)—Ph-o-I | N[(CH₂)₀₋₅CH₃]C(O)-3-bromo-5-pyridyl | C(O)—Ph-o-I | N[(CH₂)₀₋₅CH₃]C(O)-3-fluoro-5-pyridyl |

TABLE 3-continued

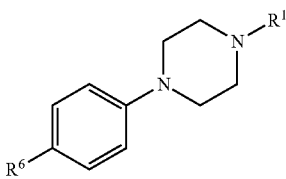

| R¹ | R⁶ | R¹ | R⁶ |
|---|---|---|---|
| C(O)—Ph-o-CF₃ | N[(CH₂)₀₋₅CH₃]C(O)-3-bromo-5-pyridyl | C(O)—Ph-o-CF₃ | N[(CH₂)₀₋₅CH₃]C(O)-3-fluoro-5-pyridyl |
| C(O)—Ph-m-Br | N[(CH₂)₀₋₅CH₃]C(O)-3-bromo-5-pyridyl | C(O)—Ph-m-Br | N[(CH₂)₀₋₅CH₃]C(O)-3-fluoro-5-pyridyl |
| C(O)—Ph-m-Cl | N[(CH₂)₀₋₅CH₃]C(O)-3-bromo-5-pyridyl | C(O)—Ph-m-Cl | N[(CH₂)₀₋₅CH₃]C(O)-3-fluoro-5-pyridyl |
| C(O)—Ph-m-F | N[(CH₂)₀₋₅CH₃]C(O)-3-bromo-5-pyridyl | C(O)—Ph-m-F | N[(CH₂)₀₋₅CH₃]C(O)-3-fluoro-5-pyridyl |
| C(O)—Ph-m-I | N[(CH₂)₀₋₅CH₃]C(O)-3-bromo-5-pyridyl | C(O)—Ph-m-I | N[(CH₂)₀₋₅CH₃]C(O)-3-fluoro-5-pyridyl |
| C(O)—Ph-m-CF₃ | N[(CH₂)₀₋₅CH₃]C(O)-3-bromo-5-pyridyl | C(O)—Ph-m-CF₃ | N[(CH₂)₀₋₅CH₃]C(O)-3-fluoro-5-pyridyl |
| H | N[(CH₂)₀₋₅CH₃]C(O)-3-bromo-5-pyridyl | H | N[(CH₂)₀₋₅CH₃]C(O)-3-fluoro-5-pyridyl |
| (CH₂)₀₋₅CH₃ | N[(CH₂)₀₋₅CH₃]C(O)-3-bromo-5-pyridyl | (CH₂)₀₋₅CH₃ | N[(CH₂)₀₋₅CH₃]C(O)-3-fluoro-5-pyridyl |

TABLE 4

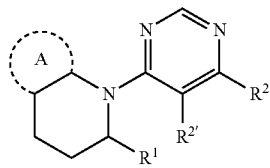

TABLE 5

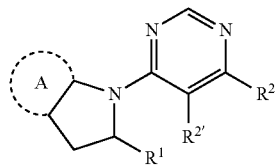

| R¹ | R² | R²' | A | R¹ | R² | R²' | A |
|---|---|---|---|---|---|---|---|
| (CH₂)₀₋₅CH₃ | NH₂ | NO₂ | Phenyl | (CH₂)₀₋₅CH₃ | NH₂ | NO₂ | Phenyl |
| (CH₂)₀₋₅CH₃ | N[(CH₂)₀₋₅CH₃]₂ | NO₂ | Phenyl | (CH₂)₀₋₅CH₃ | N[(CH₂)₀₋₅CH₃]₂ | NO₂ | Phenyl |
| (CH₂)₀₋₅CH₃ | OH | NO₂ | Phenyl | (CH₂)₀₋₅CH₃ | OH | NO₂ | Phenyl |
| (CH₂)₀₋₅CH₃ | OP(rO)(OH)₂ | NO₂ | Phenyl | (CH₂)₀₋₅CH₃ | OP(O)(OH)₂ | NO₂ | Phenyl |
| (CH₂)₀₋₅CH₃ | OC(O)C(CH₃)₃ | NO₂ | Phenyl | (CH₂)₀₋₅CH₃ | OC(O)C(CH₃)₃ | NO₂ | Phenyl |
| (CH₂)₀₋₅CH₃ | OC(O)NMe₂ | NO₂ | Phenyl | (CH₂)₀₋₅CH₃ | OC(O)NMe₂ | NO₂ | Phenyl |
| (CH₂)₀₋₅CH₃ | OMe | NO₂ | Phenyl | (CH₂)₀₋₅CH₃ | OMe | NO₂ | Phenyl |
| (CH₂)₀₋₅CH₃ | SH | NO₂ | Phenyl | (CH₂)₀₋₅CH₃ | SH | NO₂ | Phenyl |
| (CH₂)₀₋₅CH₃ | SMe | NO₂ | Phenyl | (CH₂)₀₋₅CH₃ | SMe | NO₂ | Phenyl |
| (CH₂)₀₋₅CH₃ | NH₂ | NO₂ | None | (CH₂)₀₋₅CH₃ | NH₂ | NO₂ | None |
| (CH₂)₀₋₅CH₃ | N[(CH₂)₀₋₅CH₃]₂ | NO₂ | None | (CH₂)₀₋₅CH₃ | N[(CH₂)₀₋₅CH₃]₂ | NO₂ | None |
| (CH₂)₀₋₅CH₃ | OH | NO₂ | None | (CH₂)₀₋₅CH₃ | OH | NO₂ | None |
| (CH₂)₀₋₅CH₃ | OP(O)(OH)₂ | NO₂ | None | (CH₂)₀₋₅CH₃ | OP(O)(OH)₂ | NO₂ | None |
| (CH₂)₀₋₅CH₃ | OC(O)C(CH₃)₃ | NO₂ | None | (CH₂)₀₋₅CH₃ | OC(O)C(CH₃)₃ | NO₂ | None |
| (CH₂)₀₋₅CH₃ | OC(O)NMe₂ | NO₂ | None | (CH₂)₀₋₅CH₃ | OC(O)NMe₂ | NO₂ | None |
| (CH₂)₀₋₅CH₃ | OMe | NO₂ | None | (CH₂)₀₋₅CH₃ | OMe | NO₂ | None |
| (CH₂)₀₋₅CH₃ | SH | NO₂ | None | (CH₂)₀₋₅CH₃ | SH | NO₂ | None |
| (CH₂)₀₋₅CH₃ | SMe | NO₂ | None | (CH₂)₀₋₅CH₃ | SMe | NO₂ | None |
| H | NH₂ | NO₂ | Phenyl | H | NH₂ | NO₂ | Phenyl |
| H | N[(CH₂)₀₋₅CH₃]₂ | NO₂ | Phenyl | H | N[(CH₂)₀₋₅CH₃]₂ | NO₂ | Phenyl |
| H | OH | NO₂ | Phenyl | H | OH | NO₂ | Phenyl |
| H | OP(O)(OH)₂ | NO₂ | Phenyl | H | OP(O)(OH)₂ | NO₂ | Phenyl |
| H | OC(O)C(CH₃)₃ | NO₂ | Phenyl | H | OC(O)C(CH₃)₃ | NO₂ | Phenyl |
| H | OC(O)NMe₂ | NO₂ | Phenyl | H | OC(O)NMe₂ | NO₂ | Phenyl |
| H | OMe | NO₂ | Phenyl | H | OMe | NO₂ | Phenyl |
| H | SH | NO₂ | Phenyl | H | SH | NO₂ | Phenyl |
| H | SMe | NO₂ | Phenyl | H | SMe | NO₂ | Phenyl |
| H | NH₂ | NO₂ | None | H | NH₂ | NO₂ | None |
| H | N[(CH₂)₀₋₅CH₃]₂ | NO₂ | None | H | N[(CH₂)₀₋₅CH₃]₂ | NO₂ | None |
| H | OH | NO₂ | None | H | OH | NO₂ | None |
| H | OP(O)(OH)₂ | NO₂ | None | H | OP(O)(OH)₂ | NO₂ | None |
| H | OC(O)C(CH₃)₃ | NO₂ | None | H | OC(O)C(CH₃)₃ | NO₂ | None |
| H | OC(O)NMe₂ | NO₂ | None | H | OC(O)NMe₂ | NO₂ | None |
| H | OMe | NO₂ | None | H | OMe | NO₂ | None |
| H | SH | NO₂ | None | H | SH | NO₂ | None |
| H | SMe | NO₂ | None | H | SMe | NO₂ | None |

TABLE 6A

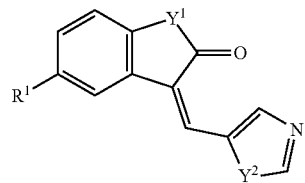

| R¹ | Y¹ | Y² | R¹ | Y¹ | Y² |
|---|---|---|---|---|---|
| O(CH$_2$)$_{0-5}$CH$_3$ | NH | NH | O(CH$_2$)$_{0-5}$CH$_3$ | NH | O |
| OH | NH | NH | OH | NH | O |
| OP(O)(OH)$_2$ | NH | NH | OP(O)(OH)$_2$ | NH | O |
| OC(O)C(CH$_3$)$_3$ | NH | NH | OC(O)C(CH$_3$)$_3$ | NH | O |
| OC(O)NMe$_2$ | NH | NH | OC(O)NMe$_2$ | NH | O |
| S(CH$_2$)$_{0-5}$CH$_3$ | NH | NH | S(CH$_2$)$_{0-5}$CH$_3$ | NH | O |
| SH | NH | NH | SH | NH | O |
| NH$_2$ | NH | NH | NH$_2$ | NH | O |
| N[(CH$_2$)$_{0-5}$CH$_3$]$_2$ | NH | NH | N[(CH$_2$)$_{0-5}$CH$_3$]$_2$ | NH | O |
| OCF$_3$ | NH | NH | OCF$_3$ | NH | O |
| CF$_3$ | NH | NH | CF$_3$ | NH | O |
| O(CH$_2$)$_{0-5}$CH$_3$ | O | O | O(CH$_2$)$_{0-5}$CH$_3$ | O | NH |
| OH | O | O | OH | O | NH |
| OP(O)(OH)$_2$ | O | O | OP(O)(OH)$_2$ | O | NH |
| OC(O)C(CH$_3$)$_3$ | O | O | OC(O)C(CH$_3$)$_3$ | O | NH |
| OC(O)NMe$_2$ | O | O | OC(O)NMe$_2$ | O | NH |
| S(CH$_2$)$_{0-5}$CH$_3$ | O | O | S(CH$_2$)$_{0-5}$CH$_3$ | O | NH |
| SH | O | O | SH | O | NH |
| NH$_2$ | O | O | NH$_2$ | O | NH |
| N[(CH$_2$)$_{0-5}$CH$_3$]$_2$ | O | O | N[(CH$_2$)$_{0-5}$CH$_3$]$_2$ | O | NH |
| OCF$_3$ | O | O | OCF$_3$ | O | NH |
| CF$_3$ | O | O | CF$_3$ | O | NH |
| O(CH$_2$)$_{0-5}$CH$_3$ | NCH$_2$OP(O)(OH)$_2$ | NH | O(CH$_2$)$_{0-5}$CH$_3$ | NCH$_2$OP(O)(OH)$_2$ | O |
| OH | NCH$_2$OP(O)(OH)$_2$ | NH | OH | NCH$_2$OP(O)(OH)$_2$ | O |
| OP(O)(OH)$_2$ | NCH$_2$OP(O)(OH)$_2$ | NH | OP(O)(OH)$_2$ | NCH$_2$OP(O)(OH)$_2$ | O |
| OC(O)C(CH$_3$)$_3$ | NCH$_2$OP(O)(OH)$_2$ | NH | OC(O)C(CH$_3$)$_3$ | NCH$_2$OP(O)(OH)$_2$ | O |
| OC(O)NMe$_2$ | NCH$_2$OP(O)(OH)$_2$ | NH | OC(O)NMe$_2$ | NCH$_2$OP(O)(OH)$_2$ | O |
| S(CH$_2$)$_{0-5}$CH$_3$ | NCH$_2$OP(O)(OH)$_2$ | NH | S(CH$_2$)$_{0-5}$CH$_3$ | NCH$_2$OP(O)(OH)$_2$ | O |
| SH | NCH$_2$OP(O)(OH)$_2$ | NH | SH | NCH$_2$OP(O)(OH)$_2$ | O |
| NH$_2$ | NCH$_2$OP(O)(OH)$_2$ | NH | NH$_2$ | NCH$_2$OP(O)(OH)$_2$ | O |
| N[(CH$_2$)$_{0-5}$CH$_3$]$_2$ | NCH$_2$OP(O)(OH)$_2$ | NH | N[(CH$_2$)$_{0-5}$CH$_3$]$_2$ | NCH$_2$OP(O)(OH)$_2$ | O |
| OCF$_3$ | NCH$_2$OP(O)(OH)$_2$ | NH | OCF$_3$ | NCH$_2$OP(O)(OH)$_2$ | O |
| CF$_3$ | NCH$_2$OP(O)(OH)$_2$ | NH | CF$_3$ | NCH$_2$OP(O)(OH)$_2$ | O |
| O(CH$_2$)$_{0-5}$CH$_3$ | NCH$_2$OP(O)(OH)$_2$ | NCH$_2$OP(O)(OH)$_2$ | O(CH$_2$)$_{0-5}$CH$_3$ | O | NCH$_2$OP(O)(OH)$_2$ |
| OH | NCH$_2$OP(O)(OH)$_2$ | NCH$_2$OP(O)(OH)$_2$ | OH | O | NCH$_2$OP(O)(OH)$_2$ |
| OP(O)(OH)$_2$ | NCH$_2$OP(O)(OH)$_2$ | NCH$_2$OP(O)(OH)$_2$ | OP(O)(OH)$_2$ | O | NCH$_2$OP(O)(OH)$_2$ |
| OC(O)C(CH$_3$)$_3$ | NCH$_2$OP(O)(OH)$_2$ | NCH$_2$OP(O)(OH)$_2$ | OC(O)C(CH$_3$)$_3$ | O | NCH$_2$OP(O)(OH)$_2$ |
| OC(O)NMe$_2$ | NCH$_2$OP(O)(OH)$_2$ | NCH$_2$OP(O)(OH)$_2$ | OC(O)NMe$_2$ | O | NCH$_2$OP(O)(OH)$_2$ |
| S(CH$_2$)$_{0-5}$CH$_3$ | NCH$_2$OP(O)(OH)$_2$ | NCH$_2$OP(O)(OH)$_2$ | S(CH$_2$)$_{0-5}$CH$_3$ | O | NCH$_2$OP(O)(OH)$_2$ |
| SH | NCH$_2$OP(O)(OH)$_2$ | NCH$_2$OP(O)(OH)$_2$ | SH | O | NCH$_2$OP(O)(OH)$_2$ |
| NH$_2$ | NCH$_2$OP(O)(OH)$_2$ | NCH$_2$OP(O)(OH)$_2$ | NH$_2$ | O | NCH$_2$OP(O)(OH)$_2$ |
| N[(CH$_2$)$_{0-5}$CH$_3$]$_2$ | NCH$_2$OP(O)(OH)$_2$ | NCH$_2$OP(O)(OH)$_2$ | N[(CH$_2$)$_{0-5}$CH$_3$]$_2$ | O | NCH$_2$OP(O)(OH)$_2$ |
| OCF$_3$ | NCH$_2$OP(O)(OH)$_2$ | NCH$_2$OP(O)(OH)$_2$ | OCF$_3$ | O | NCH$_2$OP(O)(OH)$_2$ |
| CF$_3$ | NCH$_2$OP(O)(OH)$_2$ | NCH$_2$OP(O)(OH)$_2$ | CF$_3$ | O | NCH$_2$OP(O)(OH)$_2$ |
| O(CH$_2$)$_{0-5}$CH$_3$ | S | O | O(CH$_2$)$_{0-5}$CH$_3$ | S | NH |
| OH | S | O | OH | S | NH |
| OP(O)(OH)$_2$ | S | O | OP(O)(OH)$_2$ | S | NH |
| OC(O)C(CH$_3$)$_3$ | S | O | OC(O)C(CH$_3$)$_3$ | S | NH |
| OC(O)NMe$_2$ | S | O | OC(O)NMe$_2$ | S | NH |
| S(CH$_2$)$_{0-5}$CH$_3$ | S | O | S(CH$_2$)$_{0-5}$CH$_3$ | S | NH |
| SH | S | O | SH | S | NH |
| NH$_2$ | S | O | NH$_2$ | S | NH |
| N[(CH$_2$)$_{0-5}$CH$_3$]$_2$ | S | O | N[(CH$_2$)$_{0-5}$CH$_3$]$_2$ | S | NH |
| OCF$_3$ | S | O | OCF$_3$ | S | NH |
| CF$_3$ | S | O | CF$_3$ | S | NH |
| O(CH$_2$)$_{0-5}$CH$_3$ | S | NCH$_2$OP(O)(OH)$_2$ | O(CH$_2$)$_{0-5}$CH$_3$ | S | S |
| OH | S | NCH$_2$OP(O)(OH)$_2$ | OH | S | S |
| OP(O)(OH)$_2$ | S | NCH$_2$OP(O)(OH)$_2$ | OP(O)(OH)$_2$ | S | S |
| OC(O)C(CH$_3$)$_3$ | S | NCH$_2$OP(O)(OH)$_2$ | OC(O)C(CH$_3$)$_3$ | S | S |
| OC(O)NMe$_2$ | S | NCH$_2$OP(O)(OH)$_2$ | OC(O)NMe$_2$ | S | S |
| S(CH$_2$)$_{0-5}$CH$_3$ | S | NCH$_2$OP(O)(OH)$_2$ | S(CH$_2$)$_{0-5}$CH$_3$ | S | S |
| SH | S | NCH$_2$OP(O)(OH)$_2$ | SH | S | S |
| NH$_2$ | S | NCH$_2$OP(O)(OH)$_2$ | NH$_2$ | S | S |
| N[(CH$_2$)$_{0-5}$CH$_3$]$_2$ | S | NCH$_2$OP(O)(OH)$_2$ | N[(CH$_2$)$_{0-5}$CH$_3$]$_2$ | S | S |
| OCF$_3$ | S | NCH$_2$OP(O)(OH)$_2$ | OCF$_3$ | S | S |
| CF$_3$ | S | NCH$_2$OP(O)(OH)$_2$ | CF$_3$ | S | S |

III. Methods of Use i. Methods of Treating Muscular Dystrophy

The α7β1 integrin has been shown to be a major modifier of disease progression in patients with muscular dystrophy. Increased expression of the α7 integrin in muscle can alleviate muscle disease in mouse models of muscular dystrophy. By use of a muscle cell-based assay (described in Example 1 below), the inventors identified the following molecules that up-regulate α7β1 integrin expression in muscle: laminin-111; valproic acid; ciclopirox ethanolamine; deferoxamine; 2,2-dipyridyl; 5α-cholestan-3β-ol-6-one; Compound ID #1001; Compound ID #1002; Compound ID #1003; and analogs of cholestan (see Table 9). Based on these observations, methods of treatment of muscular dystrophy by increasing the expression or activity of α7β1 integrin are disclosed.

In particular, methods are disclosed herein for treating muscular dystrophy, such as DMD, FCMD, LGMD, FHMD, BMD, MDC1A or MDC1D. In one example, the method includes administering an effective amount of a α7β1 integrin modulatory agent to a subject with muscular dystrophy or suspected of having or developing muscular dystrophy, in which the agent increases the biological activity or expression of α7β1 integrin and thereby, treating the muscular dystrophy in the subject. In some example, the method of treatment inhibits or reduces one or more signs or symptoms associated with muscular dystrophy in the subject.

Figure 10:
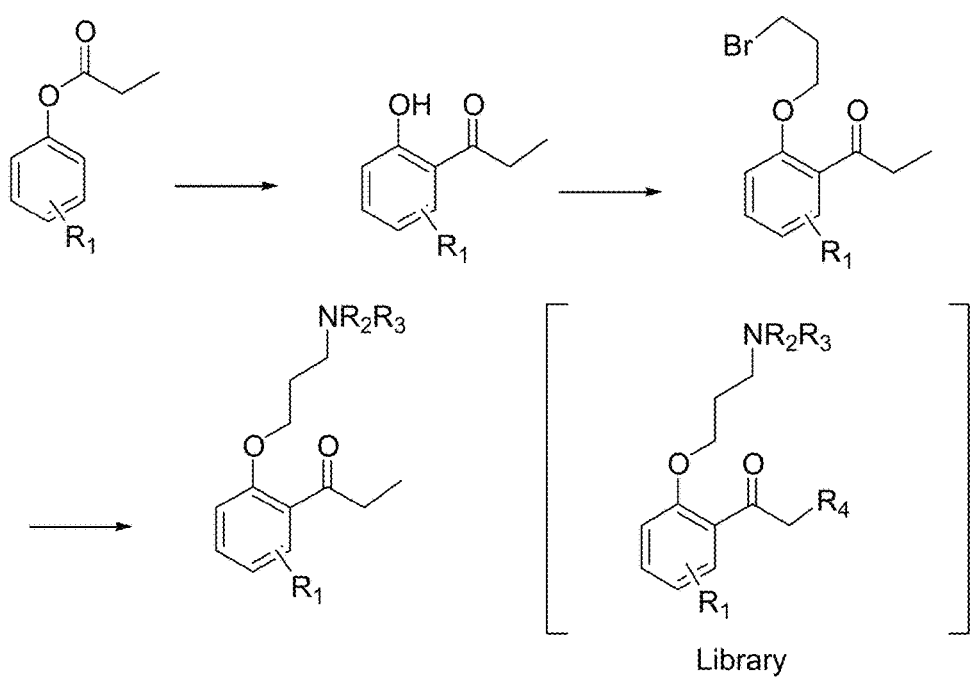
FIG. 10 is an exemplary synthesis pathway for analogs of compounds 1002 and 1003.
Figure 11:
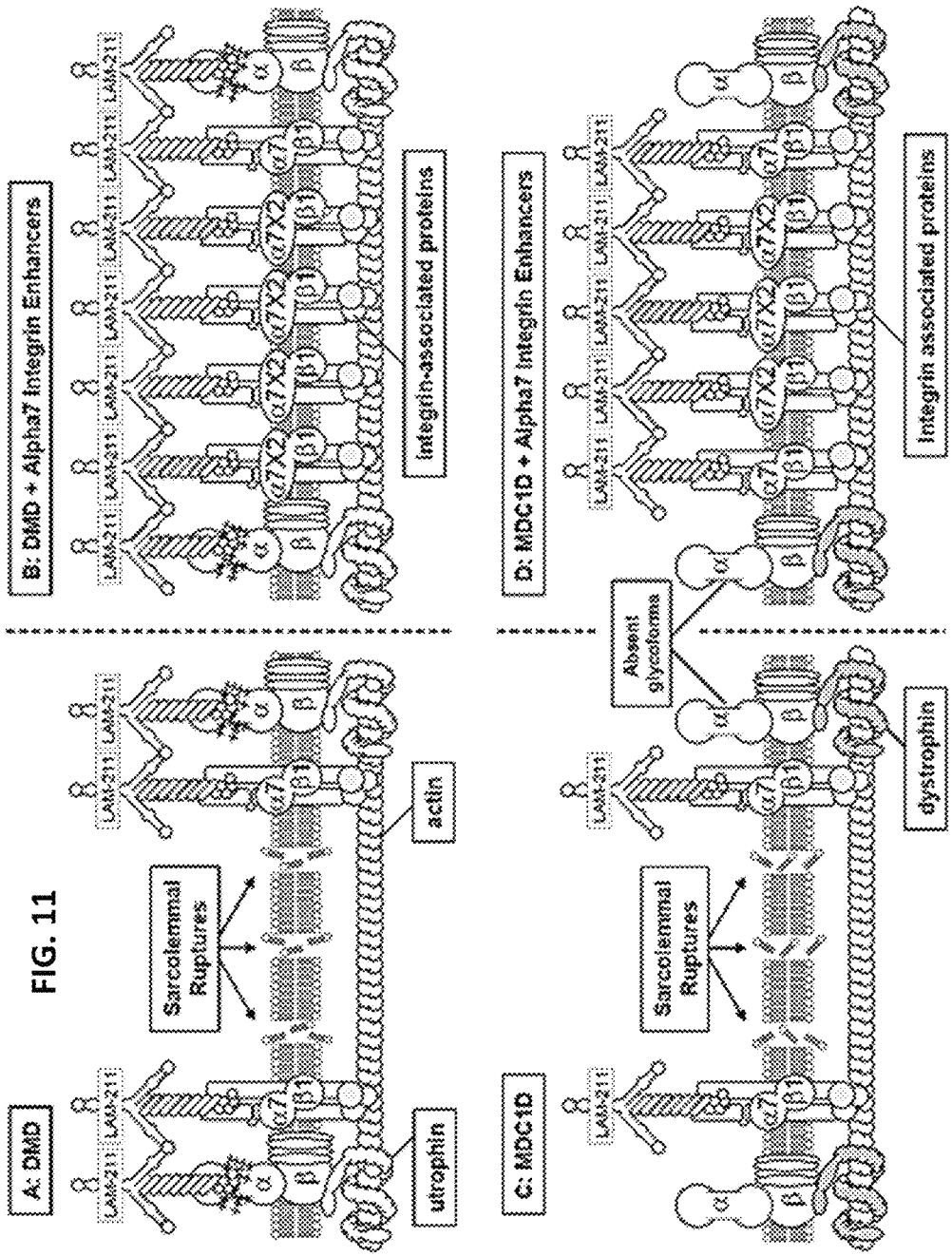
FIG. 11 is a schematic illustrating two examples of muscular dystrophy in which enhanced α7 integrin is therapeutic. Loss of dystrophin in DMD (A) or glycosylation of α dystroglycan in MDC1D (B) results in defective membrane integrity and sarcolemma disruptures. Enhancement of α7β1 integrin improves membrane integrity, minimize sarcolemma ruptures and mitigate the progression of disease in DMD (B) and MDC1D (D).

In some examples, the α7β1 integrin modulatory agent includes one or more of the following molecules: ciclopirox ethanolamine, deferoxamine, 2,2-dipyridyl; 5α-cholestan-3β-ol-6-one, Compound ID #1001, Compound ID #1002, Compound ID #1003, an analog of Compound ID #1001, an analog of Compound ID #1002, an analog of Compound ID #1003, an analog of cholestan (see Table 9), laminin-111, laminin-111 fragments, valproic acid, or a valproic acid analog. Tables 8 and 9 and FIGS. 3A-3C, 4A-4B, 5, 6A-6B, and 7-9 provide the chemical structures and characterization data for such compounds. Exemplary valproic acid analogs are disclosed in U.S. Patent Publication 2006/0223888 and International Patent Application No. 2010/080581, each of which is incorporated herein by reference in its entirety. Table 11 provides analogs of disclosed Compound ID #1001. Exemplary laminin-111 fragments are disclosed in U.S. Patent Publication US-2009-0092587-A1, which is incorporated herein by reference in its entirety. In some examples, an analog of Compound ID #1002 or #1003 is synthesized according to the general synthesis pathway shown in FIG. 10. In some examples, an analog is synthesized according to the synthesis pathway shown in the Examples below. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1. For examples, in some examples, the α7β1 integrin modulatory agent includes one or more molecules provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or combinations thereof. In further embodiments, the α7β1 integrin modulatory agent may be selected from any one or more of the compounds within any one of Formulas 1-16, as provided herein.

The disclosed α7β1 integrin modulatory agents can alter the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

In a particular example, the subject is a human.

In additional aspects, the method involves selecting a subject with muscular dystrophy. In some example, a subject is selected for treatment following diagnosing the subject with muscular dystrophy. For example, the method can include diagnosing the subject as suffering from muscular dystrophy, such as DMD, MDC1A, MDC1D, LGMD, DMD, FCMD or FHMD.

Methods of diagnosing a subject with muscular dystrophy are known to those of skill in the art and include, but are not limited to, muscle biopsies and measuring serum creatine kinase levels. Additionally, alterations in biomarker known to be associated with muscular dystrophy may be detected by measuring such levels in serum or urine sample.

In a further implementation, the method involves diagnosing the subject as suffering from a disease, disorder, or condition characterized by a mutation in the gene encoding α7 integrin. In another implementation, the method involves diagnosing the subject as suffering from a disease, disorder, or condition characterized by a decreased level of α7 integrin expression.

Alterations in the expression can be measured at the nucleic acid level (such as by real time quantitative polymerase chain reaction or microarray analysis) or at the protein level (such as by Western blot analysis or ELISA). These methods are known to those of skill in the art.

In some examples, following the measurement of the expression levels of α7 integrin expression or serum creatine kinase levels, the assay results, findings, diagnoses, predictions and/or treatment recommendations are recorded and communicated to technicians, physicians and/or patients, for example. In certain embodiments, computers are used to communicate such information to interested parties, such as, patients and/or the attending physicians. The therapy selected for administered is then based upon these results.

In one embodiment, the results and/or related information is communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having muscular dystrophy, such as DMD, LGMD, FHMD, BMD, FCMD, MDC1D or MDC1A, results in the physician treating the subject, such as prescribing one or more disclosed α7β1 agents for inhibiting or delaying one or more signs and symptoms associated with muscular dystrophy. In additional embodiments, the dose or dosing regimen is modified based on the information obtained using the methods disclosed herein.

ii Methods of Enhancing Muscle Regeneration, Repair, or Maintenance

Also disclosed are methods of enhancing muscle regeneration, repair or maintenance in a subject. In some examples, the method includes administering an effective amount of an α7β1 integrin modulatory agent to a subject in need of muscle regeneration, repair or maintenance, wherein the α7β1 integrin modulatory agent includes ciclopirox ethanolamine, deferoxamine, 2,2-dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, or any one of the compounds provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or a combination thereof, wherein the α7β1 integrin modulatory agent increases α7β1 integrin expression or activity as compared to α7β1 integrin expression or activity prior to treatment, thereby enhancing muscle regeneration, repair or maintenance in a subject.

In some examples, the α7β1 integrin modulatory agent includes one or more of the following molecules: ciclopirox ethanolamine, deferoxamine, 2,2-dipyridyl; 5α-cholestan-3β-ol-6-one, Compound ID #1001, Compound ID #1002, Compound ID #1003, an analog of Compound ID #1001, an analog of Compound ID #1002, an analog of Compound ID #1003, an analog of cholestan (see Table 9), laminin-111, laminin-111 fragments, valproic acid, or a valproic acid analog. Tables 8 and 9 and FIGS. 3A-3C, 4A-4B, 5, 6A-6B, and 7-9 provide the chemical structures and characterization data for such compounds. Exemplary valproic acid analogs are disclosed in U.S. Patent Publication 2006/0223888 and International Patent Application No. 2010/080581, each of which is incorporated herein by reference in its entirety. Exemplary laminin-111 fragments are disclosed in U.S. Patent Publication US-2009-0092587-A1, which is incorporated herein by reference in its entirety. In some examples, an analog of Compound ID #1002 or #1003 is synthesized according to the general synthesis pathway shown in FIG. 10. In some examples, an analog is synthesized according to the synthesis pathway provided in the Examples below. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1. For examples, in some examples, the α7β1 integrin modulatory agent includes one or more molecules provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or combinations thereof.

The disclosed α7β1 integrin modulatory agents can increase the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

Muscle regeneration may benefit, for example, geriatric or other patient populations with reduced muscle repair capability, or simply speed the muscle repair process for otherwise physiologically unimpaired patients. In particular implementations, administration of a α7β1 integrin modulatory agent can aid muscle repair, or reduction of muscle damage, in athletes or others having activity-induced muscle injury or damage. In yet further implementations, muscle repair in patients suffering from muscle damage, such as through accident or injury, can be augmented by administration of a α7β1 integrin modulatory agent.

In some examples, α7β1 modulatory agent is administered prior to the subject experiencing muscle damage or disease. In some examples, the α7β1 integrin modulatory agent is administered to the subject prior to the subject exercising.

In some examples, the method further includes selecting a subject in need of enhancing muscle regeneration, repair, or maintenance. For example, in some instances, selecting a subject in need of enhancing muscle regeneration, repair, or maintenance comprises diagnosing the subject with a condition characterized by impaired muscle regeneration prior to administering an effective amount of the α7β1 integrin modulatory agent to the subject. Methods for diagnosing and selecting a subject in need of muscle regeneration, repair or maintenance are known to those of ordinary skill in the art and include those provided described herein (including those in the Methods of Treatment of Muscular Dystrophy). As stated above, subjects may be selected based upon their life style (e.g., engaged in moderate to intense exercise or physical activities), age (e.g., elderly population at more risk of experiencing muscle degeneration or injury) or predisposition to muscle degeneration or injury (e.g., genetics or previous muscle injury).

iii Methods of Prospectively Preventing or Reducing Muscle Injury or Damage

Also disclosed are methods prospectively preventing or reducing muscle injury or damage in a subject. In some embodiments, the method includes administering an effective amount of an α7β1 integrin modulatory agent to the subject wherein the α7β1 integrin modulatory agent comprises ciclopirox ethanolamine, deferoxamine, 2,2- dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, a compound provided herein, such as in Table 10, Table 11, Table 6 (see Appendix I of U.S. Provisional Pat. App. No. 61/796,476), and/or Table 7 (see Appendix II of U.S. Provisional Pat. App. No. 61/796,476), Table 13, or a combination thereof, wherein the α7β1 integrin modulatory agent increases α7β1 integrin expression or activity as compared to α7β1 integrin expression or activity prior to treatment, thereby prospectively preventing or reducing muscle injury or damage in the subject.

In some examples, the α7β1 integrin modulatory agent includes one or more of the following molecules: ciclopirox ethanolamine, deferoxamine, 2,2-dipyridyl; 5α-cholestan-3β-ol-6-one, Compound ID #1001, Compound ID #1002, Compound ID #1003, an analog of Compound ID #1001, an analog of Compound ID #1002, an analog of Compound ID #1003, an analog of cholestan (see Table 9), laminin-111, laminin-111 fragments, valproic acid, or a valproic acid analog. Tables 8 and 9 and FIGS. 3A-3C, 4A-4B, 5, 6A-6B, and 7-9 provide the chemical structures and characterization data for such compounds. Exemplary valproic acid analogs are disclosed in U.S. Patent Publication 2006/0223888 and International Patent Application No. 2010/080581, each of which is incorporated herein by reference in its entirety. Exemplary laminin-111 fragments are disclosed in U.S. Patent Publication US-2009-0092587-A1, which is incorporated herein by reference in its entirety. In some examples, an analog of Compound ID #1002 or #1003 is synthesized according to the general synthesis pathway shown in FIG. 10. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1. For examples, in some examples, the α7β1 integrin modulatory agent includes one or more molecules provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or combinations thereof.

The disclosed α7β1 integrin modulatory agents can increase the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

In some examples, the method further includes selecting a subject at risk for developing a muscle injury or damage. In some examples, the α7β1 integrin modulatory agent is administered to a subject prior to the subject exercising.

In some examples, the method further includes selecting a subject at risk for developing a muscle injury or damage. Methods for selecting such s subject are known to those of ordinary skill in the art and include those provided described herein. As stated above, subjects may be selected based upon their life style (e.g., engaged in moderate to intense exercise or physical activities), age (elderly population at more risk of experiencing muscle degeneration or injury) or predisposition to muscle degeneration or injury (e.g., genetics or previous muscle injury).

iv. Methods of Enhancing α7β1 Integrin Expression

Also disclosed herein are methods of enhancing α7β1 integrin expression. In some examples, these methods include contacting a cell with an effective amount of an α7β1 integrin modulatory agent, wherein the α7β1 integrin modulatory agent comprises ciclopirox ethanolamine, deferoxamine, 2,2-dipyridyl; 5α-cholestan-3β-ol-6-one, Compound ID #1001, Compound ID #1002, Compound ID #1003, N032-0003, N066-0070, N069-0071, N069-0075, N064-0028, N066-0053, N069-0073, 1080-0573, or any one of the compounds provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or a combination thereof and increases α7β1 integrin expression in the treated cell relative to α7β1 integrin expression in an untreated cell, thereby enhancing α7β1 integrin expression. In some examples, the cell is a muscle cell, such as a skeletal muscle cell. In some examples, the muscle cell is present in a mammal, and wherein contacting the cell with an agent comprises administering the agent to the mammal.

In some examples, the α7β1 integrin modulatory agent includes one or more of the following molecules: ciclopirox ethanolamine, deferoxamine, 2,2-dipyridyl; 5α-cholestan-3β-ol-6-one, Compound ID #1001, Compound ID #1002, Compound ID #1003, an analog of Compound ID #1001, an analog of Compound ID #1002, an analog of Compound ID #1003, an analog of cholestan (see Table 9), laminin-111, laminin-111 fragments, valproic acid, or a valproic acid analog. Tables 8-10 and FIGS. 3A-3C, 4A-4B, 5, 6A-6B, and 7-9 provide the chemical structures and characterization data for such compounds. Exemplary valproic acid analogs are disclosed in U.S. Patent Publication 2006/0223888 and International Patent Application No. 2010/080581, each of which is incorporated herein by reference in its entirety. Exemplary laminin-111 fragments are disclosed in U.S. Patent Publication US-2009-0092587-A1, which is incorporated herein by reference in its entirety. In some examples, an analog of Compound ID #1002 or #1003 is synthesized according to the general synthesis pathway shown in FIG. 10. In further examples, the α7β1 integrin modulatory agent is an analog/derivative of any of the disclosed α7β1 integrin modulatory agents which may be designed and synthesized according to the chemical principles known to one of ordinary skill in the art and identified as a α7β1 integrin modulatory agent by methods known to those of ordinary skill in the art, including the muscle cell based assay described Example 1. In some examples, the α7β1 integrin modulatory agent includes one or more molecules provided herein, such as in Table 10, Table 11, Table 6 (see Appendix I of U.S. Provisional Pat. App. No. 61/796,476), Table 7 (see Appendix II of U.S. Provisional Pat. App. No. 61/796,476), Table 13, or combinations thereof.

In some examples, the disclosed α7β1 integrin modulatory agents can increase the expression of nucleic acid sequences (such as DNA, cDNA, or mRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described in the Examples below (e.g., Western blot and ELISA assay with commercially available antibodies).

Administration of an Effective Amount of an α7β1 Integrin Modulatory Agent

For any of the disclosed methods, an effective amount of α7β1 integrin modulatory agent is one when administered by a particular route and concentration induces the desired response (e.g., treatment of muscular dystrophy, enhancing muscle regeneration, repair or maintenance, preventing or reducing muscle injury or damage, or enhancing α7β1 integrin expression).

i. Administration Routes, Formulations and Concentrations

Methods of administration of the disclosed α7β1 integrin modulatory agents are routine, and can be determined by a skilled clinician. The disclosed α7β1 integrin modulatory agents or other therapeutic substance are in general administered topically, nasally, intravenously, orally, intracranially, intramuscularly, parenterally or as implants, but even rectal or vaginal use is possible in principle. The disclosed α7β1 integrin modulatory agents also may be administered to a subject using a combination of these techniques.

Suitable solid or liquid pharmaceutical preparation forms are, for example, aerosols, (micro)capsules, creams, drops, drops or injectable solution in ampoule form, emulsions, granules, powders, suppositories, suspensions, syrups, tablets, coated tablets, and also preparations with protracted release of active compounds, in whose preparation excipients and additives and/or auxiliaries such as binders, coating agents, disintegrants, flavorings, lubricants, solubilizers, sweeteners, or swelling agents are customarily used as described above. The pharmaceutical agents are suitable for use in a variety of drug delivery systems. For a brief review of various methods for drug delivery, see Langer, "New Methods of Drug Delivery," *Science* 249:1527-1533 (1990), incorporated by reference herein to the extent not inconsistent with the present disclosure.

The disclosed α7β1 integrin modulatory agents or other therapeutic agents of the present disclosure can be formulated into therapeutically-active pharmaceutical agents that can be administered to a subject parenterally or orally. Parenteral administration routes include, but are not limited to epidermal, intraarterial, intramuscular (IM and depot IM), intraperitoneal (IP), intravenous (IV), intrasternal injection or infusion techniques, intranasal (inhalation), intrathecal, injection into the stomach, subcutaneous injections (subcutaneous (SQ and depot SQ), transdermal, topical, and ophthalmic.

The disclosed α7β1 integrin modulatory agents or other therapeutic agents can be mixed or combined with a suitable pharmaceutically acceptable excipients to prepare pharmaceutical agents. Pharmaceutically acceptable excipients include, but are not limited to, alumina, aluminum stearate, buffers (such as phosphates), glycine, ion exchangers (such as to help control release of charged substances), lecithin, partial glyceride mixtures of saturated vegetable fatty acids, potassium sorbate, serum proteins (such as human serum albumin), sorbic acid, water, salts or electrolytes such as cellulose-based substances, colloidal silica, disodium hydrogen phosphate, magnesium trisilicate, polyacrylates, polyalkylene glycols, such as polyethylene glycol, polyethylene-polyoxypropylene-block polymers, polyvinyl pyrrolidone, potassium hydrogen phosphate, protamine sulfate, group 1 halide salts such as sodium chloride, sodium carboxymethylcellulose, waxes, wool fat, and zinc salts, for example. Liposomal suspensions may also be suitable as pharmaceutically acceptable carriers.

Upon mixing or addition of one or more disclosed α7β1 integrin modulatory agents and/or or other therapeutic agents, the resulting mixture may be a solid, solution, suspension, emulsion, or the like. These may be prepared according to methods known to those of ordinary skill in the art. The form of the resulting mixture depends upon a number of factors, including the intended mode of administration and the solubility of the agent in the selected carrier. Pharmaceutical carriers suitable for administration of the disclosed α7β1 integrin modulatory agents or other therapeutic agents include any such carriers known to be suitable for the particular mode of administration. In addition, the disclosed α7β1 integrin modulatory agents or other therapeutic substance can also be mixed with other inactive or active materials that do not impair the desired action, or with materials that supplement the desired action, or have another action.

Methods for solubilizing may be used where the agents exhibit insufficient solubility in a carrier. Such methods are known and include, but are not limited to, dissolution in aqueous sodium bicarbonate, using cosolvents such as dimethylsulfoxide (DMSO), and using surfactants such as TWEEN® (ICI Americas, Inc., Wilmington, Del.).

The disclosed α7β1 integrin modulatory agents or other therapeutic agents can be prepared with carriers that protect them against rapid elimination from the body, such as coatings or time-release formulations. Such carriers include controlled release formulations, such as, but not limited to, microencapsulated delivery systems. A disclosed α7β1 integrin modulatory agents or other therapeutic agent is included in the pharmaceutically acceptable carrier in an amount sufficient to exert a therapeutically useful effect, typically in an amount to avoid undesired side effects, on the treated subject. The therapeutically effective concentration may be determined empirically by testing the compounds in known in vitro and in vivo model systems for the treated condition. For example, mouse models of muscular dystrophy may be used to determine effective amounts or concentrations that can then be translated to other subjects, such as humans, as known in the art.

Injectable solutions or suspensions can be formulated, using suitable non-toxic, parenterally-acceptable diluents or solvents, such as 1,3-butanediol, isotonic sodium chloride solution, mannitol, Ringer's solution, saline solution, or water; or suitable dispersing or wetting and suspending agents, such as sterile, bland, fixed oils, including synthetic mono- or diglycerides, and fatty acids, including oleic acid; a naturally occurring vegetable oil such as coconut oil, cottonseed oil, peanut oil, sesame oil, and the like; glycerine; polyethylene glycol; propylene glycol; or other synthetic solvent; antimicrobial agents such as benzyl alcohol and methyl parabens; antioxidants such as ascorbic acid and sodium bisulfite; buffers such as acetates, citrates, and phosphates; chelating agents such as ethylenediaminetetraacetic acid (EDTA); agents for the adjustment of tonicity such as sodium chloride and dextrose; and combinations thereof. Parenteral preparations can be enclosed in ampoules, disposable syringes, or multiple dose vials made of glass, plastic, or other suitable material. Buffers, preservatives, antioxidants, and the like can be incorporated as required. Where administered intravenously, suitable carriers include physiological saline, phosphate-buffered saline (PBS), and solutions containing thickening and solubilizing agents such as glucose, polyethylene glycol, polypropyleneglycol, and mixtures thereof. Liposomal suspensions, including tissue-targeted liposomes, may also be suitable as pharmaceutically acceptable carriers.

For topical application, one or more disclosed α7β1 integrin modulatory agents, or other therapeutic agent may be made up into a cream, lotion, ointment, solution, or suspension in a suitable aqueous or non-aqueous carrier. Topical application can also be accomplished by transdermal patches or bandages which include the therapeutic substance. Additives can also be included, e.g., buffers such as sodium metabisulphite or disodium edetate; preservatives such as bactericidal and fungicidal agents, including phenyl mercuric acetate or nitrate, benzalkonium chloride, or chlorhexidine; and thickening agents, such as hypromellose.

If the disclosed α7β1 integrin modulatory agent, or other therapeutic agent is administered orally as a suspension, the pharmaceutical agents can be prepared according to techniques well known in the art of pharmaceutical formulation and may contain a suspending agent, such as alginic acid or sodium alginate, bulking agent, such as microcrystalline cellulose, a viscosity enhancer, such as methylcellulose, and sweeteners/flavoring agents. Oral liquid preparations can contain conventional additives such as suspending agents, e.g., gelatin, glucose syrup, hydrogenated edible fats, methyl cellulose, sorbitol, and syrup; emulsifying agents, e.g., acacia, lecithin, or sorbitan monooleate; non-aqueous carriers (including edible oils), e.g., almond oil, fractionated coconut oil, oily esters such as glycerine, propylene glycol, or ethyl alcohol; preservatives such as methyl or propyl p-hydroxybenzoate or sorbic acid; and, if desired, conventional flavoring or coloring agents. When formulated as immediate release tablets, these agents can contain dicalcium phosphate, lactose, magnesium stearate, microcrystalline cellulose, and starch and/or other binders, diluents, disintegrants, excipients, extenders, and lubricants.

If oral administration is desired, one or more disclosed α7β1 integrin modulatory agents, or other therapeutic substances can be provided in a composition that protects it from the acidic environment of the stomach. For example, he disclosed α7β1 integrin modulatory agents or other therapeutic agents can be formulated with an enteric coating that maintains its integrity in the stomach and releases the active compound in the intestine. The disclosed α7β1 integrin modulatory agents, or other therapeutic agent can also be formulated in combination with an antacid or other such ingredient.

Oral compositions generally include an inert diluent or an edible carrier and can be compressed into tablets or enclosed in gelatin capsules. For the purpose of oral therapeutic administration, one or more of the disclosed α7β1 integrin modulatory agents, or other therapeutic substances can be incorporated with excipients and used in the form of capsules, tablets, or troches. Pharmaceutically compatible adjuvant materials or binding agents can be included as part of the composition.

The capsules, pills, tablets, troches, and the like can contain any of the following ingredients or compounds of a similar nature: a binder such as, but not limited to, acacia, corn starch, gelatin, gum tragacanth, polyvinylpyrrolidone, or sorbitol; a filler such as calcium phosphate, glycine, lactose, microcrystalline cellulose, or starch; a disintegrating agent such as, but not limited to, alginic acid and corn starch; a lubricant such as, but not limited to, magnesium stearate, polyethylene glycol, silica, or talc; a gildant, such as, but not limited to, colloidal silicon dioxide; a sweetening agent such as sucrose or saccharin; disintegrants such as potato starch; dispersing or wetting agents such as sodium lauryl sulfate; and a flavoring agent such as peppermint, methyl salicylate, or fruit flavoring.

When the dosage unit form is a capsule, it can contain, in addition to material of the above type, a liquid carrier, such as a fatty oil. In addition, dosage unit forms can contain various other materials that modify the physical form of the dosage unit, for example, coatings of sugar and other enteric agents. One or more of the disclosed α7β1 integrin modulatory agents, or other therapeutic agent can also be administered as a component of an elixir, suspension, syrup, wafer, tea, chewing gum, or the like. A syrup may contain, in addition to the active compounds, sucrose or glycerin as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, they can be of the sustained release type so that the compounds need to be administered less frequently.

In some examples, one or more of the disclosed α7β1 integrin modulatory agents and/or a therapeutic agent is injected into the stomach of a subject is incorporated systemically in the subject, such as in diverse muscle groups. Examples of methods and compositions for administering therapeutic substances which include proteins include those discussed in Banga, *Therapeutic Peptides and Proteins: Formulation, Processing, and Delivery Systems* 2ed. (2005); Mahato, *Biomaterials for Delivery and Targeting of Proteins and Nucleic Acids* (2004); McNally, *Protein Formulation and Delivery*, 2ed. (2007); and Kumar et al., "Novel Delivery Technologies for Protein and Peptide Therapeutics," *Current Pharm. Biotech.*, 7:261-276 (2006); each of which is incorporated by reference herein to the extent not inconsistent with the present disclosure.

In some implementations, the effective amount of one or more of the disclosed α7β1 integrin modulatory agents is administered as a single dose per time period, such as every three or four months, month, week, or day, or it can be divided into at least two unit dosages for administration over a period. Treatment may be continued as long as necessary to achieve the desired results. For instance, treatment may continue for about 3 or 4 weeks up to about 12-24 months or longer, including ongoing treatment. The compound can also be administered in several doses intermittently, such as every few days (for example, at least about every two, three, four, five, or ten days) or every few weeks (for example at least about every two, three, four, five, or ten weeks).

Particular dosage regimens can be tailored to a particular subject, condition to be treated, or desired result. For example, when the methods of the present disclosure are used to treat muscular dystrophy or similar conditions, an initial treatment regimen can be applied to arrest the condition. Such initial treatment regimen may include administering a higher dosage of one or more of the disclosed α7β1 integrin modulatory agents, or administering such material more frequently, such as daily. After a desired therapeutic result has been obtained, such as a desired level of muscle regeneration, a second treatment regimen may be applied, such as administering a lower dosage of one or more of the disclosed α7β1 integrin modulatory agents or administering such material less frequently, such as monthly, bi-monthly, quarterly, or semi-annually In such cases, the second regimen may serve as a "booster" to restore or maintain a desired level of muscle regeneration Similar treatment regimens may be used for other subjects with reduced or impaired muscle regeneration capabilities, such as geriatric subjects.

When particular methods of the present disclosure are used to prevent or mitigate muscle damage, such as damage caused by exertion or injury, the subject is typically treated a sufficient period of time before the exertion or injury in order to provide therapeutic effect. For example, the subject may be treated at least about 24 hours before the expected activity or potential injury, such as at least about 48 hours, about 72 hours, about 1 week, about 2 weeks, about three weeks, or about 4 weeks or more prior.

When embodiments of the method of the present disclosure are used to prevent or treat a muscle injury, one or more of the disclosed α7β1 integrin modulatory agents or other therapeutic substance can be applied directly to, or proximately to, the area to be treated. For example, the substance can be injected into or near the area. In further examples, the substance can be applied topically to the area to be treated. Treatment is typically initiated prior to the injury to several weeks following the injury. In more specific implementations, the treatment is initiated between about 12 and about 72 hours following injury, such as between about 24 and about 48 hours following injury. In some cases, a single administration of the substance is effective to provide the desired therapeutic effect. In further examples, additional administrations are provided in order to achieve the desired therapeutic effect.

Amounts effective for various therapeutic treatments of the present disclosure may, of course, depend on the severity of the disease and the weight and general state of the subject, as well as the absorption, inactivation, and excretion rates of the therapeutically-active compound or component, the dosage schedule, and amount administered, as well as other factors known to those of ordinary skill in the art. It also should be apparent to one of ordinary skill in the art that the exact dosage and frequency of administration will depend on the particular α7β1 integrin modulatory agent, or other therapeutic substance being administered, the particular condition being treated, the severity of the condition being treated, the age, weight, general physical condition of the particular subject, and other medication the subject may be taking. Typically, dosages used in vitro may provide useful guidance in the amounts useful for in vivo administration of the pharmaceutical composition, and animal models may be used to determine effective dosages for treatment of particular disorders. For example, mouse models of muscular dystrophy may be used to determine effective dosages that can then be translated to dosage amount for other subjects, such as humans, as known in the art. Various considerations in dosage determination are described, e.g., in Gilman et al., eds., *Goodman And Gilman's: The Pharmacological Bases of Therapeutics,* 8th ed., Pergamon Press (1990); and *Remington's Pharmaceutical Sciences,* 17th ed., Mack Publishing Co., Easton, Pa. (1990), each of which is herein incorporated by reference to the extent not inconsistent with the present disclosure.

In specific examples, the one or more disclosed α7β1 integrin modulatory agents is administered to a subject in an amount sufficient to provide a dose of the agent of between about 10 fmol/g and about 500 nmol/g, such as between about 2 nmol/g and about 20 nmol/g or between about 2 nmol/g and about 10 nmol/g. In additional examples, the α7β1 integrin modulatory agent is administered to a subject in an amount sufficient to provide a dose of between about 0.01 μg/kg and about 1000 mg/kg or between about 0.1 mg/kg and about 1000 mg/kg, in particular examples this amount is provided per day or per week. In another example, the disclosed α7β1 integrin modulatory agent is administered to a subject in an amount sufficient to provide a dose of agent of between about 0.2 mg/kg and about 2 mg/kg. In further examples, the α7β1 integrin modulatory agent is administered to a subject in an amount sufficient to provide a concentration of α7β1 integrin modulatory agent in the administrated material of between about 5 nM and about 500 nM, such as between about 50 nM and about 200 nm, or about 100 nM. In other examples, the α7β1 integrin modulatory agent is administered to a subject between about 500 μg/ml and about 1 μg/ml, such as about 300 μg/ml and about 3 μg/ml, about 200 μg/ml and about 20 μg/ml, including 500 μg/ml, 400 μg/ml, 300 μg/ml, 250 μg/ml, 200 μg/ml, 150 μg/ml, 100 μg/ml, 50 μg/ml, 25 μg/ml, 12.5 μg/ml, 6.25 μg/ml, 3.125 μg/ml, 2.5 μg/ml and 1.25 μg/ml.

ii. Desired Response

One or more disclosed α7β1 integrin modulatory agents and/or additional therapeutic agents are administered by a specific route and/or concentration to generate a desired response. In some examples, a desired response refers to an amount effective for lessening, ameliorating, eliminating, preventing, or inhibiting at least one symptom of a disease, disorder, or condition treated and may be empirically determined. In various embodiments of the present disclosure, a desired response is muscle regeneration, reductions or prevention of muscle degeneration, promotion of muscle maintenance, reduction or prevention of muscle injury or damage, reduction or prevention in one more signs or symptoms associated with muscular dystrophy.

In particular, indicators of muscular health, such as muscle cell regeneration, maintenance, or repair, can be assessed through various means, including monitoring markers of muscle regeneration, such as transcription factors such as Pax7, Pax3, MyoD, MRF4, and myogenin. For example, increased expression of such markers can indicate that muscle regeneration is occurring or has recently occurred. Markers of muscle regeneration, such as expression of embryonic myosin heavy chain (eMyHC), can also be used to gauge the extent of muscle regeneration, maintenance, or repair. For example, the presence of eMyHC can indicate that muscle regeneration has recently occurred in a subject.

Muscle cell regeneration, maintenance, or repair can also be monitored by determining the girth, or mean cross sectional area, of muscle cells or density of muscle fibers. Additional indicators of muscle condition include muscle weight and muscle protein content. Mitotic index (such as by measuring BrdU incorporation) and myogenesis can also be used to evaluate the extent of muscle regeneration.

In particular examples, the improvement in muscle condition, such as regeneration, compared with a control is at least about 10%, such as at least about 30%, or at least about 50% or more, including an at least 15%, at least 20%, at least 25%, at least 30%, at least 40%, at least 45%, at least 50%, at least 60%, at least 70%, at least 80%, at least 90%, including a 10% to 90% decrease, 20% to 80% increase, 30% to 70% increase or a 40% to 60% increase (e.g., a 10%, 20%, 30%, 40%, 50%, 60%, 70%, 80%, 90%, 95%, 100%, 200% or more increase).

iii. Additional Treatments or Therapeutic Agents

In particular examples, prior to, during, or following administration of an effective amount of an agent that reduces or inhibits one or more signs or symptoms associated with muscular dystrophy, the subject can receive one or more other therapies. In one example, the subject receives one or more treatments prior to administration of a disclosed α7β1 modulatory agent. Examples of such therapies include, but are not limited to, laminin-111 protein therapy, which works to stabilize the sarcolemma and reduce muscle degeneration. In some examples, a source of muscle cells can be added to aid in muscle regeneration and repair. In some aspects of the present disclosure, satellite cells are administered to a subject in combination with laminin therapy. U.S. Patent Publication 2006/0014287, incorporated by reference herein to the extent not inconsistent with the present disclosure, provides methods of enriching a collection of cells in myogenic cells and administering those cells to a subject. In further aspects, stem cells, such as adipose-derived stem cells, are administered to the subject. Suitable methods of preparing and administering adipose-derived stem cells are disclosed in U.S. Patent Publication 2007/0025972, incorporated by reference herein to the extent not inconsistent with the present disclosure. Additional cellular materials, such as fibroblasts, can also be administered, in some examples.

Additional therapeutic agents include agents which enhance the effect of the disclosed α7β1 modulatory agents, such as a component of the extracellular matrix, such as an integrin, dystrophin, dystroglycan, utrophin, or a growth factor. In some examples, the additional therapeutic agent reduces or enhances expression of a substance that enhances the formation or maintenance of the extracellular matrix. In some examples, the additional substance can include aggrecan, angiostatin, cadherins, collagens (including collagen I, collagen III, or collagen IV), decorin, elastin, enactin, endostatin, fibrin, fibronectin, osteopontin, tenascin, thrombospondin, vitronectin, and combinations thereof. Biglycans, glycosaminoglycans (such as heparin), glycoproteins (such as dystroglycan), proteoglycans (such as heparan sulfate), and combinations thereof can also be administered.

In some examples, growth stimulants such as cytokines, polypeptides, and growth factors such as brain-derived neurotrophic factor (BDNF), CNF (ciliary neurotrophic factor), EGF (epidermal growth factor), FGF (fibroblast growth factor), glial growth factor (GGF), glial maturation factor (GMF) glial-derived neurotrophic factor (GDNF), hepatocyte growth factor (HGF), insulin, insulin-like growth factors, kerotinocyte growth factor (KGF), nerve growth factor (NGF), neurotropin-3 and -4, PDGF (platelet-derived growth factor), vascular endothelial growth factor (VEGF), and combinations thereof may be administered with one of the disclosed methods.

IV. Clinical Trials

To obtain regulatory approval for the use of one or more of the disclosed α7β1 modulatory agents to treat a muscular disorder, clinical trials are performed. As is known in the art, clinical trials progress through phases of testing, which are identified as Phases I, II, III, and IV.

Initially the disclosed α7β1 modulatory agent is evaluated in a Phase I trial. Typically Phase I trials are used to determine the best mode of administration (for example, by pill or by injection), the frequency of administration, and the toxicity for the compounds. Phase I studies frequently include laboratory tests, such as blood tests and biopsies, to evaluate the effects of the potential therapeutic in the body of the patient. For a Phase I trial, a small group of patients with a muscular disorder are treated with a specific dose of a disclosed α7β1 modulatory agent. During the trial, the dose is typically increased group by group in order to determine the maximum tolerated dose (MTD) and the dose-limiting toxicities (DLT) associated with the compound. This process determines an appropriate dose to use in a subsequent Phase II trial.

A Phase II trial can be conducted to further evaluate the effectiveness and safety of the disclosed α7β1 modulatory agent. In Phase II trials, a disclosed α7β1 modulatory agent is administered to groups of patients with a muscular disorder using the dosage found to be effective in Phase I trials.

Phase III trials focus on determining how a disclosed α7β1 modulatory agent compares to the standard, or most widely accepted, treatment. In Phase III trials, patients are randomly assigned to one of two or more "arms". In a trial with two arms, for example, one arm will receive the standard treatment (control group) and the other arm will receive a disclosed α7β1 modulatory agent treatment (investigational group).

Phase IV trials are used to further evaluate the long-term safety and effectiveness of a disclosed α7β1 modulatory agent. Phase IV trials are less common than Phase I, II and III trials and take place after a disclosed α7β1 modulatory agent has been approved for standard use.

Eligibility of Patients for Clinical Trials

Participant eligibility criteria can range from general (for example, age, sex, type of disease) to specific (for example, type and number of prior treatments, disease characteristics, blood cell counts, organ function). In one embodiment, eligible patients have been diagnosed with a muscular disorder. Eligibility criteria may also vary with trial phase. Patients eligible for clinical trials can also be chosen based on objective measurement of a muscular disorder and failure to respond to other muscular disorder treatments. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I trials usually include 15 to 30 participants for whom other treatment options have not been effective. Phase II trials typically include up to 100 participants who have already received drug therapy, but for whom the treatment has not been effective.

Participation in Phase III trials is often restricted based on the previous treatment received. Phase III trials usually include hundreds to thousands of participants. This large number of participants is necessary in order to determine whether there are true differences between the effectiveness of a disclosed α7β1 modulatory agent and the standard treatment. Phase III can include patients ranging from those newly diagnosed with a muscular disorder to those with re-occurring signs and/or symptoms associated with a muscular disorder or a muscular disorder that did not respond to prior treatment.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

Assessment of Patients Prior to Treatment

Prior to commencement of the study, several measures known in the art can be used to first classify the patients. Patients can first be assessed, for example by determining serum creatine kinase (CK) levels or other indicators of a muscle disorder, such as increased levels of muscle inflammation, apoptosis, muscle loss, myotube hypertrophy, and/or decreased myofibers stability and cell survival.

Administration of a Disclosed α7β1 Modulatory Agent in Clinical Trials

A disclosed α7β1 modulatory agent is typically administered to the trial participants orally. A range of doses of the agent can be tested. Provided with information from pre-clinical testing, a skilled practitioner can readily determine appropriate dosages of agent for use in clinical trials. In one embodiment, a dose range is from about 100 µg/kg and about 5000 mg/kg of the subject's weight, such as 1 mg/kg and about 2000 mg/kg of the subject's weight, about 100 mg/kg and about 1500 mg/kg of the subject's weight, about 100 µg/kg and about 2000 mg/kg of the subject's weight, about 200 mg/kg and about 1000 mg/kg of the subject's weight, about 200 mg/kg and about 750 mg/kg of the subject's weight, about 250 mg/kg and about 500 mg/kg of the subject's weight, about 100 µm and about 500 mM. In some embodiments, subjects are given a disclosed α7β1 modulatory agent orally at 10 to 60 mg/kg of body weight per day. For example, 10-15 mg/kg of a disclosed α7β1 modulatory agent is administered for two weeks and if well tolerated the dose is increased by 5-10 mg/kg/week to achieve optimal clinical response. In some examples, the daily dose does not exceed 60 mg/kg of body weight and is given for a minimum of 6 months with liver function monitored every two weeks to monthly.

Pharmacokinetic Monitoring

To fulfill Phase I criteria, distribution of the disclosed α7β1 modulatory agent is monitored, for example, by chemical analysis of samples, such as blood, collected at regular intervals. For example, samples can be taken at regular intervals up until about 72 hours after the start of treatment.

If analysis is not conducted immediately, the samples can be placed on dry ice after collection and subsequently transported to a freezer to be stored at −70° C. until analysis can be conducted. Samples can be prepared for analysis using standard techniques known in the art and the amount of the disclosed α7β1 modulatory agent present can be determined, for example, by high-performance liquid chromatography (HPLC). Pharmacokinetic data can be generated and analyzed in collaboration with an expert clinical pharmacologist and used to determine, for example, clearance, half-life and maximum plasma concentration.

Monitoring of Patient Outcome

The endpoint of a clinical trial is a measurable outcome that indicates the effectiveness of a compound under evaluation. The endpoint is established prior to the commencement of the trial and will vary depending on the type and phase of the clinical trial. Examples of endpoints include, for example, decline in serum CK levels, inflammation, apoptosis, and muscle loss. For example, at least a 10% reduction in serum CK levels indicates the patient is responsive to the treatment.

The following examples are provided to illustrate certain particular features and/or embodiments. These examples should not be construed to limit the invention to the particular features or embodiments described.

EXAMPLES

Example 1

LacZ Reporter Gene in α7βgal$^{+/-}$ Muscle Cells Reports the Transcriptional Activity of the α7 Integrin Promoter This Example shows that the LacZ reporter gene in α7βgal$^{+/-}$ muscle cells faithfully reports the transcriptional activity of the α7 integrin promoter and can be used screen for α7β1 enhancer molecules.

Figure 1B:
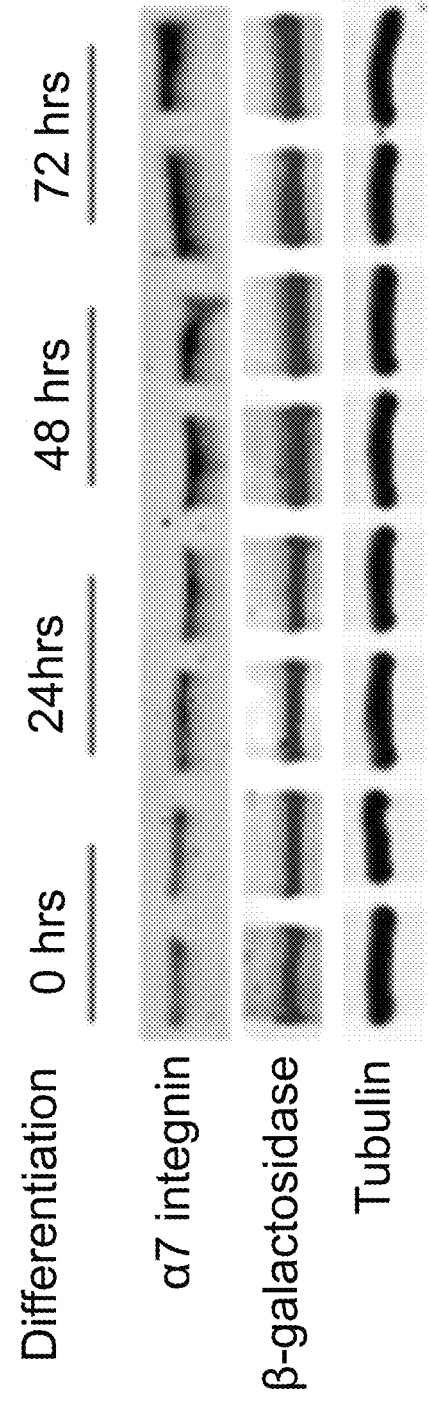
FIG. 1B is a digital image of a Western analysis of α7βgal$^{+/-}$ myoblasts differentiated from 0-72 hours shows a corresponding increase in both α7 integrin and β-galactosidase. α-Tubulin was used as a loading control.
Figure 2A:
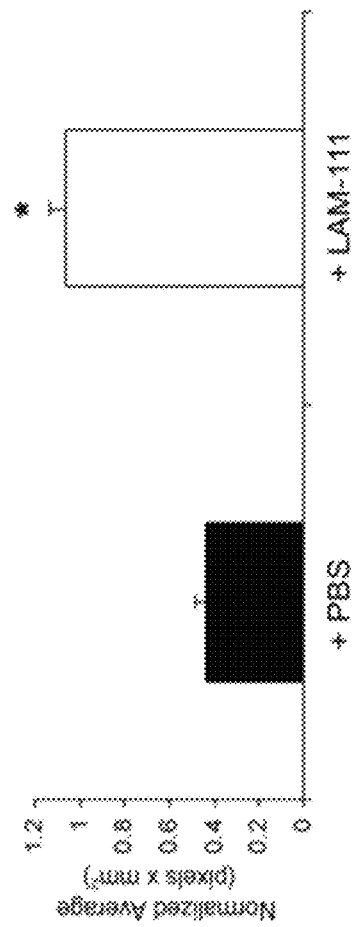
FIGS. 2A-2D demonstrate Laminin-111 increases α7 integrin levels in mouse and human muscle cells. (2A) Western blotting reveals increased levels of α7β integrin in laminin-111 treated myoblasts compared to controls. Cox-1 was used as a loading control. (2B) Quantitation shows a two-fold increase in α7β integrin in C2C12 myoblasts treated with laminin-111. (2C) Western blotting reveals increased α7β integrin in laminin-111 treated DMD myoblasts compared to control. Cox-1 was used as a loading control. (2D) Quantitation shows a 2-fold increase in α7β integrin in DMD myoblasts treated with laminin-111.
Figure 2B:
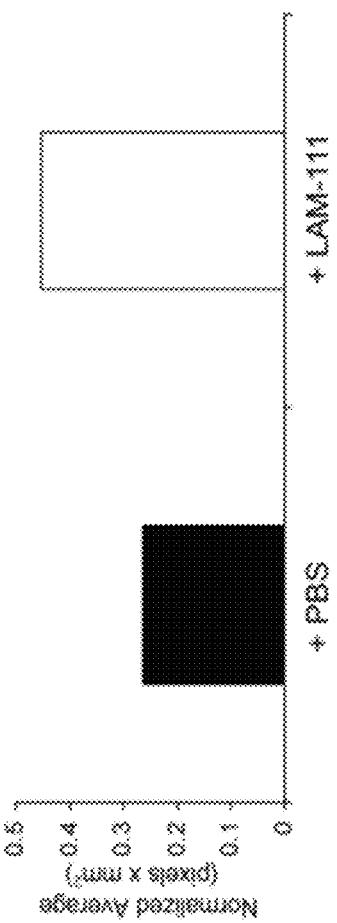
Figure 2C:
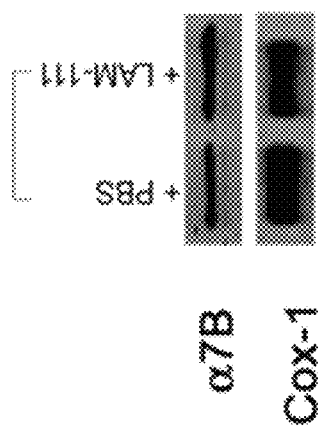
Figure 2D:
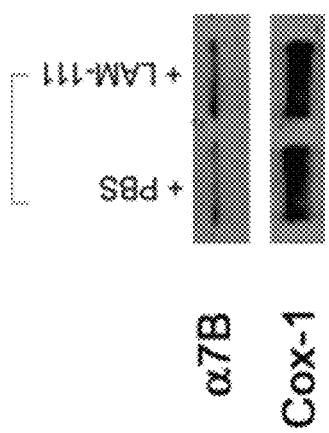

An α7 integrin null mouse was produced in which exon 1 of the gene encoding the α7 integrin was replaced by the LacZ reporter. In these mice, all the transcriptional regulatory elements of the α7 integrin promoter were retained, allowing β-galactosidase to report expression of 7 integrin. A primary myoblast cell line (designated α7βgal$^{+/-}$) isolated from 10 day old α7$^{+/-}$ pups were analyzed for the ability of β-galactosidase to report α7 integrin expression. α7βgal$^{+/-}$ myoblasts were differentiated and subjected to X-gal staining and western analysis (FIGS. 1A and 1B).

These results demonstrate that β-galactosidase expression in α7βgal$^{+/-}$ muscle cells increased upon myogenic differentiation consistent with the expression pattern of α7 integrin in myoblasts and myotubes. These results confirm that the LacZ reporter gene in α7βgal$^{+/-}$ muscle cells faithfully reports the transcriptional activity of the α7 integrin promoter. The activity of the α7 integrin promoter was measured by β-galactosidase cleavage of the non-fluorescent compound fluorescein di-β-D-galactopyranoside (FDG) to fluorescein. This assay was used to screen compound libraries to identify molecules that up-regulate α7 integrin expression in muscle.

Example 2

Identification of Compounds that Promote α7β1 Integrin Expression

This example describes multiple compounds identified as α7β1 integrin expression enhancers.

Using the muscle cell based assay described in Example 1, the following compound libraries were screened: Prestwick Chemical and Microsource Spectrum Libraries from BioFocus DPI (Leiden Netherlands with facilities in UK, Basel, Heidelberg); the DIVERSet library (Chembridge Corp., San Diego, Calif.) and compounds from the ChemDiv library. Also evaluated was the effect of various isoforms of laminin and the ligand for α7β1 integrin on integrin expression. Positive hits were subjected to dose-response analysis, western analysis and a myostatin counterscreen (a negative regulator of muscle growth). To quantify myostatin expression a western blot based assay was utilized (however, an ELISA assay is now available). α7βgal+/− and C2C12 myotubes were treated with the optimal drug concentration (see Table 8 below) for 24 hours, conditioned media removed and subjected to western analysis using an anti-myostatin antibody (AB3239, Millipore). As a positive control, cells were treated with 200 mM Dexamethasone, which has been shown to increase myostatin expression in C2C12 myotubes. The results indicate that at the EC$_{100}$ concentrations used, none of the lead compounds increased myostatin expression.

From these studies nine molecules were identified that increased α7 integrin using our muscle cell-based assay as summarized in Table 8.

TABLE 8

Molecules identified as enhances of α7 integrin expression in muscle

| Compound | Optimal Concentration | $EC_{50}$ | FDA approved | Drug Family |
|---|---|---|---|---|
| Laminin-111 | 100 nM | 50 nM | No | Extracellular matrix protein |
| Valproic acid | 2 mM | 0.5 mM | Yes | HDAC inhibitor |
| Ciclopirox ethanolamine | 4 µg/ml | 0.6 µg/ml | Yes | Iron chelator, Anti-fungal, Antibiotic |
| Deferoxamine | 20 µM | 10 µM | Yes | Iron chelator |
| 2,2-Dipyridyl | 125 µM | 62.5 µM | No | Iron chelator |
| 5α-cholestan-3β-ol-6-one | 20 µM | 6 µM | No | Plant derived compound |
| Compound ID# 1001 | 12.5 µM | 3 µM | No | Unknown |
| Compound ID# 1002 | 12.5 µM | 1.5 µM | No | Unknown |
| Compound ID# 1003 | 25 µM | 5 µM | No | Unknown |

Example 3

Intramuscular Injection of Laminin-111 Prevents Muscular Dystrophy in mdx Mice

This example demonstrates that intramuscular injection of laminin-111 prevents muscular dystrophy in mdx mice. Although this example describes studies particular to laminin-111 it is contemplated that similar studies can be performed based upon the methods described herein and the optimal concentrations of the particular α7β1 intregin enhancer molecules provided in Table 8 for the other α7β1 intregin enhancer molecules and similar effects on muscular dystrophy are predicted.

The ability of laminin to regulate α7 integrin expression, α7βgal$^{+/-}$ myoblasts were exposed to 0-200 nM laminin-111 for 24 hours. The activity of the α7 integrin promoter was measured by β-galactosidase cleavage of the non-fluorescent compound fluorescein di-β-D-galactopyranoside (FDG) to fluorescein. Fluorescence activated cell sorting (FACS) demonstrated that α7βgal$^{+/-}$ myoblasts treated for 24 hours with 100 nM laminin-111 produced the maximal increase in α7 integrin promoter activity. These results indicate laminin-111 promotes expression of α7 integrin in isolated mouse muscle cells. The ability of laminin-111 to increase α7 integrin expression was confirmed by western analysis using mouse and human DMD muscle cells (FIGS. 2A-2D). These data indicate that the mechanism by which laminin-111 increases α7 integrin expression is conserved between mouse and human muscle cells and suggests that laminin-111 is highly likely to increase α7β1 integrin expression in the skeletal muscle of DMD patients.

Figure 3A:
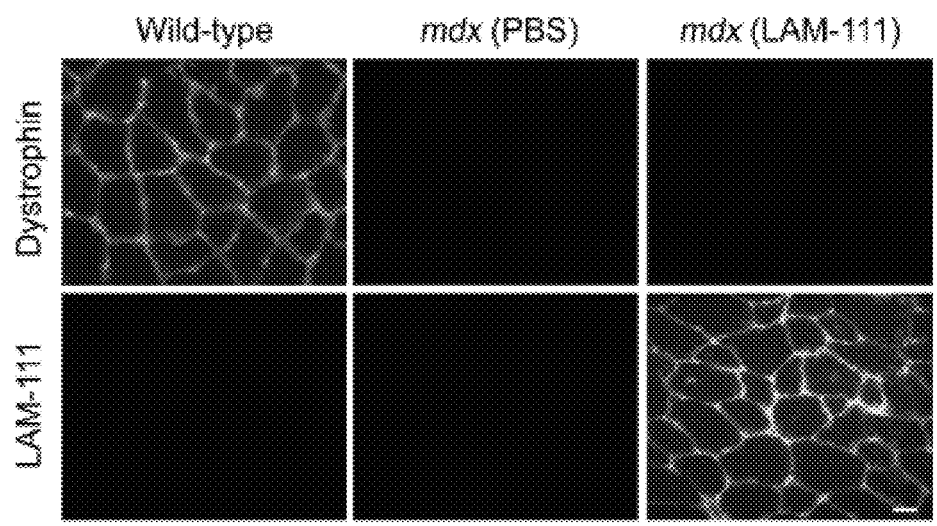
FIGS. 3A-3C demonstrate that intramuscular injection of laminin-111 prevents muscle disease in mdx mice. (3A) Immunofluorescence of the TA muscles of control and laminin-111 treated mice confirm the absence dystrophin in mdx muscle treated with LAM-111 or PBS Laminin-111 was not present in wild-type or PBS injected mdx muscle but was detected in the extracellular matrix of laminin-111-injected mdx muscle. Scale bar=10 μm. (3B) Evans blue dye (EBD) uptake reveals mdx muscle injected with laminin-111 exhibits reduced EBD uptake compared to control. Scale bar=10 μm. H&E staining reveals that mdx muscle treated with laminin-111 contains few muscle fibers with centrally located nuclei and mononuclear cell infiltrate compared to control. (3C) Quantitation reveals wild-type and mdx muscle treated with laminin-111 contained significantly fewer EBD positive fibers and myofibers with centrally located nuclei compared to control. *P<0.05, **P<0.001, n=5 mice/group.
Figure 3B:
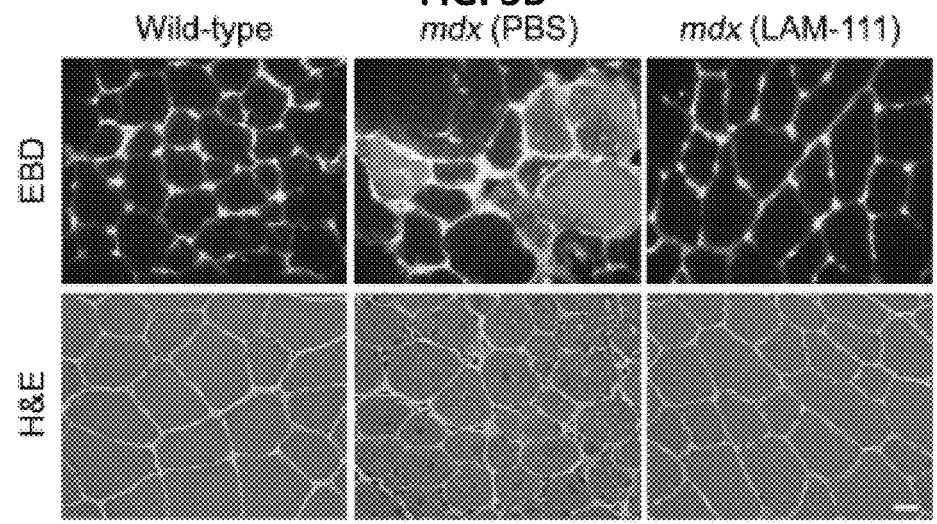
Figure 3C:
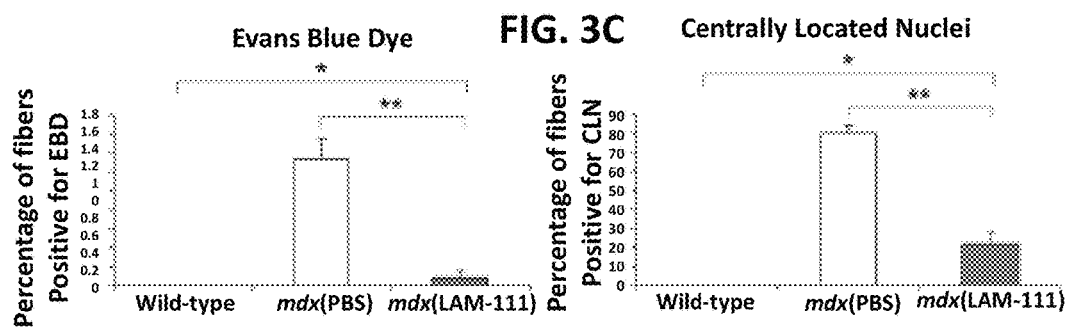

To determine if laminin-111 prevented muscle pathology in mdx mice, Evans blue dye (EBD) uptake and Hemotoxylin and Eosin (H&E) staining were performed on cryosections from PBS and laminin-111 injected TA muscle (FIG. 3A). Analysis revealed that mdx muscles injected with laminin-111 had a 12-fold reduction in the percentage of fibers positive for EBD compared to the contralateral controls (FIGS. 3B & 3C). In addition, mdx muscles injected with laminin-111 showed a 4-fold decrease in the percentage of muscle fibers with centrally located nuclei (FIG. 3C). These results indicate intramuscular injection of laminin-111 protein dramatically increased sacrolemmal integrity and reduced myofiber degeneration.

Injection of laminin-111 protein into the mdx mouse model of DMD increased expression of α7 integrin, stabilized the sarcolemma, restored serum creatine kinase to wild-type levels and protected muscle from exercise induced damage. These findings demonstrate that laminin-111 is a highly potent therapeutic for the mdx mouse model of DMD and represents a paradigm for the systemic delivery of extracellular matrix proteins as therapies for genetic diseases.

Example 4

Valproic Acid as a Treatment for Muscular Dystrophy

This example describes studies indicating the ability of valproic acid to be used to treat muscular dystrophy.

Figure 4A:
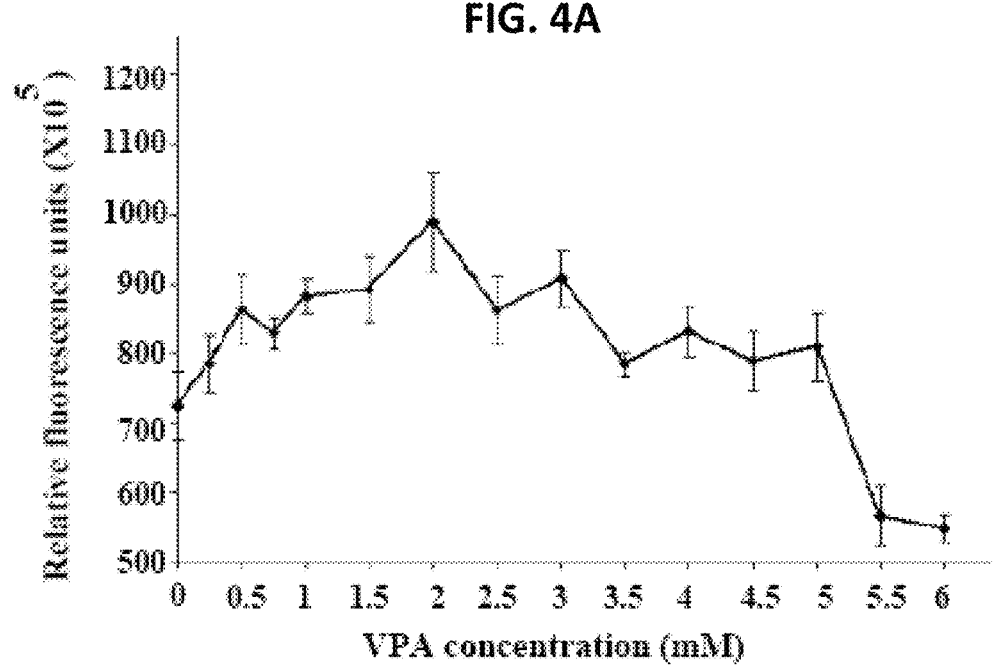
FIGS. 4A and 4B demonstrate Valproic Acid increases α7 integrin expression in muscle cells. (4A) Dose response curve for Valproic Acid using α7βgal$^{+/-}$ myotubes. (4B) Valproic acid increases α7 integrin protein in C2C12 myotubes.
Figure 4B:
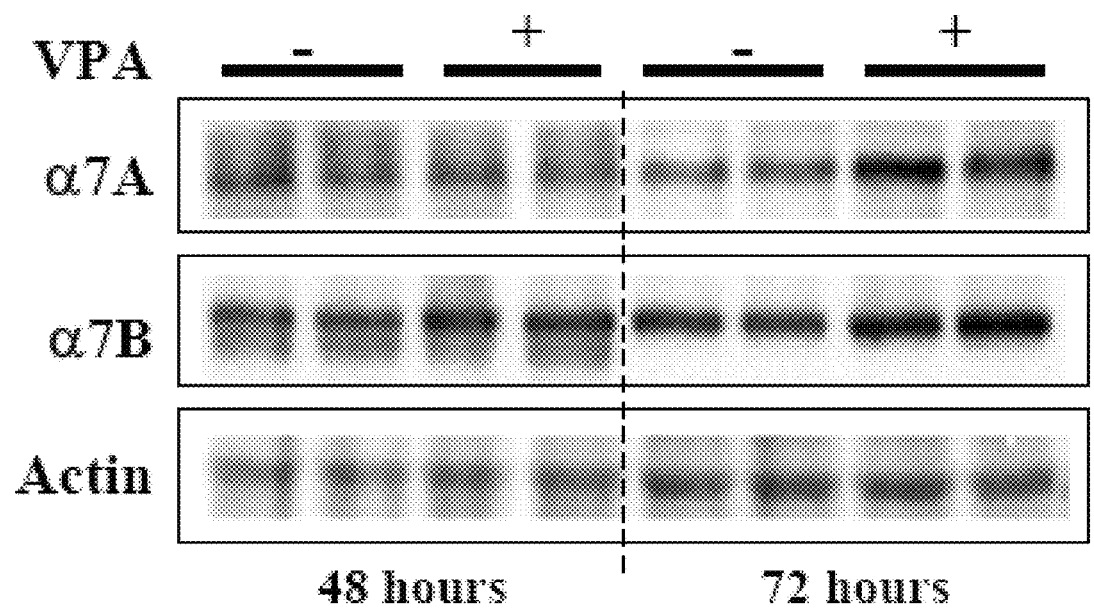

Valproic acid (VPA) is a branched chain fatty acid that is FDA approved for treating epilepsy and bipolar disorders. VPA activates Akt in neurons and promotes their survival is also known to have histone deacetylase (HDAC) inhibitor activity. Using our muscle cell-based assay we identified that valproic acid activates α7 integrin expression in muscle cells. Valproic acid gave a dose-response curve and increased α7 integrin in C2C12 myotubes (FIGS. 4A and 4B). Mdx/utr$^{-/-}$ mice treated with Valproic Acid showed reduced muscle disease, improved mobility, reduced fibrosis and activation of the Akt signaling pathway in muscle. These results indicate that valproic acid is a candidate for the treatment of DMD.

Example 5

Ciclopirox, Deferoxamine and 2,2-dipyridyl Increase α7 Integrin Expression

This example shows that ciclopirox, 2,2-dipyridyl and deferoxamine increase α7 integrin expression through a common pathway.

Figure 6A:
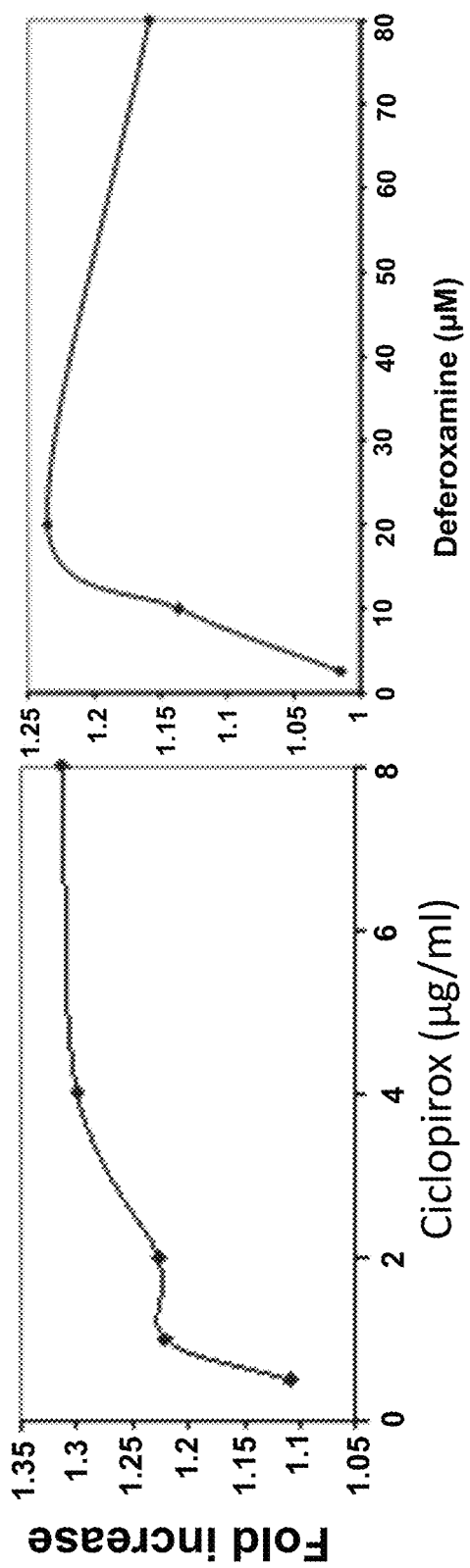
FIGS. 6A and 6B show dose-response curves for Ciclopirox, Deferoxamine and 2,2-dipyridyl using α7βgal$^{+/-}$ myotubes and the FDG assay.
Figure 6B:
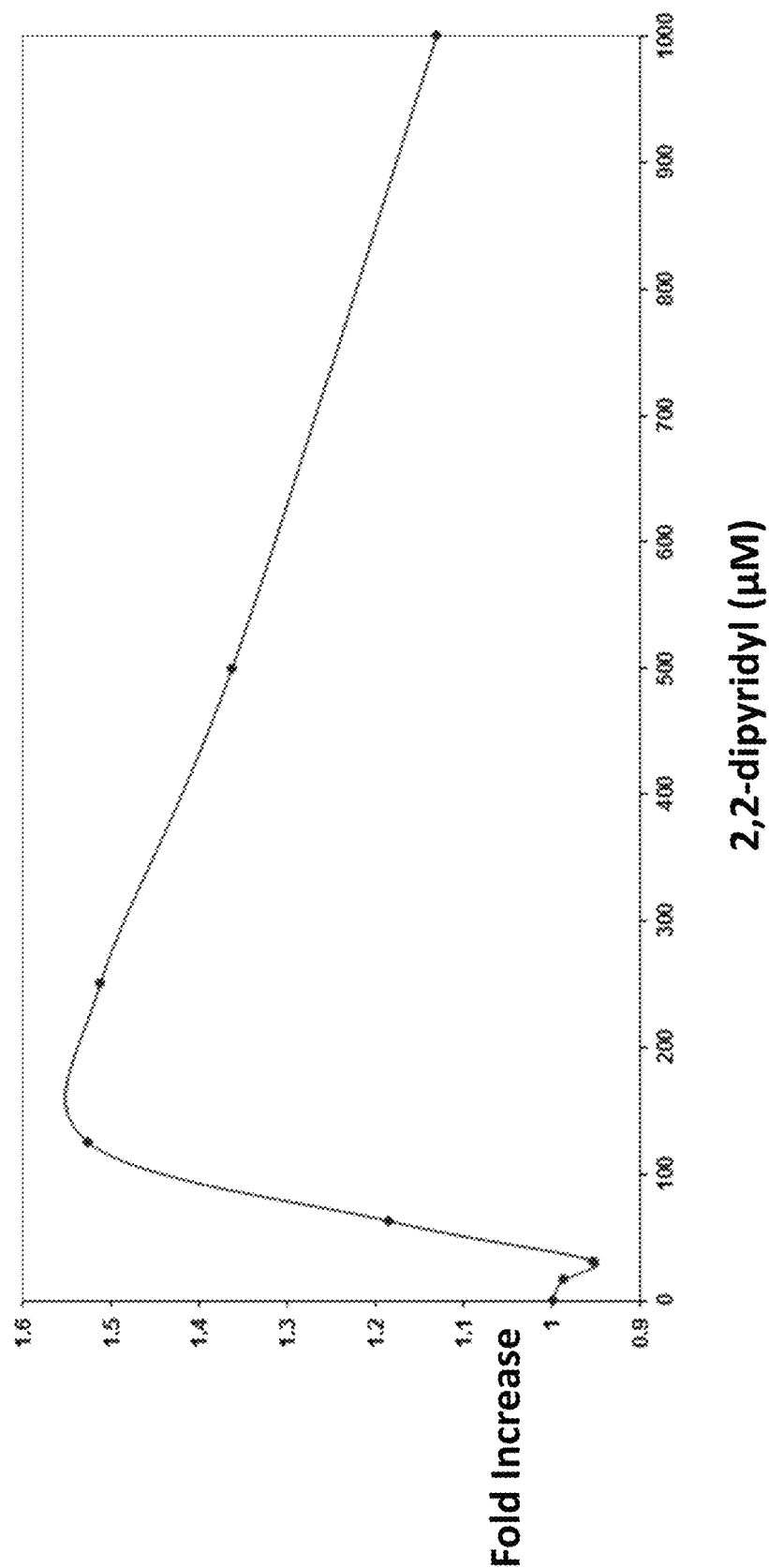

As stated in Example 2 ciclopirox and deferoxamine are as activators of α7 integrin promoter activity using α7βgal$^{+/-}$ myotubes. Both ciclopirox and deferoxamine are iron chelating drugs. Ciclopirox was independently identified in two compound libraries and is FDA approved as an antibiotic and anti-fungal drug. Deferoxamine is an FDA approved drug used to treat iron toxicity. Typical dose-response curves were obtained for both ciclopirox and deferoxamine with $EC_{50}$ of 0.6 µg/ml and 10 µM respectively (FIG. 5). A dose response curve for 2,2-dipyridyl (also an iron chelating molecule, but is not FDA approved) is shown in FIGS. 6A and 6B.

These results suggest ciclopirox, deferoxamine and 2,2-dipyridyl act through a common pathway to activate α7 integrin expression. Ciclopirox, deferoxamine and 2,2-dipyridyl have been shown to increase stability of the transcription factor hypoxia inducible factor-1 (HIF-1) by preventing its breakdown. To determine if α7 integrin expression was responsive to HIF-1, bioinformatic analysis was performed on the α7 integrin promoter. A 2.8 kb fragment of the mouse α7 integrin promoter was analyzed using MATINSPECTOR (Genomatix) for the presence of HIF-1 binding sites. The consensus DNA sequence for HIF-1 binding in the hypoxia-response element is 5'-[–A/G]CGTG-3' flanked with or without a second consensus site 5'[A/C]ACAG-3'. Analysis of the α7 integrin promoter sequence revealed the presence of a HIF-1 binding site along with flanking sequences that promote HIF-1 binding. MATINSPECTOR analysis gave these sequences a perfect score for HIF-1 binding. These results suggest ciclopirox, deferoxamine and 2,2-dipyridyl may act to increase α7 integrin gene expression by inhibiting proteosomal breakdown of HIF-1 in muscle cells resulting in increased cellular levels of HIF-1 protein. The overall result would increase α7 integrin protein on the surface of muscle cells increasing membrane stability. Further studies to determine if these drugs can experimentally increase HIF-1 protein levels in muscle cells need to be undertaken to add support to this mechanism of drug action. Interestingly, increased HIF-1 levels are associated with increased angiogenesis. Increasing HIF-1 levels in dystrophic muscle may not only increase membrane stability through increased α7 integrin expression, but increased muscle vascularization, improving blood flow and reducing the ischemia associated with dystrophic muscle.

DMD primary myotubes were exposed to the iron chelators 2,2-dipyridyl (31.25 µM) and deferoxamine (5 and 10 µM) for 132 hrs to determine if they increased α7 integrin. Protein was extracted from the cells and subjected to western blotting using antibodies against α7 integrin. α-tubulin was used as a loading control. Results showed that both 2,2-dipyridyl and deferoxamine increased α7 integrin in DMD myotubes (FIG. 7). These results indicate the mechanism(s) by which the iron chelators act to increase integrin expression are conserved between mouse and human muscle cells.

Example 6

Cholestan (5α-cholestan-3β-ol-6-one) and Cholestan Analogs Effect on α7 Integrin Expression This Example demonstrates the ability of cholestan and specific cholestan analogs to increase α7 integrin expression in myoblasts and myotubes.

The studies described in Example 2 identified cholestan as an enhancer of α7 integrin expression as determined by the muscle cell based assay. Cholestan is a plant-derived compound of unknown function and gave a typical dose-response curve using α7βgal$^{+/-}$ myotubes and increased α7 integrin protein in DMD myotubes (FIG. 8). In addition, specific analogs of cholestan retained the ability to activate expression of α7β1 integrin (see Table 9 below). One hundred and nineteen analogs of cholestan were obtained from Chemical Diversity laboratories and assessed for their ability to activate the expression of the α7 integrin in α7betagal+/− myoblasts and myotubes. Four of 119 analogs retained the ability to activate α7 integrin expression in myoblasts and myotubes, and an additional 4 of 119 retained the ability to activate α7 integrin expression in myoblasts only (Table 9).

TABLE 9

Analogs of cholestan that retained the ability to activate expression of the α7 integrin

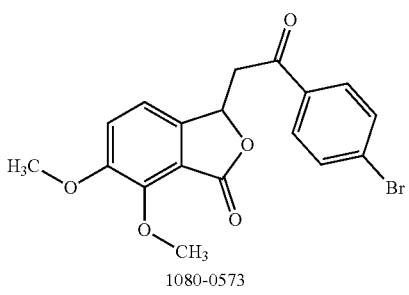

1080-0573

| Compound (Obtained Commercially from ChemDiv Library) | EC100 | Increased A7 Expression Myotubes + Myoblasts | Myoblasts Only |
|---|---|---|---|
| 5α-cholestan-3β-ol-6-one | 20 uM | + | NA |
| N032-0003 | 12.5 uM | + | + |
| N066-0070 | 12.5 uM | + | + |
| N069-0071 | 3.13 uM | + | + |
| N069-0075 | 12.5 uM | + | + |
| 1080-0573 | 50 uM | − | + |
| N064-0028 | 50 uM | − | + |
| N066-0053 | 50 uM | − | + |

TABLE 9-continued

Analogs of cholestan that retained the ability to activate expression of the α7 integrin

| | | | | | R₁ | R₂ |
|---|---|---|---|---|---|---|
| N069-0073 | 10 uM | − | + | N032-0003 | OH | O-C(=O)-CH₃ (acetoxyethyl) |
| | | | | N066-0070 | OH | CH₂-CHO |
| | | | | N069-0071 | HO-N= | =N-OH |
| | | | | N069-0075 | HO-N= | C(=O)-O-ethyl |
| | | | | 8011-0437 | Structure Unavailable | |
| | | | | N064-0028 | OH | isopropyl |
| | | | | N066-0053 | OH | C(=O)-OH |
| | | | | N069-0073 | O-C(=O)-CH₃ | =N-OH |

Example 7

Compounds #1001, 1002 & 1003 Increased α7 Integrin Expression in Muscle

Using the muscle cell based assay to screen the DIVER-Set library of compounds (as described in Example 2), three compounds designed 1001, 1002 and 1003 all increased α7 integrin expression in muscle. Compound Nos. 1001, 1002 and 1003 are commercially available from ChemBridge Corporation (San Diego, Calif.). Compound No. 1001 is 3-methyl-2-[(2-oxo-2-phenylethyl)thio]-3H-spiro[benzo[h]quinazoline-5,1"-cyclopentan]-4(6H)-one (MW=417). Compound No. 1002 is 1-{2-[3-(4-methyl-1-piperazinyl)propoxy]Phenyl}-1-propanone hydrochloride (MW=327). Compound 1003 is 1{2-[3-(1-piperidinyl)propoxy}phenyl}-1-propanone hydrochloride (MW=312).

The dose-response curves to activate integrin expression by these compounds (as well as the chemical structures of such compounds) are provided in FIG. 9. These studies demonstrate the ability of such compounds to increase α7 integrin expression in muscle and support their use as agents to regulate α7 integrin modulated conditions, including muscular dystrophy. It is contemplated that analogs of compounds 1001, 1002 and 1003 could have similar effects. For example, it is contemplated that analogs of compounds 1001, 1002 and 1003 could be synthesized such as by the synthesis pathway provided in FIG. 10 and evaluated by the muscle cell base assay provided in Example 1 to determine their effects on α7 integrin expression in muscle.

Example 8

Laminin-111 Effects on α7 Integrin Expression and Muscular Dystrophy

The studies described in this example demonstrate the effectiveness of LAM-111 to increase α7 integrin levels and ameliorate the symptoms of disease in mdx and dy$^W$ mice. This data is included to demonstrate that enhancement of the α7 integrin is possible in vivo and as a therapeutic for muscular dystrophy. Thus, any of the disclosed α7β1 enhancers are believed to have similar in vivo effects as LAM-111 and thus, useful therapeutic agents for muscular dystrophy.

FACS analysis demonstrated that a 24 hour treatment of α7betaβ1-gal+/− myoblasts with 100 nM LAM-111 and a fluorescent β-gal substrate resulted in a nearly 10-fold increase in α7 integrin expression compared to PBS treatment (FIGS. 12A-12D) Immunoblot analysis demonstrated that a 24 hour treatment of C2C12 or DMD myoblasts with 100 nM LAM-111 resulted in an approximately 2-fold increase in α7B integrin expression compared to PBS treatment (FIGS. 13A-13D). Overall, these results demonstrated that application of LAM-111 to myogenic cells results in an enhancement of α7 integrin protein expression that acted at the level of transcription or mRNA stability. It is contemplated that the identified parent scaffolds (Tables 8 and 9) increase α7 integrin expression through a similar mechanism.

Figure 14V:
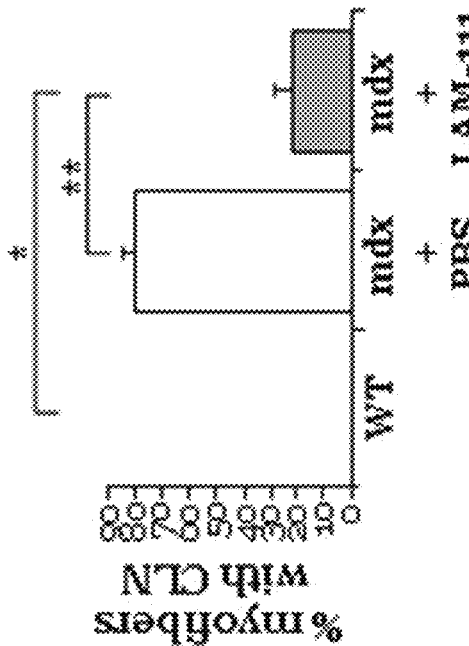
FIGS. 14V and 14W show percentage of Evans blue dye (EBD) positive myofibers (Panel V) and percentage of centrally-located nuclei (CLN) (Panel W) in the TA muscle of wild-type (black bar), PBS-treated mdx (white bar), and LAM-111 treated (gray bar) mdx mice. n=5 mice per group, 1000 fibers were counted per animal, *=p<0.05, **=p<0.001.
Figure 14W:
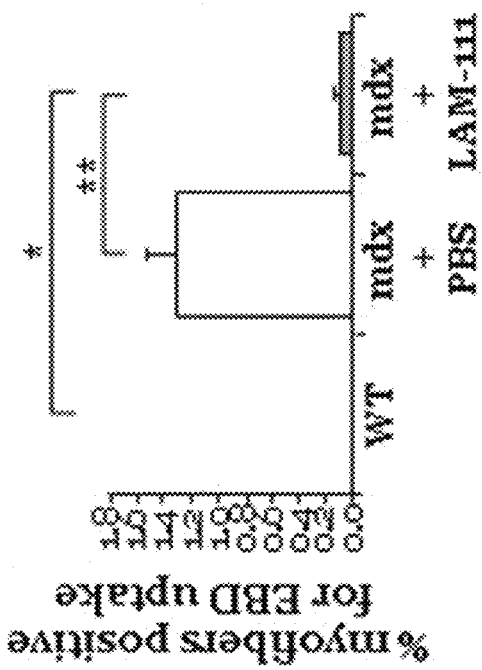
Figures 15A, 15B, 15C, 15D:
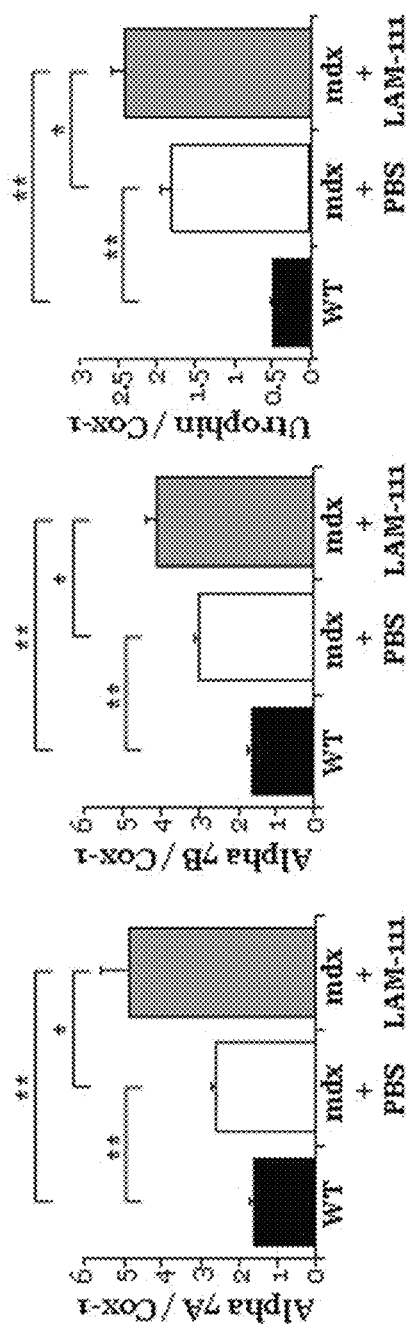
FIGS. 15A-15D shows the results of immunoblot detection and quantitation of skeletal muscle protein. Four weeks after one intramuscular injection of the TA muscle with PBS or LAM-111, TA muscles were subjected to western analysis (A), followed by densitometry of α7A (B), α7B (C), and utrophin (D). Densitometry values were normalized to a Cox-1 standard. *=p<0.05.

One intramuscular dose of 100 nM (100 ul) of purified LAM-111 into the tibialis anterior (TA) of 10 day old mdx mice resulted in distribution of LAM-111 to all myofibers, and resulted in a substantial reduction in the number of centrally nucleated and Evans blue dye (EBD) positive myofibers (FIGS. 14A-14W). These studies demonstrate that intramuscular delivery of LAM-111 protects mdx myofibers from degeneration.

Immunofluorescence analysis of both mdx treatment groups demonstrated enhancements of α7A and α7B integrin, and utrophin compared to wild-type animals, and LAM-111 treated mdx mice demonstrated a further increase in α7A and α7B integrin, and utrophin beyond PBS-treated mdx mice (FIGS. 14A-14W). Densitometry of immunoblots from protein extracts of PBS and LAM-111 treated TA demonstrated that both mdx treatment groups showed a statistically significant increase in expression of α7A and α7B integrin and utrophin compared to wild-type animals, and treatment of mdx mice with LAM-111 resulted in a further 100% increase in α7A, a 50% increase in α7B and 33% increase in utrophin beyond PBS-treated mdx mice (FIGS. 15A-15D). Characterization of mdx/utro−/− dKO mouse expressing transgenic (rat) α7X2B integrin demonstrated that the 150% increase in α7X2B could fully account for the amelioration of disease, and is consistent with the presented data demonstrating that the enhanced expression of α7 integrin in LAM-111 treated mdx mice likely accounts for the observed therapeutic effect.

Four weeks following a single systemic dose (i.p) of 1.0 mg/kg LAM-111 to mdx mice, immunofluorescence analysis demonstrated continued localization of LAM-111 around all cardiac myofibers, and myofibers of the diaphragm and gastrocnemius (FIGS. 16A-16K). LAM-111 was absent from wild-type muscles and PBS-treated mdx mice (59). These studies demonstrate that systemic delivery of LAM-111 prevents sarcolemmal disruption of mdx myofibers.

Figure 17A:
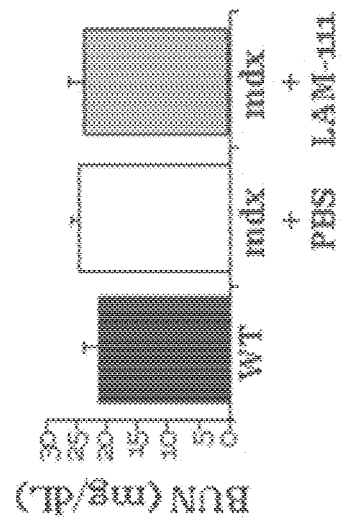
FIGS. 17A-17C includes three bar graphs illustrating the blood chemistry following intraperitoneal delivery of LAM-111. Serum creatine kinase (CK) activity (FIG. 17A), creatine (FIG. 17B) and Blood Urea Nitrogen (BUN) (FIG. 17C) in wild-type (black bars), PBS-treated mdx mice (white bars), and LAM-111-treated mdx mice (gray bars). n=5 mice per group, *=p<0.05 (59).
Figure 17B:
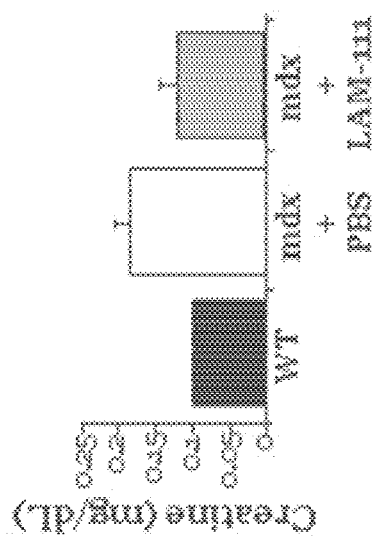
Figure 17C:
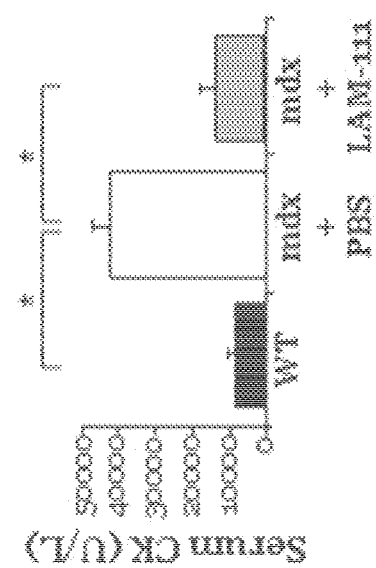

Systemic treatment of mdx mice with LAM-111 demonstrated a near normalization of serum creatine kinase activity compared to PBS-treated mdx mice, and LAM-111-treated mdx mice showed no significant change in serum creatine or blood urea nitrogen (BUN) (FIGS. 17A-17C). These data suggest that a single systemic dose of LAM-111 provided a body-wide stabilization of sarcolemma integrity without affecting kidney function.

Figures 18A, 18B:
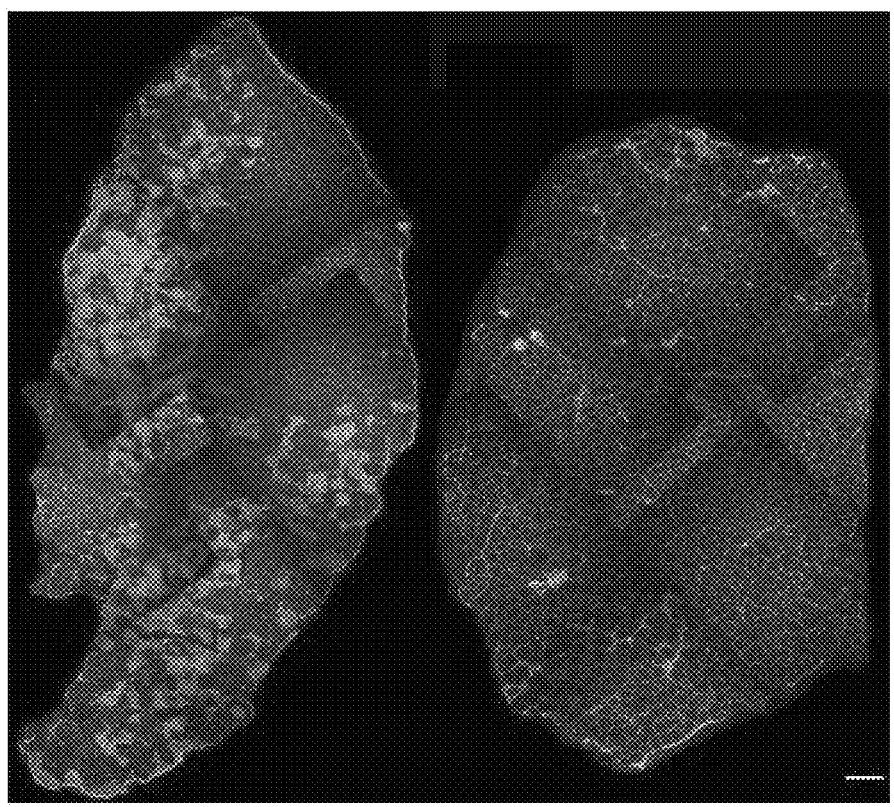
FIGS. 18A-18C shows that pretreatment with LAM-111 protects mdx TA from eccentric exercise-induced damage. Uptake of Evans blue dye in the TA of the mdx mice pretreated with PBS (FIG. 18A) or LAM-111 (FIG. 18B) and exercised on a downhill treadmill 4 weeks later. Percentage uptake of Evans blue dye in the TA of the mdx mice pretreated with PBS or LAM-111 and remained sedentary or were exercised on a downhill treadmill 2 weeks later (FIG. 18C). n=4 mice per group. Scale bar=200 um. **=p<0.001 (59).
Figure 18C:
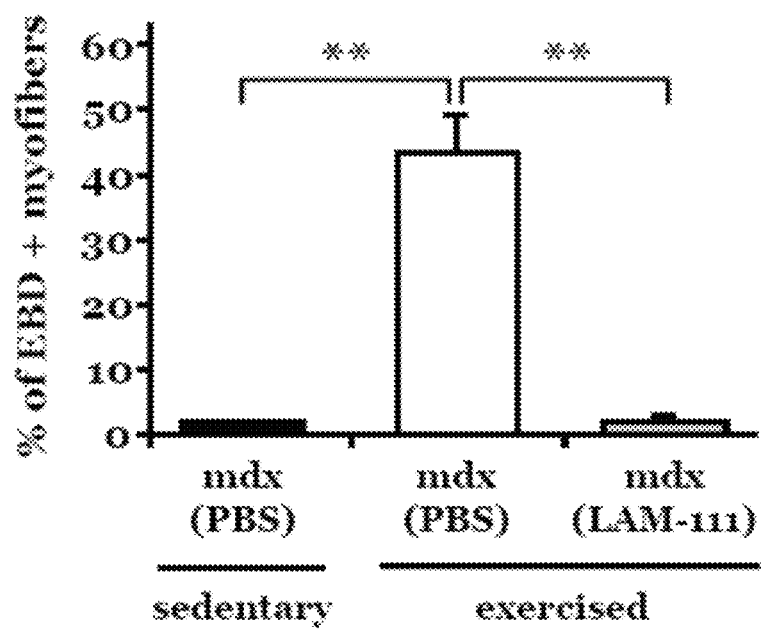

Ten day old mdx mice pretreated with a single systemic dose of PBS or 1.0 mg/kg LAM-111, and four weeks later subjected to eccentric downhill treadmill exercise, injection of Evan's blue dye and sacrifice 24 hours later were completely protected from sarcolemmal ruptures (FIGS. 18A-18C). These data suggest that a systemic delivery of LAM-111 protects myofibers from damaging eccentric exercise. It is contemplated that systemic delivery of the other disclosed α7β1 integrin expression enhancers would have similar protective effects on myofibers during exercise.

Treatment of mdx/utro−/− dKO mice with valproic acid resulted in activation of the AKT signaling pathway in muscle, improved mobility, reduced fibrosis, and reduced overall muscle disease. These results indicate that VPA is a candidate for the treatment of DMD and existing human safety data may expedite its development for treatment of DMD.

Figure 19:
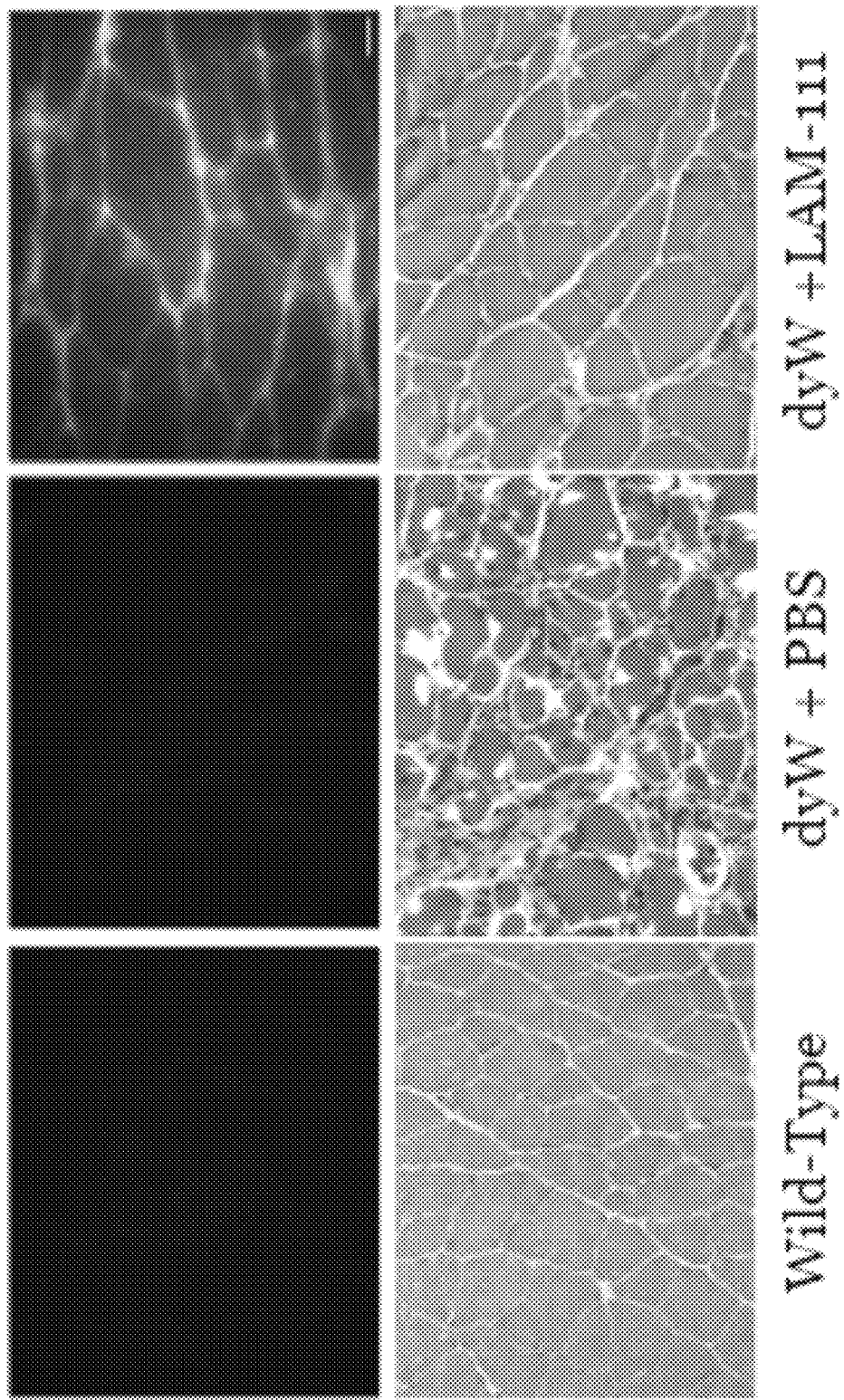
FIG. 19 shows that LAM-111 ameliorates muscle disease in the dyW mouse model for MDC1A. Immunofluorescence detection of LAM-111 (top) and H&E staining (bottom) of the skeletal muscle of WT, PBS-treated dyW, and LAM-111-treated dyW mice. Animals were injected i.p. twice weekly with 1 mg/kg of LAM-111 beginning at 10 days of age. Tissues were harvested at 7 weeks of age. Scale bar=20 uM
Figure 20A:
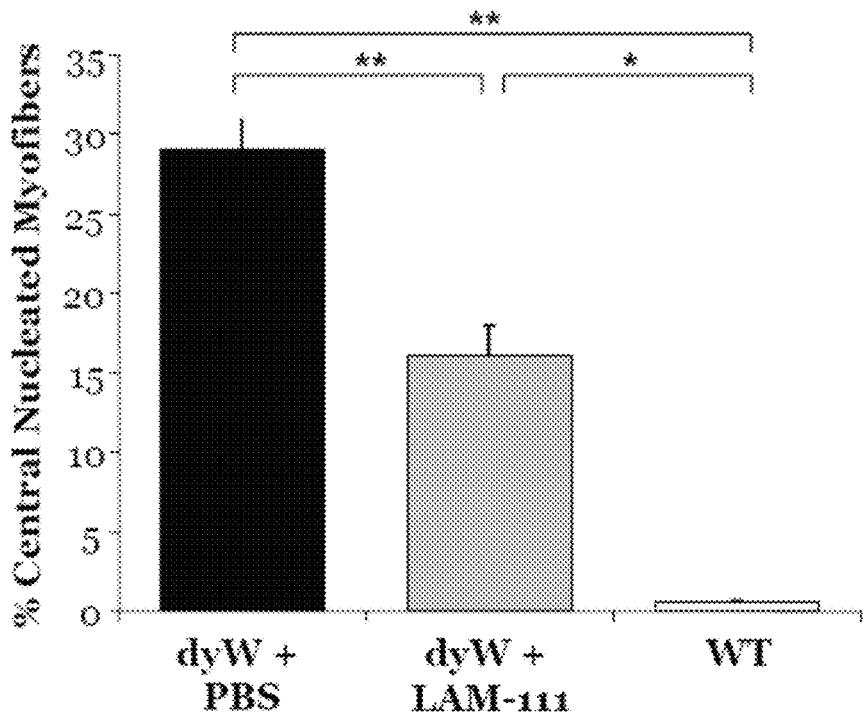
Figure 20A:
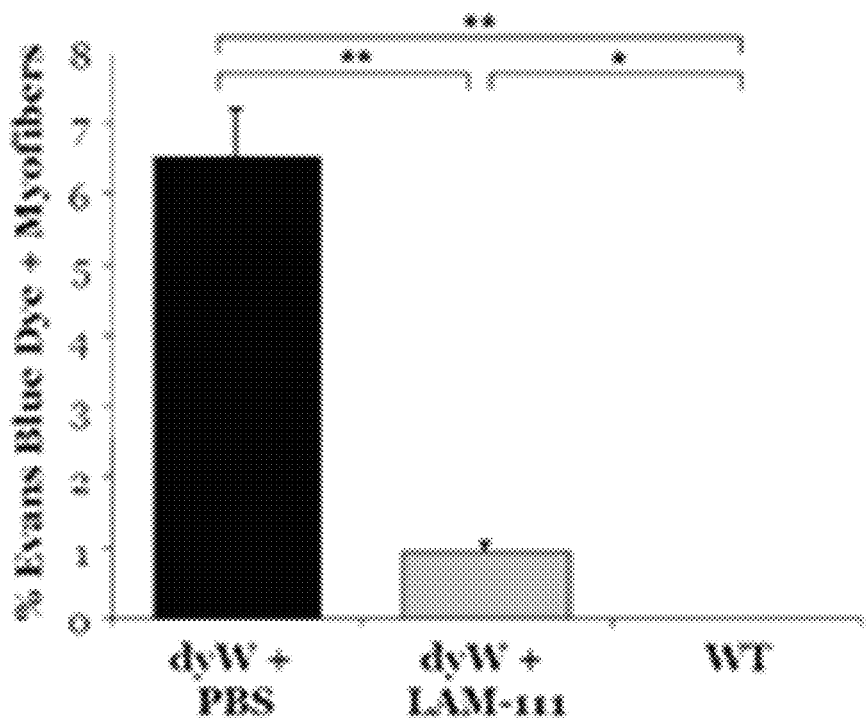
Figure 20C:
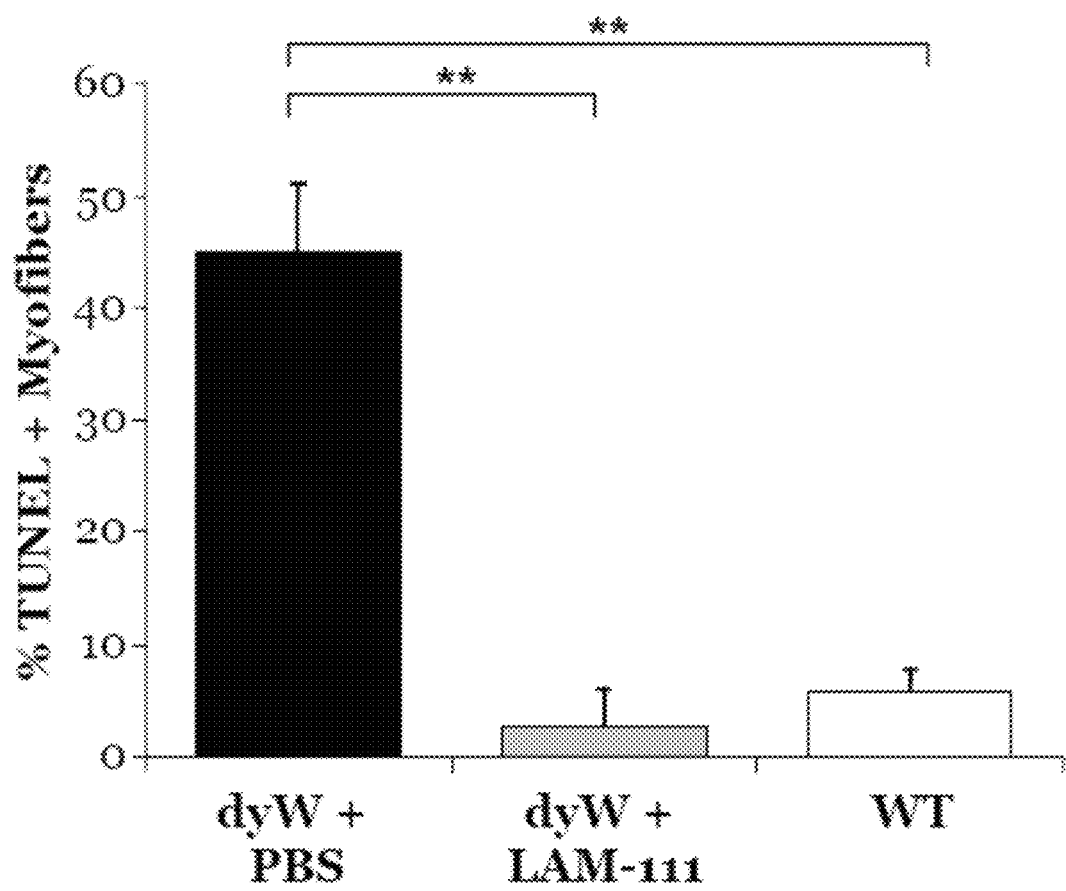
Figure 21:
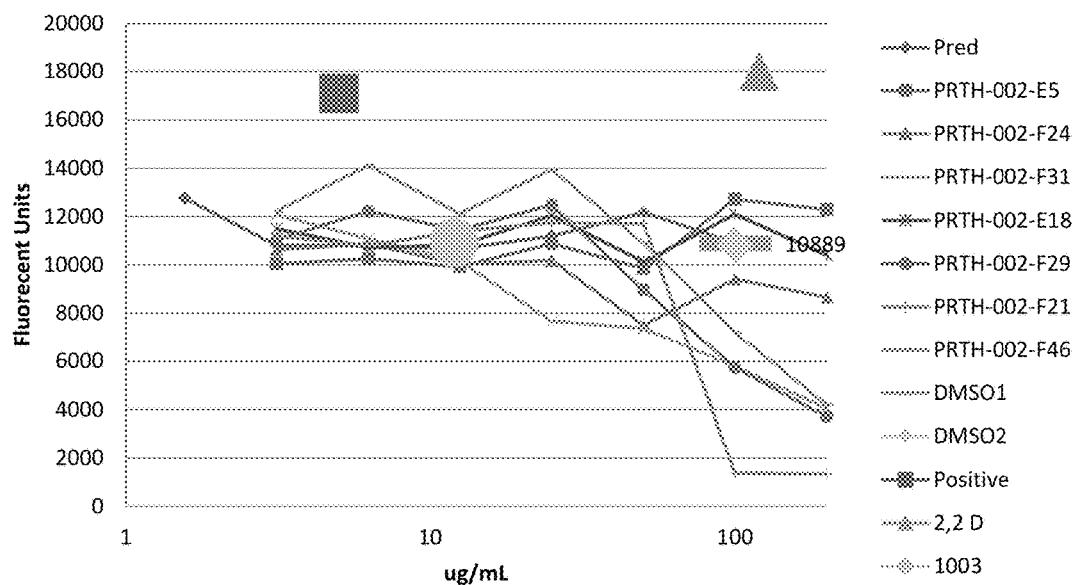
FIGS. 21-28 are dose response graphs illustrating the effect of disclosed analogs on α7 integrin promoter activity. Typical dose response curves showing the fold increase in reporter activity vs drug dose were obtained for specific analogs using α7βgal$^{+/-}$ myotubes.
Figure 22:
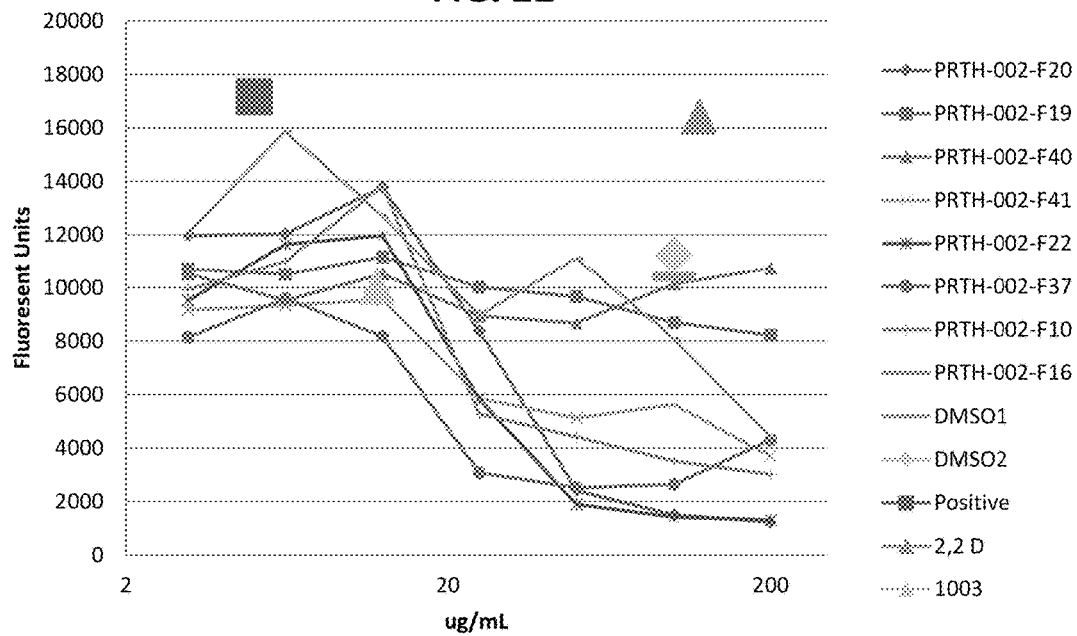
Figure 23:
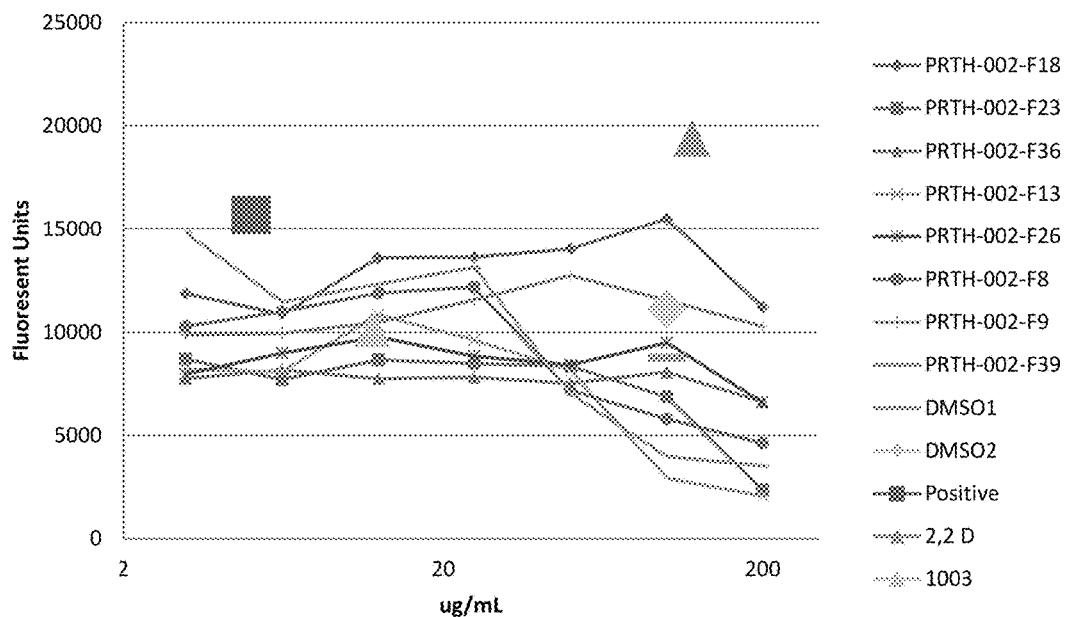
Figure 24:
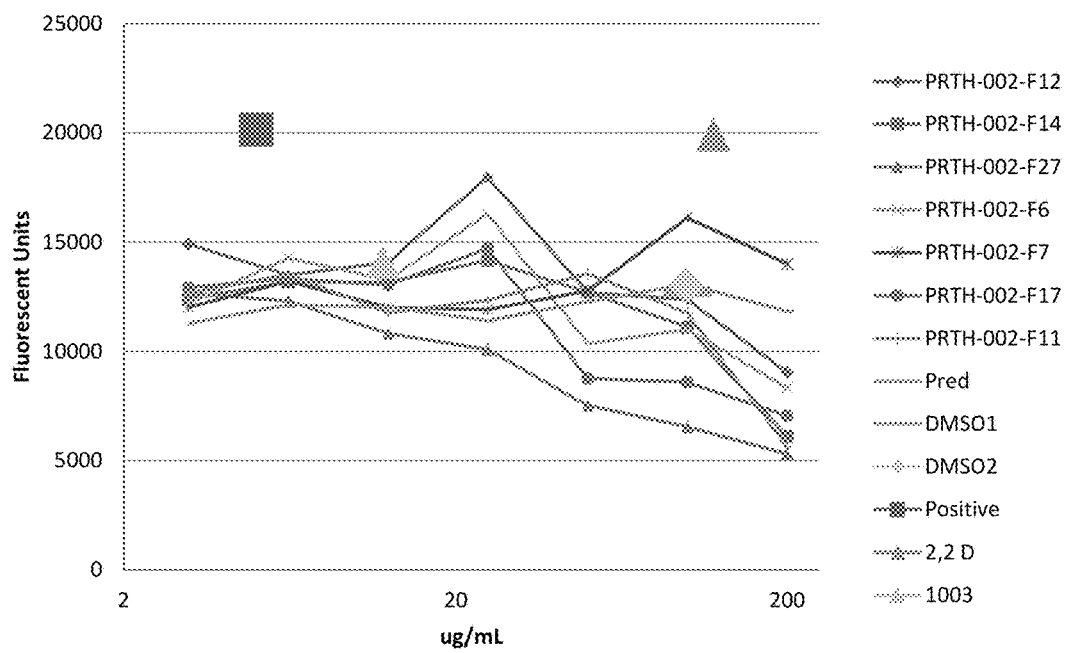
Figure 25:
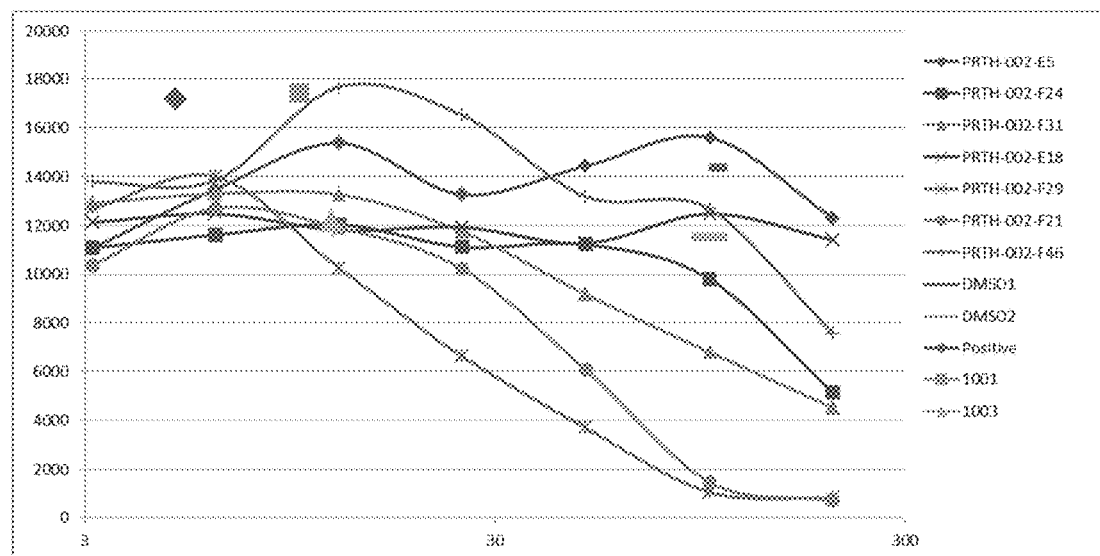
Figure 26:
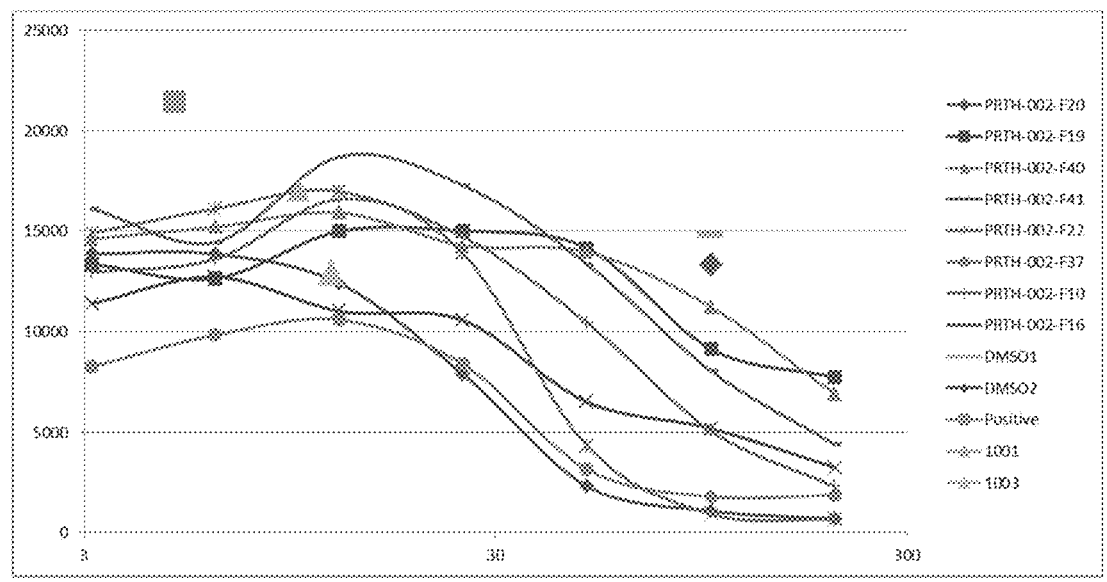
Figure 27:
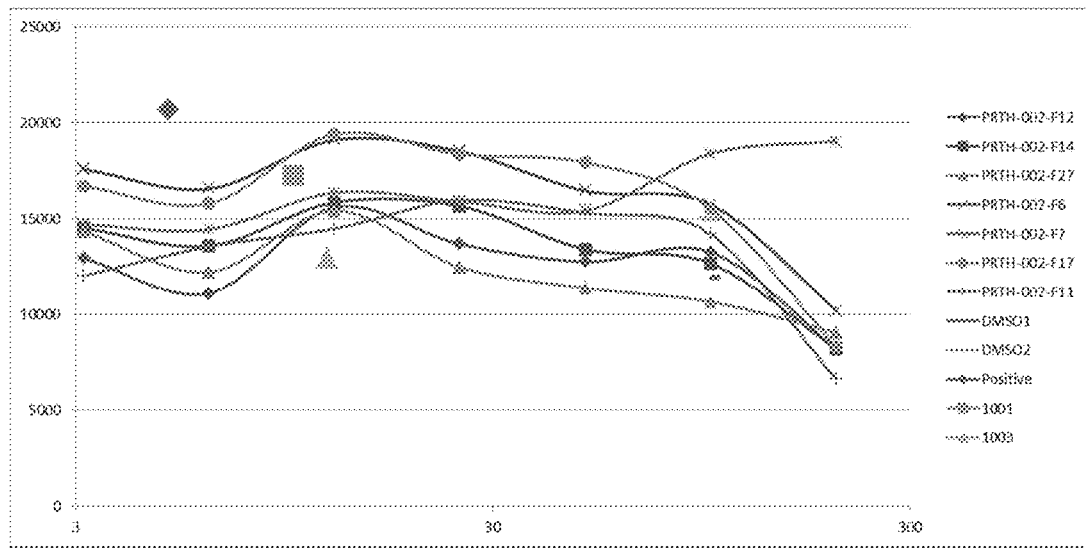
Figure 28:
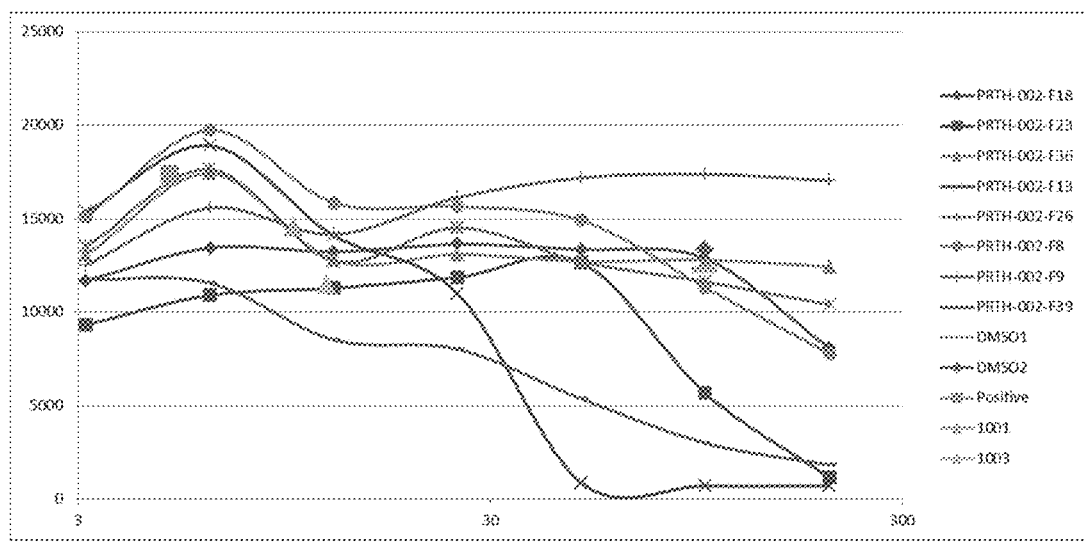
Figure 29A:
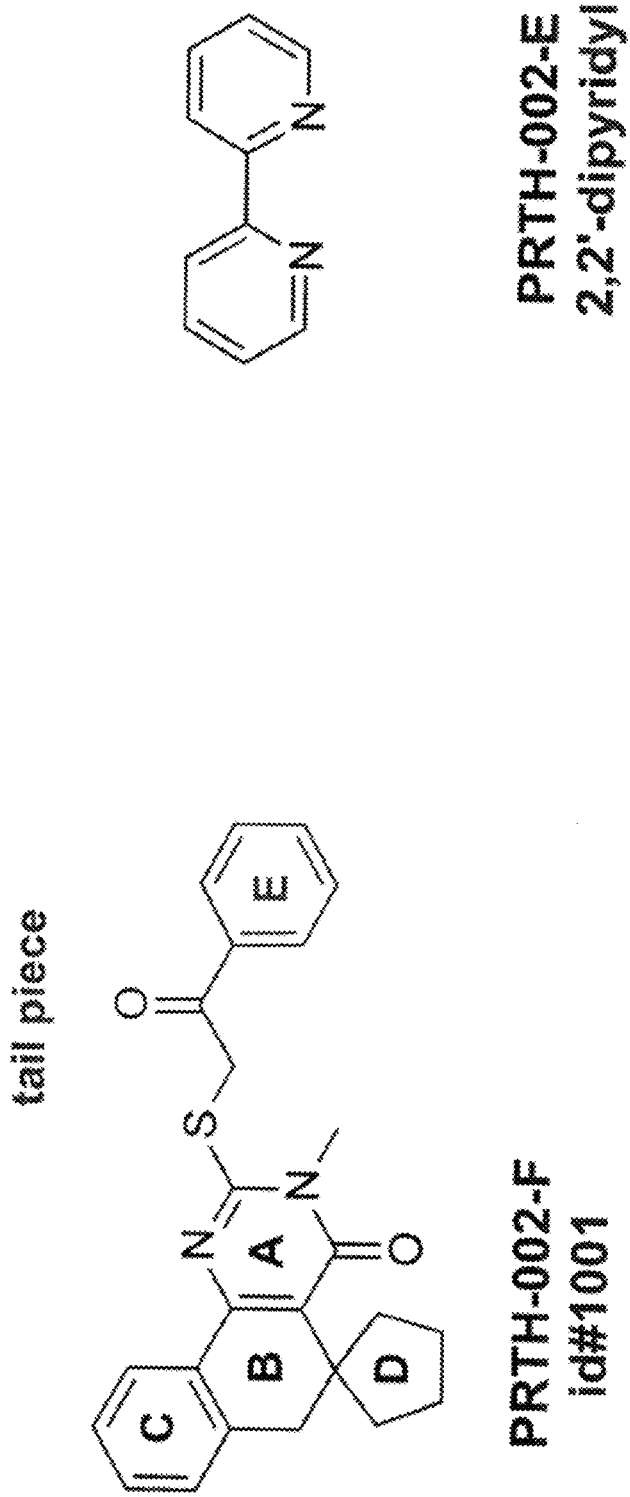
Figure 29B:
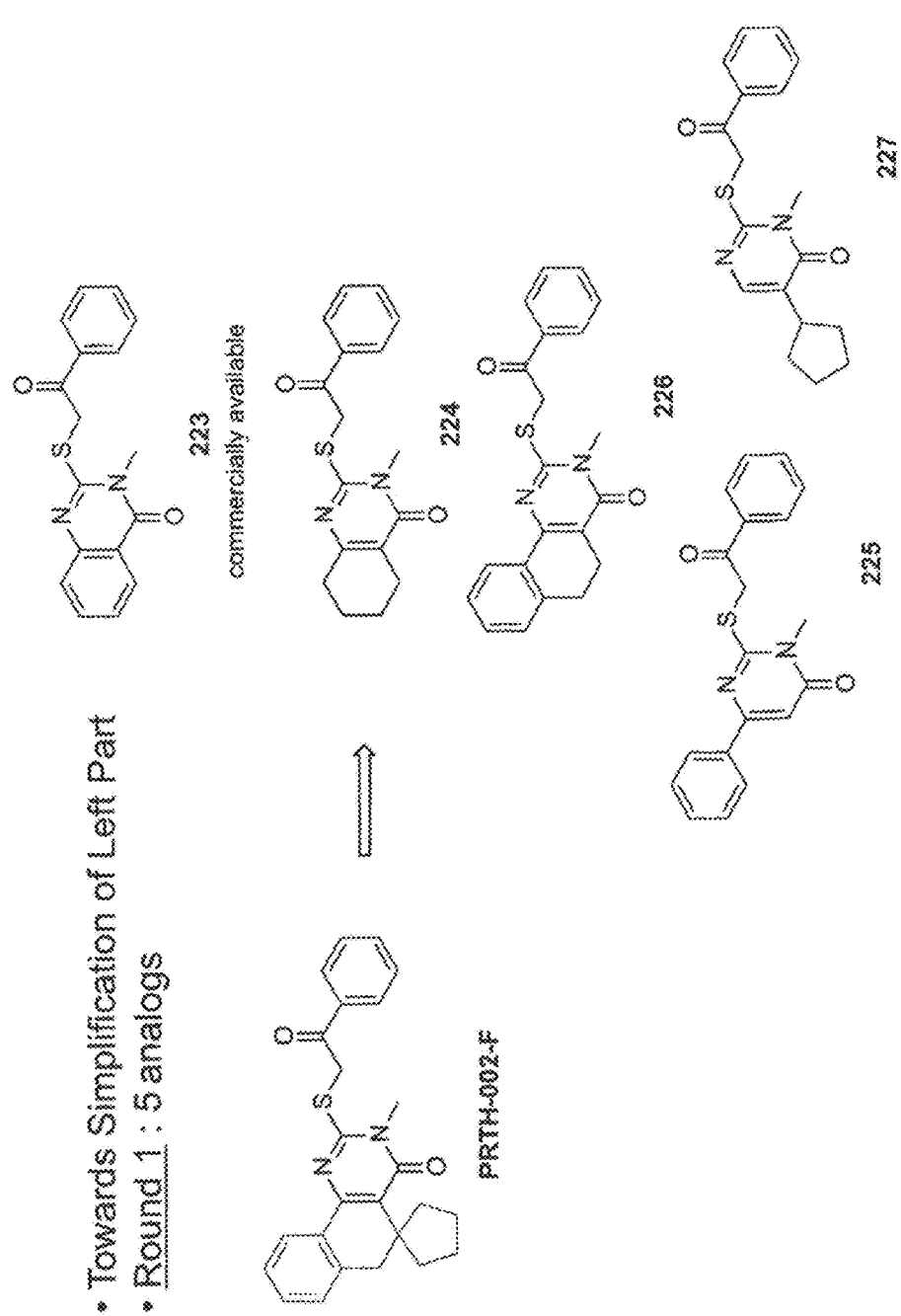
Figure 29F:
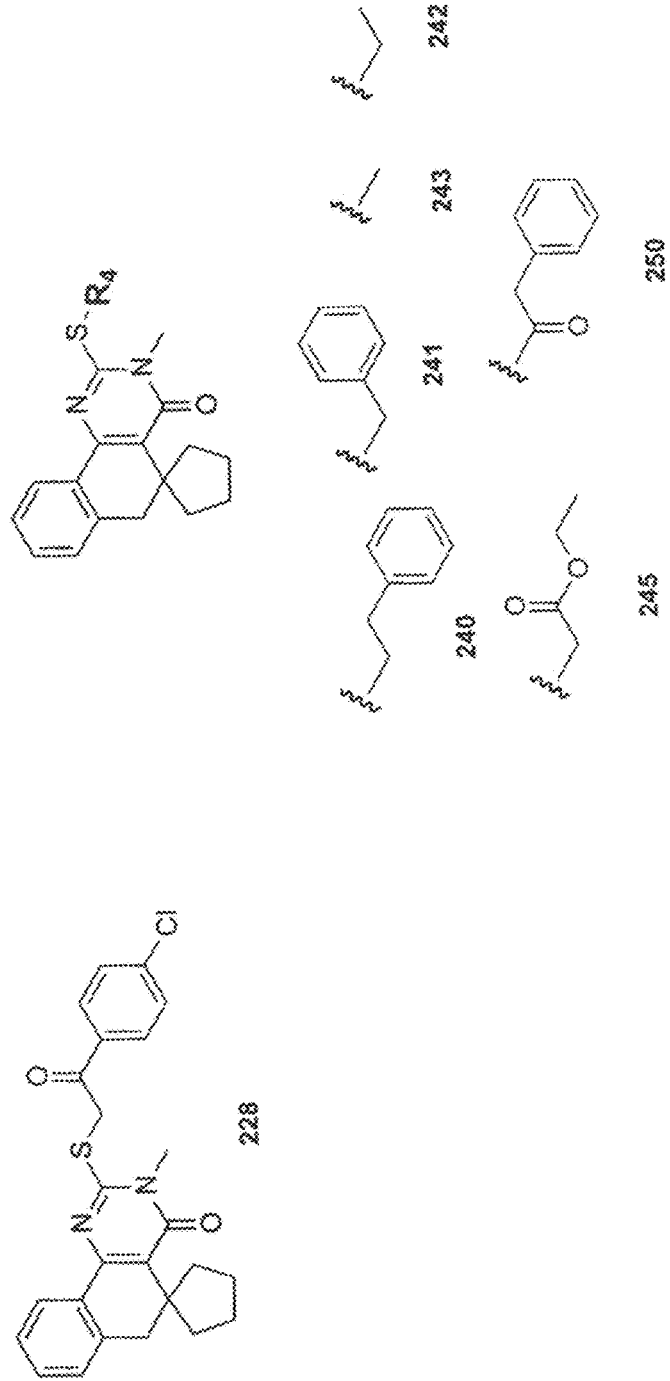
Figure 29G:
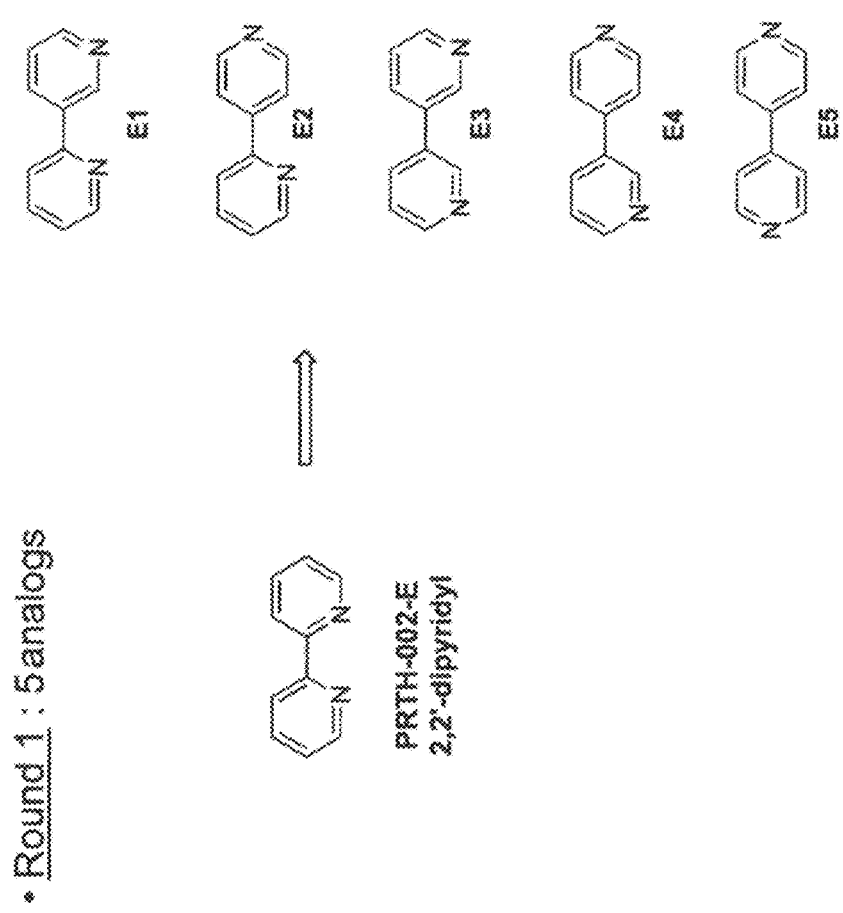
Figure 29H:
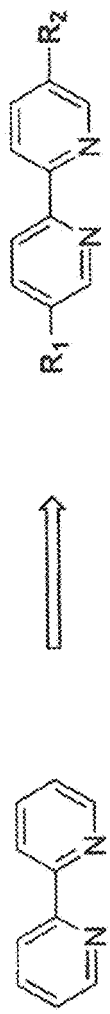

Systemically delivered LAM-111 localizes to skeletal muscle of dy$^W$ mice (FIG. 19-top panels), but required twice weekly doses to improve muscle pathology (FIG. 19-bottom panels) and reduce the percentage of myofibers containing centrally nucleated myofibers (FIG. 20A), Evans blue dye (FIG. 20B), and a TUNEL (apoptosis) reaction (FIG. 20C). Although body weights of LAM-111-treated dy$^W$ mice were not significantly different from PBS-treated dy$^W$ mice, PBS-treated dy$^W$ mice became moribund at 7 weeks of age (5.5 weeks post-injection) and had to be sacrificed while LAM-111-treated dy$^W$ mice sacrificed at 7 weeks of age as age matched controls were in much better health. These studies demonstrate that systemic delivery of LAM-111 prevents myofiber degeneration of dy$^W$ myofibers. It is contemplated that systemic delivery of the other disclosed α7β1 integrin expression enhancers would have similar effects on myofiber degeneration.

Figure 31:
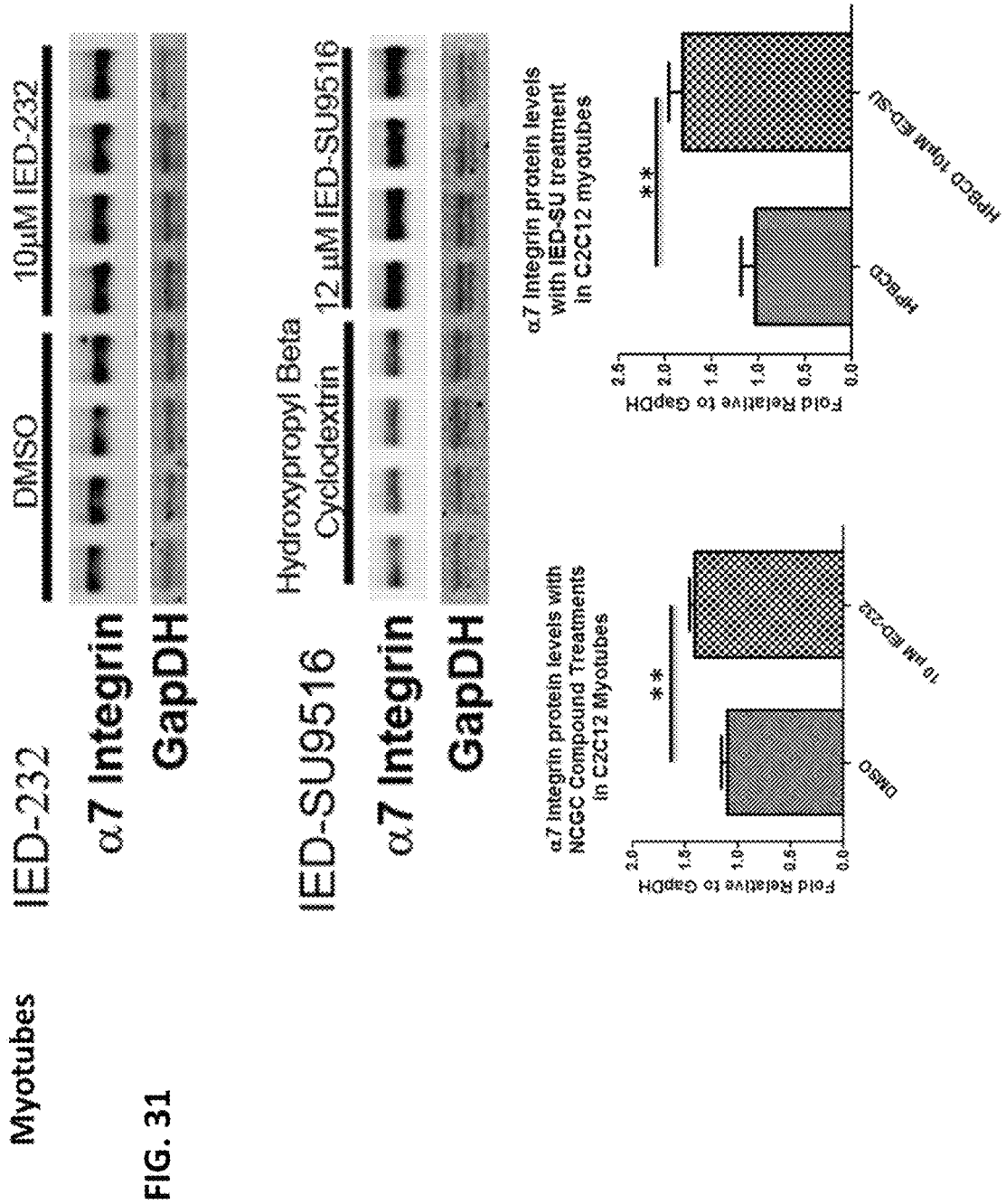
FIG. 31 is a digital image of Western Blots and quantitative analysis of α7 Integrin and GAPDH protein levels in C2C12 myotubes treated for 48 hours with DMSO control, 10 μM MLS000683232-01 (IED-232), Hydroxylpropyl-Beta-Cyclodextrin (HPBCD) control, or 12 μM SU9516 in HPBCD. Bands were quantified using Image J software and then graphed as α7 Integrin protein levels relative to GAPDH protein levels. * denotes a significant difference in relative protein levels with **p <0.01.
Figure 32:
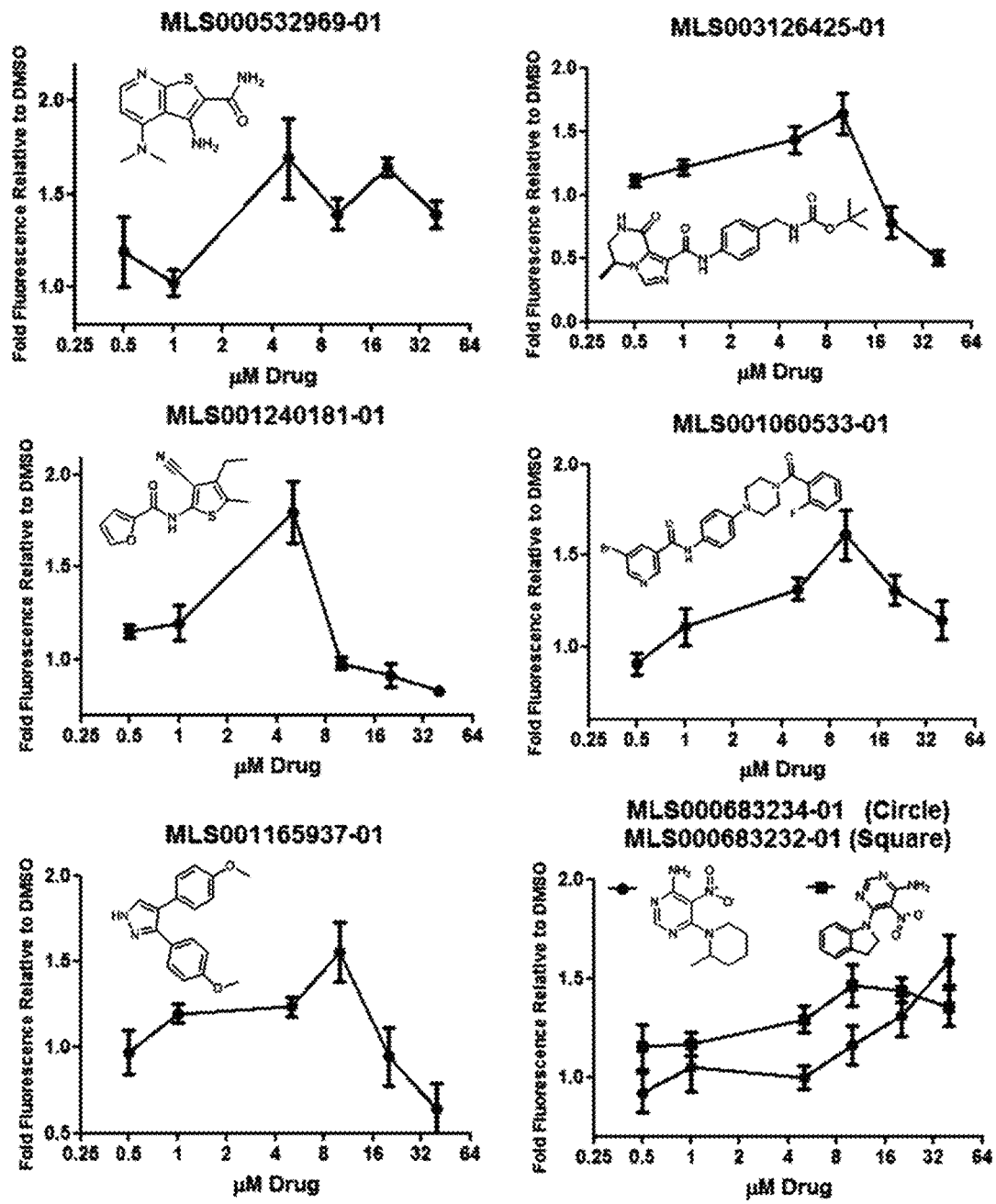
FIG. 32 is an image of results (fluorescence relative to DMSO at various concentrations of the agent) from a screen using particular embodiments of the disclosed α7β1 integrin modulatory agents.

FIG. 30 is a digital image illustrating the results of quantitative real-time PCR used to assess Itga7, Itgb1, and Lama2 transcript levels in C2C12 myoblasts and myotubes treated for 24 hours with DMSO control, 10 µM MLS000683232-01 (IED-232), 10 µM MLS001165937-01 (IED-937), Hydroxylpropyl-Beta-Cyclodextrin (HPBCD) control, or 12 µM SU9516 in HPBCD. FIG. 31 is a digital image of Western Blots and quantitative analysis of α7 Integrin and GAPDH protein levels in C2C12 myotubes treated for 48 hours with DMSO control, 10 µM MLS000683232-01 (IED-232), Hydroxylpropyl-Beta-Cyclodextrin (HPBCD) control, or 12 µM SU9516 in HPBCD. Bands were quantified using Image J software and then graphed as α7 Integrin protein levels relative to GAPDH protein levels. * denotes a significant difference in relative protein levels with **p <0.01.

Example 9

Additional Compounds for Increasing α7 Integrin Expression in Muscle

This example provides the structures (Table 11 below), exemplary synthesis reactions (FIGS. 29A-29H) and characterization studies (see FIGS. 21-28) for additional compounds for increasing α7 integrin expression in muscle. In TABLE 10
Exemplary Compounds
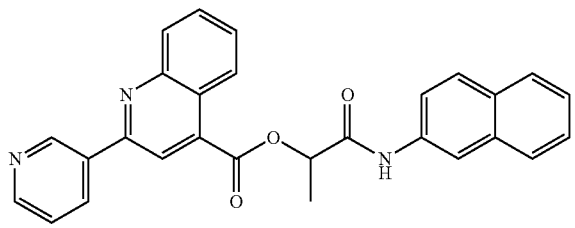 [SMILES: CC(OC(=O)c1cc(-c2cccnc2)nc2ccccc12)C(=O)Nc1ccc2ccccc2c1]
Compound 1
Potency: 1.122
Efficacy: 198.146
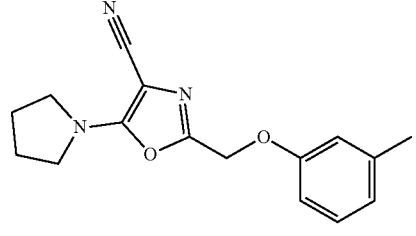 [SMILES: Cc1cccc(OCc2nc(C#N)c(N3CCCC3)o2)c1]
Compound 2
Potency: 3.5481
Efficacy: 228.085
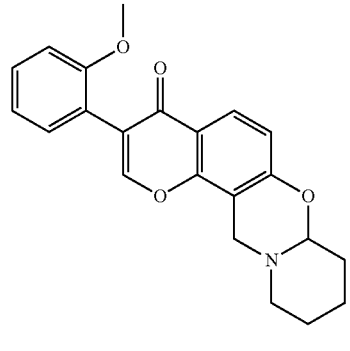 [SMILES: COc1ccccc1-c1coc2c3c(ccc2c1=O)OC1CCCCN1C3]
Compound 3
Potency: 2.2387
Efficacy: 193.433
Compound 4
Potency: 2.8184
Efficacy: 129.298

TABLE 10-continued
Exemplary Compounds
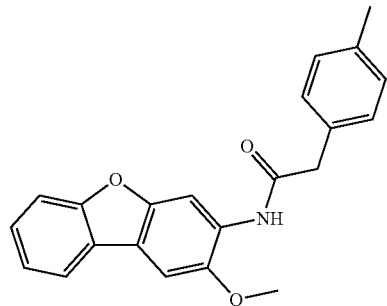 [SMILES: COc1cc2c(cc1NC(=O)Cc1ccc(C)cc1)oc1ccccc12]
Compound 5
Potency: 1.122
Efficacy: 92.4838
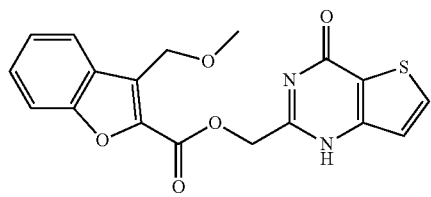 [SMILES: COCc1c(C(=O)OCc2nc(=O)c3sccc3[nH]2)oc2ccccc12]
Compound 6
Potency: 1.122
Efficacy: 128.12
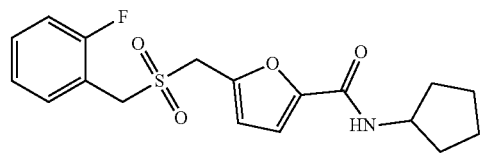 [SMILES: O=C(NC1CCCC1)c1ccc(CS(=O)(=O)Cc2ccccc2F)o1]
Compound 7
Potency: 4.4668
Efficacy: 94.9208
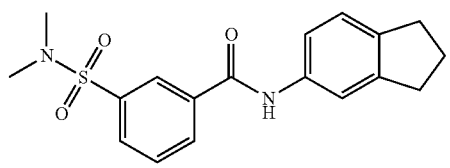 [SMILES: CN(C)S(=O)(=O)c1cccc(C(=O)Nc2ccc3c(c2)CCC3)c1]
Compound 8
Potency: 2.8184
Efficacy: 111.685
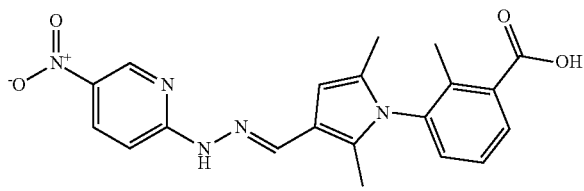
Compound 9
Potency: 2.8184
Efficacy: 122.703

TABLE 10-continued
Exemplary Compounds
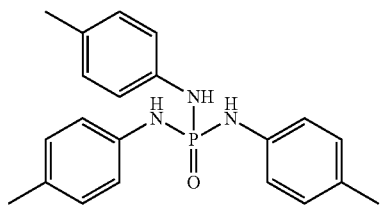
Compound 10
Potency: 3.1623
Efficacy: 102.022
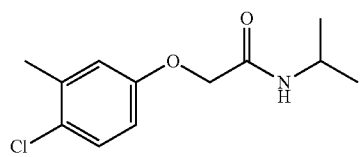 [SMILES: Cc1cc(OCC(=O)NC(C)C)ccc1Cl]
Compound 11
Potency: 3.9811
Efficacy: 101.893
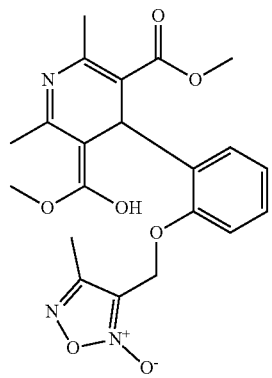 [SMILES: COC(=O)C1=C(C)N=C(C)/C(=C(/O)OC)C1c1ccccc1OCc1c(C)no[n+]1[O-]]
Compound 12
Potency: 2.8184
Efficacy: 92.9057
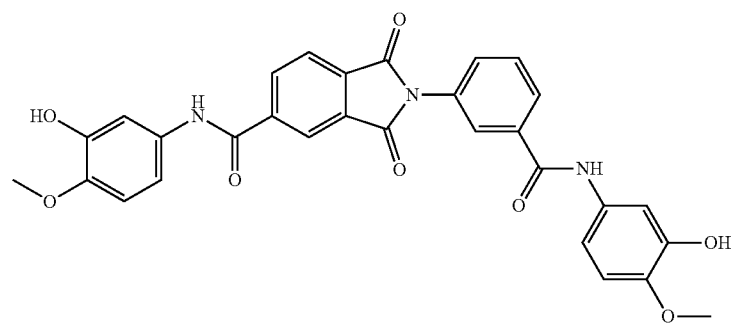
Compound 13
Potency: 4.4668
Efficacy: 121.996

TABLE 10-continued
Exemplary Compounds
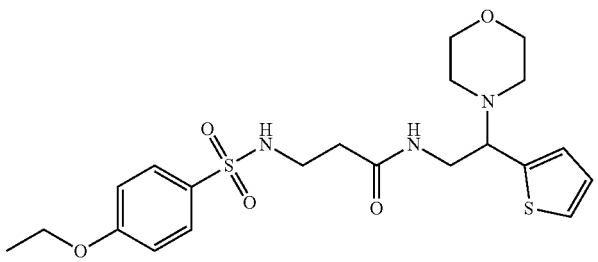 [SMILES: CCOc1ccc(S(=O)(=O)NCCC(=O)NCC(c2cccs2)N2CCOCC2)cc1]
Compound 14
Potency: 2.2387
Efficacy: 84.7736
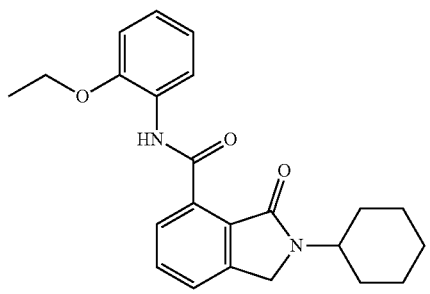 [SMILES: CCOc1ccccc1NC(=O)c1cccc2c1C(=O)N(C1CCCCC1)C2]
Compound 15
Potency: 3.1623
Efficacy: 91.3808
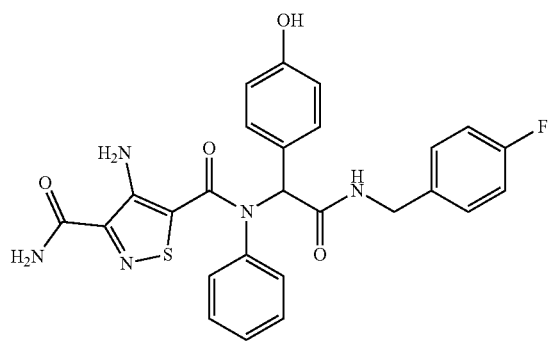 [SMILES: NC(=O)c1nsc(C(=O)N(c2ccccc2)C(C(=O)NCc2ccc(F)cc2)c2ccc(O)cc2)c1N]
Compound 16
Potency: 2.2387
Efficacy: 115.349
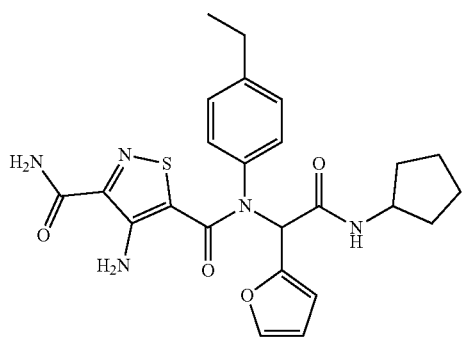 [SMILES: CCc1ccc(N(C(=O)c2snc(C(N)=O)c2N)C(C(=O)NC2CCCC2)c2ccco2)cc1]
Compound 17
Potency: 2.5119
Efficacy: 96.1948

TABLE 10-continued
Exemplary Compounds
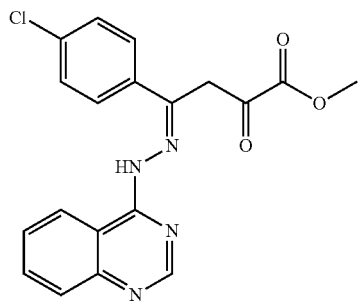 [SMILES: COC(=O)C(=O)C/C(=N/Nc1ncnc2ccccc12)c1ccc(Cl)cc1]
Compound 18
Potency: 10
Efficacy: 1751.56
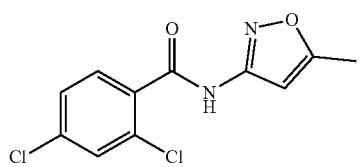 [SMILES: Cc1cc(NC(=O)c2ccc(Cl)cc2Cl)no1]
Compound 19
Potency: 1.4125
Efficacy: 81.6138
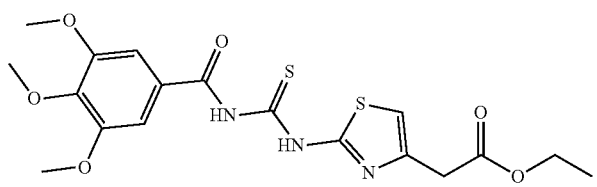 [SMILES: CCOC(=O)Cc1csc(NC(=S)NC(=O)c2cc(OC)c(OC)c(OC)c2)n1]
Compound 20
Potency: 3.5481
Efficacy: 101.579
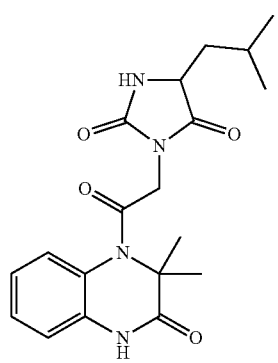 [SMILES: CC(C)CC1NC(=O)N(CC(=O)N2c3ccccc3NC(=O)C2(C)C)C1=O]
Compound 21
Potency: 5.6234
Efficacy: 92.2825
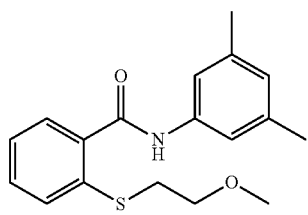 [SMILES: COCCSc1ccccc1C(=O)Nc1cc(C)cc(C)c1]
Compound 22
Potency: 4.4668
Efficacy: 83.4252

TABLE 10-continued
Exemplary Compounds
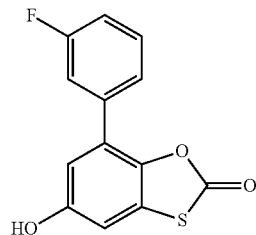 [SMILES: O=c1oc2c(-c3cccc(F)c3)cc(O)cc2s1]
Compound 23
Potency: 3.9811
Efficacy: 85.1623
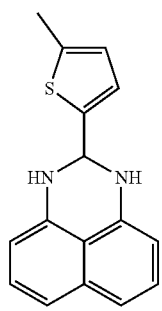 [SMILES: Cc1ccc(C2Nc3cccc4cccc(c34)N2)s1]
Compound 24
Potency: 3.1623
Efficacy: 76.9771
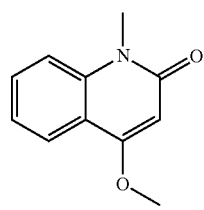
Compound 25
Potency: 2.2387
Efficacy: 82.8995
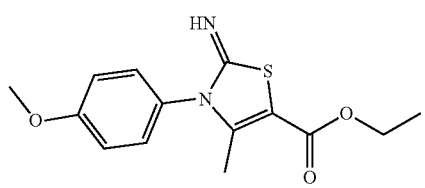 [SMILES: CCOC(=O)c1sc(=N)n(-c2ccc(OC)cc2)c1C]
Compound 26
Potency: 1.9953
Efficacy: 95.7363
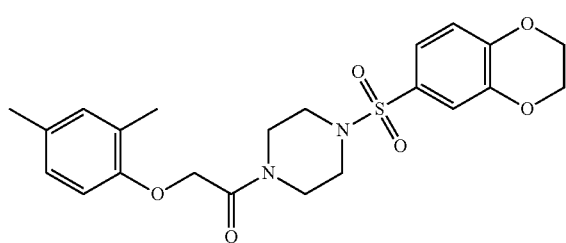 [SMILES: Cc1ccc(OCC(=O)N2CCN(S(=O)(=O)c3ccc4c(c3)OCCO4)CC2)c(C)c1]
Compound 27
Potency: 1.9953
Efficacy: 81.8506

TABLE 10-continued
Exemplary Compounds
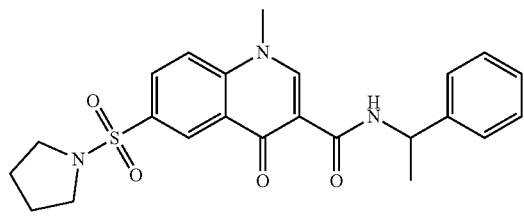 [SMILES: CC(NC(=O)c1cn(C)c2ccc(S(=O)(=O)N3CCCC3)cc2c1=O)c1ccccc1]
Compound 28
Potency: 2.8184
Efficacy: 92.0171
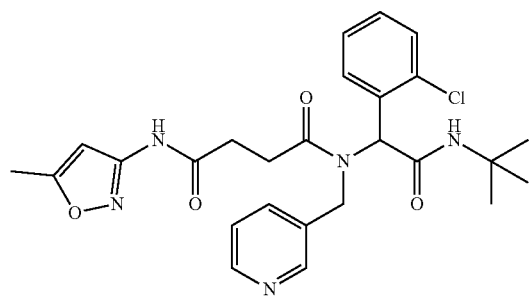 [SMILES: Cc1cc(NC(=O)CCC(=O)N(Cc2cccnc2)C(C(=O)NC(C)(C)C)c2ccccc2Cl)no1]
Compound 29
Potency: 3.9811
Efficacy: 81.1658
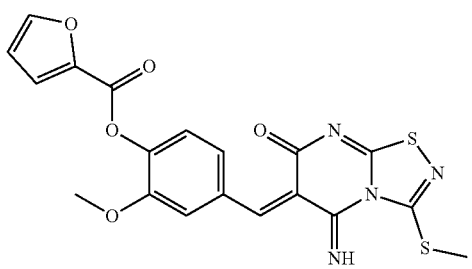 [SMILES: COc1cc(/C=C2/C(=N)N3C(SC)=NSC3=NC2=O)ccc1OC(=O)c1ccco1]
Compound 30
Potency: 3.9811
Efficacy: 92.7977
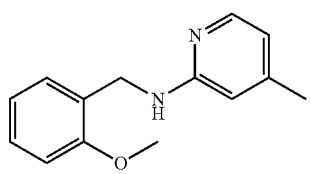 [SMILES: COc1ccccc1CNc1cc(C)ccn1]
Compound 31
Potency: 2.5119
Efficacy: 86.4354
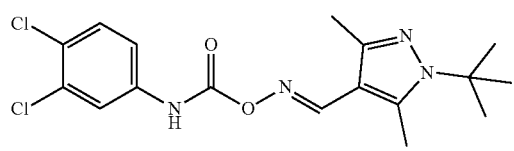 [SMILES: Cc1nn(C(C)(C)C)c(C)c1/C=N/OC(=O)Nc1ccc(Cl)c(Cl)c1]
Compound 32
Potency: 2.8184
Efficacy: 88.796

TABLE 10-continued
Exemplary Compounds
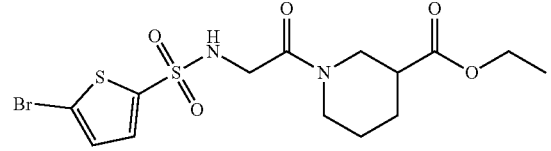 [SMILES: CCOC(=O)C1CCCN(C(=O)CNS(=O)(=O)c2ccc(Br)s2)C1]
Potency: 1.9953
Efficacy: 83.3258
Compound 33
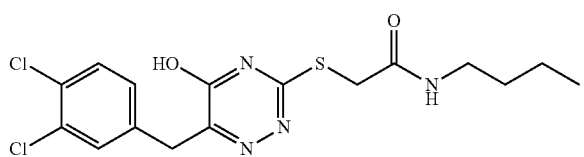 [SMILES: CCCCNC(=O)CSc1nnc(Cc2ccc(Cl)c(Cl)c2)c(O)n1]
Potency: 1.4125
Efficacy: 70.4537
Compound 34
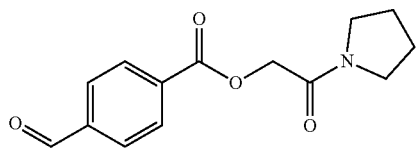 [SMILES: O=Cc1ccc(C(=O)OCC(=O)N2CCCC2)cc1]
Potency: 2.5119
Efficacy: 72.7515
Compound 35
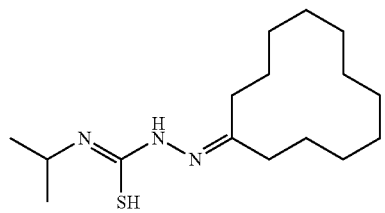 [SMILES: CC(C)/N=C(\S)NN=C1CCCCCCCCCCC1]
Potency: 3.1623
Efficacy: 75.7047
Compound 36
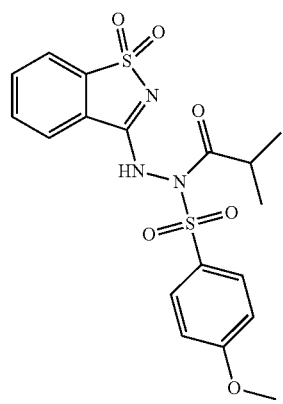 [SMILES: COc1ccc(S(=O)(=O)N(NC2=NS(=O)(=O)c3ccccc32)C(=O)C(C)C)cc1]
Potency: 2.5119
Efficacy: 77.0458
Compound 37

TABLE 10-continued

Exemplary Compounds

Compound 38

Potency: 4.4668
Efficacy: 75.5605

Compound 39

Potency: 3.5481
Efficacy: 78.5404

Compound 40

Potency: 14.1254
Efficacy: 436.691

Compound 41

Potency: 14.1254
Efficacy: 447.862

Compound 42

Potency: 14.1254
Efficacy: 475.262

Compound 43

Potency: 3.9811
Efficacy: 148.01

TABLE 10-continued
Exemplary Compounds
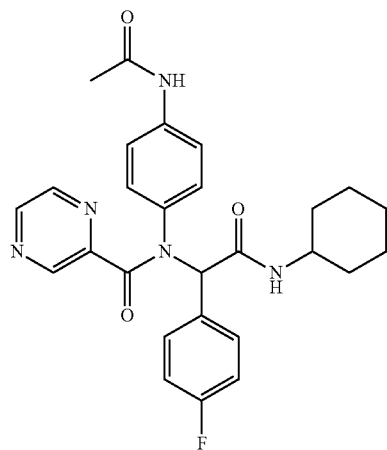 [SMILES: CC(=O)Nc1ccc(N(C(=O)c2cnccn2)C(C(=O)NC2CCCCC2)c2ccc(F)cc2)cc1]
Compound 44
Potency: 11.2202
Efficacy: 328.277
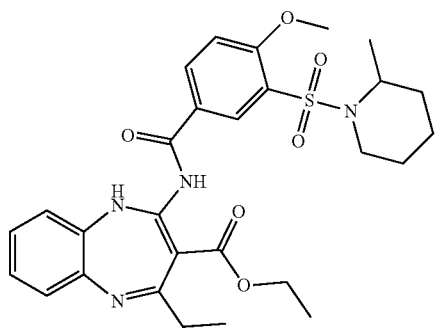 [SMILES: CCOC(=O)C1=C(NC(=O)c2ccc(OC)c(S(=O)(=O)N3CCCCC3C)c2)Nc2ccccc2N=C1CC]
Compound 45
Potency: 14.1254
Efficacy: 426.535
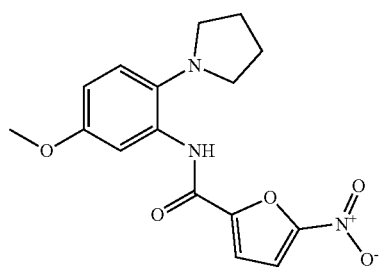 [SMILES: COc1ccc(N2CCCC2)c(NC(=O)c2ccc([N+](=O)[O-])o2)c1]
Compound 46
Potency: 7.9433
Efficacy: 231.415
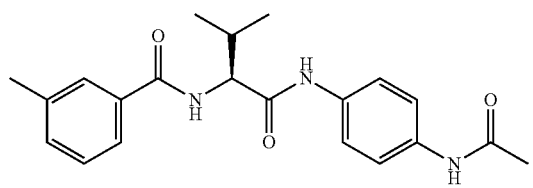 [SMILES: CC(=O)Nc1ccc(NC(=O)[C@@H](NC(=O)c2cccc(C)c2)C(C)C)cc1]
Compound 47
Potency: 5.6234
Efficacy: 141.317

TABLE 10-continued
Exemplary Compounds
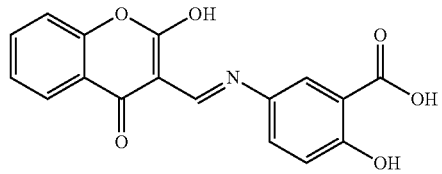 [SMILES: O=C(O)c1cc(/N=C/c2c(O)oc3ccccc3c2=O)ccc1O]
Potency: 7.0795
Efficacy: 214.145
Compound 48
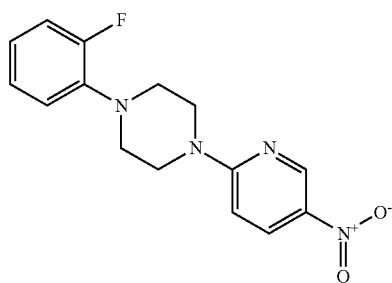 [SMILES: O=[N+]([O-])c1ccc(N2CCN(c3ccccc3F)CC2)nc1]
Potency: 5.6234
Efficacy: 150.998
Compound 49
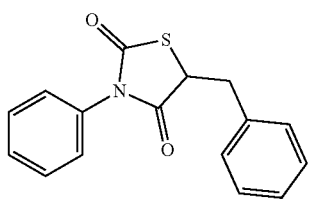 [SMILES: O=C1SC(Cc2ccccc2)C(=O)N1c1ccccc1]
Potency: 7.9433
Efficacy: 181.323
Compound 50
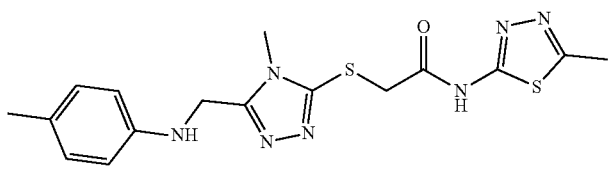
Potency: 10
Efficacy: 273.425
Compound 51
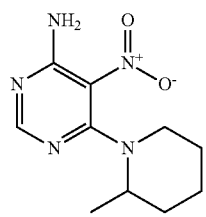 [SMILES: CC1CCCCN1c1ncnc(N)c1[N+](=O)[O-]]
Potency: 4.4668
Efficacy: 165.293
Compound 52

TABLE 10-continued

Exemplary Compounds

Compound 53

Potency: 7.0795
Efficacy: 163.55

Compound 54

Potency: 12.5893
Efficacy: 222.708

Compound 55

Potency: 12.5893
Efficacy: 271.246

Compound 56

Potency: 3.9811
Efficacy: 88.764

Compound 57

Potency: 4.4668
Efficacy: 115.732

TABLE 10-continued
Exemplary Compounds
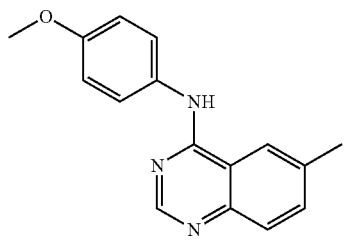
Potency: 3.5481
Efficacy: 137.991
Compound 58
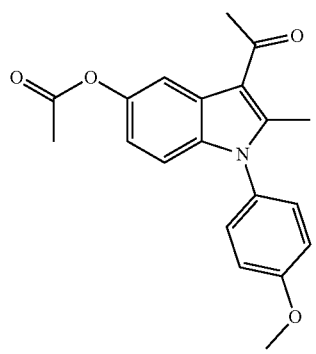 [SMILES: COc1ccc(-n2c(C)c(C(C)=O)c3cc(OC(C)=O)ccc32)cc1]
Potency: 10
Efficacy: 188.981
Compound 59
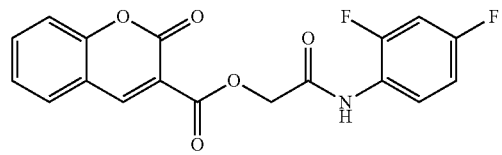 [SMILES: O=C(COC(=O)c1cc2ccccc2oc1=O)Nc1ccc(F)cc1F]
Potency: 4.4668
Efficacy: 128.904
Compound 60
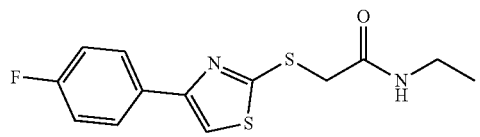 [SMILES: CCNC(=O)CSc1nc(-c2ccc(F)cc2)cs1]
Potency: 5.0119
Efficacy: 140.322
Compound 61
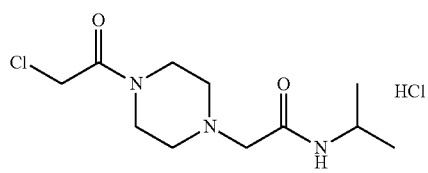 [SMILES: CC(C)NC(=O)CN1CCN(C(=O)CCl)CC1 ; Cl]
Potency: 7.0795
Efficacy: 186.257
Compound 62

TABLE 10-continued
Exemplary Compounds
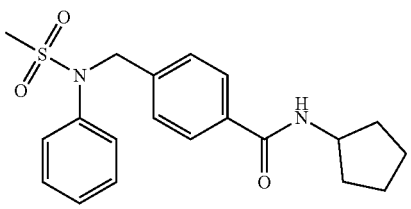 [SMILES: CS(=O)(=O)N(Cc1ccc(C(=O)NC2CCCC2)cc1)c1ccccc1]
Potency: 10
Efficacy: 200.43
Compound 63
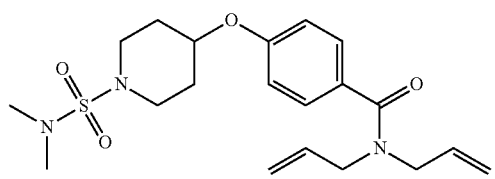 [SMILES: C=CCN(CC=C)C(=O)c1ccc(OC2CCN(S(=O)(=O)N(C)C)CC2)cc1]
Potency: 5.0119
Efficacy: 134.919
Compound 64
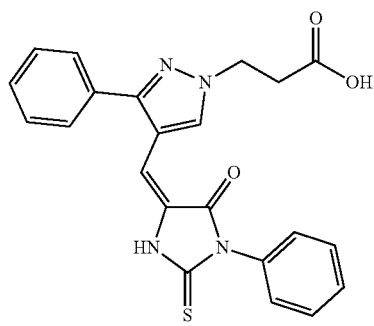 [SMILES: O=C(O)CCn1cc(/C=C2/NC(=S)N(c3ccccc3)C2=O)c(-c2ccccc2)n1]
Potency: 19.9526
Efficacy: 491.985
Compound 65
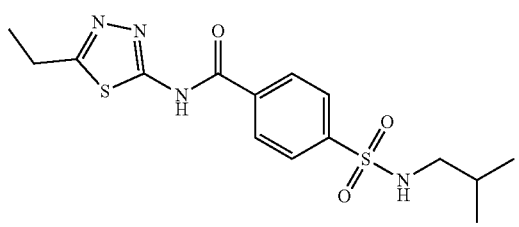 [SMILES: CCc1nnc(NC(=O)c2ccc(S(=O)(=O)NCC(C)C)cc2)s1]
Potency: 12.5893
Efficacy: 215.25
Compound 66
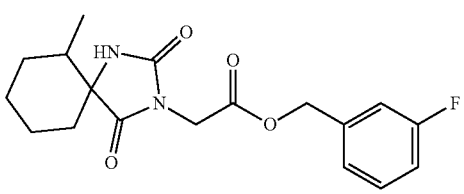 [SMILES: CC1CCCCC12NC(=O)N(CC(=O)OCc1cccc(F)c1)C2=O]
Potency: 10
Efficacy: 157.616
Compound 67

TABLE 10-continued
Exemplary Compounds
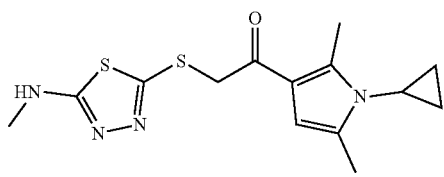 [SMILES: CNc1nnc(SCC(=O)c2cc(C)n(C3CC3)c2C)s1]
Compound 68
Potency: 12.5893
Efficacy: 239.617
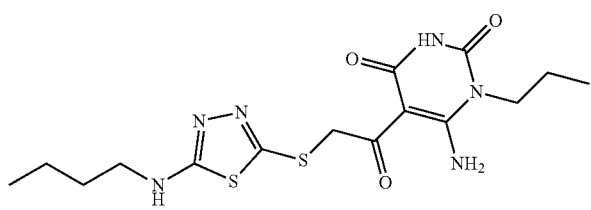 [SMILES: CCCCNc1nnc(SCC(=O)c2c(N)n(CCC)c(=O)[nH]c2=O)s1]
Compound 69
Potency: 3.9811
Efficacy: 90.5081
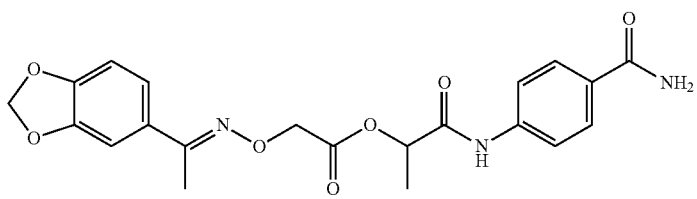 [SMILES: C/C(=N\OCC(=O)OC(C)C(=O)Nc1ccc(C(N)=O)cc1)c1ccc2c(c1)OCO2]
Compound 70
Potency: 4.4668
Efficacy: 115.234
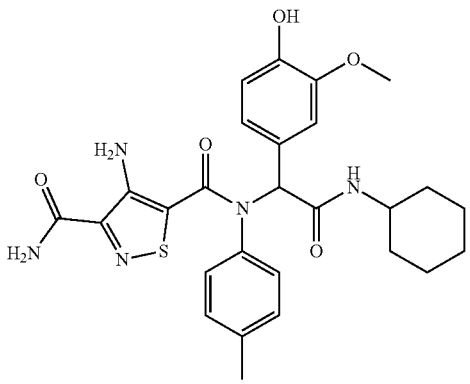 [SMILES: COc1cc(C(C(=O)NC2CCCCC2)N(C(=O)c2snc(C(N)=O)c2N)c2ccc(C)cc2)ccc1O]
Compound 71
Potency: 7.9433
Efficacy: 124.512
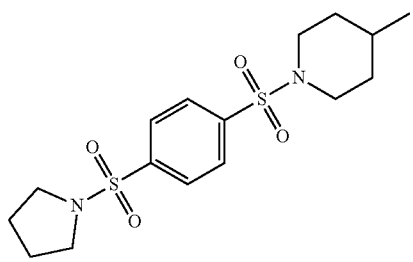 [SMILES: CC1CCN(S(=O)(=O)c2ccc(S(=O)(=O)N3CCCC3)cc2)CC1]
Compound 72
Potency: 8.9125
Efficacy: 138.663

TABLE 10-continued
Exemplary Compounds
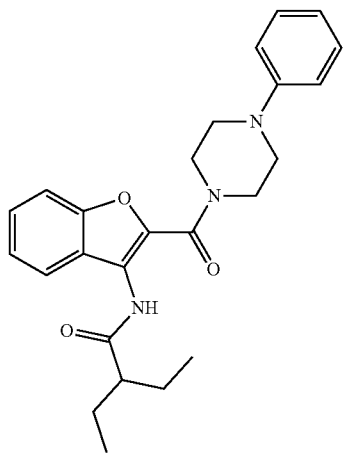 [SMILES: CCC(CC)C(=O)Nc1c(C(=O)N2CCN(c3ccccc3)CC2)oc2ccccc12]
Compound 73
Potency: 12.5893
Efficacy: 170.328
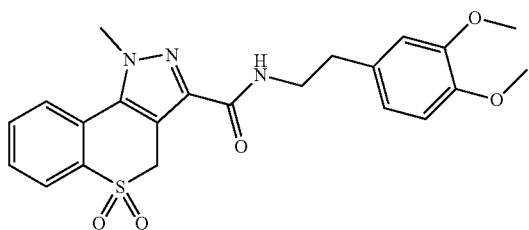 [SMILES: COc1ccc(CCNC(=O)c2nn(C)c3c2CS(=O)(=O)c2ccccc2-3)cc1OC]
Compound 74
Potency: 4.4668
Efficacy: 109.274
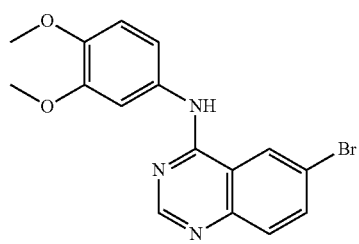 [SMILES: COc1ccc(Nc2ncnc3ccc(Br)cc23)cc1OC]
Compound 75
Potency: 3.9811
Efficacy: 71.4431
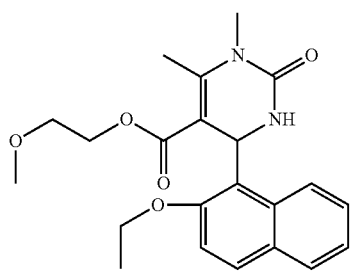 [SMILES: CCOc1ccc2ccccc2c1C1NC(=O)N(C)C(C)=C1C(=O)OCCOC]
Compound 76
Potency: 6.3096
Efficacy: 114.425

TABLE 10-continued
Exemplary Compounds
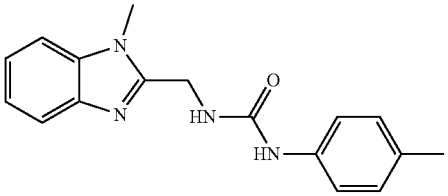 [SMILES: Cc1ccc(NC(=O)NCc2nc3ccccc3n2C)cc1]
Potency: 4.4668
Efficacy: 121.35
Compound 77
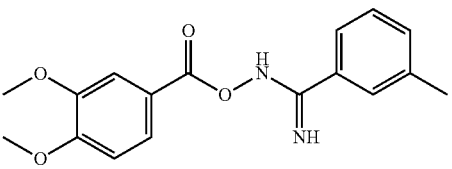
Potency: 10
Efficacy: 152.941
Compound 78
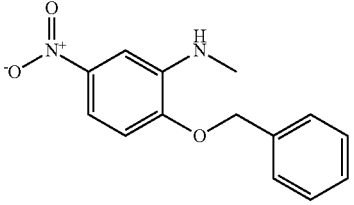
Potency: 4.4668
Efficacy: 85.208
Compound 79
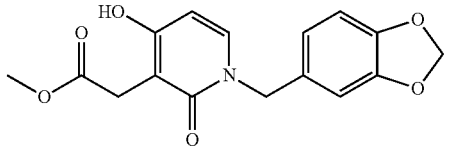 [SMILES: COC(=O)Cc1c(O)ccn(Cc2ccc3c(c2)OCO3)c1=O]
Potency: 10
Efficacy: 175.516
Compound 80
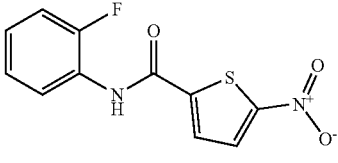 [SMILES: O=C(Nc1ccccc1F)c1ccc([N+](=O)[O-])s1]
Potency: 12.5893
Efficacy: 213.226
Compound 81
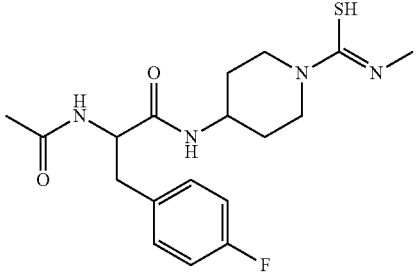 [SMILES: C/N=C(\S)N1CCC(NC(=O)C(Cc2ccc(F)cc2)NC(C)=O)CC1]
Potency: 3.1623
Efficacy: 96.4736
Compound 82

TABLE 10-continued
Exemplary Compounds
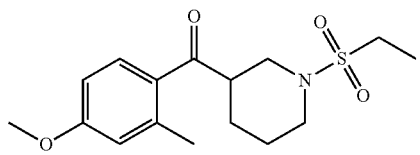 [SMILES: CCS(=O)(=O)N1CCCC(C(=O)c2ccc(OC)cc2C)C1]
Compound 83
Potency: 11.2202
Efficacy: 175.054
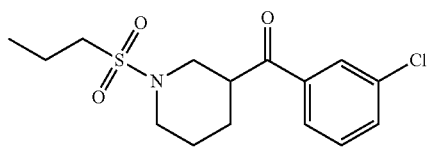 [SMILES: CCCS(=O)(=O)N1CCCC(C(=O)c2cccc(Cl)c2)C1]
Compound 84
Potency: 6.3096
Efficacy: 122.242
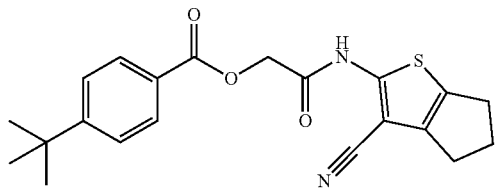 [SMILES: CC(C)(C)c1ccc(C(=O)OCC(=O)Nc2sc3c(c2C#N)CCC3)cc1]
Compound 85
Potency: 5.0119
Efficacy: 99.705
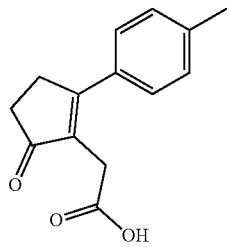 [SMILES: Cc1ccc(C2=C(CC(=O)O)C(=O)CC2)cc1]
Compound 86
Potency: 4.4668
Efficacy: 94.2018
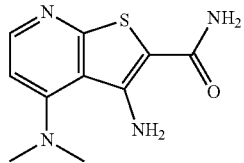 [SMILES: CN(C)c1ccnc2sc(C(N)=O)c(N)c12]
Compound 87
Potency: 5.0119
Efficacy: 66.4058
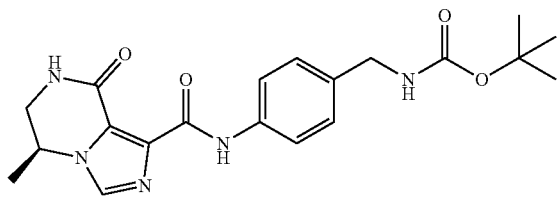 [SMILES: C[C@H]1CNC(=O)c2c(C(=O)Nc3ccc(CNC(=O)OC(C)(C)C)cc3)ncn21]
Compound 88
Potency: 8.9125
Efficacy: 88.9864

TABLE 10-continued
Exemplary Compounds
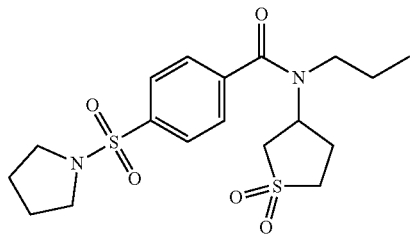 [SMILES: CCCN(C(=O)c1ccc(S(=O)(=O)N2CCCC2)cc1)C1CCS(=O)(=O)C1]
Compound 89
Potency: 5.0119
Efficacy: 86.1979
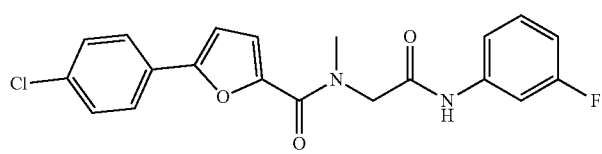 [SMILES: CN(CC(=O)Nc1cccc(F)c1)C(=O)c1ccc(-c2ccc(Cl)cc2)o1]
Compound 90
Potency: 11.2202
Efficacy: 140.713
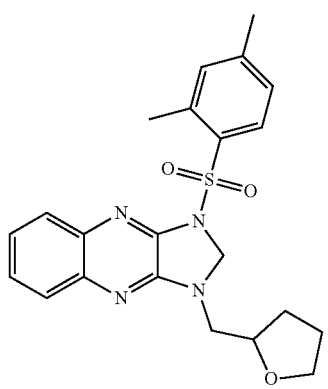 [SMILES: Cc1ccc(S(=O)(=O)N2CN(CC3CCCO3)c3nc4ccccc4nc32)c(C)c1]
Compound 91
Potency: 11.2202
Efficacy: 139.097
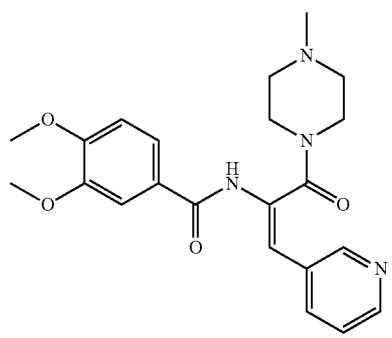 [SMILES: COc1ccc(C(=O)N/C(=C/c2cccnc2)C(=O)N2CCN(C)CC2)cc1OC]
Compound 92
Potency: 4.4668
Efficacy: 75.211

TABLE 10-continued
| Exemplary Compounds |
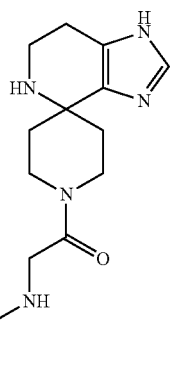
Compound 93
Potency: 11.2202
Efficacy: 117.921
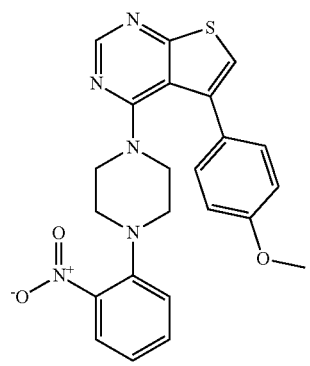
Compound 94
Potency: 10
Efficacy: 128.349
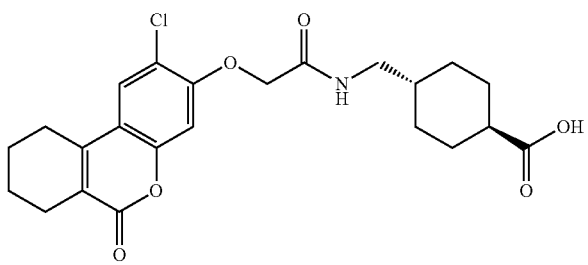 [SMILES: O=C(COc1cc2oc(=O)c3c(c2cc1Cl)CCCC3)NC[C@H]1CC[C@H](C(=O)O)CC1]
Compound 95
Potency: 7.0795
Efficacy: 98.2729
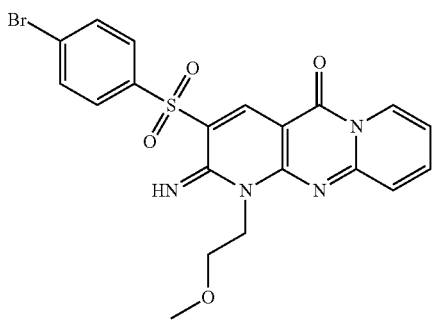 [SMILES: COCCn1c(=N)c(S(=O)(=O)c2ccc(Br)cc2)cc2c(=O)n3ccccc3nc21]
Compound 96
Potency: 4.4668
Efficacy: 83.068

TABLE 10-continued
Exemplary Compounds
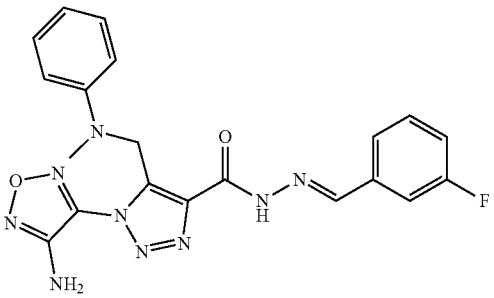 [SMILES: CN(Cc1c(C(=O)N/N=C/c2cccc(F)c2)nnn1-c1nonc1N)c1ccccc1]
Compound 97
Potency: 5.6234
Efficacy: 78.6154
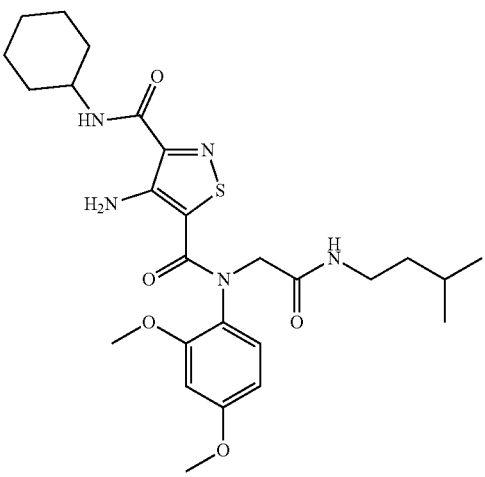 [SMILES: COc1ccc(N(CC(=O)NCCC(C)C)C(=O)c2snc(C(=O)NC3CCCCC3)c2N)c(OC)c1]
Compound 98
Potency: 10
Efficacy: 125.681
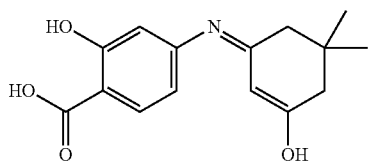 [SMILES: CC1(C)CC(O)=C/C(=N\c2ccc(C(=O)O)c(O)c2)C1]
Compound 99
Potency: 10
Efficacy: 121.073
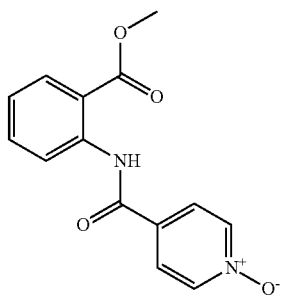 [SMILES: COC(=O)c1ccccc1NC(=O)c1cc[n+]([O-])cc1]
Compound 100
Potency: 3.9811
Efficacy: 95.5318

TABLE 10-continued
Exemplary Compounds
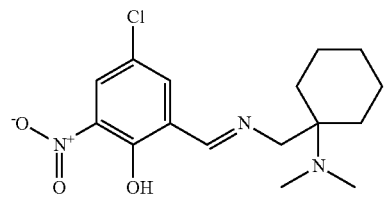
Compound 101
Potency: 8.9125
Efficacy: 131.53
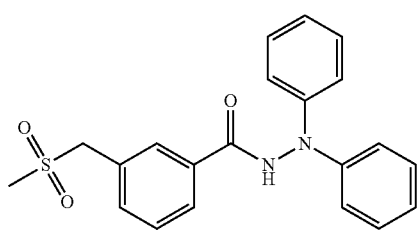 [SMILES: CS(=O)(=O)Cc1cccc(C(=O)NN(c2ccccc2)c2ccccc2)c1]
Compound 102
Potency: 12.5893
Efficacy: 149.767
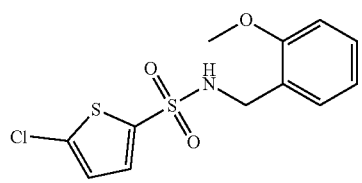 [SMILES: COc1ccccc1CNS(=O)(=O)c1ccc(Cl)s1]
Compound 103
Potency: 6.3096
Efficacy: 119.897
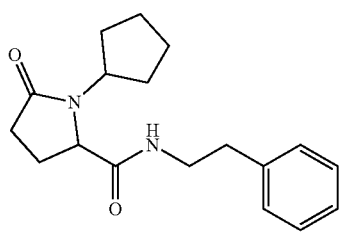 [SMILES: O=C(NCCc1ccccc1)C1CCC(=O)N1C1CCCC1]
Compound 104
Potency: 10
Efficacy: 137.595
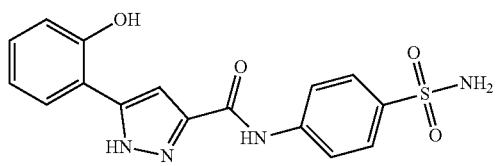 [SMILES: NS(=O)(=O)c1ccc(NC(=O)c2cc(-c3ccccc3O)[nH]n2)cc1]
Compound 105
Potency: 10
Efficacy: 96.3714

TABLE 10-continued
Exemplary Compounds
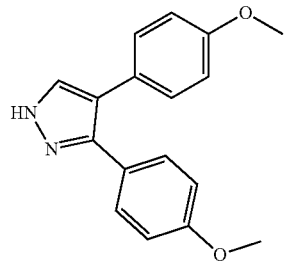 [SMILES: COc1ccc(-c2c[nH]nc2-c2ccc(OC)cc2)cc1]
Compound 106
Potency: 7.0795
Efficacy: 81.3792
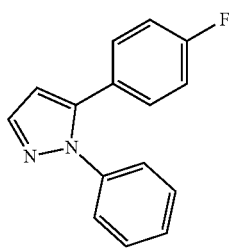 [SMILES: Fc1ccc(-c2ccnn2-c2ccccc2)cc1]
Compound 107
Potency: 4.4668
Efficacy: 95.5906
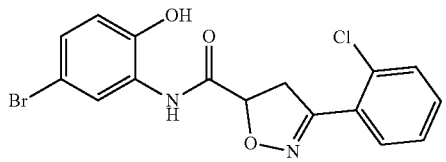 [SMILES: O=C(Nc1cc(Br)ccc1O)C1CC(c2ccccc2Cl)=NO1]
Compound 108
Potency: 12.5893
Efficacy: 139.967
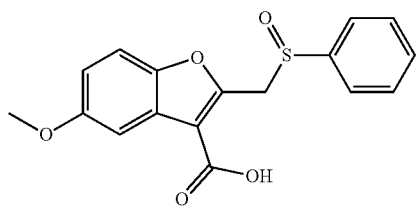 [SMILES: COc1ccc2oc(CS(=O)c3ccccc3)c(C(=O)O)c2c1]
Compound 109
Potency: 12.5893
Efficacy: 166.495
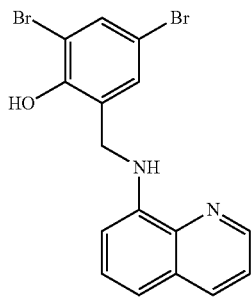 [SMILES: Oc1c(Br)cc(Br)cc1CNc1cccc2cccnc12]
Compound 110
Potency: 12.5893
Efficacy: 180.783

TABLE 10-continued
Exemplary Compounds
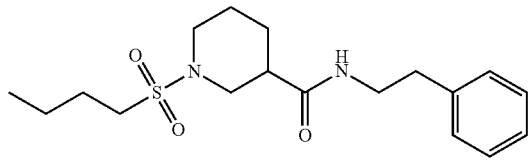 [SMILES: CCCCS(=O)(=O)N1CCCC(C(=O)NCCc2ccccc2)C1]
Compound 111
Potency: 7.0795
Efficacy: 99.2205
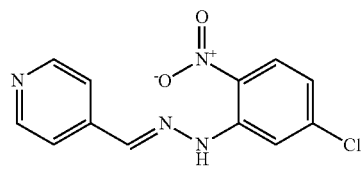
Compound 112
Potency: 5.6234
Efficacy: 73.9187
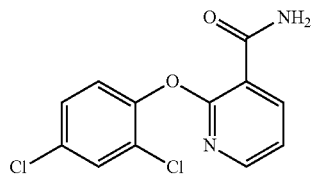 [SMILES: NC(=O)c1cccnc1Oc1ccc(Cl)cc1Cl]
Compound 113
Potency: 10
Efficacy: 111.758
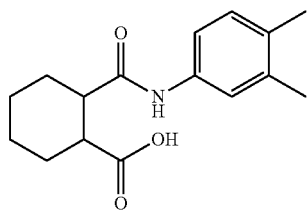 [SMILES: Cc1ccc(NC(=O)C2CCCCC2C(=O)O)cc1C]
Compound 114
Potency: 11.2202
Efficacy: 138.65
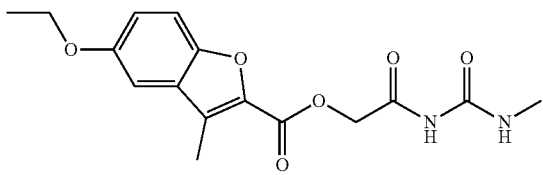 [SMILES: CCOc1ccc2oc(C(=O)OCC(=O)NC(=O)NC)c(C)c2c1]
Compound 115
Potency: 7.0795
Efficacy: 85.5436
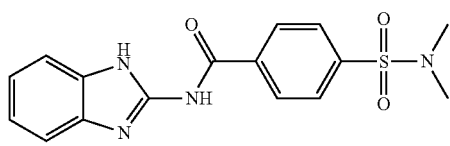 [SMILES: CN(C)S(=O)(=O)c1ccc(C(=O)Nc2nc3ccccc3[nH]2)cc1]
Compound 116
Potency: 8.9125
Efficacy: 104.576

TABLE 10-continued
Exemplary Compounds
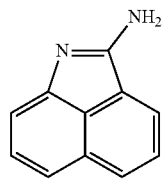 [SMILES: NC1=Nc2cccc3cccc1c23]
Potency: 7.9433
Efficacy: 88.998
Compound 117
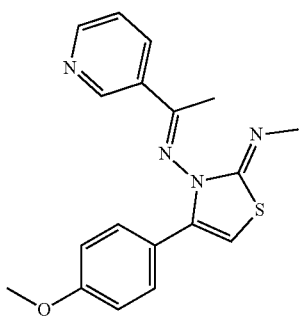
Potency: 5.0119
Efficacy: 82.7908
Compound 118
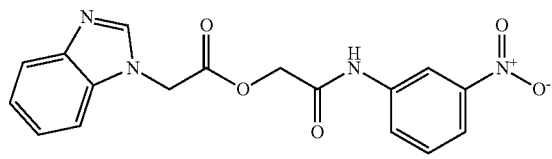 [SMILES: O=C(COC(=O)Cn1cnc2ccccc21)Nc1cccc([N+](=O)[O-])c1]
Potency: 11.2202
Efficacy: 127.904
Compound 119
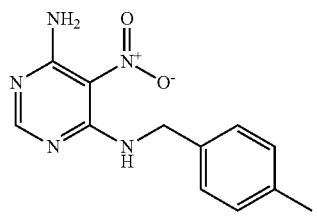 [SMILES: Cc1ccc(CNc2ncnc(N)c2[N+](=O)[O-])cc1]
Potency: 10
Efficacy: 114.827
Compound 120
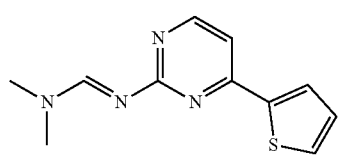 [SMILES: CN(C)/C=N/c1nccc(-c2cccs2)n1]
Potency: 8.9125
Efficacy: 92.062
Compound 121

TABLE 10-continued
Exemplary Compounds
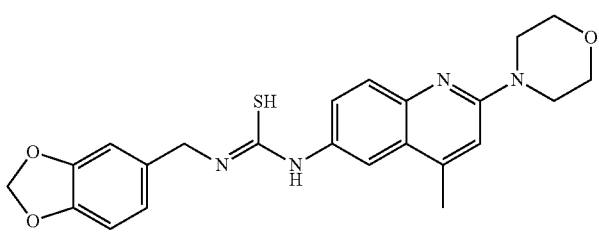 [SMILES: Cc1cc(N2CCOCC2)nc2ccc(N/C(S)=N/Cc3ccc4c(c3)OCO4)cc12]
Compound 122
Potency: 10
Efficacy: 127.132
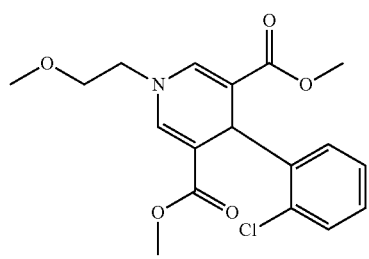 [SMILES: COCCN1C=C(C(=O)OC)C(c2ccccc2Cl)C(C(=O)OC)=C1]
Compound 123
Potency: 8.9125
Efficacy: 92.918
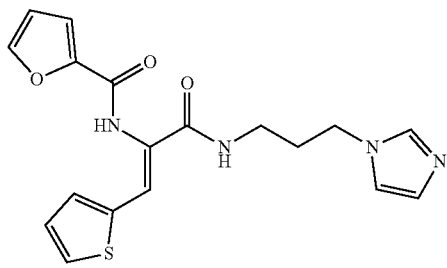 [SMILES: O=C(NCCCn1ccnc1)/C(=C/c1cccs1)NC(=O)c1ccco1]
Compound 124
Potency: 8.9125
Efficacy: 123.416
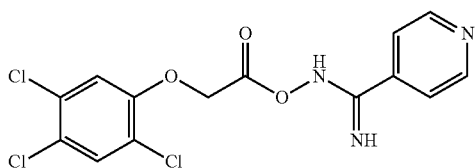 [SMILES: N=C(NOC(=O)COc1cc(Cl)c(Cl)cc1Cl)c1ccncc1]
Compound 125
Potency: 11.2202
Efficacy: 136.36
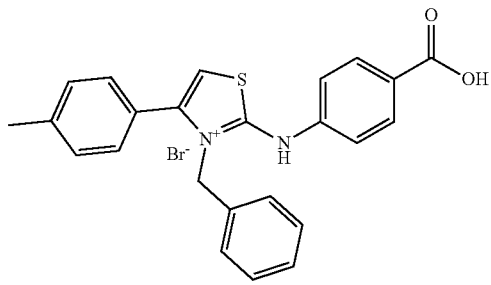 [SMILES: Cc1ccc(-c2csc(Nc3ccc(C(=O)O)cc3)[n+]2Cc2ccccc2)cc1 ; [Br-]]
Compound 126
Potency: 8.9125
Efficacy: 124.439

TABLE 10-continued
| Exemplary Compounds | |
|---|---|
| 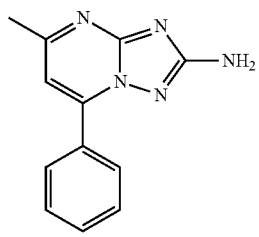 [SMILES: Cc1cc(-c2ccccc2)n2nc(N)nc2n1]
Potency: 12.5893
Efficacy: 171.242 | Compound 127 |
| 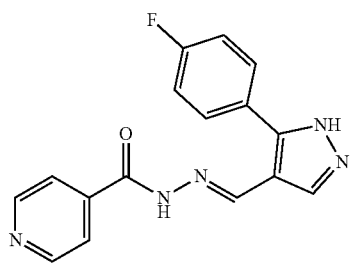 [SMILES: O=C(N/N=C/c1cn[nH]c1-c1ccc(F)cc1)c1ccncc1]
Potency: 14.1254
Efficacy: 138.869 | Compound 128 |
| 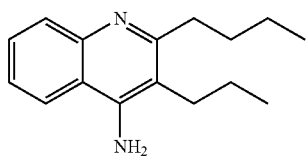 | Compound 129 |
| 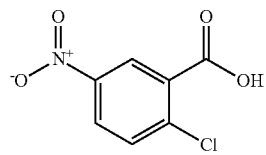
Potency: 11.2202
Efficacy: 145.936 | |
| 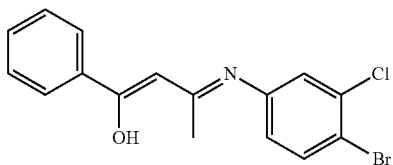 [SMILES: CC(/C=C(\O)c1ccccc1)=N\c1ccc(Br)c(Cl)c1]
Potency: 11.2202
Efficacy: 119.808 | Compound 130 |
| 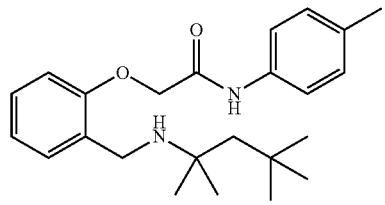 [SMILES: Cc1ccc(NC(=O)COc2ccccc2CNC(C)(C)CC(C)(C)C)cc1]
Potency: 14.1254
Efficacy: 175.002 | Compound 131 |

TABLE 10-continued
Exemplary Compounds
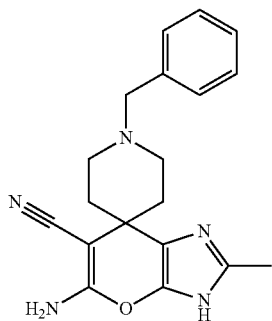 [SMILES: Cc1nc2c([nH]1)OC(N)=C(C#N)C21CCN(Cc2ccccc2)CC1]
Compound 132
Potency: 12.5893
Efficacy: 120.609
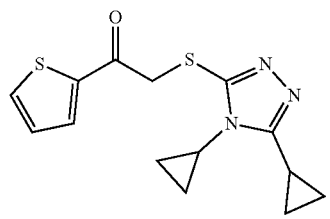 [SMILES: O=C(CSc1nnc(C2CC2)n1C1CC1)c1cccs1]
Compound 133
Potency: 10
Efficacy: 100.712
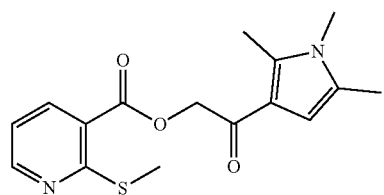 [SMILES: CSc1ncccc1C(=O)OCC(=O)c1cc(C)n(C)c1C]
Compound 134
Potency: 10
Efficacy: 95.4818
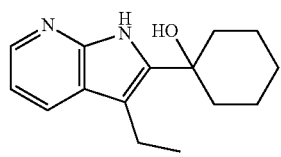 [SMILES: CCc1c(C2(O)CCCCC2)[nH]c2ncccc12]
Compound 135
Potency: 10
Efficacy: 91.1222
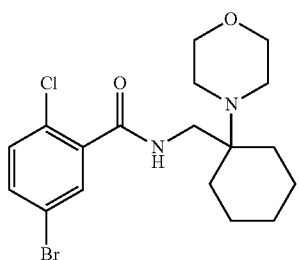 [SMILES: O=C(NCC1(N2CCOCC2)CCCCC1)c1cc(Br)ccc1Cl]
Compound 136
Potency: 8.9125
Efficacy: 89.1179

TABLE 10-continued
Exemplary Compounds
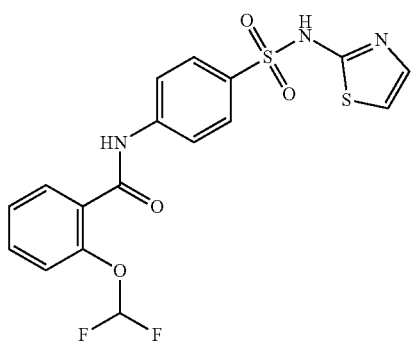 [SMILES: O=C(Nc1ccc(S(=O)(=O)Nc2nccs2)cc1)c1ccccc1OC(F)F]
Compound 137
Potency: 10
Efficacy: 81.023
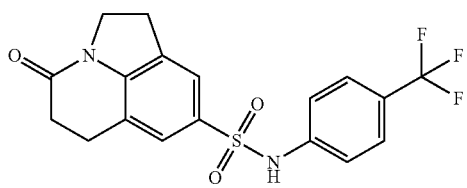 [SMILES: O=C1CCc2cc(S(=O)(=O)Nc3ccc(C(F)(F)F)cc3)cc3c2N1CC3]
Compound 138
Potency: 11.2202
Efficacy: 135.363
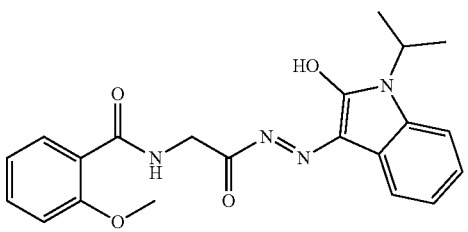 [SMILES: COc1ccccc1C(=O)NCC(=O)/N=N/c1c(O)n(C(C)C)c2ccccc12]
Compound 139
Potency: 11.2202
Efficacy: 67.3145
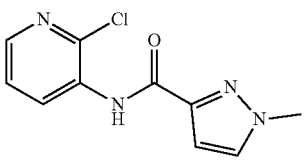 [SMILES: Cn1ccc(C(=O)Nc2cccnc2Cl)n1]
Compound 140
Potency: 10
Efficacy: 81.9056
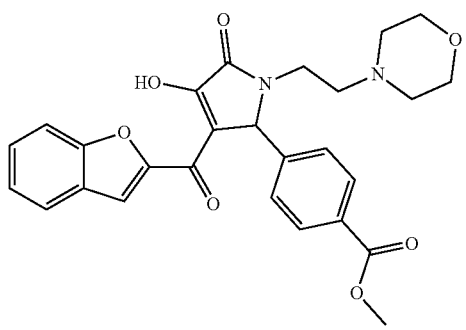 [SMILES: COC(=O)c1ccc(C2C(C(=O)c3cc4ccccc4o3)=C(O)C(=O)N2CCN2CCOCC2)cc1]
Compound 141
Potency: 10
Efficacy: 100.669

TABLE 10-continued
Exemplary Compounds
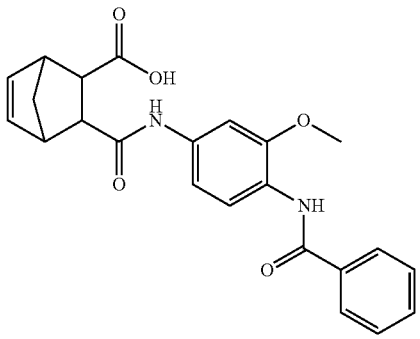 [SMILES: COc1cc(NC(=O)C2C3C=CC(C3)C2C(=O)O)ccc1NC(=O)c1ccccc1]
Compound 142
Potency: 8.9125
Efficacy: 89.9548
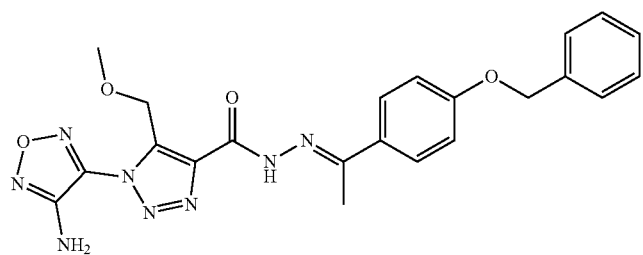 [SMILES: COCc1c(C(=O)N/N=C(\C)c2ccc(OCc3ccccc3)cc2)nnn1-c1nonc1N]
Compound 143
Potency: 10
Efficacy: 76.5877
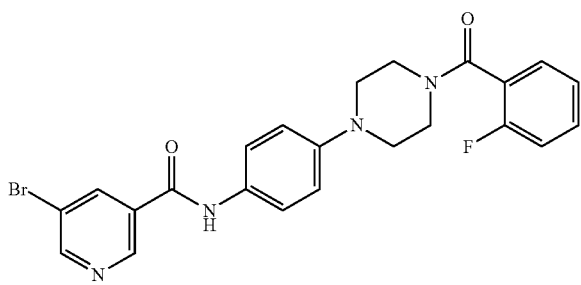 [SMILES: O=C(Nc1ccc(N2CCN(C(=O)c3ccccc3F)CC2)cc1)c1cncc(Br)c1]
Compound 144
Potency: 12.5893
Efficacy: 94.0383
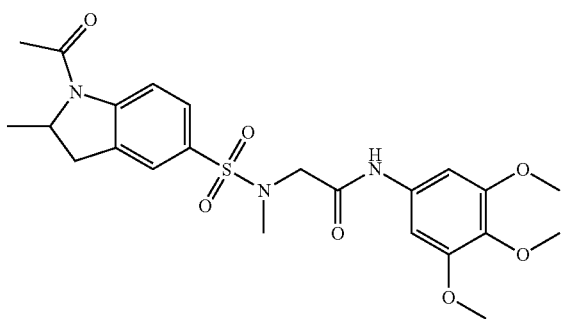
Compound 145
Potency: 10
Efficacy: 69.9943

TABLE 10-continued
Exemplary Compounds
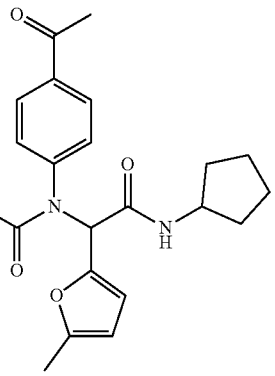
Compound 146
Potency: 10
Efficacy: 96.4095
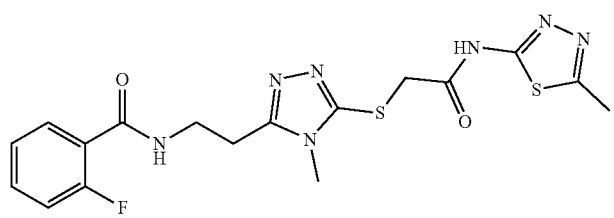 [SMILES: Cc1nnc(NC(=O)CSc2nnc(CCNC(=O)c3ccccc3F)n2C)s1]
Compound 147
Potency: 11.2202
Efficacy: 90.1504
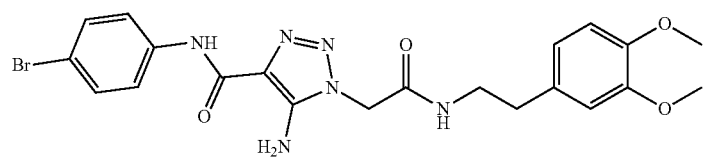 [SMILES: COc1ccc(CCNC(=O)Cn2nnc(C(=O)Nc3ccc(Br)cc3)c2N)cc1OC]
Compound 148
Potency: 11.2202
Efficacy: 138.741
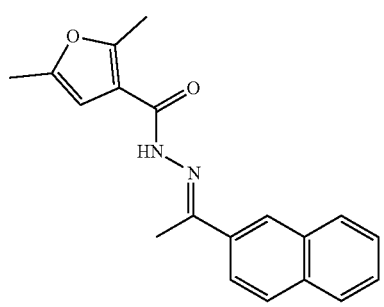 [SMILES: C/C(=N\NC(=O)c1cc(C)oc1C)c1ccc2ccccc2c1]
Compound 149
Potency: 8.9125
Efficacy: 84.3701

TABLE 10-continued
Exemplary Compounds
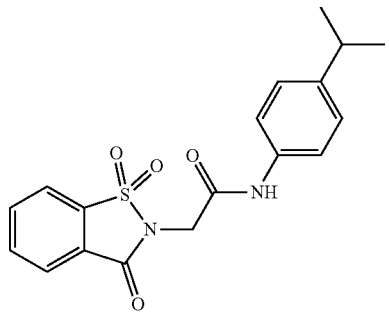 [SMILES: CC(C)c1ccc(NC(=O)CN2C(=O)c3ccccc3S2(=O)=O)cc1]
Compound 150
Potency: 10
Efficacy: 67.6116
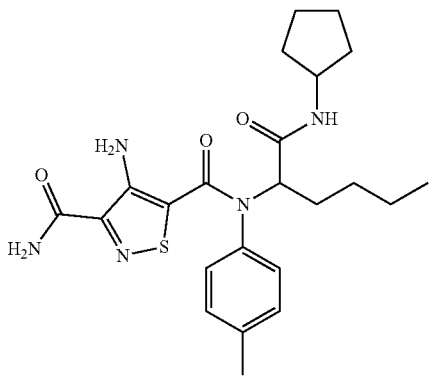 [SMILES: CCCCC(C(=O)NC1CCCC1)N(C(=O)c1snc(C(N)=O)c1N)c1ccc(C)cc1]
Compound 151
Potency: 10
Efficacy: 91.5246
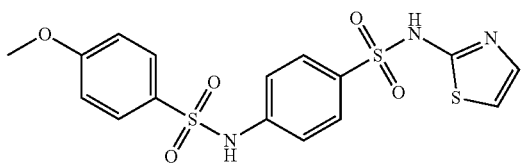 [SMILES: COc1ccc(S(=O)(=O)Nc2ccc(S(=O)(=O)Nc3nccs3)cc2)cc1]
Compound 152
Potency: 12.5893
Efficacy: 97.2406
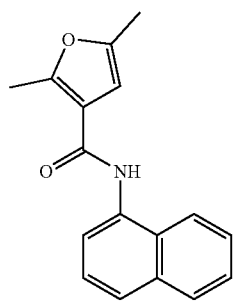 [SMILES: Cc1cc(C(=O)Nc2cccc3ccccc23)c(C)o1]
Compound 153
Potency: 7.9433
Efficacy: 95.7207

TABLE 10-continued
Exemplary Compounds
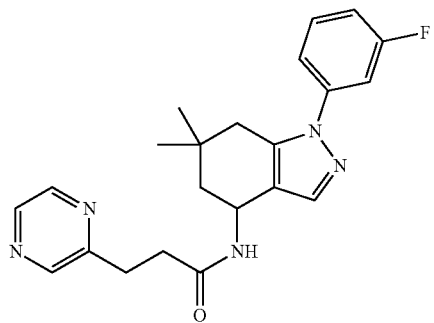 [SMILES: CC1(C)Cc2c(cnn2-c2cccc(F)c2)C(NC(=O)CCc2cnccn2)C1]
Compound 154
Potency: 3.1623
Efficacy: 93.8685
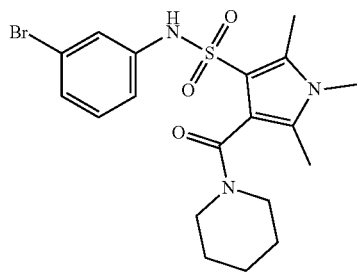 [SMILES: Cc1c(C(=O)N2CCCCC2)c(S(=O)(=O)Nc2cccc(Br)c2)c(C)n1C]
Compound 155
Potency: 10
Efficacy: 93.0585
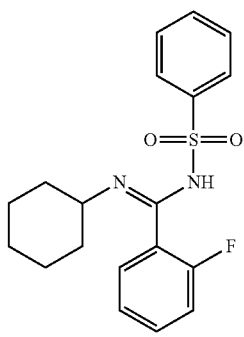 [SMILES: O=S(=O)(N/C(=N/C1CCCCC1)c1ccccc1F)c1ccccc1]
Compound 156
Potency: 10
Efficacy: 67.8359
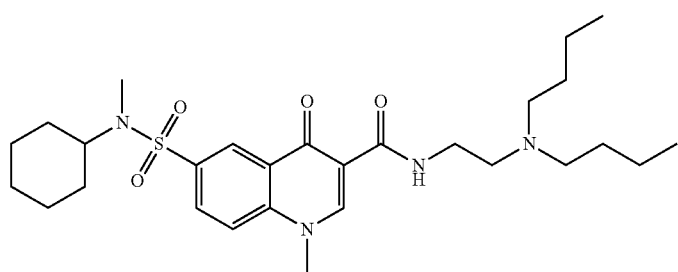 [SMILES: CCCCN(CCCC)CCNC(=O)c1cn(C)c2ccc(S(=O)(=O)N(C)C3CCCCC3)cc2c1=O]
Compound 157
Potency: 10
Efficacy: 70.1776

TABLE 10-continued
Exemplary Compounds
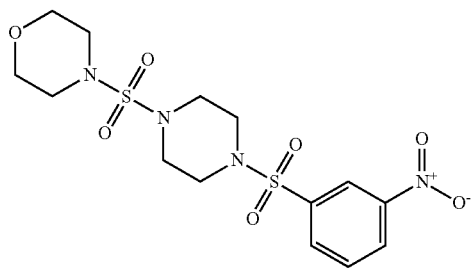 [SMILES: O=[N+]([O-])c1cccc(S(=O)(=O)N2CCN(S(=O)(=O)N3CCOCC3)CC2)c1]
Compound 158
Potency: 10
Efficacy: 71.256
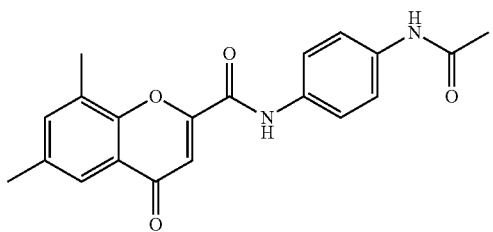 [SMILES: CC(=O)Nc1ccc(NC(=O)c2cc(=O)c3cc(C)cc(C)c3o2)cc1]
Compound 159
Potency: 11.2202
Efficacy: 109.576
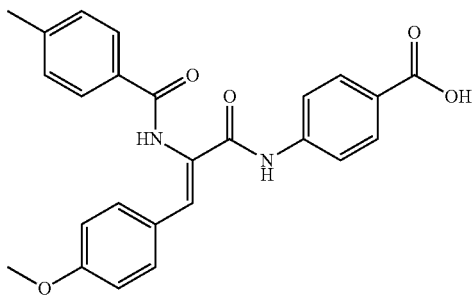 [SMILES: COc1ccc(/C=C(\NC(=O)c2ccc(C)cc2)C(=O)Nc2ccc(C(=O)O)cc2)cc1]
Compound 160
Potency: 11.2202
Efficacy: 103.065
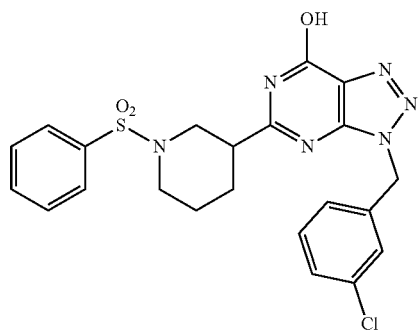 [SMILES: O=S(=O)(c1ccccc1)N1CCCC(c2nc(O)c3nnn(Cc4cccc(Cl)c4)c3n2)C1]
Compound 161
Potency: 3.9811
Efficacy: 97.9916

TABLE 10-continued
| Exemplary Compounds | |
|---|---|
| 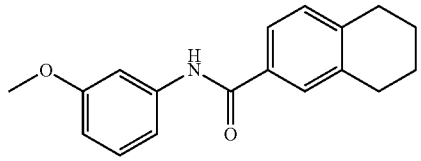 [SMILES: COc1cccc(NC(=O)c2ccc3c(c2)CCCC3)c1]<br>Potency: 5.6234<br>Efficacy: 87.0645 | Compound 162 |
| 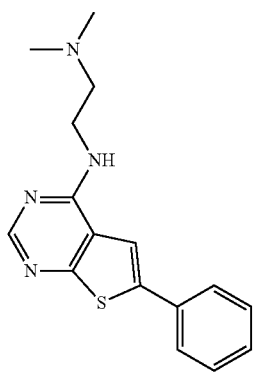 [SMILES: CN(C)CCNc1ncnc2sc(-c3ccccc3)cc12]<br>Potency: 10<br>Efficacy: 79.1483 | Compound 163 |
| 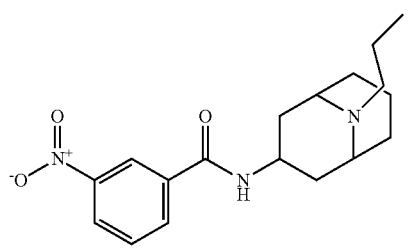<br>Potency: 10<br>Efficacy: 90.988 | Compound 164 |
| 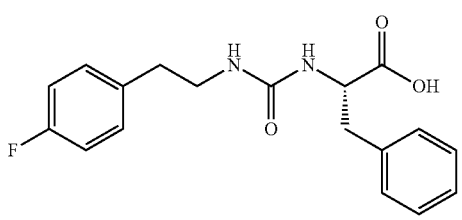 [SMILES: O=C(NCCc1ccc(F)cc1)N[C@@H](Cc1ccccc1)C(=O)O]<br>Potency: 11.2202<br>Efficacy: 128.695 | Compound 165 |
| 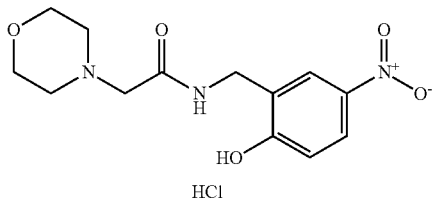 [SMILES: O=C(CN1CCOCC1)NCc1cc([N+](=O)[O-])ccc1O ; Cl]<br>HCl<br>Potency: 12.5893<br>Efficacy: 93.7937 | Compound 166 |

TABLE 10-continued
Exemplary Compounds
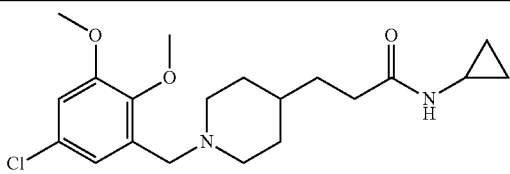
Potency: 7.0795
Efficacy: 86.8199
Compound 167
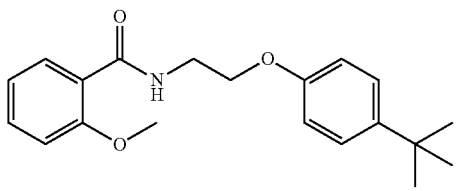 [SMILES: COc1ccccc1C(=O)NCCOc1ccc(C(C)(C)C)cc1]
Potency: 8.9125
Efficacy: 83.6415
Compound 168
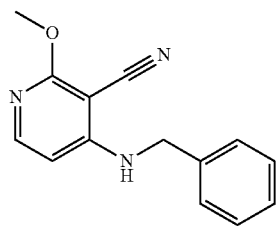 [SMILES: COc1nccc(NCc2ccccc2)c1C#N]
Potency: 10
Efficacy: 84.5587
Compound 169
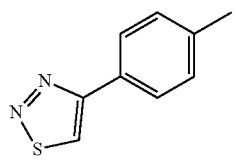
Potency: 10
Efficacy: 84.3344
Compound 170
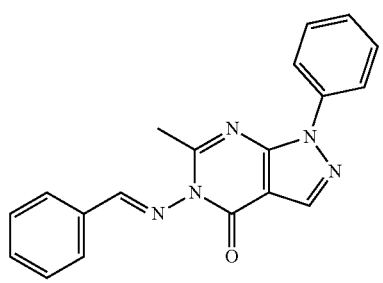 [SMILES: Cc1nc2c(cnn2-c2ccccc2)c(=O)n1/N=C/c1ccccc1]
Potency: 10
Efficacy: 59.61
Compound 171
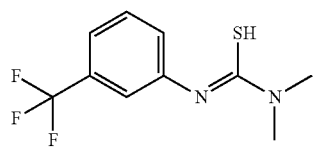
Potency: 10
Efficacy: 65.8043
Compound 172

TABLE 10-continued
Exemplary Compounds
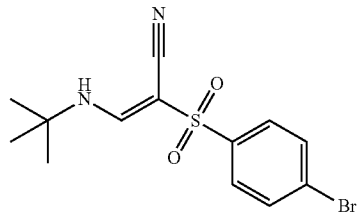 [SMILES: CC(C)(C)N/C=C(\C#N)S(=O)(=O)c1ccc(Br)cc1]
Potency: 11.2202
Efficacy: 85.4536
Compound 173
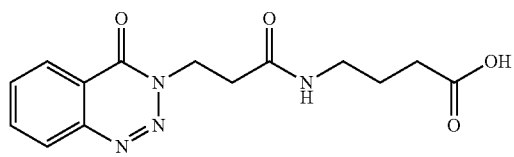 [SMILES: O=C(O)CCCNC(=O)CCn1nnc2ccccc2c1=O]
Potency: 11.2202
Efficacy: 104.045
Compound 174
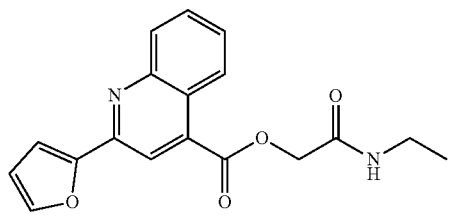 [SMILES: CCNC(=O)COC(=O)c1cc(-c2ccco2)nc2ccccc12]
Potency: 5.6234
Efficacy: 116.69
Compound 175
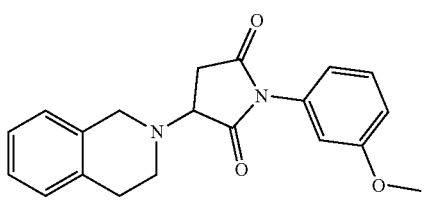 [SMILES: COc1cccc(N2C(=O)CC(N3CCc4ccccc4C3)C2=O)c1]
Potency: 10
Efficacy: 115.567
Compound 176
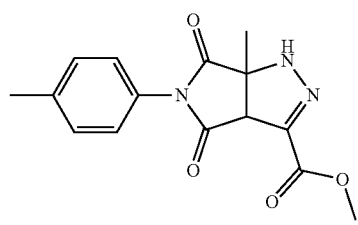
Potency: 10
Efficacy: 70.6131
Compound 177

TABLE 10-continued
Exemplary Compounds
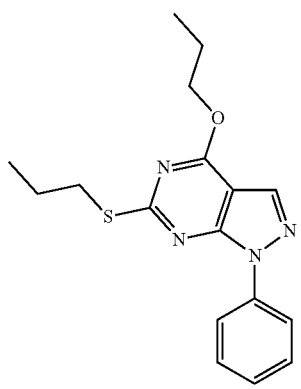 [SMILES: CCCOc1nc(SCCC)nc2c1cnn2-c1ccccc1]
Compound 178
Potency: 11.2202
Efficacy: 107.982
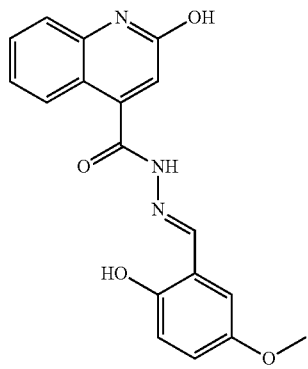 [SMILES: COc1ccc(O)c(/C=N/NC(=O)c2cc(O)nc3ccccc23)c1]
Compound 179
Potency: 5.6234
Efficacy: 84.0774
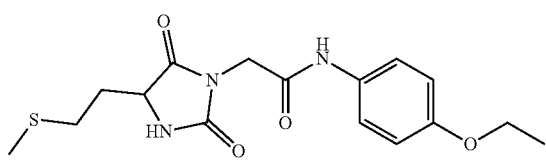 [SMILES: CCOc1ccc(NC(=O)CN2C(=O)NC(CCSC)C2=O)cc1]
Compound 180
Potency: 10
Efficacy: 77.6845
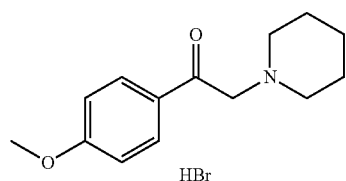 [SMILES: COc1ccc(C(=O)CN2CCCCC2)cc1 ; Br]
Compound 181
Potency: 12.5893
Efficacy: 80.5239

TABLE 10-continued
Exemplary Compounds
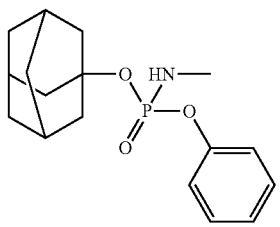 [SMILES: CNP(=O)(Oc1ccccc1)OC12CC3CC(CC(C3)C1)C2]
Compound 182
Potency: 10
Efficacy: 99.1066
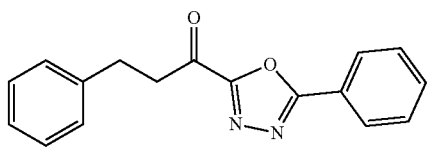 [SMILES: O=C(CCc1ccccc1)c1nnc(-c2ccccc2)o1]
Compound 183
Potency: 10
Efficacy: 98.6809
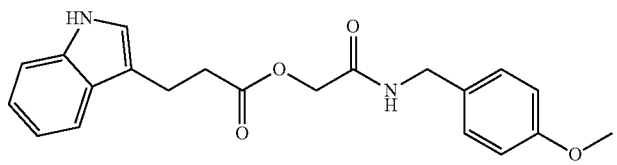 [SMILES: COc1ccc(CNC(=O)COC(=O)CCc2c[nH]c3ccccc23)cc1]
Compound 184
Potency: 10
Efficacy: 86.1315
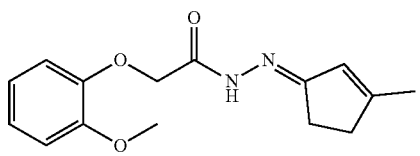 [SMILES: COc1ccccc1OCC(=O)N/N=C1/C=C(C)CC1]
Compound 185
Potency: 10
Efficacy: 117.72
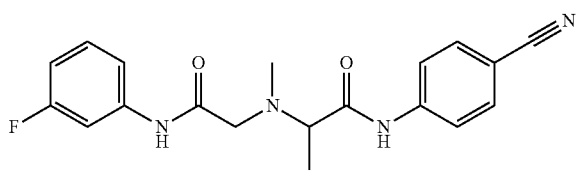 [SMILES: CC(C(=O)Nc1ccc(C#N)cc1)N(C)CC(=O)Nc1cccc(F)c1]
Compound 186
Potency: 3.9811
Efficacy: 93.5129
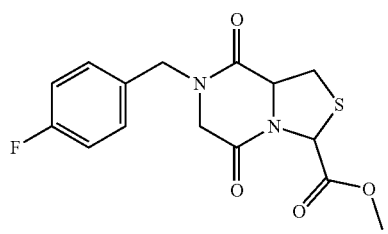 [SMILES: COC(=O)C1SCC2C(=O)N(Cc3ccc(F)cc3)CC(=O)N21]
Compound 187
Potency: 8.9125
Efficacy: 120.104

TABLE 10-continued
Exemplary Compounds
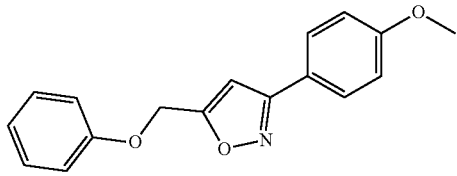 [SMILES: COc1ccc(-c2cc(COc3ccccc3)on2)cc1]
Compound 188
Potency: 10
Efficacy: 88.0312
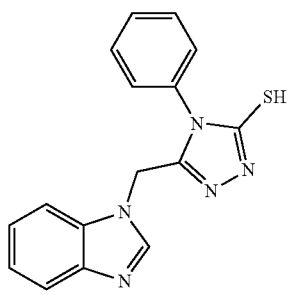 [SMILES: Sc1nnc(Cn2cnc3ccccc32)n1-c1ccccc1]
Compound 189
Potency: 8.9125
Efficacy: 76.0346
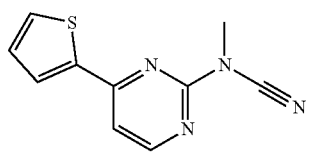
Compound 190
Potency: 11.2202
Efficacy: 116.431
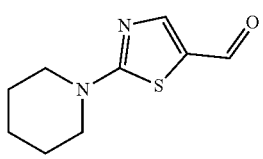 [SMILES: O=Cc1cnc(N2CCCCC2)s1]
Compound 191
Potency: 11.2202
Efficacy: 115.598
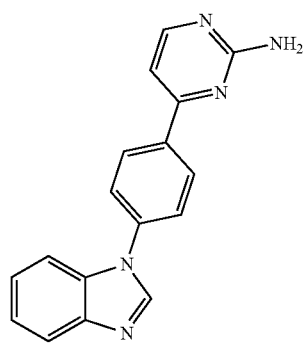 [SMILES: Nc1nccc(-c2ccc(-n3cnc4ccccc43)cc2)n1]
Compound 192
Potency: 11.2202
Efficacy: 74.0117

TABLE 10-continued
Exemplary Compounds
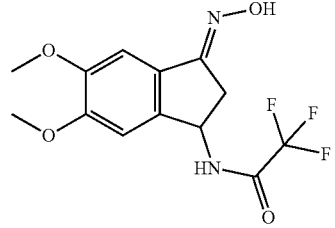 [SMILES: COc1cc2c(cc1OC)C(NC(=O)C(F)(F)F)C/C2=N\O]
Compound 193
Potency: 11.2202
Efficacy: 89.7146
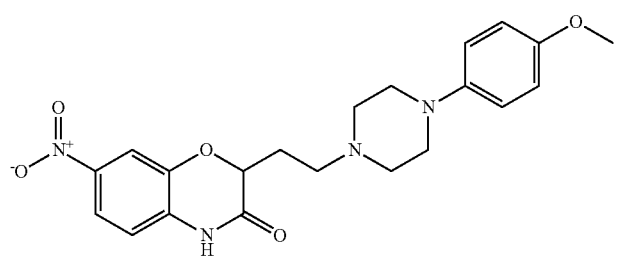
Compound 194
Potency: 8.9125
Efficacy: 76.8665
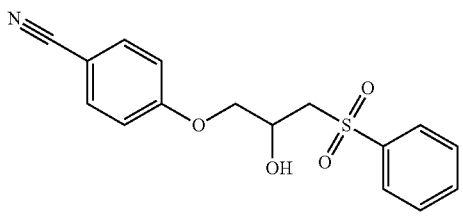 [SMILES: N#Cc1ccc(OCC(O)CS(=O)(=O)c2ccccc2)cc1]
Compound 195
Potency: 10
Efficacy: 99.4569
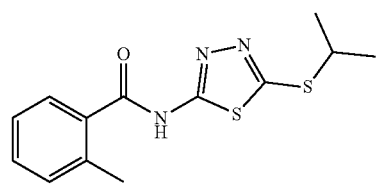 [SMILES: Cc1ccccc1C(=O)Nc1nnc(SC(C)C)s1]
Compound 196
Potency: 10
Efficacy: 67.0912
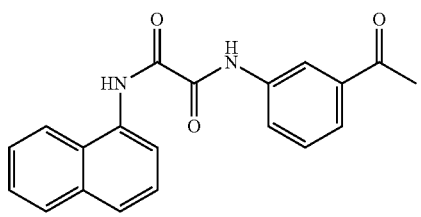 [SMILES: CC(=O)c1cccc(NC(=O)C(=O)Nc2cccc3ccccc23)c1]
Compound 197
Potency: 8.9125
Efficacy: 83.2038

TABLE 10-continued
Exemplary Compounds
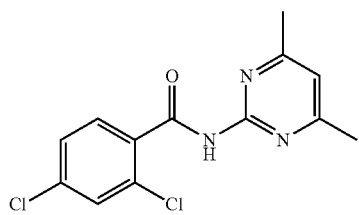 [SMILES: Cc1cc(C)nc(NC(=O)c2ccc(Cl)cc2Cl)n1]
Compound 198
Potency: 10
Efficacy: 78.0861
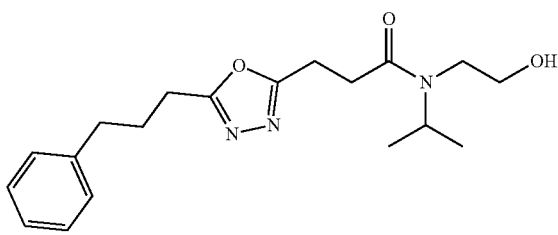 [SMILES: CC(C)N(CCO)C(=O)CCc1nnc(CCCc2ccccc2)o1]
Compound 199
Potency: 12.5893
Efficacy: 96.0151
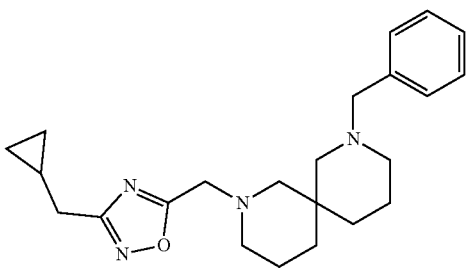 [SMILES: c1ccc(CN2CCCC3(CCCN(Cc4nc(CC5CC5)no4)C3)C2)cc1]
Compound 200
Potency: 8.9125
Efficacy: 98.6316
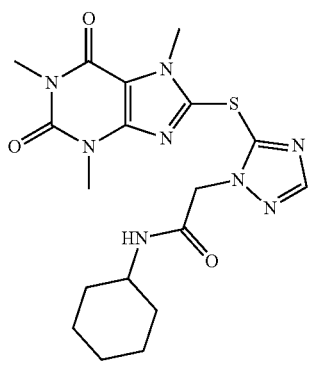 [SMILES: Cn1c(=O)c2c(nc(Sc3ncnn3CC(=O)NC3CCCCC3)n2C)n(C)c1=O]
Compound 201
Potency: 11.2202
Efficacy: 94.7942
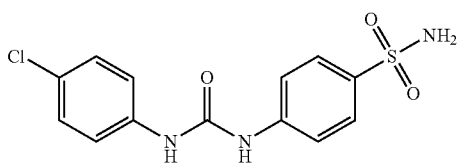 [SMILES: NS(=O)(=O)c1ccc(NC(=O)Nc2ccc(Cl)cc2)cc1]
Compound 202
Potency: 10
Efficacy: 83.9426

TABLE 10-continued
Exemplary Compounds
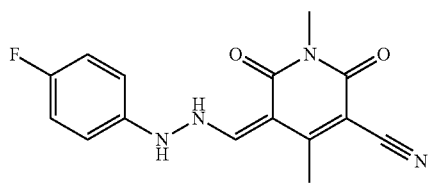 [SMILES: CC1=C(C#N)C(=O)N(C)C(=O)/C1=C\NNc1ccc(F)cc1]
Compound 203
Potency: 7.0795
Efficacy: 106.69
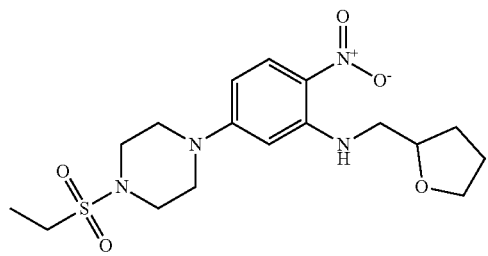 [SMILES: CCS(=O)(=O)N1CCN(c2ccc([N+](=O)[O-])c(NCC3CCCO3)c2)CC1]
Compound 204
Potency: 10
Efficacy: 70.2778
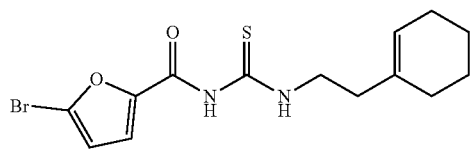 [SMILES: O=C(NC(=S)NCCC1=CCCCC1)c1ccc(Br)o1]
Compound 205
Potency: 7.0795
Efficacy: 98.0553
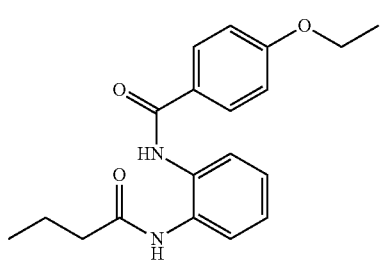 [SMILES: CCCC(=O)Nc1ccccc1NC(=O)c1ccc(OCC)cc1]
Compound 206
Potency: 11.2202
Efficacy: 77.9394
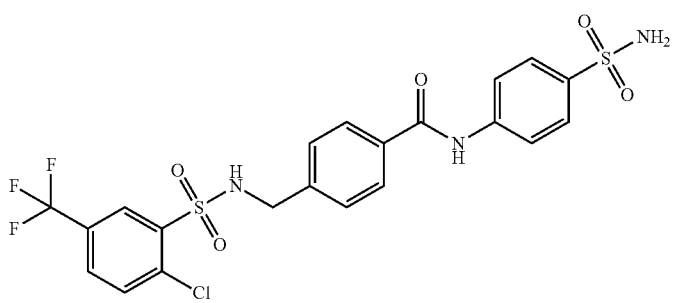 [SMILES: NS(=O)(=O)c1ccc(NC(=O)c2ccc(CNS(=O)(=O)c3cc(C(F)(F)F)ccc3Cl)cc2)cc1]
Compound 207
Potency: 10
Efficacy: 75.3009

TABLE 10-continued
Exemplary Compounds
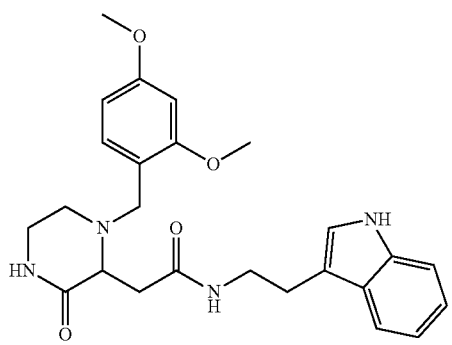 [SMILES: COc1ccc(CN2CCNC(=O)C2CC(=O)NCCc2c[nH]c3ccccc23)c(OC)c1]
Compound 208
Potency: 10
Efficacy: 83.7154
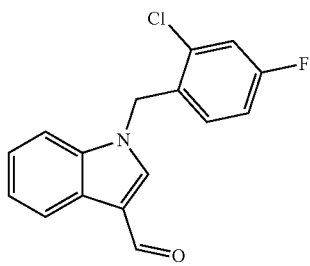 [SMILES: O=Cc1cn(Cc2ccc(F)cc2Cl)c2ccccc12]
Compound 209
Potency: 15.8489
Efficacy: 130.232
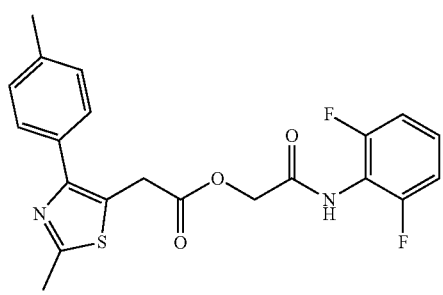 [SMILES: Cc1ccc(-c2nc(C)sc2CC(=O)OCC(=O)Nc2c(F)cccc2F)cc1]
Compound 210
Potency: 12.5893
Efficacy: 101.354
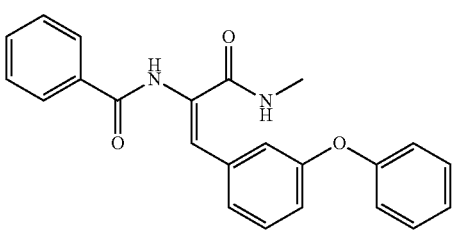 [SMILES: CNC(=O)/C(=C\c1cccc(Oc2ccccc2)c1)NC(=O)c1ccccc1]
Compound 211
Potency: 11.2202
Efficacy: 109.939

TABLE 10-continued
Exemplary Compounds
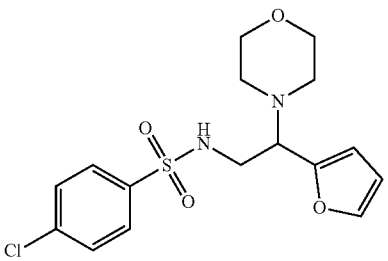 [SMILES: O=S(=O)(NCC(c1ccco1)N1CCOCC1)c1ccc(Cl)cc1]
Compound 212
Potency: 14.1254
Efficacy: 119.538
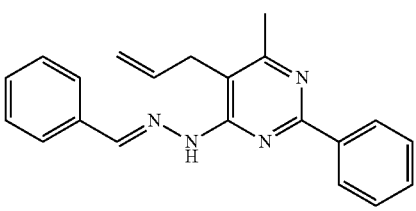 [SMILES: C=CCc1c(C)nc(-c2ccccc2)nc1N/N=C/c1ccccc1]
Compound 213
Potency: 11.2202
Efficacy: 110.24
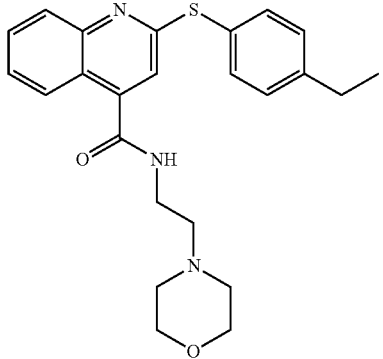 [SMILES: CCc1ccc(Sc2cc(C(=O)NCCN3CCOCC3)c3ccccc3n2)cc1]
Compound 214
Potency: 11.2202
Efficacy: 94.2928
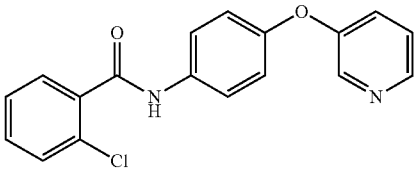 [SMILES: O=C(Nc1ccc(Oc2cccnc2)cc1)c1ccccc1Cl]
Compound 215
Potency: 10
Efficacy: 73.527
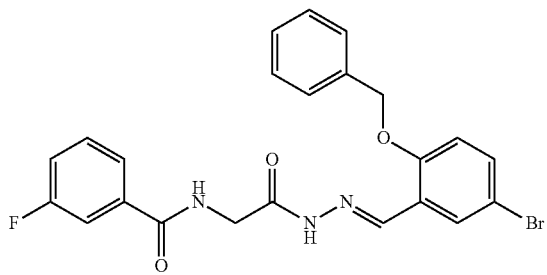 [SMILES: O=C(CNC(=O)c1cccc(F)c1)N/N=C/c1cc(Br)ccc1OCc1ccccc1]
Compound 216
Potency: 10
Efficacy: 90.7389

TABLE 10-continued
Exemplary Compounds
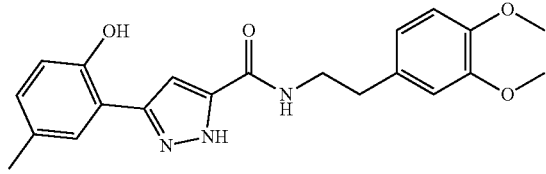
Potency: 10
Efficacy: 56.3855
Compound 217
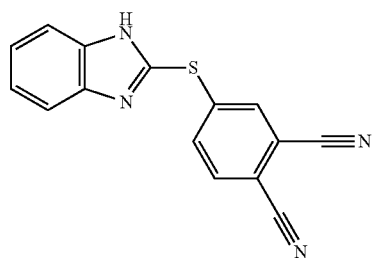 [SMILES: N#Cc1ccc(Sc2nc3ccccc3[nH]2)cc1C#N]
Potency: 10
Efficacy: 58.0835
Compound 218
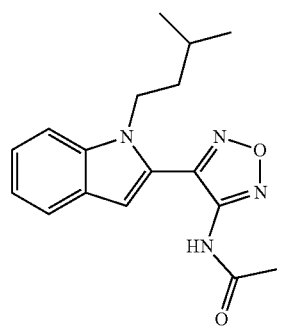 [SMILES: CC(=O)Nc1nonc1-c1cc2ccccc2n1CCC(C)C]
Potency: 11.2202
Efficacy: 83.9475
Compound 219
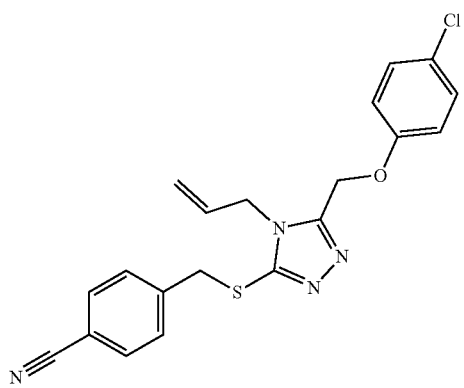 [SMILES: C=CCn1c(COc2ccc(Cl)cc2)nnc1SCc1ccc(C#N)cc1]
Potency: 11.2202
Efficacy: 86.9112
Compound 220

TABLE 10-continued
Exemplary Compounds
Compound 221
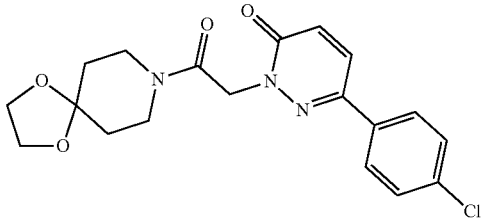 [SMILES: O=C(Cn1nc(-c2ccc(Cl)cc2)ccc1=O)N1CCC2(CC1)OCCO2]
Potency: 11.2202
Efficacy: 59.5046
Compound 222
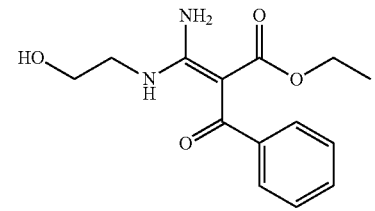 [SMILES: CCOC(=O)/C(C(=O)c1ccccc1)=C(\N)NCCO]
Potency: 12.5893
Efficacy: 56.9925
TABLE 11
Additional Exemplary Analogs
Compound 223
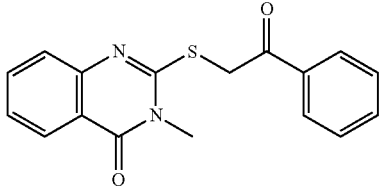
(PRTH-002-F1)
Compound 224
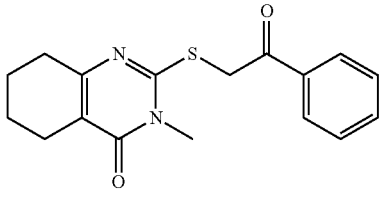
(PRTH-002-F2)
Compound 225
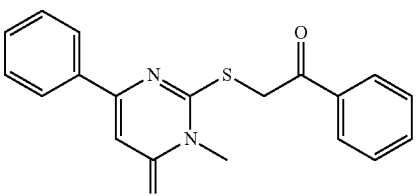
(PRTH-002-F4)
TABLE 11-continued
Additional Exemplary Analogs
Compound 226
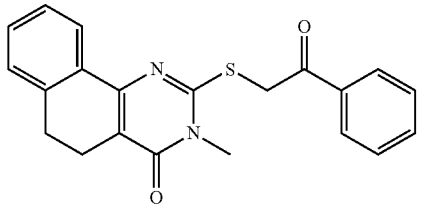
(PRTH-002-F3)
Compound 227
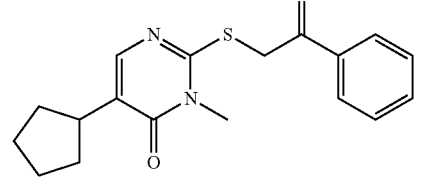
(PRTH-002-F5)
Compound 228
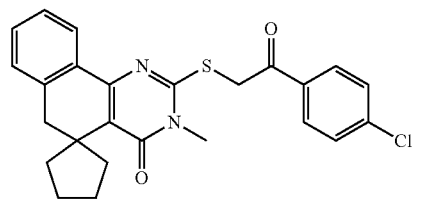 [SMILES: Cn1c(SCC(=O)c2ccc(Cl)c(Cl)c2)nc2c(c1=O)C1(CCCC1)Cc1ccccc1-2]
(PRTH-002-F6)

TABLE 11-continued

Additional Exemplary Analogs

Compound 229

Compound 230

Compound 231

Compound 232

Compound 233

Compound 234

Compound 235

Compound 236

Compound 237

Compound 238

Compound 239

Compound 240
(PRTH-002-F18)

Compound 241
(PRTH-002-F19)

TABLE 11-continued
Additional Exemplary Analogs
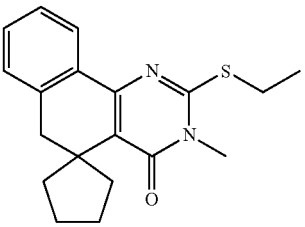
(PRTH-002-F21)
Compound 242
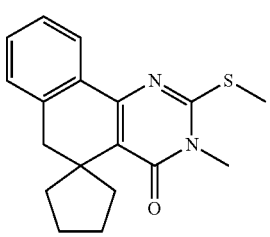
(PRTH-002-F20)
Compound 243
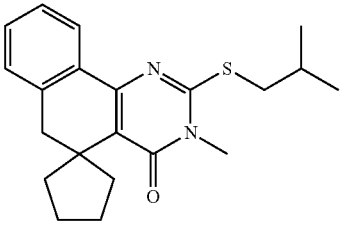
(PRTH-002-F22)
Compound 244
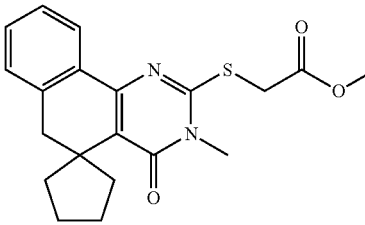
(PRTH-002-F23)
Compound 245
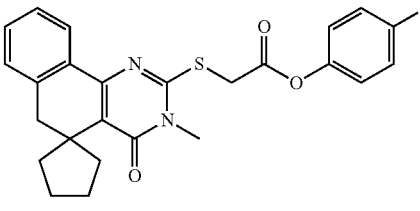
(PRTH-002-F25)
Compound 246
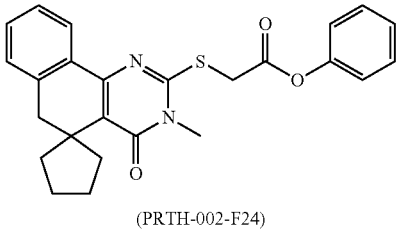 [SMILES: Cn1c(SCC(=O)Oc2ccccc2)nc2c(c1=O)C1(CCCC1)Cc1ccccc1-2]
(PRTH-002-F24)
Compound 247
TABLE 11-continued
Additional Exemplary Analogs
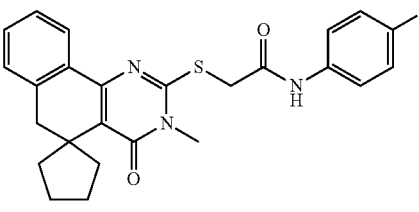
(PRTH-002-F27)
Compound 248
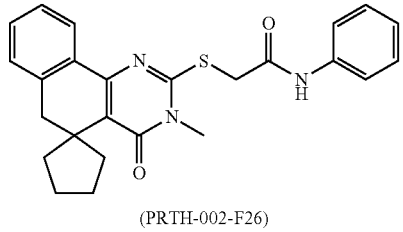 [SMILES: Cn1c(SCC(=O)Nc2ccccc2)nc2c(c1=O)C1(CCCC1)Cc1ccccc1-2]
(PRTH-002-F26)
Compound 249
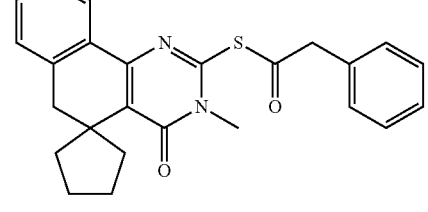
(PRTH-002-F28)
Compound 250
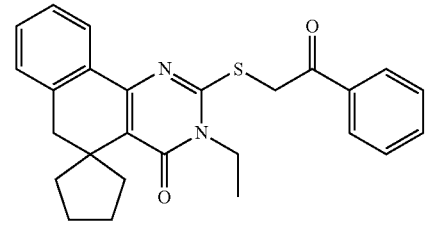
(PRTH-002-F29)
Compound 251
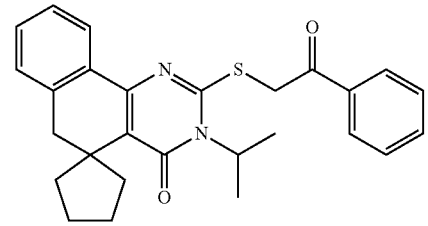
(PRTH-002-F30)
Compound 252
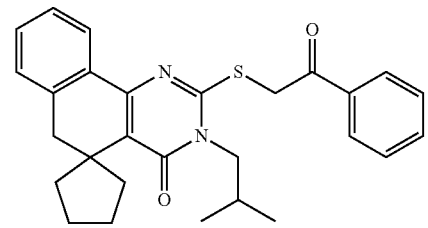
(PRTH-002-F31)
Compound 253

TABLE 11-continued
Additional Exemplary Analogs
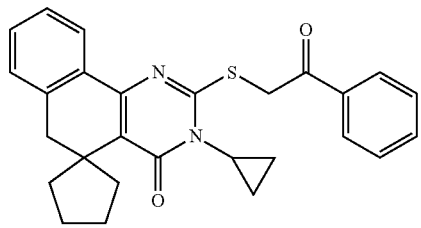
Compound 254
(PRTH-002-F32)
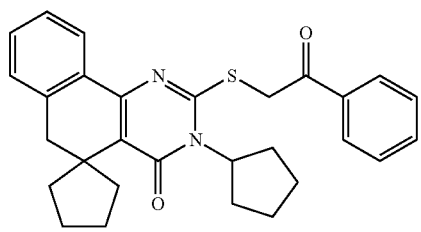
Compound 255
(PRTH-002-F33)
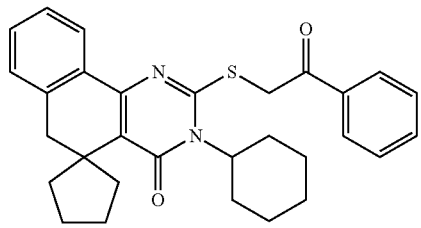
Compound 256
(PRTH-002-F34)
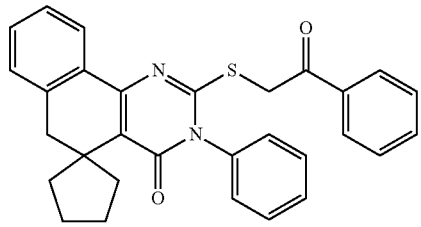
Compound 257
(PRTH-002-F35)
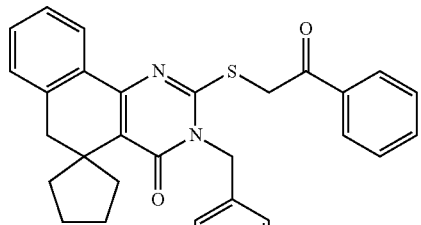
Compound 258
(PRTH-002-F36)
TABLE 11-continued
Additional Exemplary Analogs
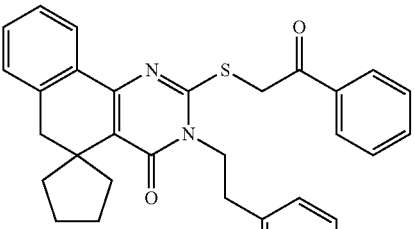
Compound 259
(PRTH-002-F37)
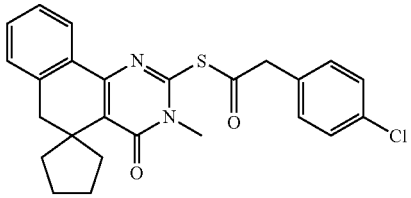 [SMILES: Cn1c(SC(=O)Cc2ccc(Cl)cc2)nc2c(c1=O)C1(CCCC1)Cc1ccccc1-2]
Compound 260
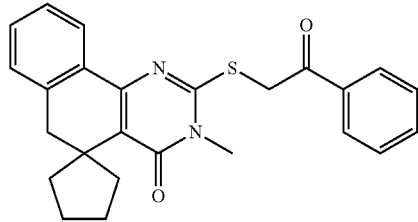 [SMILES: Cn1c(SCC(=O)c2ccccc2)nc2c(c1=O)C1(CCCC1)Cc1ccccc1-2]
Compound 261
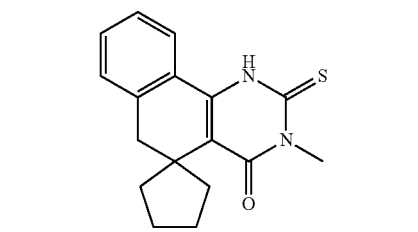 [SMILES: Cn1c(=S)[nH]c2c(c1=O)C1(CCCC1)Cc1ccccc1-2]
Compound 262
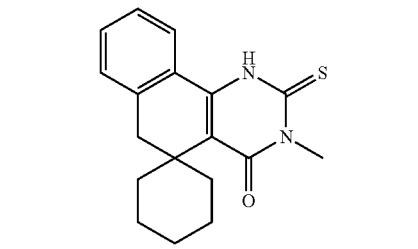 [SMILES: Cn1c(=S)[nH]c2c(c1=O)C1(CCCCC1)Cc1ccccc1-2]
Compound 263
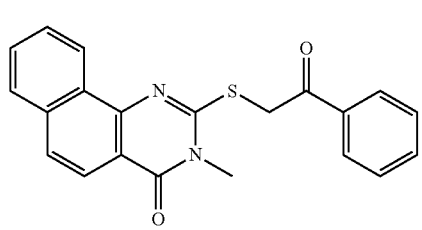 [SMILES: Cn1c(SCC(=O)c2ccccc2)nc2c(ccc3ccccc32)c1=O]
Compound 264

TABLE 11-continued

Additional Exemplary Analogs

Compound 265
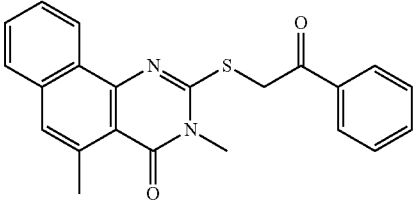 [SMILES: Cc1cc2ccccc2c2nc(SCC(=O)c3ccccc3)n(C)c(=O)c12]

Compound 266
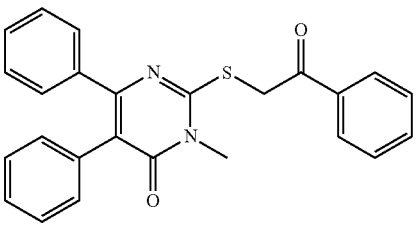 [SMILES: Cn1c(SCC(=O)c2ccccc2)nc(-c2ccccc2)c(-c2ccccc2)c1=O]

Compound 267
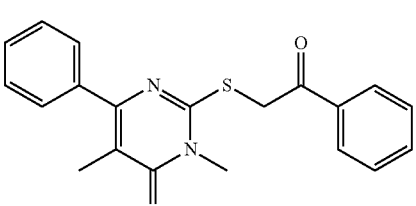

Compound 268
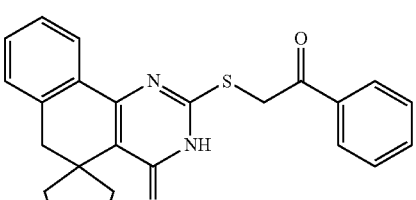

Compound 269
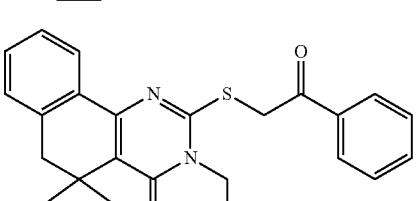

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of enhancing muscle regeneration, repair, or maintenance in a subject, comprising:
administering an effective amount of an α7β1 integrin modulatory agent to the subject in need of muscle regeneration, repair, or maintenance, wherein the α7β1 integrin modulatory agent is selected from the group consisting of MLS003126425-01, MLS000683234-01, MLS001060533, MLS001240181-01, MLS001165937-01, MLS000763405-01, and MLS000695955-01; and wherein the α7β1 integrin modulatory agent increases α7β1 integrin expression or activity as compared to α7β1 integrin expression or activity prior to treatment, thereby enhancing muscle regeneration, repair or maintenance in a subject.

2. The method of claim 1, wherein the α7β1 integrin modulatory agent is administered prior to the subject experiencing muscle damage or disease.

3. The method of claim 1, wherein the method is a method of enhancing muscle maintenance in a subject.

4. The method of claim 3, wherein the α7β1 integrin modulatory agent is administered to the subject prior to the subject exercising.

5. The method of claim 3, wherein the α7β1 integrin modulatory agent is administered to a subject at risk of acquiring a muscle disease or damage.

6. The method of claim 1, further comprising selecting a subject in need of enhancing muscle regeneration, repair, or maintenance.

7. The method of claim 6, wherein selecting a subject in need of enhancing muscle regeneration, repair, or maintenance comprises diagnosing the subject with a condition characterized by impaired muscle regeneration prior to administering an effective amount of the α7β1 integrin modulatory agent to the subject.

8. The method of claim 6, wherein selecting a subject in need of enhancing muscle regeneration, repair, or maintenance comprises diagnosing the subject with a condition characterized by impaired production of a component of α7β1 integrin prior to administering an effective amount of the α7β1 integrin modulatory agent to the subject.

9. The method of claim 1, wherein the α7β1 integrin modulatory agent is administered with an additional therapeutic agent.

10. The method of claim 9, wherein the additional therapeutic agent is a costameric protein, a growth factor, satellite cells, stem cells, myocytes or an additional α7β1 integrin modulatory agent.

11. The method of claim 10, wherein the additional α7β1 integrin modulatory agent is laminin-111, a laminin-111 fragment, valproic acid, or a valproic acid analog.

12. The method of claim 1, wherein the method is a method of enhancing muscle regeneration.

13. The method of claim 12, wherein the α7β1 integrin modulatory agent is administered to a subject with a muscle disease or damage.

14. The method of claim 13, wherein the muscle disease is a muscular dystrophy.

15. The method of claim 14, wherein the muscular dystrophy is merosin deficient congenital muscular dystrophy Type 1A (MDC1A), merosin deficient congenital muscular dystrophy Type 1D (MDC1D), limb-girdle muscular dystrophy (LGMD), Duchenne muscular dystrophy (DMD), Fukuyama congenital muscular dystrophy (FCMD) or Facioscapulohumeral muscular dystrophy (FHMD).

16. The method of claim 15, wherein the muscular dystrophy is DMD, MDC1A or FCMD.

17. The method of claim 15, wherein the muscular dystrophy is DMD.

18. The method of claim 1, wherein the α7β1 integrin modulatory agent is MLS00160533-01.

* * * * *